United States Patent
Jin

(10) Patent No.: US 12,089,489 B2
(45) Date of Patent: Sep. 10, 2024

(54) ORGANIC ELECTROLUMINESCENCE DEVICE AND DIAMINE COMPOUND FOR ORGANIC ELECTROLUMINESCENCE DEVICE

(71) Applicant: Samsung Display Co., LTD., Yongin-si (KR)

(72) Inventor: XiuLan Jin, Yokohama (JP)

(73) Assignee: SAMSUNG DISPLAY CO., LTD., Yongin-si (KR)

( * ) Notice: Subject to any disclaimer, the term of this patent is extended or adjusted under 35 U.S.C. 154(b) by 663 days.

(21) Appl. No.: 17/097,647

(22) Filed: Nov. 13, 2020

(65) Prior Publication Data

US 2021/0280786 A1    Sep. 9, 2021

(30) Foreign Application Priority Data

Feb. 20, 2020 (KR) .......................... 10-2020-0021050

(51) Int. Cl.
*H01L 51/00* (2006.01)
*C07C 211/58* (2006.01)
(Continued)

(52) U.S. Cl.
CPC .......... *H10K 85/633* (2023.02); *C07C 211/58* (2013.01); *C07D 307/91* (2013.01);
(Continued)

(58) Field of Classification Search
None
See application file for complete search history.

(56) References Cited

U.S. PATENT DOCUMENTS 6,849,345 B2   2/2005 Parton et al.
7,470,472 B2  12/2008 Funahashi
(Continued)

FOREIGN PATENT DOCUMENTS

CN    1906153   1/2007
CN  101163664   4/2008
(Continued)

OTHER PUBLICATIONS

Machine English translation of Zhou et al. (CN 107778212 A). Jan. 10, 2023.*

*Primary Examiner* — Jay Yang
(74) *Attorney, Agent, or Firm* — KILE PARK REED & HOUTTEMAN PLLC

(57) ABSTRACT

An organic electroluminescence device is provided, which may include a first electrode, a hole transport region disposed on the first electrode, an emission layer disposed on the hole transport region, an electron transport region disposed on the emission layer, and a second electrode disposed on the electron transport region. The hole transport region may include a diamine compound represented by Formula 1, thereby exhibiting high light emission efficiency.

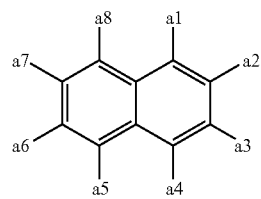

[Formula 1]

11 Claims, 2 Drawing Sheets

(51) Int. Cl.
  *C07D 307/91* (2006.01)
  *C07D 333/76* (2006.01)
  *C09K 11/06* (2006.01)
  *H10K 85/60* (2023.01)
  *H10K 50/11* (2023.01)
  *H10K 50/15* (2023.01)
  *H10K 50/17* (2023.01)

(52) U.S. Cl.
  CPC ............ *C07D 333/76* (2013.01); *C09K 11/06* (2013.01); *H10K 85/636* (2023.02); *C09K 2211/1007* (2013.01); *C09K 2211/1011* (2013.01); *C09K 2211/1014* (2013.01); *C09K 2211/1018* (2013.01); *H10K 50/11* (2023.02); *H10K 50/15* (2023.02); *H10K 50/17* (2023.02); *H10K 85/615* (2023.02); *H10K 85/626* (2023.02); *H10K 85/6574* (2023.02); *H10K 85/6576* (2023.02)

(56) References Cited

U.S. PATENT DOCUMENTS

| | | | |
|---|---|---|---|
| 8,614,009 | B2 | 12/2013 | Funahashi |
| 8,911,885 | B2 | 12/2014 | Kim et al. |
| 10,062,850 | B2 | 8/2018 | Jung et al. |
| 10,297,765 | B2 | 5/2019 | Mizuki et al. |
| 2006/0177693 | A1* | 8/2006 | Funahashi ............ C07C 211/58 564/429 |
| 2009/0072716 | A1* | 3/2009 | Funahashi ............ H10K 85/633 564/429 |
| 2019/0189927 | A1 | 6/2019 | Lee et al. |

FOREIGN PATENT DOCUMENTS

| | | |
|---|---|---|
| CN | 101910147 | 12/2010 |
| CN | 107778212 | 3/2018 |
| CN | 107778212 A * | 3/2018 |
| CN | 107778213 | 3/2018 |
| CN | 112142605 | 12/2020 |
| JP | 2006-306745 | 11/2006 |
| JP | 4415582 | 2/2010 |
| JP | 5088097 | 12/2012 |
| KR | 10-0670185 | 2/2007 |
| KR | 10-2008-0005227 | 1/2008 |
| WO | 2010/068000 | 6/2010 |
| WO | 2018/021737 | 2/2018 |

* cited by examiner

ORGANIC ELECTROLUMINESCENCE DEVICE AND DIAMINE COMPOUND FOR ORGANIC ELECTROLUMINESCENCE DEVICE

CROSS-REFERENCE TO RELATED APPLICATION(S)

This claims priority to and benefits of Korean Patent Application No. 10-2020-0021050 under 35 U.S.C. § 119, filed on Feb. 20, 2020 in the Korean Intellectual Property Office, the entire contents of which are incorporated herein by reference.

BACKGROUND

1. Technical Field

The disclosure relates to an organic electroluminescence device and a diamine compound for the organic electroluminescence device.

2. Description of the Related Art

Recently, active development is being conducted for an organic electroluminescence display as an image display device. Unlike liquid crystal display devices and the like, the organic electroluminescence display is a so-called self-luminescent display device in which holes and electrons injected from a first electrode and a second electrode recombine in an emission layer, and thus a luminescent material including an organic compound in the emission layer emits light to implement display.

In the application of an organic electroluminescence device to a display device, there is continuous demand for an organic electroluminescence device having a low driving voltage, high light emission efficiency, and a long service life. There is also continuous demand for the development of materials for an organic electroluminescence device that are capable of stably attaining such characteristics.

SUMMARY

The disclosure provides an organic electroluminescence device and a diamine compound for the organic electroluminescence device. The disclosure also provides an organic electroluminescence device having high efficiency and a diamine compound included in a hole transport region of the organic electroluminescence device.

An embodiment of the inventive concept provides an organic electroluminescence device that may include a first electrode, a hole transport region disposed on the first electrode, an emission layer disposed on the hole transport region, an electron transport region disposed on the emission layer, and a second electrode disposed on the electron transport region The hole transport region may include a diamine compound represented by Formula 1 below:

[Formula 1]

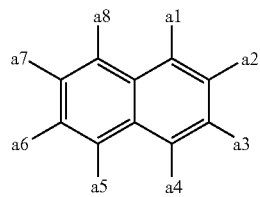

In Formula 1, a1 to a4 may each independently be a hydrogen atom, a deuterium atom, a substituted or unsubstituted aryl group having 6 to 30 ring-forming carbon atoms, or a group represented by Formula 2-1, where one of a1 to a4 may be a group represented by Formula 2-1, and another one of a1 to a4 may be a substituted or unsubstituted aryl group having 6 to 30 ring-forming carbon atoms. In Formula 1, a5 to a8 may each independently be a hydrogen atom, a deuterium atom, a substituted or unsubstituted aryl group having 6 to 30 ring-forming carbon atoms, or a group represented by Formula 2-2, where one of a5 to a8 may be a group represented by Formula 2-2, and another one of a5 to a8 may be a substituted or unsubstituted aryl group having 6 to 30 ring-forming carbon atoms:

[Formula 2-1]

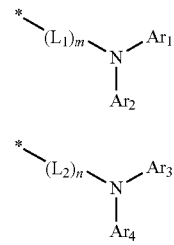

[Formula 2-2]

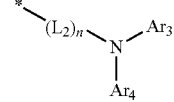

In Formula 2-1 and Formula 2-2, $L_1$ and $L_2$ may each independently be a direct linkage, a substituted or unsubstituted arylene group having 6 to 30 ring-forming carbon atoms, or a substituted or unsubstituted heteroarylene group having 2 to 30 ring-forming carbon atoms, m and n may each independently be an integer from 0 to 4, $Ar_1$ to $Ar_4$ may each independently be a substituted or unsubstituted aryl group having 6 to 30 ring-forming carbon atoms, or a substituted or unsubstituted heteroaryl group having 2 to 30 ring-forming carbon atoms. When a1 is represented by Formula 2-1, and a5 is represented by Formula 2-2, and a7 is a substituted or unsubstituted aryl group having 6 to 30 ring-forming carbon atoms, then one of a2 to a4 may be a substituted or unsubstituted aryl group having 6 to 30 ring-forming carbon atoms, and at least one of $Ar_1$ to $Ar_4$ may be a substituted or unsubstituted heteroaryl group having 2 to 30 ring-forming carbon atoms.

In an embodiment, when one of a1 to a4 is a substituted or unsubstituted aryl group having 6 to 30 ring-forming carbon atoms, then the substituted or unsubstituted aryl group having 6 to 30 ring-forming carbon atoms may be represented by Formula 2-3, and when one of a5 to a8 is a substituted or unsubstituted aryl group having 6 to 30 ring-forming carbon atoms, then the substituted or unsubstituted aryl group having 6 to 30 ring-forming carbon atoms may be represented by Formula 2-4:

[Formula 2-3]

[Formula 2-4]

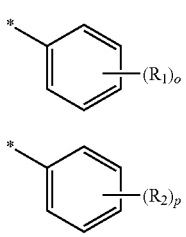

In Formula 2-3 and Formula 2-4, $R_1$ and $R_2$ may each independently be a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, a substituted or unsubstituted heteroaryl group having 2 to 30 ring-forming carbon atoms, or bonded to an adjacent group to form a ring, and o and p may each independently be an integer from 0 to 5.

In an embodiment, Formula 1 may be represented by Formula 3-1 or Formula 3-2:

[Formula 3-1]

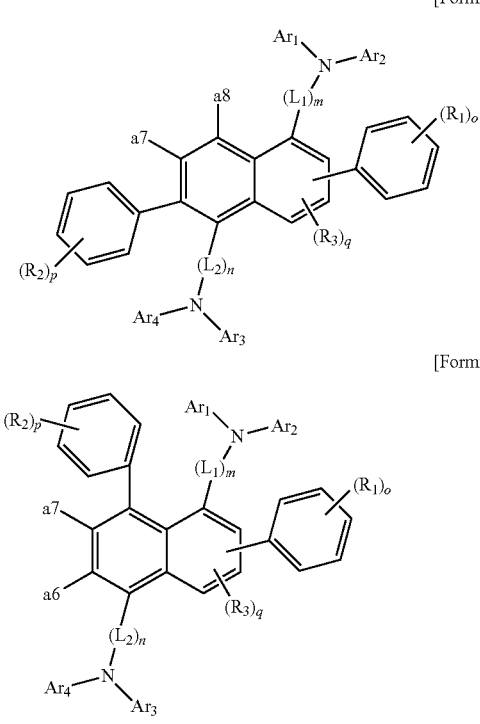

[Formula 3-2]

In Formula 3-1 and Formula 3-2, a6 to a8 may each independently be a hydrogen atom or a deuterium atom, $R_3$ may be a hydrogen atom or a deuterium atom, q may be an integer from 0 to 2, and $Ar_1$ to $Ar_4$, $L_1$, $L_2$, $R_1$, $R_2$, and m to p may be the same as defined in Formula 1 and Formula 2-1 to Formula 2-4.

In an embodiment, Formula 1 may be represented by Formula 4:

[Formula 4]

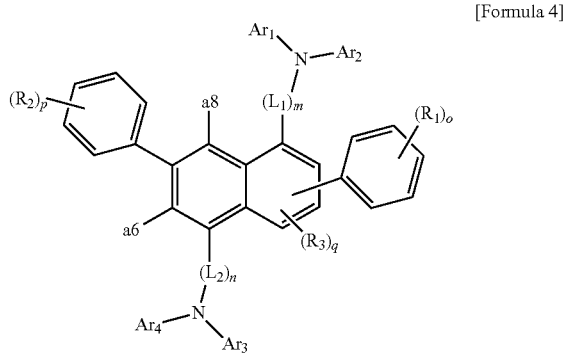

In Formula 4, $Ar_1$ to $Ar_4$ may each independently be a substituted or unsubstituted aryl group having 6 to 30 ring-forming carbon atoms or a substituted or unsubstituted aryl group having 2 to 30 ring-forming carbon atoms, at least one of $Ar_1$ to $Ar_4$ may be a substituted or unsubstituted heteroaryl group having 2 to 30 ring-forming carbon atoms, a6 and a8 may each independently be a hydrogen atom or a deuterium atom, $R_3$ may be a hydrogen atom or a deuterium atom, q may be an integer from 0 to 2, and $L_1$, $L_2$, $R_1$, $R_2$, and m to p may be the same as defined in Formula 1 and Formula 2-1 to Formula 2-4.

In an embodiment, Formula 1 may be represented by one of Formula 5 to Formula 7:

[Formula 5]

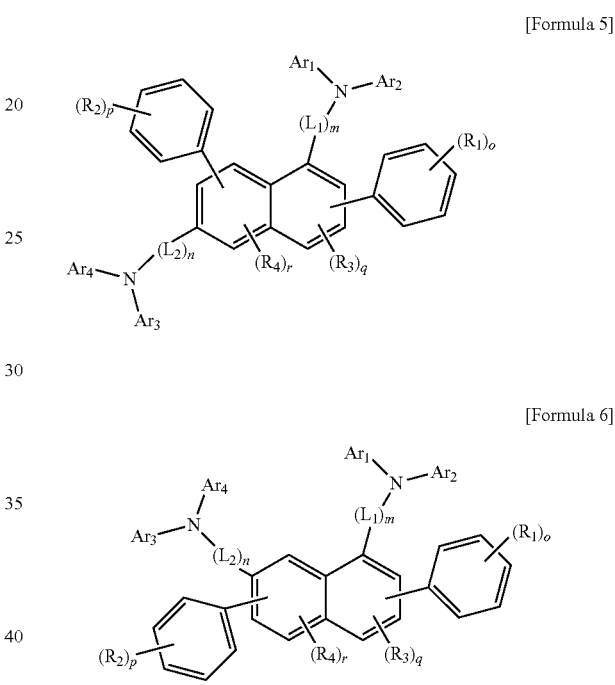

[Formula 6]

[Formula 7]

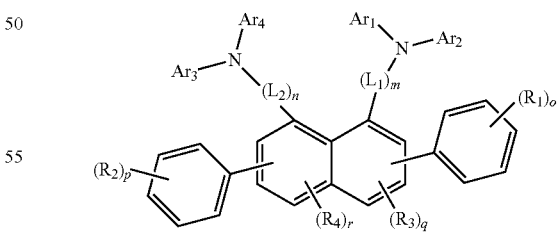

In Formula 5 to Formula 7, $R_5$ and $R_4$ may each independently be a hydrogen atom or a deuterium atom, q and r may each independently be an integer from 0 to 2, and $Ar_1$ to $Ar_4$, $L_1$, $L_2$, $R_1$, $R_2$, and m to p may be the same as defined in Formula 1 and Formula 2-1 to Formula 2-4.

In an embodiment, Formula 1 may be represented by one of Formula 8 to Formula 11:

[Formula 8]

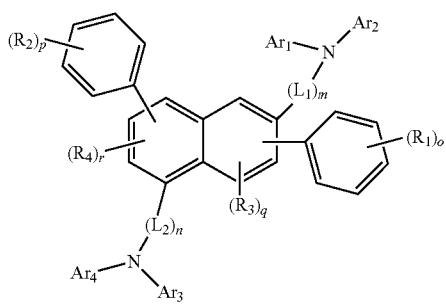

[Formula 9]

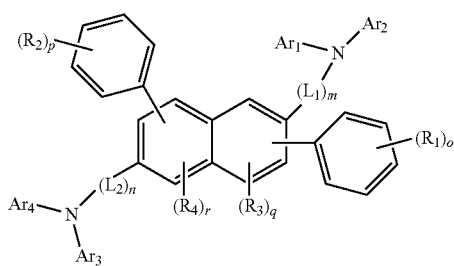

[Formula 10]

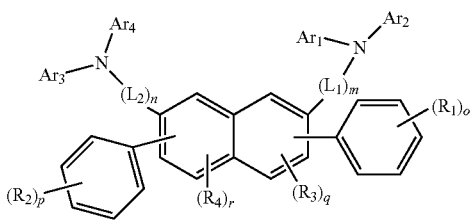

[Formula 11]

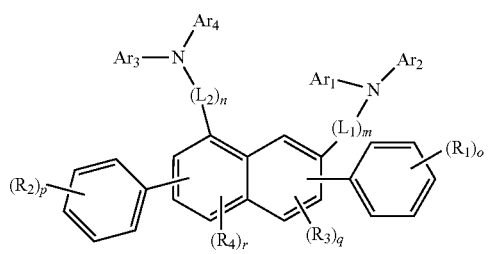

In Formula 8 to Formula 11, $R_3$ and $R_4$ may each independently be a hydrogen atom or a deuterium atom, q and r may each independently an of from 0 to 2, and $Ar_1$ to $Ar_4$, $L_1$, $L_2$, $R_1$, $R_2$, and m to p may be the same as defined in Formula 1 and Formula 2-1 to Formula 2-4.

In an embodiment, $L_1$ and $L_2$ may each independently be a direct linkage, a substituted or unsubstituted phenylene group, or a substituted or unsubstituted biphenylene group.

In an embodiment, Formula 6 may be represented by Formula 6-1 or Formula 6-2:

[Formula 6-1]

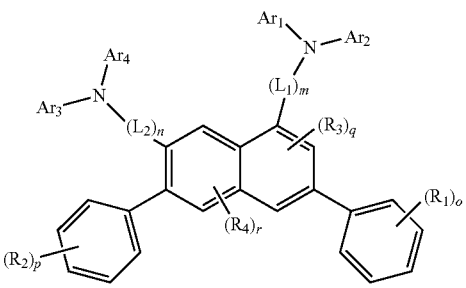

[Formula 6-2]

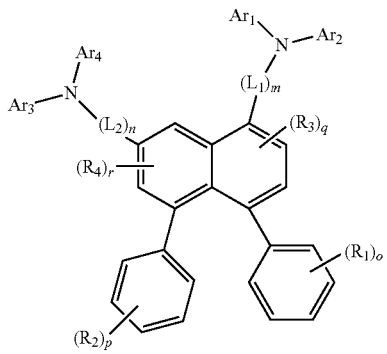

In Formula 6-1 and Formula 6-2, $Ar_1$ to $Ar_4$, $L_1$, $L_2$, $R_1$ to $R_4$, and m tor may be the same as defined in Formula 6.

In an embodiment, Formula 9 may be represented by Formula 9-1:

[Formula 9-1]

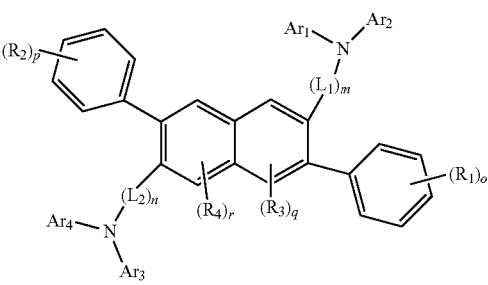

In Formula 9-1, $Ar_1$ to $Ar_4$, $L_1$, $L_2$, $R_1$ to $R_4$, and m to r may be the same as defined in Formula 9.

In an embodiment, Formula 10 may be represented by one of Formula 10-1 to Formula 10-3:

[Formula 10-1]

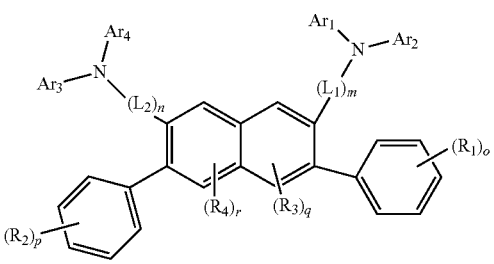

[Formula 10-2]

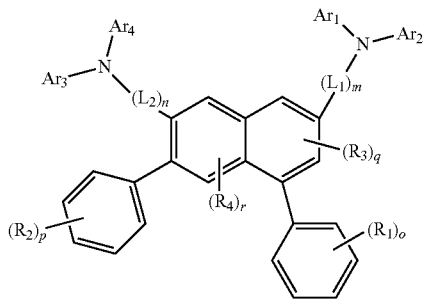

[Formula 10-3]

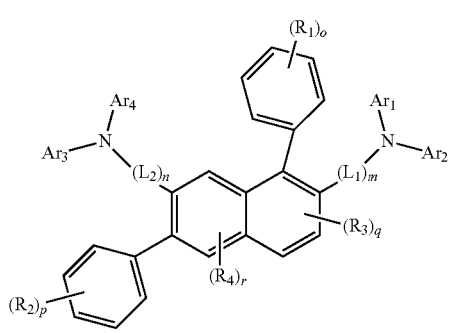

In Formula 10-1 to Formula 10-3, $Ar_1$ to $Ar_4$, $L_1$, $L_2$, $R_1$ to $R_4$, and m to r may be the same as defined in Formula 10.

In an embodiment, the hole transport region may include a hole injection layer disposed on the first electrode and a hole transport layer disposed on the hole injection layer, wherein the hole transport layer may include a diamine compound represented by Formula 1.

In an embodiment, the diamine compound represented by Formula 1 may be one selected from the compounds represented by Compound Group 1 below.

An embodiment of the inventive concept provides a diamine compound represented by Formula 1.

BRIEF DESCRIPTION OF THE DRAWINGS

The accompanying drawings are included to provide a further understanding of the inventive concept, and are incorporated in and constitute a part of this specification. The drawings illustrate embodiments of the inventive concept and, together with the description, serve to explain principles of the inventive concept. In the drawings.

DETAILED DESCRIPTION OF THE EMBODIMENTS

Figure 1:
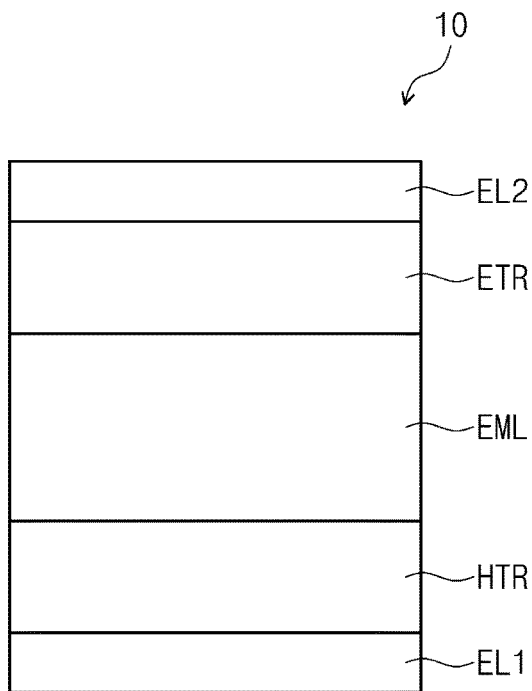
FIG. 1 is a schematic cross-sectional view illustrating an organic electroluminescence device according to an embodiment of the inventive concept.

The inventive concept may have various modifications and may be embodied in different forms, and example embodiments will be explained in detail with reference to the accompanying drawings. The inventive concept may, however, be embodied in different forms and should not be construed as limited to the embodiments set forth herein. Rather, all modifications, equivalents, and substituents which are included in the spirit and technical scope of the inventive concept should be included in the inventive concept.

In the description, it will be understood that when an element (a region, a layer, a section, or the like) is referred to as being "on", "connected to" or "coupled to" another element, it can be directly on, connected or coupled to the other element, or an intervening third element may be disposed therebetween.

Like numbers refer to like elements throughout. In the drawings, the thickness, the ratio, and the dimensions of elements may be exaggerated for an effective description of technical contents.

As used herein, the term "and/or" includes any and all combinations of one or more of the associated listed items. For example, "A and/or B" may be understood to mean "A, B, or A and B." The terms "and" and "or" may be used in the conjunctive or disjunctive sense and may be understood to be equivalent to "and/or". Throughout the disclosure, the expression "at least one of A, B, and C" may indicate only A, only B, only C, both A and B, both A and C, both B and C, all of A, B, and C, or variations thereof.

The term "at least one of" is intended to include the meaning of "at least one selected from the group consisting of" for the purpose of its meaning and interpretation. For example, "at least one of A and B" may be understood to mean "A, B, or A and B." When preceding a list of elements, the term, "at least one of," modifies the entire list of elements and does not modify the individual elements of the list.

It will be understood that, although the terms "first", "second", etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the inventive concept. The terms of a singular form may include plural forms unless the context clearly indicates otherwise.

Terms such as "below," "lower," "above," "upper," and the like are used to describe the relationship of the configurations shown in the drawings. The terms are used as a relative concept and are described with reference to the direction indicated in the drawings.

The terms "about" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" may mean within one or more standard deviations, or within +20%, 10%, or 5% of the stated value.

Unless otherwise defined, all terms (including technical and scientific terms) used herein have the same meaning as commonly understood by one of ordinary skill in the art to which the inventive concept pertains. It is also to be understood that terms defined in commonly used dictionaries should be interpreted as having meanings consistent with the meanings in the context of the related art, and are expressly defined herein unless they are interpreted in an ideal or overly formal sense.

It should be understood that the terms "comprises," "comprising," "includes," "including," "have," "having," "contains," and/or "containing" are intended to specify the presence of stated features, integers, steps, operations, elements, components, or combinations thereof in the disclosure, but do not preclude the presence or addition of one or more other features, integers, steps, operations, elements, components, or combinations thereof.

Hereinafter, an organic electroluminescence device according to an embodiment of the inventive concept and a compound of an embodiment included therein will be described with reference to the accompanying drawings.

FIGS. 1 to 4 are schematic cross-sectional views illustrating organic electroluminescence devices according to embodiments of the inventive concept. Referring to FIGS. 1 to 4, in each of organic electroluminescence devices 10 according to embodiments, a first electrode EL1 and a second electrode EL2 are disposed to face each other and an emission layer EML may be disposed between the first electrode EL1 and the second electrode EL2.

Each of the organic electroluminescence devices 10 of embodiments may further include functional layers between the first electrode EL1 and the second electrode EL2 in addition to the emission layer EML. The functional layers may include a hole transport region HTR and an electron transport region ETR. Each of the organic electroluminescence devices 10 according to embodiments may include the first electrode EL1, the hole transport region HTR, the emission layer EML, the electron transport region ETR, and the second electrode EL2 in a sequentially stacked embodiment. The organic electroluminescence device 10 of an embodiment may include a capping layer CPL disposed on the second electrode EL2.

The organic electroluminescence device 10 of an embodiment may include a diamine compound of an embodiment, which will be described later, in the hole transfer region HTR disposed between the first electrode EL1 and the second electrode EL2. However, the embodiment is not limited thereto, and the organic electroluminescence device 10 of an embodiment may include a compound according to an embodiment, which will be described later, not only in the hole transport region HTR but also in the emission layer EML or electron transport region ETR, which may be included in the functional layers disposed between the first electrode EL 1 and the second electrode EL2, or in the capping layer CPL disposed on the second electrode EL2.

Figure 2:
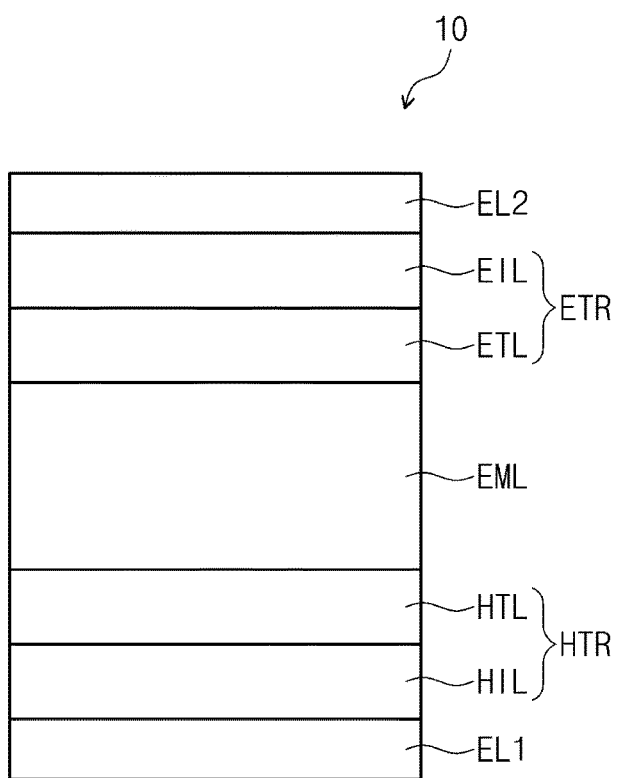
FIG. 2 is a schematic cross-sectional view illustrating an organic electroluminescence device according to an embodiment of the inventive concept.
Figure 3:
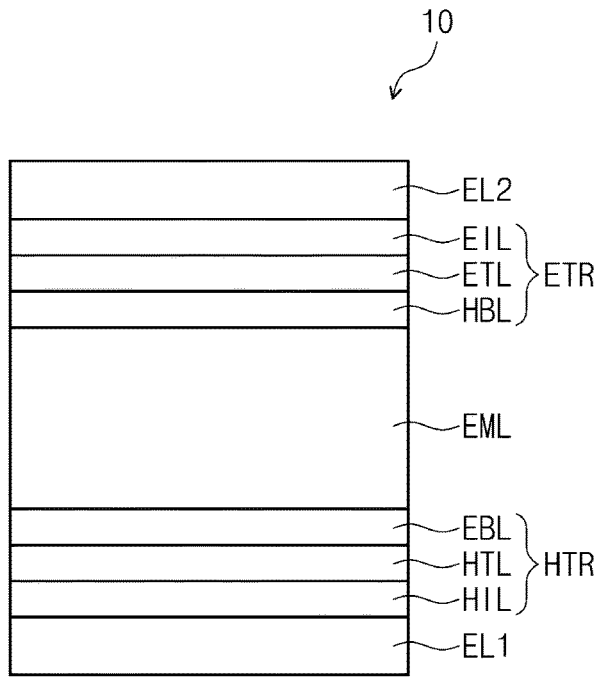
FIG. 3 is a schematic cross-sectional view illustrating an organic electroluminescence device according to an embodiment of the inventive concept.
Figure 4:
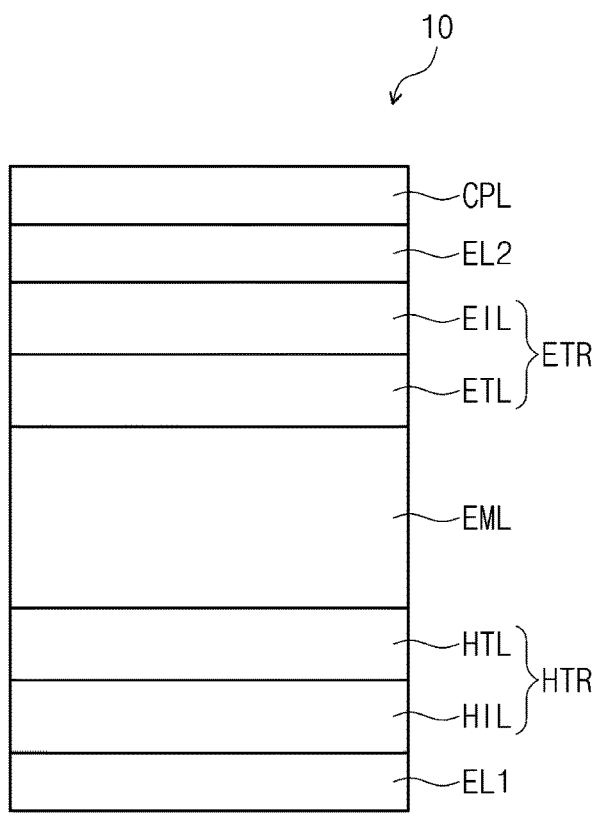
FIG. 4 is a schematic cross-sectional view illustrating an organic electroluminescence device according to an embodiment of the inventive concept.

In comparison to FIG. 1, FIG. 2 illustrates a cross-sectional view of an organic electroluminescence device 10 of an embodiment, in which a hole transport region HTR includes a hole injection layer HIL and a hole transport layer HTL, and an electron transport region ETR includes an electron injection layer EIL and an electron transport layer ETL. In comparison to FIG. 1, FIG. 3 illustrates a cross-sectional view of an organic electroluminescence device 10 of an embodiment, in which a hole transport region HTR includes a hole injection layer HIL, a hole transport layer HTL, and an electron blocking layer EBL, and an electron transport region ETR includes an electron injection layer EIL, an electron transport layer ETL, and a hole blocking layer HBL. In comparison to FIG. 2, FIG. 4 illustrates a cross-sectional view of an organic electroluminescence device 10 of an embodiment including a capping layer CPL disposed on the second electrode EL2.

The first electrode EL1 has conductivity. The first electrode EL1 may be formed of a metal alloy or a conductive compound. The first electrode EL1 may be a pixel electrode or positive electrode. The first electrode EL1 may be a transmissive electrode, a transflective electrode, or a reflective electrode. When the first electrode EL1 is a transmissive electrode, the first electrode EL1 may include a transparent metal oxide, such as indium tin oxide (ITO), indium zinc oxide (IZO), zinc oxide (ZnO), and indium tin zinc oxide (ITZO). When the first electrode EL1 is a transflective electrode or a reflective electrode, the first electrode EL1 may include Ag, Mg Cu, Al, Pt, Pd, Au, Ni, Nd, Ir, Cr, Li, Ca, LiF/Ca, LiF/Al, Mo, Ti, a compound thereof, or a mixture thereof (e.g., a mixture of Ag and Mg). The first electrode EL1 may have a multilayer structure including a reflective layer or a transflective layer formed of the above-described materials, and a transparent conductive layer formed of ITO, IZO, ZnO, ITZO, etc. For example, the first electrode EL1 may have a three-layer structure of ITO/Ag/ITO, but is not limited thereto. The thickness of the first electrode EL1 may be in a range of about 1,000 Å to about 10,000 Å. For example, the thickness of the first electrode EL1 may be in a range of about 1,000 Å to about 3,000 Å.

The hole transport region HTR may be provided on the first electrode EL1. The hole transport region HTR may include at least one of a hole injection layer HIL, a hole transport layer HTL, a hole buffer layer (not shown), or an electron blocking layer.

The hole transport region HTR may have a single layer formed of a single material, a single layer formed of different materials, or a multilayer structure including multiple layers formed of different materials.

For example, the hole transport region HTR may have a single layer structure of a hole injection layer HIL or a hole transport layer HTL, or a single layer structure formed of a hole injection material and a hole transport material. The hole transport region HTR may have a single layer structure formed of different materials, or a structure of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer EBL which may be sequentially laminated from the first electrode EL1, but embodiments are not limited thereto.

The hole transport region HTR in the organic electroluminescence device 10 of an embodiment may include a diamine compound according to an embodiment of the inventive concept.

In the description, the term "substituted or unsubstituted" may indicate that one is substituted or unsubstituted with at least one substituent selected from the group consisting of a deuterium atom, a halogen atom, a cyano group, a nitro group, an amino group, a silyl group, oxy group, thio group, sulfinyl group, sulfonyl group, carbonyl group, a boron group, a phosphine oxide group, a phosphine sulfide group, an alkyl group, an alkenyl group, an alkoxy group, a hydrocarbon ring group, an aryl group, and a heterocyclic group. Each of the substituents above may be substituted or unsubstituted. For example, a biphenyl group may be interpreted as an aryl group or a phenyl group substituted with a phenyl group.

In the description, examples of the halogen atom may include a fluorine atom, a chlorine atom, a bromine atom, and an iodine atom.

In the description, the alkyl group may be a linear, branched, or cyclic type. The number of carbons in the alkyl group may be from 1 to 50, 1 to 30, 1 to 20, 1 to 10, or 1 to 6. Examples of the alkyl group may include, but are not limited to, methyl group, ethyl group, n-propyl group, isopropyl group, n-butyl group, s-butyl group, t-butyl group, i-butyl group, 2-ethylbutyl group, 3,3-dimethylbutyl group, n-pentyl group, i-pentyl group, neopentyl group, t-pentyl group, cyclopentyl group, 1-methylpentyl group, 3-methylpentyl group, 2-ethylpentyl group, 4-methyl-2-pentyl group, n-hexyl group, 1-methylhexyl group, 2-ethylhexyl group, 2-butylhexyl group, cyclohexyl group, 4-methylcyclohexyl group, 4-t-butylcyclohexyl group, n-heptyl group, 1-methylheptyl group, 2,2-dimethylheptyl group, 2-ethylheptyl group, 2-butylheptyl group, n-octyl group, t-octyl group, 2-ethyloctyl group, 2-butyloctyl group, 2-hexyloctyl group, 3,7-dimethyloctyl group, Zcyclooctyl group, n-nonyl group, n-decyl group, adamantyl group, 2-ethyldecyl group, 2-butyldecyl group, 2-hexyldecyl group, 2-octyldecyl group, n-undecyl group, n-dodecyl group, 2-ethyldodecyl group, 2-butyldodecyl group, 2-hexyldocecyl group, 2-octyldodecyl group, n-tridecyl group, n-tetradecyl group, n-pentadecyl group, n-hexadecyl group, 2-ethylhexadecyl group, 2-butylhexadecyl group, 2-hexylhexadecyl group, 2-octylhexadecyl group, n-heptadecyl group, n-octadecyl group, n-nonadecyl group, n-eicosyl group, 2-ethyleicosyl group, 2-butyleicosyl group, 2-hexyleicosyl group, 2-octyleicosyl group, n-henicosyl group, n-docosyl group, n-tricosyl group, n-tetracosyl group, n-pentacosyl group, n-hexacosyl group, n-heptacosyl group, n-octacosyl group, n-nonacosyl group, n-triacontyl group, etc.

In the description, an alkenyl group means a hydrocarbon group including at least one carbon double bond in the middle or terminal of an alkyl group having 2 or more carbon atoms. The alkenyl group may be linear or branched. Although the number of carbon atoms is not specifically limited, it may be from 2 to 30, 2 to 20, or 2 to 10. Examples of the alkenyl group include a vinyl group, a 1-butenyl group, a 1-pentenyl group, a 1,3-butadienyl aryl group, a styrenyl group, a styryl vinyl group, etc., but are not limited thereto.

In the description, an alkynyl group means a hydrocarbon group including at least one carbon triple bond in the middle or terminal of an alkyl group having 2 or more carbon atoms. The alkynyl group may be linear or branched. Although the number of carbon atoms is not specifically limited, it may be from 2 to 30, 2 to 20, or 2 to 10. Specific examples of the alkynyl group may include an ethynyl group, a propynyl group, etc., but are not limited thereto.

In the description, a hydrocarbon ring group may be an any functional group or substituent derived from an aliphatic hydrocarbon ring, or an any functional group or substituent derived from an aromatic hydrocarbon ring. The number of ring-forming carbon atoms in the hydrocarbon ring group may be from 5 to 60, 5 to 30, or 5 to 20.

In the description, an aryl group means any functional group or substituent derived from an aromatic hydrocarbon ring. The aryl group may be a monocyclic aryl group or a polycyclic aryl group. The number of ring-forming carbon atoms in the aryl group may be from 6 to 30, 6 to 20, or 6 to 15. Examples of the aryl group may include phenyl, naphthyl, fluorenyl, anthracenyl, phenanthryl, biphenyl, terphenyl, quaterphenyl, quinqphenyl, sexiphenyl, triphenylenyl, pyrenyl, benzofluoranthenyl, chrysenyl, etc., but are not limited thereto.

In the description, the fluorenyl group may be substituted, and two substituents may be combined with each other to form a spiro structure. Examples of the substituted fluorenyl group are as follows However, an embodiment of the inventive concept is not limited thereto.

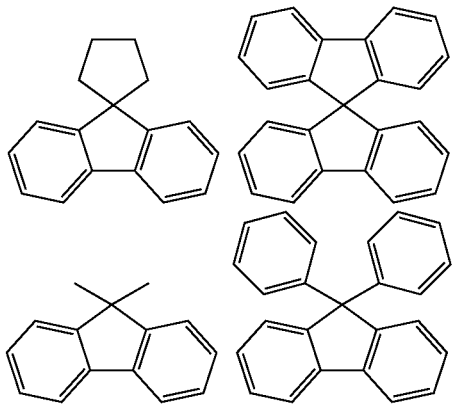

In the description, a heterocyclic group means any functional group or substituent derived from a ring containing at least one of B, O, N, P, Si, or S as a hetero atom. The heterocyclic group includes an aliphatic heterocyclic group and an aromatic heterocyclic group. The aromatic heterocyclic group may be a heteroaryl group. The aliphatic heterocycle and aromatic heterocycle may be monocyclic or polycyclic.

In the description, the heterocyclic group may include at least one of B, O, N, P, Si or S as a hetero atom. When the heterocyclic group contains two or more hetero atoms, the two or more hetero atoms may be the same as or different from each other. The heterocyclic group may be a monocyclic heterocyclic group or a polycyclic heterocyclic group, and includes a heteroaryl group. The number of ring-forming carbon atoms in in the heterocyclic group may be from 2 to 30, 2 to 20, or 2 to 10.

In the description, the aliphatic heterocyclic group may include at least one of B, O, N, P, Si, or S as a hetero atom. The number of ring-forming carbon atoms in the aliphatic heterocyclic group may be from 2 to 30, 2 to 20, or 2 to 10. Examples of the aliphatic heterocyclic group include an oxirane group, a tyran group, a pyrrolidine group, a piperidine group, a tetrahydrofuran group, a tetrahydrothiophene group, a thian group, a tetrahydropyran group, a 1,4-dioxane group, etc., but are not limited to thereto.

In the description, the heteroaryl group may include at least one of B, O, N, P, Si, or S as a hetero atom. When the heteroaryl group contains two or more hetero atoms, the two or more hetero atoms may be the same as or different from each other. The heteroaryl group may be a monocyclic heteroaryl group or a polycyclic heteroaryl group. The number of ring-forming carbon atoms in the heteroaryl group may be from 2 to 30, 2 to 20, or 2 to 10. Examples of the heteroaryl group may include thiophene, furan, pyrrole, imidazole, thiazole, oxazole, oxadiazole, triazole, pyridyl, bipyridyl, pyrimidyl, triazine, triazole, acridyl, pyridazine, pyrazinyl, quinolinyl, quinazoline, quinoxalinyl, phenoxazyl, phthalazinyl, pyrido pyrimidyl, pyrido pyrazinyl, pyrazino pyrazinyl, isoquinoline, indole, carbazole, N-arylcarbazole, N-heteroarylcarbazole, N-alkylcarbazole, benzoxazole, benzoimidazole, benzothiazole, benzocarbazole, benzothiophene, dibenzothiophenyl, thienothiophene, benzofuranyl, phenanthroline, thiazolyl, isooxazolyl, oxadiazolyl, thiadiazolyl, phenothiazolyl, phenothiazinyl, dibenzosilole, dibenzofuranyl, etc., but are not limited thereto.

In the description, the number of carbon atoms in an amine group is not specifically limited, but may be from 1 to 30. The amine group may include an alkyl amine group, an aryl amine group, or a heteroaryl amine group. Examples of the amine group include a methylamine group, a dimethylamine group, a phenylamine group, a diphenylamine group, a naphthylamine group, a 9-methyl-anthracenylamine group, a triphenylamine group, etc., but are not limited thereto.

In the description, the above description with respect to the aryl group is applied to an arylene group except that the arylene group is a divalent group.

In the description, the above description with respect to the heteroaryl group is applied to a heteroarylene group except that the heteroarylene group is a divalent group.

In the description, "—*" refers to a position to be connected, and * indicates a binding site to a neighboring atom.

The diamine compound according to an embodiment of the inventive concept is represented by Formula 1 below:

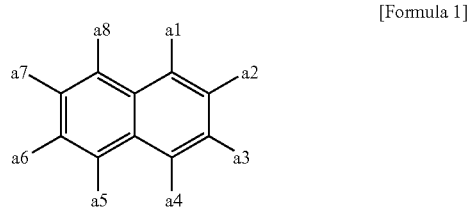

[Formula 1]

In Formula 1, a1 to a4 may each independently be a hydrogen atom, a deuterium atom, a substituted or unsubstituted aryl group having 6 to 30 ring-forming carbon atoms, or a group represented by Formula 2-1 below, wherein one of a1 to a4 is a group represented by Formula 2-1 below, and another one of a1 to a4 is a substituted or unsubstituted aryl group having 6 to 30 ring-forming carbon atoms.

In Formula 1, a5 to a8 may each independently be a hydrogen atom, a deuterium atom, a substituted or unsubstituted aryl group having 6 to 30 ring-forming carbon atoms, or represented by Formula 2-2 below, wherein one of a5 to a8 is a group represented by Formula 2-2 below, and another one of a5 to a8 is an aryl group having 6 to 30 ring-forming carbon atoms.

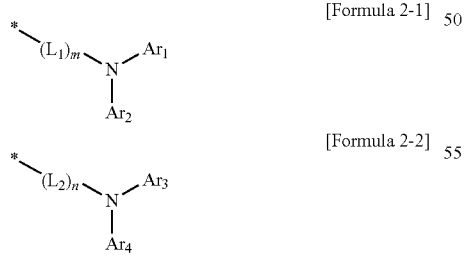

[Formula 2-1]

[Formula 2-2]

In Formula 2-1 and Formula 2-2, $L_1$ and $L_2$ may each independently be a direct linkage, a substituted or unsubstituted arylene group having 6 to 30 ring-forming carbon atoms, or a substituted or unsubstituted heteroarylene group having 2 to 30 ring-forming carbon atoms.

In Formula 2-1 and Formula 2-2, m and n may each independently be an integer from 0 to 4. When m is 2 or more, the $L_1$'s may be the same as or different from each other, and when n is 2 or more, the $L_2$'s may be the same as or different from each other.

In Formula 2-2 and Formula 2-2, $Ar_1$ to $Ar_2$ may each independently be a substituted or unsubstituted aryl group having 6 to 30 ring-forming carbon atoms, or a substituted or unsubstituted heteroaryl group having 2 to 30 ring-forming carbon atoms.

When a1 above is a group represented by Formula 2-1 above, a5 above is a group represented by Formula 2-2 above, and a7 above is a substituted or unsubstituted aryl group having 6 to 30 ring-forming carbon atoms, then any one of a2 to a4 may be a substituted or unsubstituted aryl group having 6 to 30 ring-forming carbon atoms, and at least one of $Ar_1$ to $Ar_4$ may be a substituted or unsubstituted heteroaryl group having 2 to 30 ring-forming carbon atoms.

In an embodiment, the diamine compound represented by Formula 1 may include only the amine group represented by Formula 2-1 and Formula 2-2. In an embodiment, the diamine compound represented by Formula 1 may not include a substituent including N other than the amine group represented by Formula 2-1 and Formula 2-2. In an embodiment, the diamine compound represented by Formula 1 may not include an alkylamine group and/or an arylamine group as a substituent other than the amine group represented by Formula 2-1 and Formula 2-2. In an embodiment, the diamine compound represented by Formula 1 may not include an heteroaryl group including N.

In an embodiment, $Ar_1$ to $Ar_4$ in Formula 2-1 and Formula 2-2 may not be bonded to each other to form a ring.

In an embodiment, $L_1$ and $L_2$ in Formula 2-1 and Formula 2-2 may be each independently a direct linkage, a substituted or unsubstituted phenylene group, or a substituted or unsubstituted biphenylene group.

In an embodiment, when one of a1 to a4 in Formula 1 is a substituted or unsubstituted aryl group having 6 to 30 ring-forming carbon atoms, then the substituted or unsubstituted aryl group having 6 to 30 ring-forming carbon atoms may be represented by Formula 2-3 below, and when one of a5 to a8 in Formula 1 is a substituted or unsubstituted aryl group having 6 to 30 ring-forming carbon atoms, then the substituted or unsubstituted aryl group having 6 to 30 ring-forming carbon atoms may be represented by Formula 2-4 below:

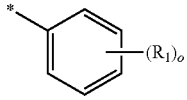

[Formula 2-3]

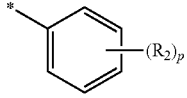

[Formula 2-4]

In Formula 2-3 and Formula 2-4, $R_1$ and $R_2$ may each independently be a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, a substituted or unsubstituted heteroaryl group having 2 to 30 ring-forming carbon atoms, or bonded to an adjacent group to form a ring.

In Formula 2-3 and Formula 2-4, o and p may each independently be an integer from 0 to 5. When o is 2 or more, the $R_1$'s may be the same as or different from each other, and when p is 2 or more, the $R_2$'s may be the same as or different from each other.

In an embodiment, when a1 in Formula 1 is a group represented by Formula 2-1, and a5 in Formula 1 is a group represented by Formula 2-2, then one of a2 to a4 in Formula 1 may be a substituted or unsubstituted aryl group having 6 to 30 ring-forming carbon atoms, and a6 or a8 in Formula 1 may be a substituted or unsubstituted aryl group having 6 to 30 ring-forming carbon atoms. Formula 1 may be represented by one of Formula 3-1 or Formula 3-2 below:

[Formula 3-1]

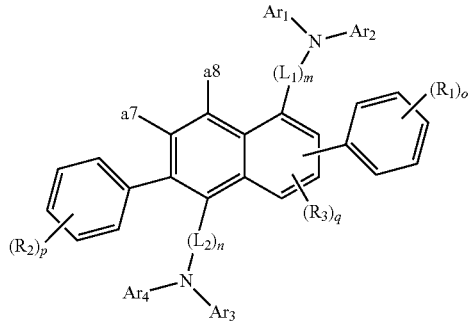

[Formula 3-2]

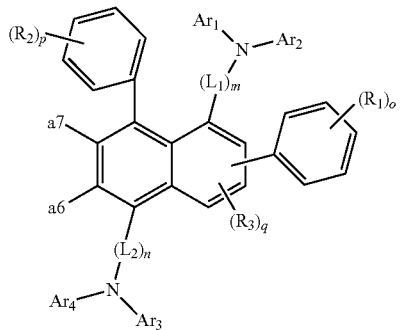

In Formula 3-1 and Formula 3-2, a6 to a8 may each independently be a hydrogen atom or a deuterium atom.

In Formula 3-1 and Formula 3-2, $R_3$ may be a hydrogen atom or a deuterium atom.

In Formula 3-1 and Formula 3-2, q may be an integer from 0 to 2. When q is 2, the $R_3$'s may be the same as or different from each other.

In Formula 3-1 and Formula 3-2 above, $Ar_1$ to $Ar_4$, $L_1$, $L_2$, $R_1$ to $R_4$, and m to p may be the same as defined in Formula 1 and Formula 2-1 to Formula 2-4.

In an embodiment, when a1 in Formula 1 is a group represented by Formula 2-1, a5 in Formula 1 is a group represented by Formula 2-2, and a7 in Formula 1 is a substituted or unsubstituted aryl group having 6 to 30 ring-forming carbon atoms, then one of a2 to a4 in Formula 1 may be a substituted or unsubstituted aryl group having 6 to 30 ring-forming carbon atoms, and at least one of $Ar_1$ to $Ar_4$ may be a substituted or unsubstituted heteroaryl group having 2 to 30 ring-forming carbon atoms. Formula 1 may be represented by Formula 4 below:

[Formula 4]

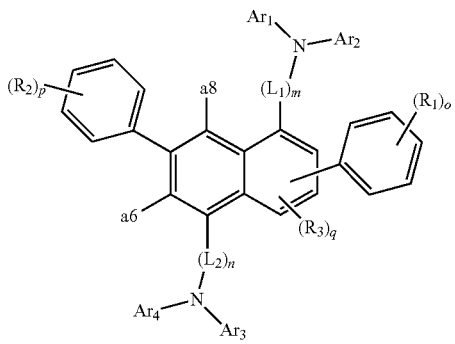

In Formula 4, $Ar_1$ to $Ar_4$ may each independently be a substituted or unsubstituted aryl group having 6 to 30 ring-forming carbon atoms, or a substituted or unsubstituted heteroaryl group having 2 to 30 ring-forming carbon atoms, and at least one of $Ar_1$ to $Ar_4$ may be a substituted or unsubstituted heteroaryl group having 2 to 30 ring-forming carbon atoms.

In Formula 4, a6 and a8 may each independently be a hydrogen atom or a deuterium atom.

In Formula 4, $R_3$ may be a hydrogen atom or a deuterium atom.

In Formula 4, q may be an integer of 0 to 2. When q is 2, the $R_3$'s may be the same as or different from each other.

In Formula 4, $L_1$, $L_2$, $R_1$, $R_2$, and m to p may be the same as defined in Formula 1 and Formula 2-1 to Formula 2-4.

In an embodiment, when a1 in Formula 1 is a group represented by Formula 2-1 and one of a6 to a8 in Formula 1 is a group represented by Formula 2-2, then one of a2 to a4 in Formula 1 may be a substituted or unsubstituted aryl group having 6 to 30 ring-forming carbon atoms, and one of the group consisting of a5 and another of a6 to a8 in Formula 1 may be a substituted or unsubstituted aryl group having 6 to 30 ring-forming carbon atoms. Formula 1 may be represented by one of Formula 5 to Formula 7 below:

[Formula 5]

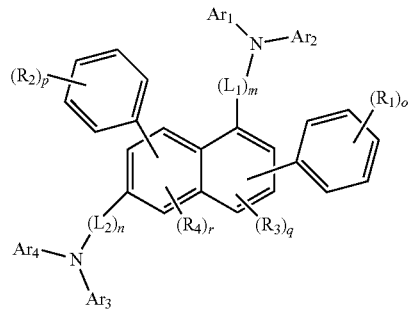

[Formula 6]

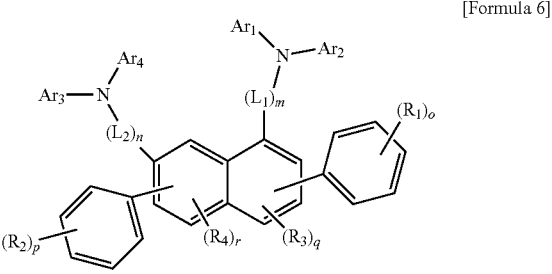

[Formula 7]

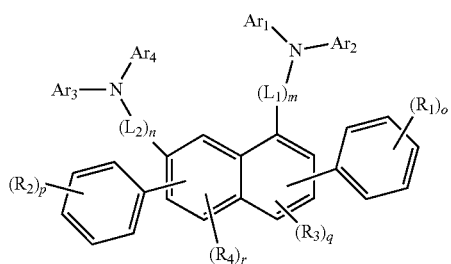

In Formula 5 to Formula 7, $R_3$ and $R_4$ may each independently be a hydrogen atom, or a deuterium atom.

In Formula 5 to Formula 7, q and r may each independently be an integer from 0 to 2. When q is 2, the $R_3$'s may be the same as or different from each other, and when r is 2, the $R_4$'s may be the same as or different from each other.

In Formula 5 to Formula 7, $Ar_1$ to $Ar_4$, $L_1$, $L_2$, $R_1$, $R_2$, and m to p may be the same as defined in Formula 1 and Formula 2-1 to Formula 2-4.

In an embodiment, when a2 in Formula 1 is a group represented by Formula 2-1 and one of a5 to a8 in Formula 1 is a group represented by Formula 2-2, then one of a1, a3, and a4 in Formula 1 may be a substituted or unsubstituted aryl group having 6 to 30 ring-forming carbon atoms, and another one of a5 to a8 in Formula 1 may be a substituted or unsubstituted aryl group having 6 to 30 ring-forming carbon atoms. Formula 1 may be represented by one of Formula 8 to Formula 11 below:

[Formula 8]

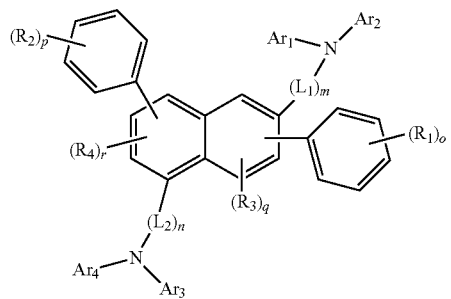

[Formula 9]

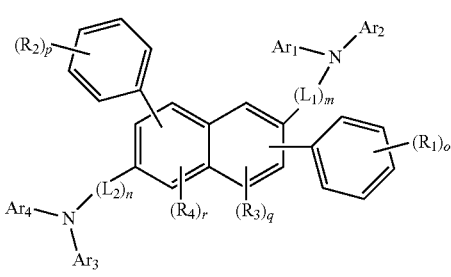

[Formula 10]

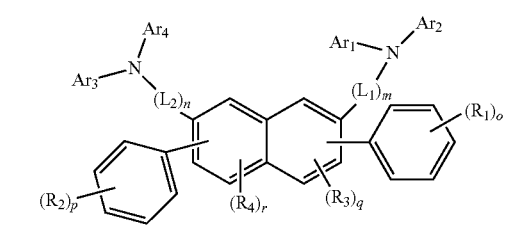

[Formula 11]

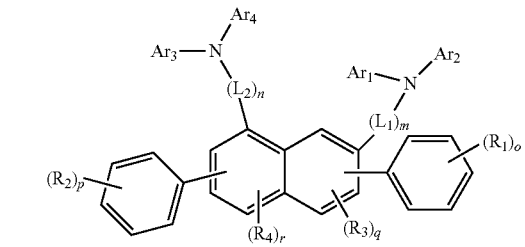

In Formula 8 to Formula 11, $R_3$ and $R_4$ may each independently be a hydrogen atom, or a deuterium atom.

In Formula 8 to Formula 11, q and r may each independently be an integer from 0 to 2. When q is 2, the $R_3$'s may be the same as or different from each other, and when r is 2, the $R_4$'s may be the same as or different from each other.

In Formula 8 to Formula 11, $Ar_1$ to $Ar_4$, $L_1$, $L_2$, $R_1$, $R_2$, and m to p may be the same as defined in Formula 1 and Formula 2-1 to Formula 2-4.

In an embodiment, Formula 6 may be represented by Formula 6-1 or Formula 6-2 below:

[Formula 6-1]

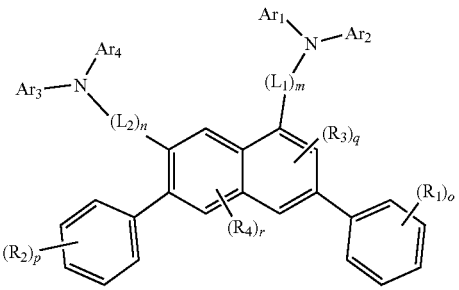

[Formula 6-2]

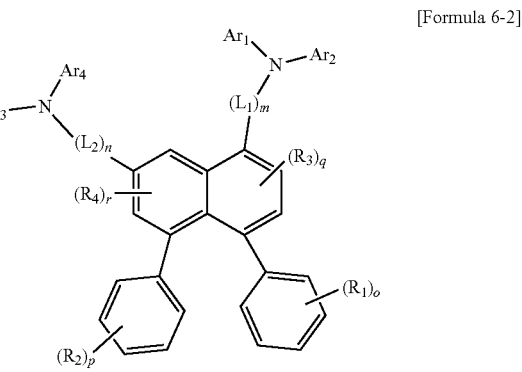

In Formula 6-1 and Formula 6-2, $Ar_1$ to $Ar_4$, $L_1$, $L_2$, $R_1$ to $R_4$, and m to r may be the same as defined in Formula 6.

In an embodiment, Formula 9 may be represented by Formula 9-1 below:

[Formula 9-1]

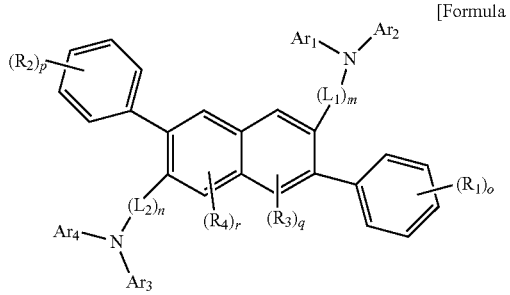

[Formula 10-2]

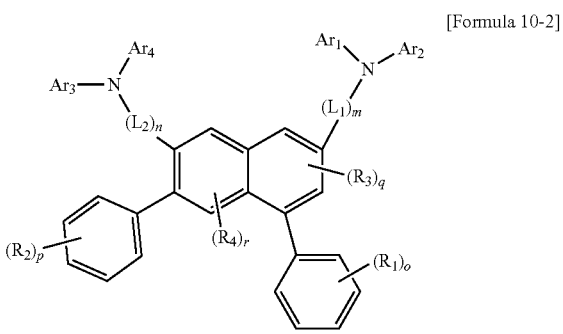

In Formula 9-1, $Ar_1$ to $Ar_4$, $L_1$, $L_2$, $R_1$ to $R_4$, and m to r may be the same as defined in Formula 9.

In an embodiment, Formula 10 may be represented by one of Formula 10-1 to Formula 10-3 below:

[Formula 10-3]

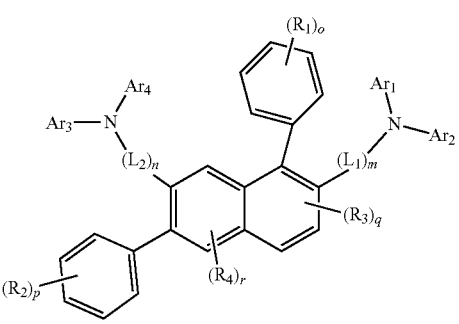

[Formula 10-1]

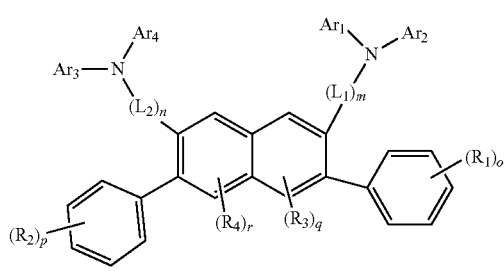

In Formula 10-1 to Formula 10-3, $Ar_1$ to $Ar_4$, $L_1$, $L_2$, $R_1$ to $R_4$, and m to r may be the same as defined in Formula 10.

The diamine compound represented by Formula 1 according to an embodiment of the inventive concept may be one selected from the compounds represented by Compound Group 1 below, which includes Compounds 1-1 to 1-35, 2-1 to 2-35, 3-1 to 3-35, 4-1 to 4-16, 5-1 to 5-35, 6-1 to 6-35, and 7-1 to 7-7. However, the embodiments are not limited thereto.

[Compound Group 1]

1-1

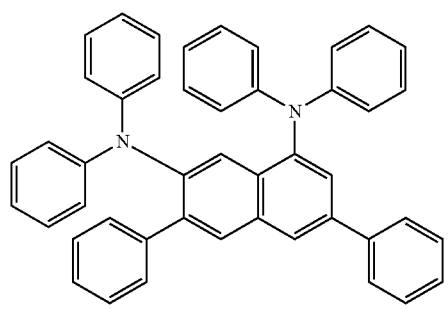

1-2

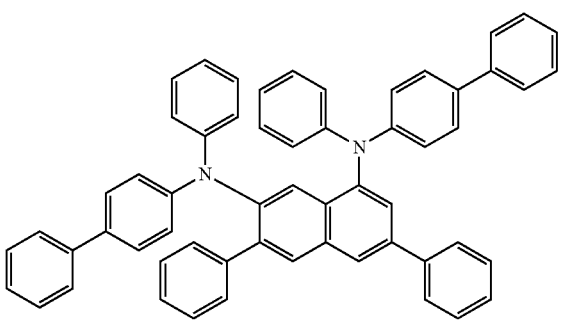

-continued
1-3
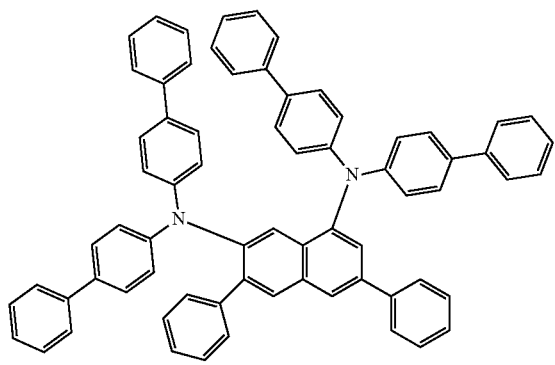
1-4
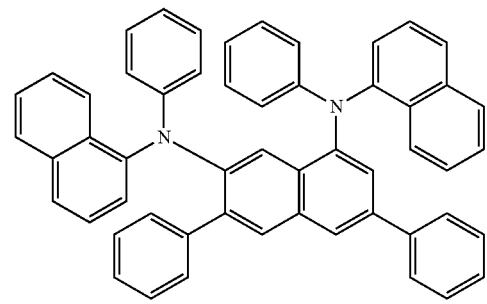
1-5
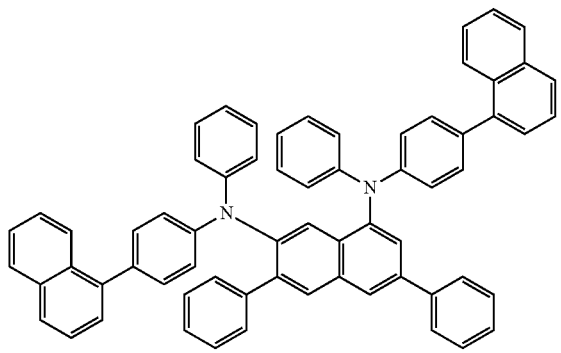
1-6
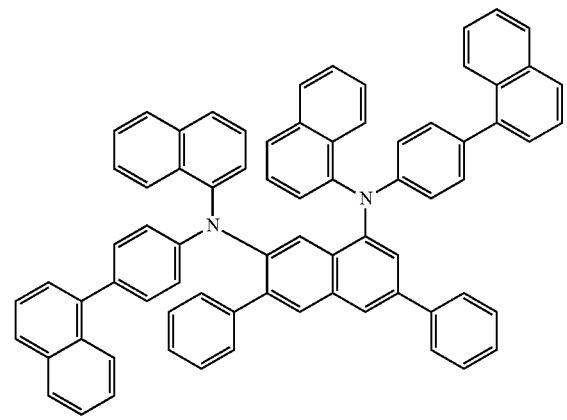
1-7
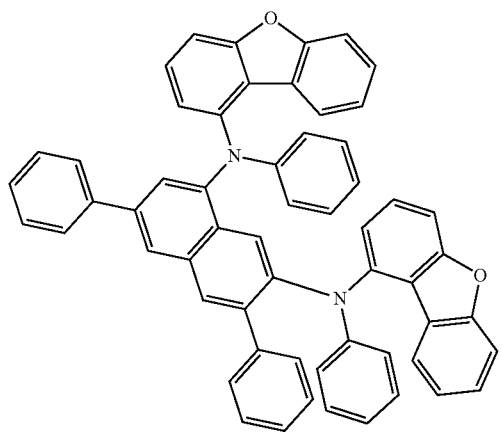
1-8
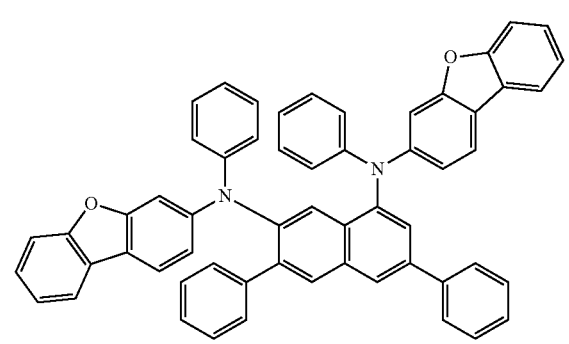

-continued
1-9
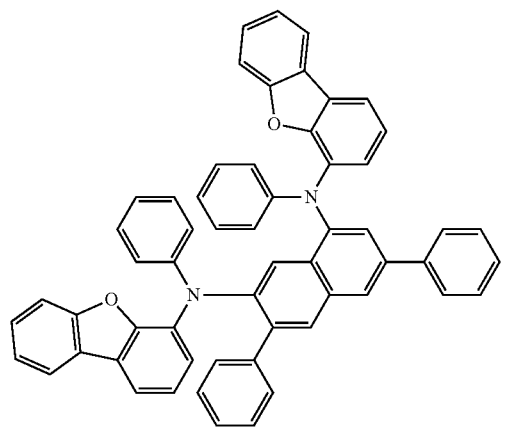
1-10
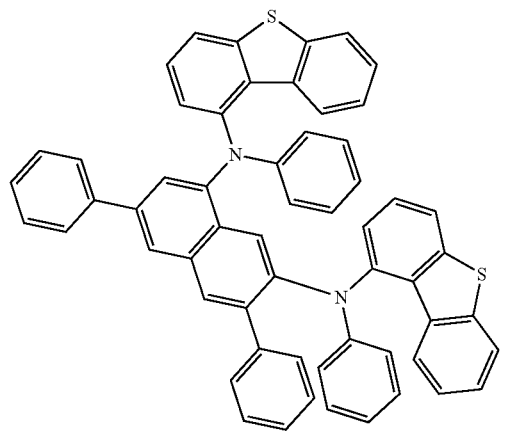
1-11
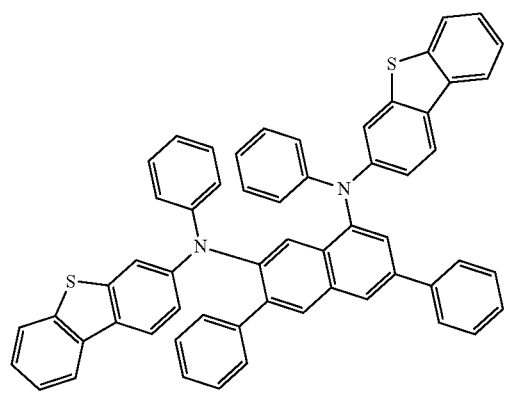
1-12
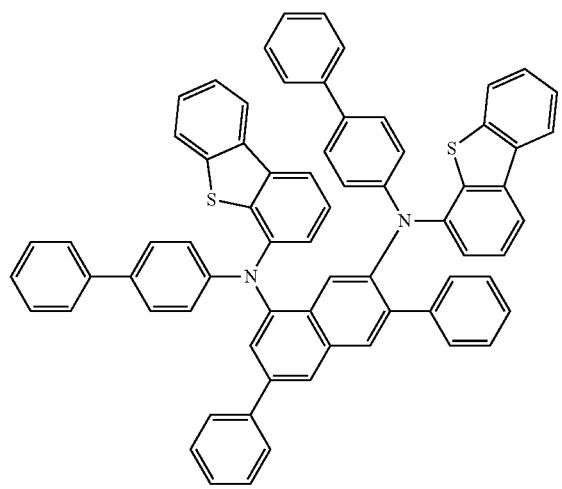
1-13
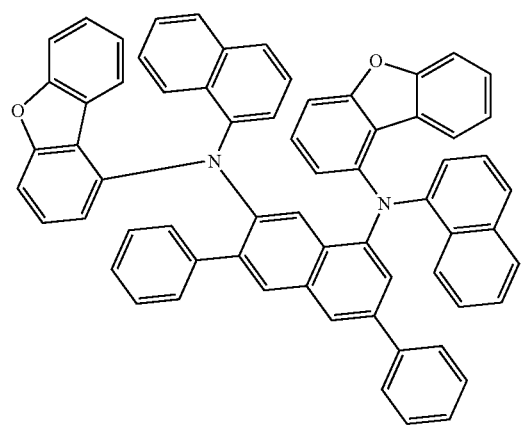
1-14
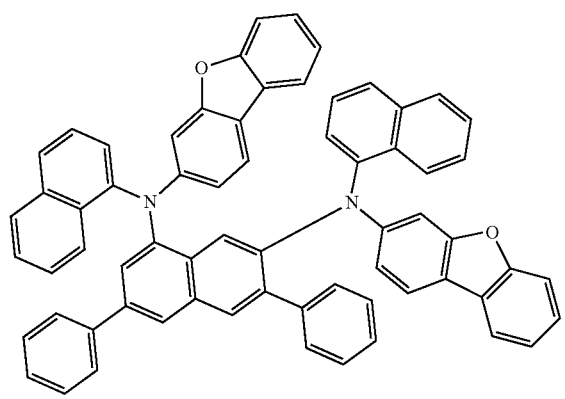

-continued
1-15
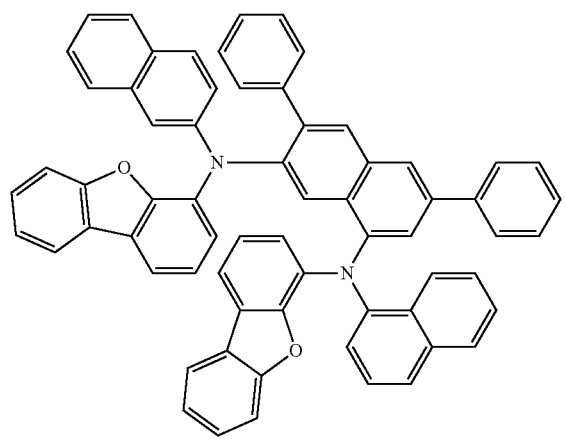
1-16
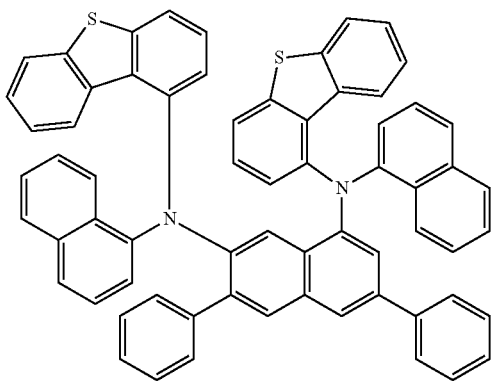
1-17
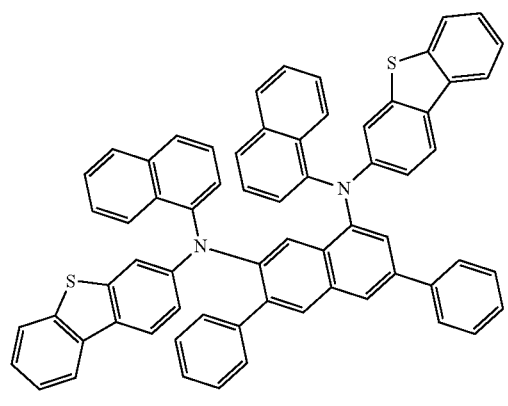
1-18
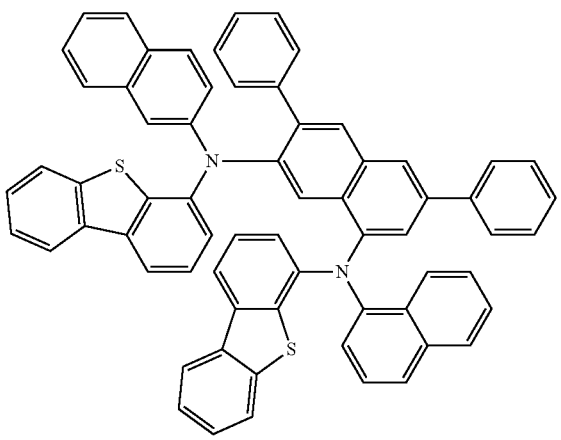
1-19
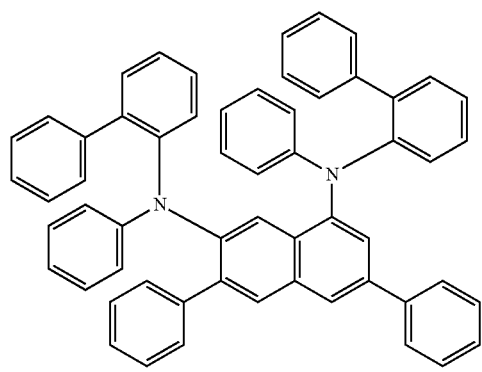
1-20
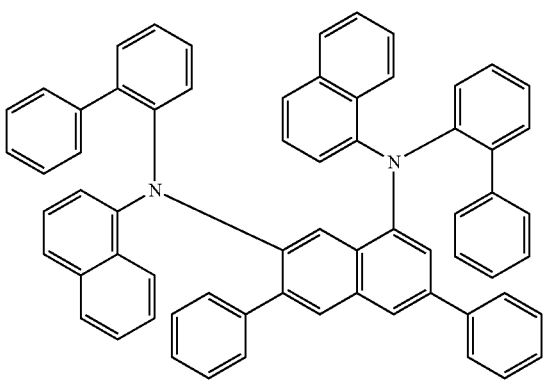

-continued
1-21
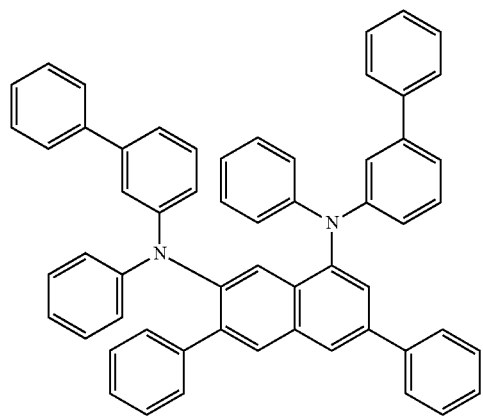
1-22
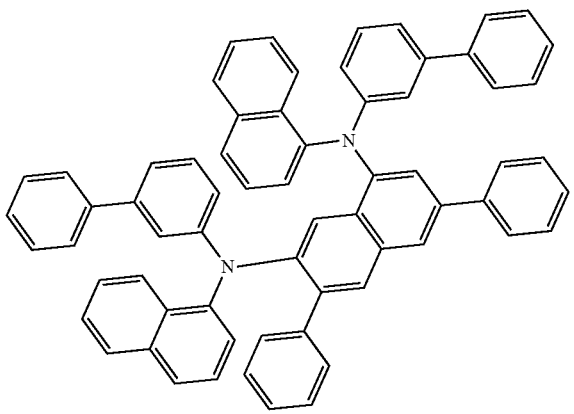
1-23
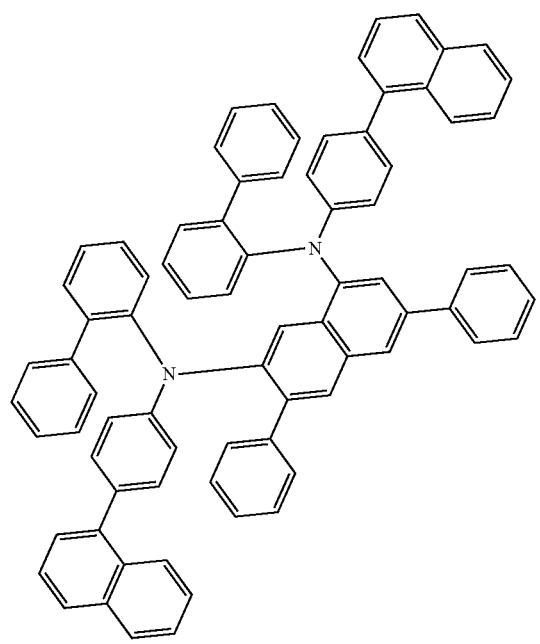
1-24
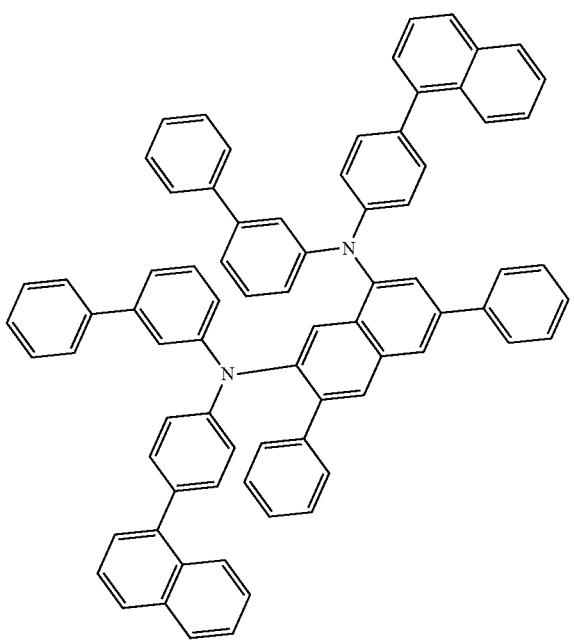
1-25
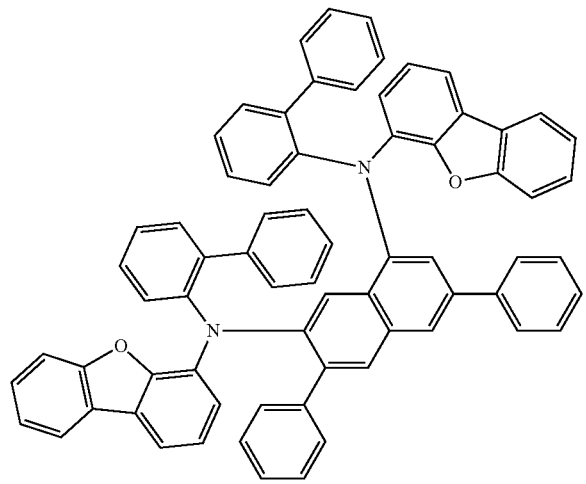
1-26
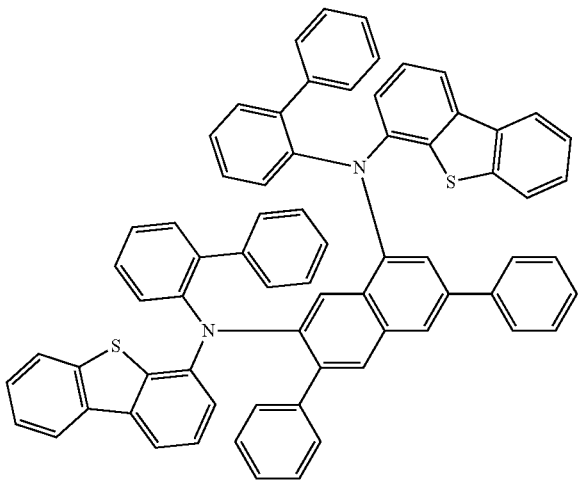

-continued
1-27
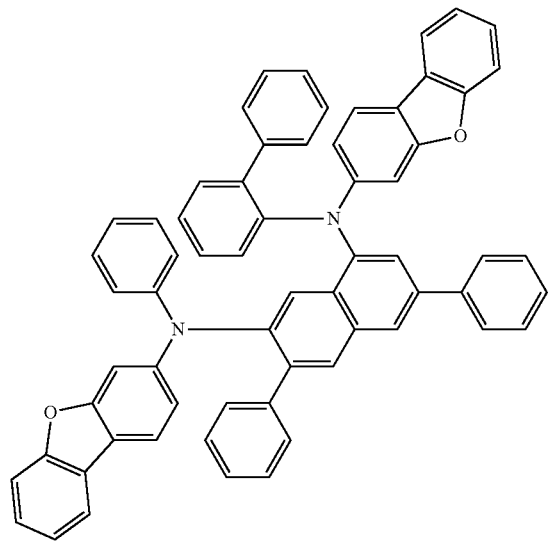
1-28
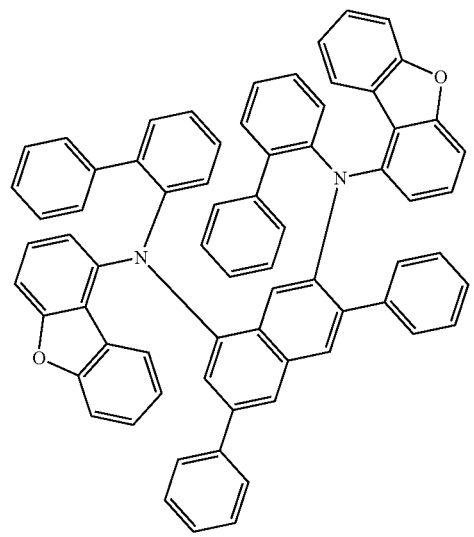
1-29
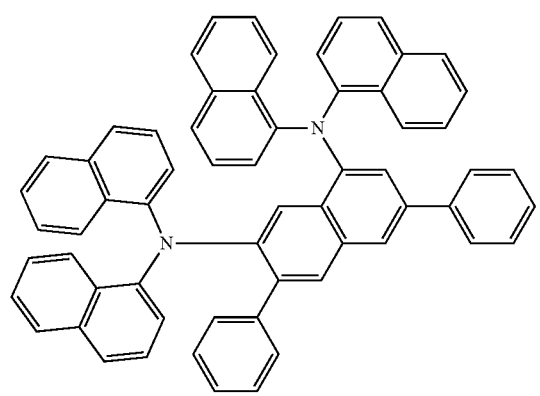
1-30
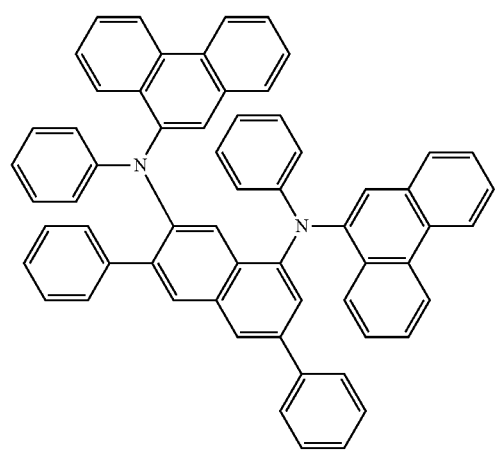
1-31
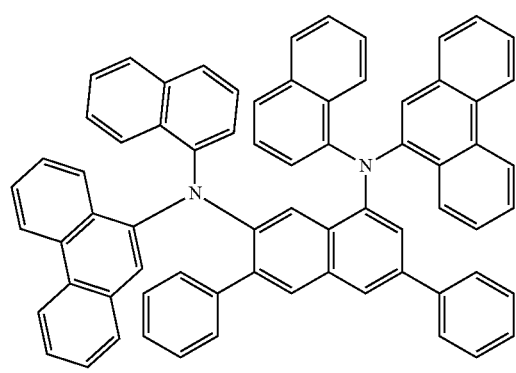
1-32
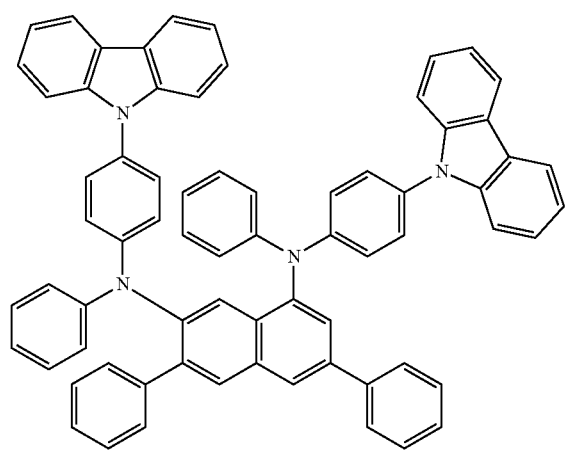

-continued
1-33
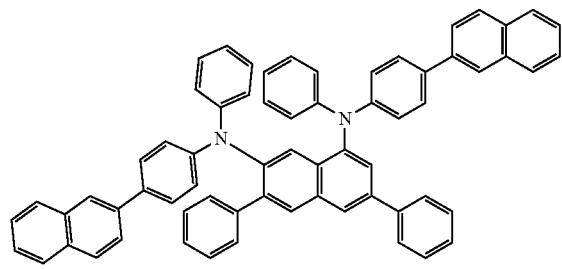
1-34
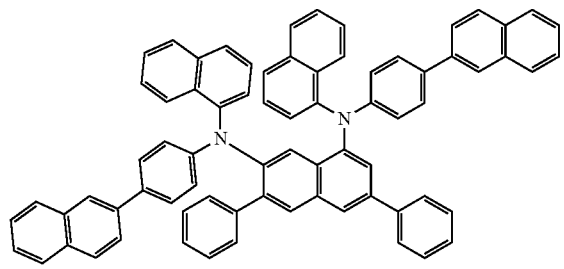
1-35
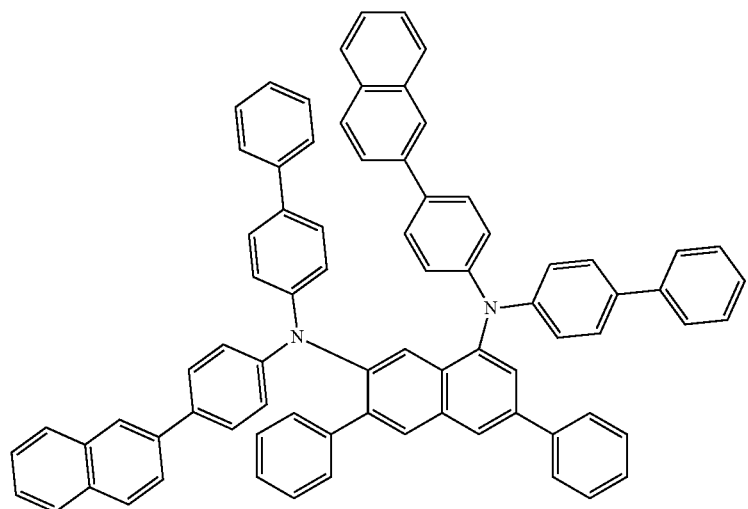
2-1
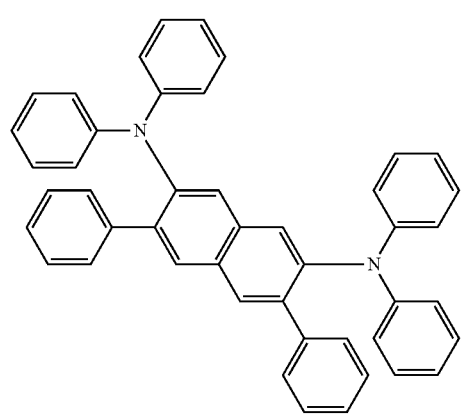
2-2
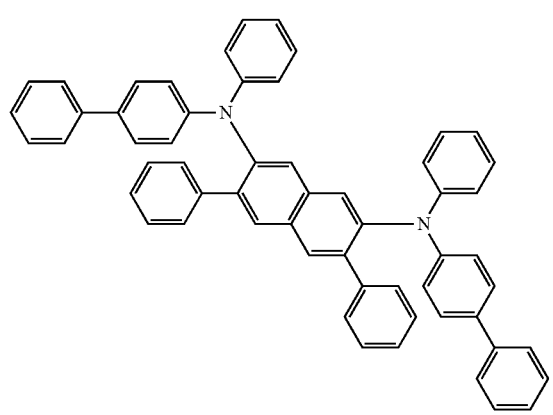

-continued
2-3
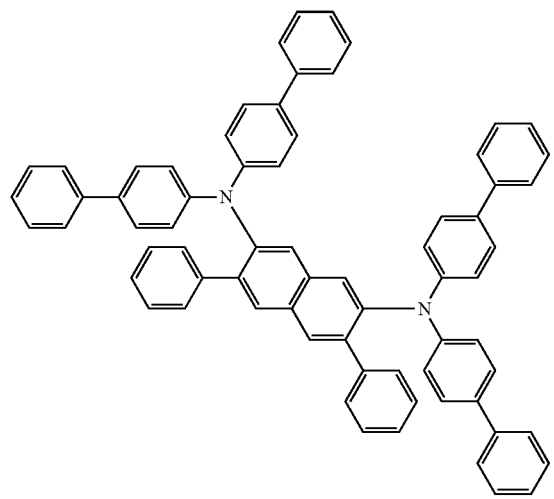
2-4
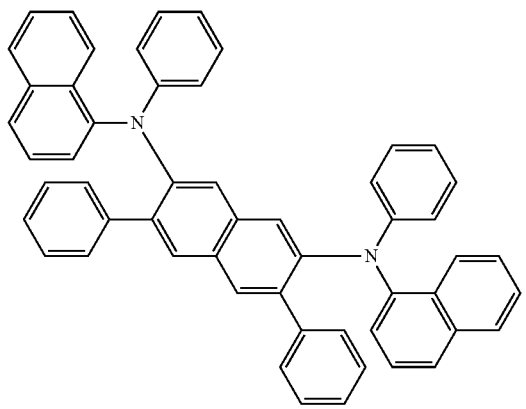
2-5
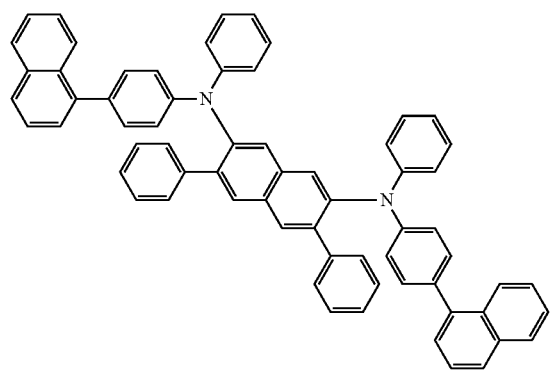
2-6
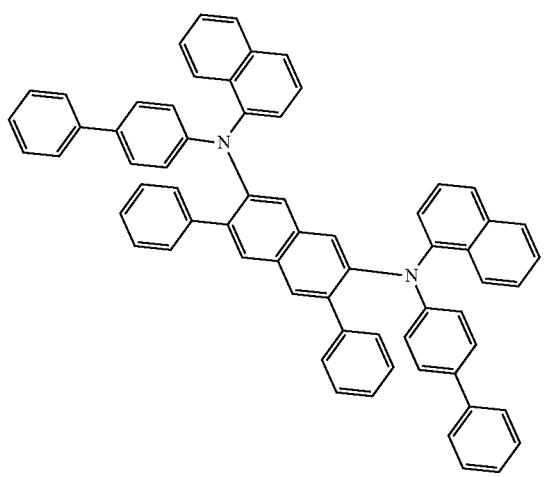
2-7
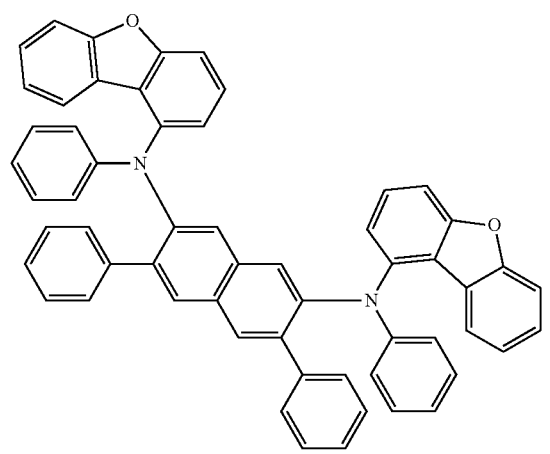
2-8
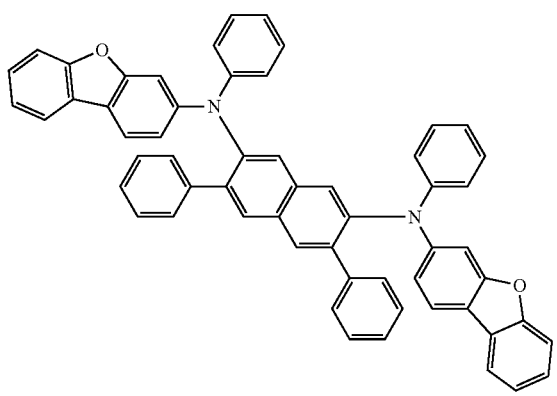

-continued
2-9
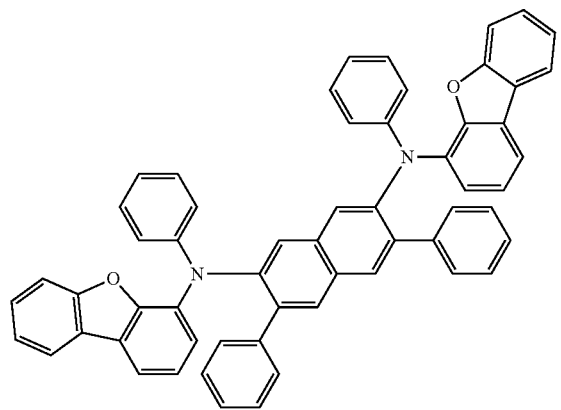
2-10
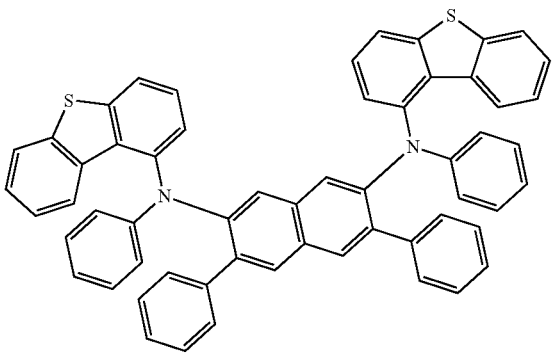
2-11
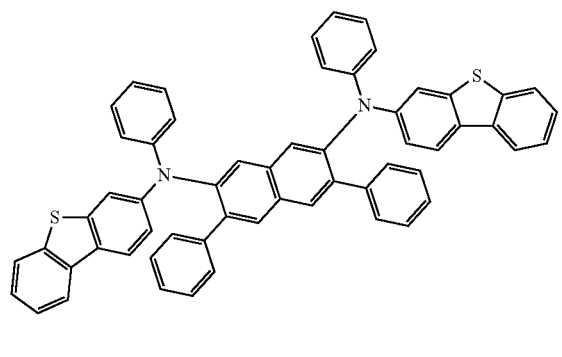
2-12
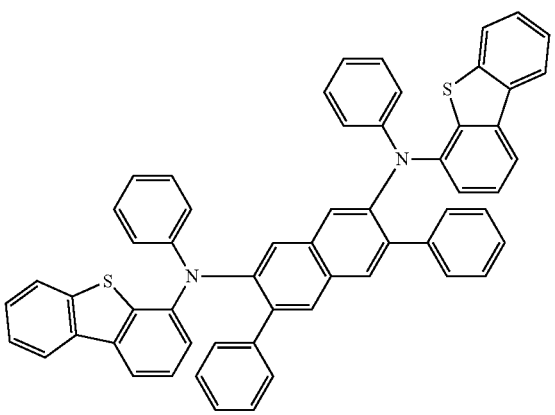
2-13
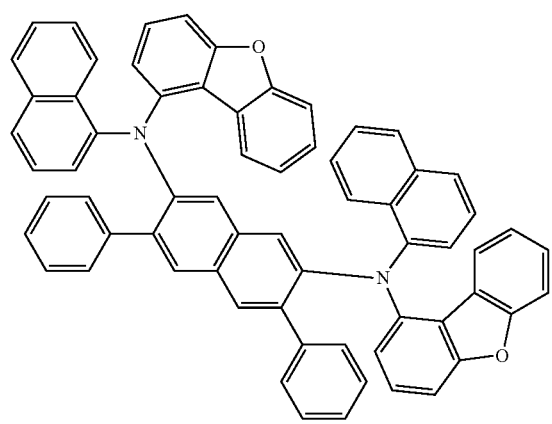
2-14
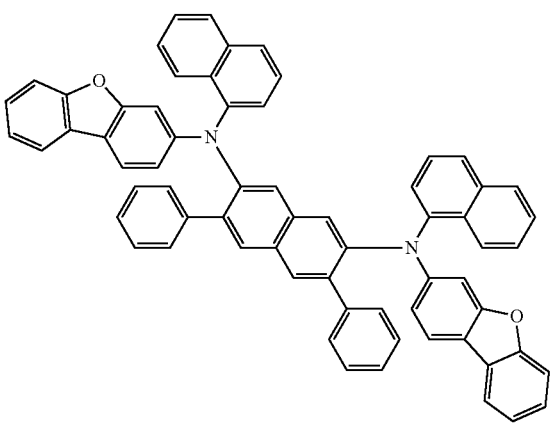

2-15
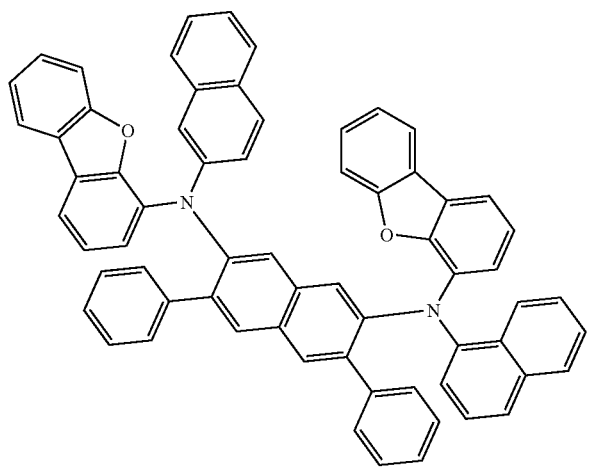
2-16
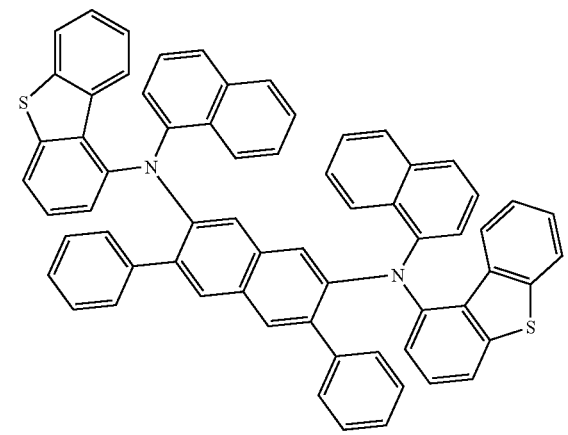
2-17
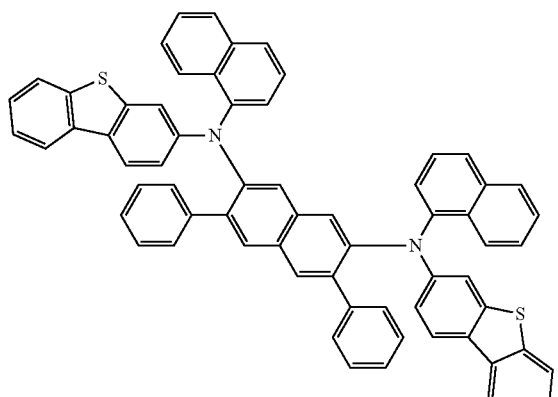
2-18
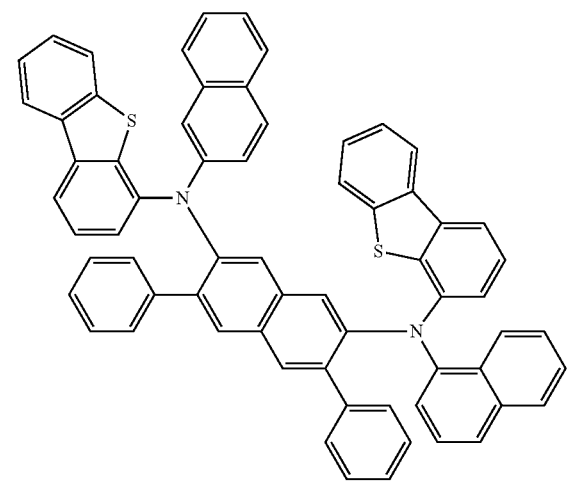
2-19
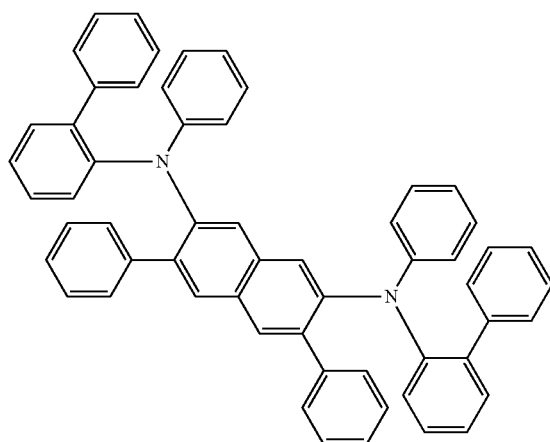
2-20
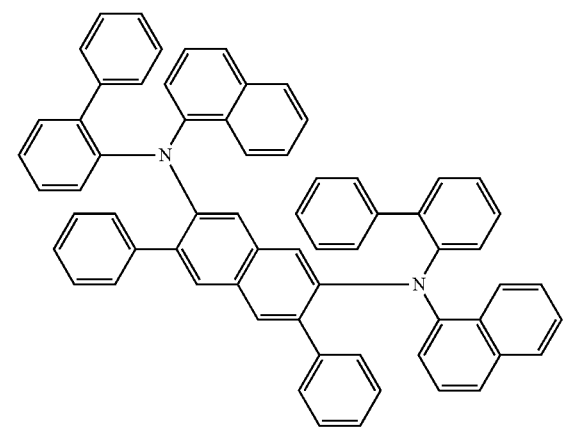

-continued
2-21
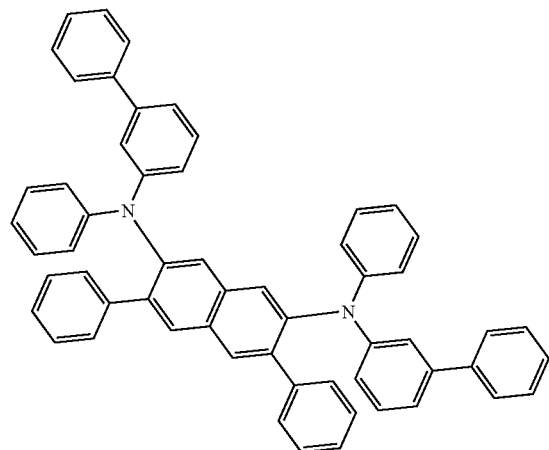
2-22
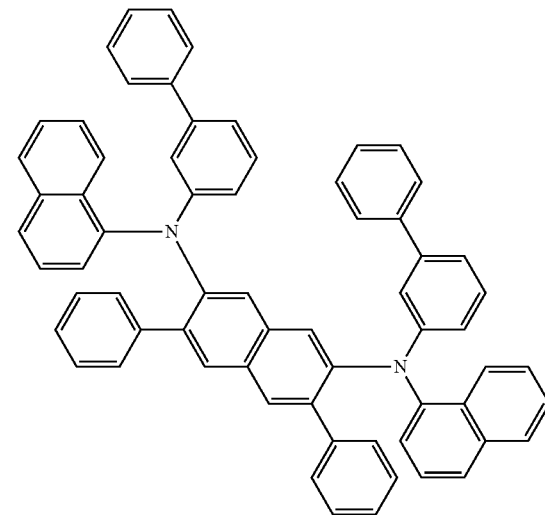
2-23
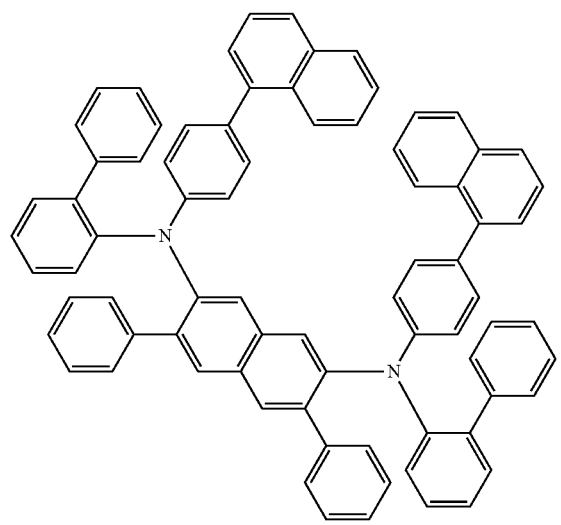
2-24
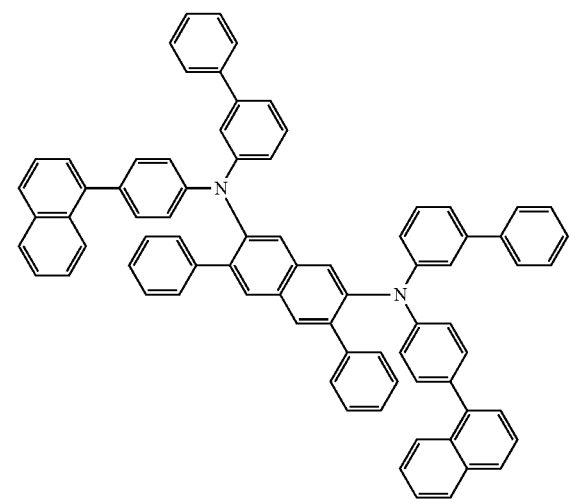
2-25
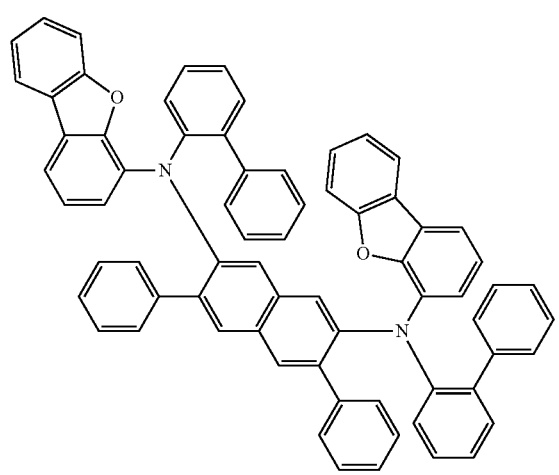
2-26
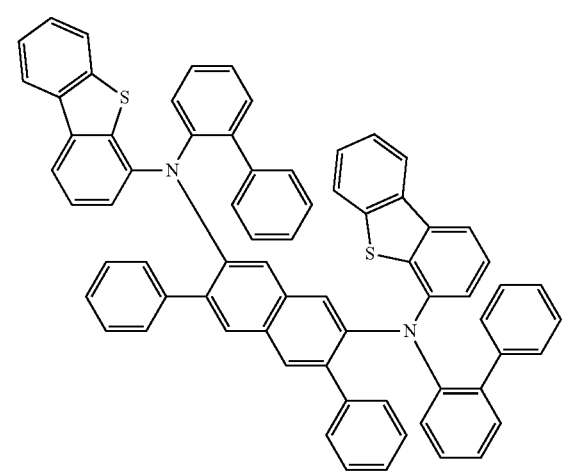

-continued
2-27
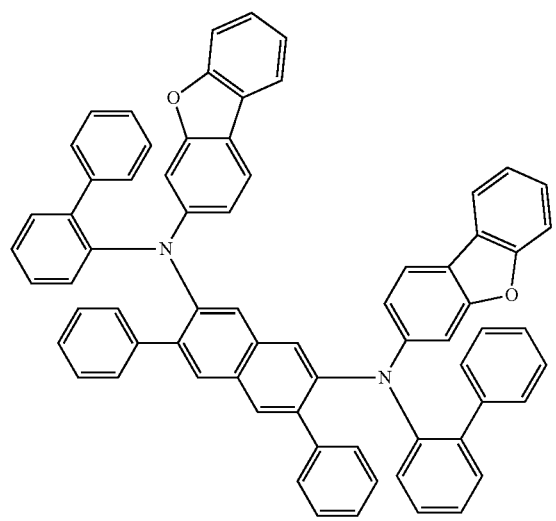
2-28
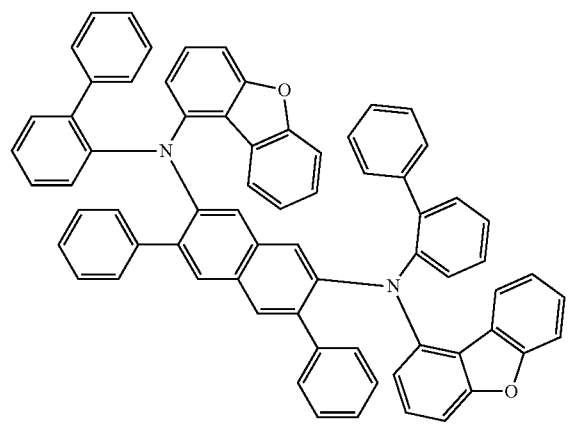
2-29
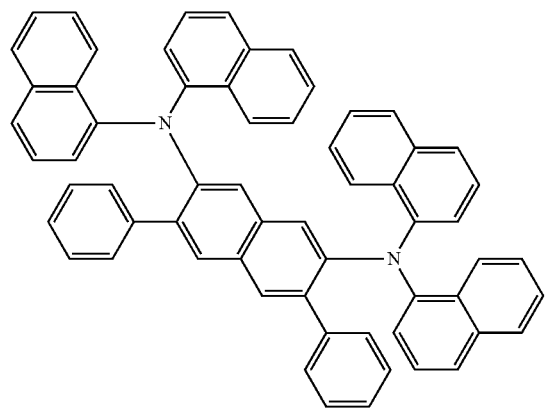
2-30
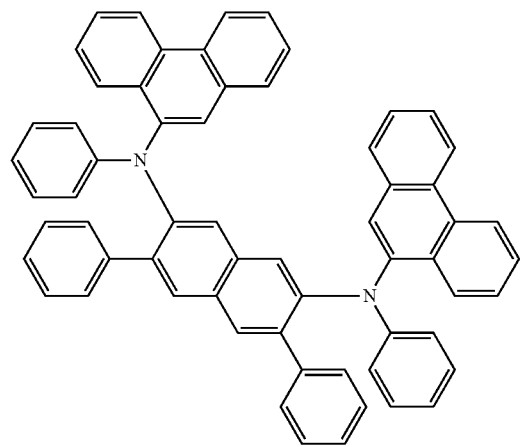
2-31
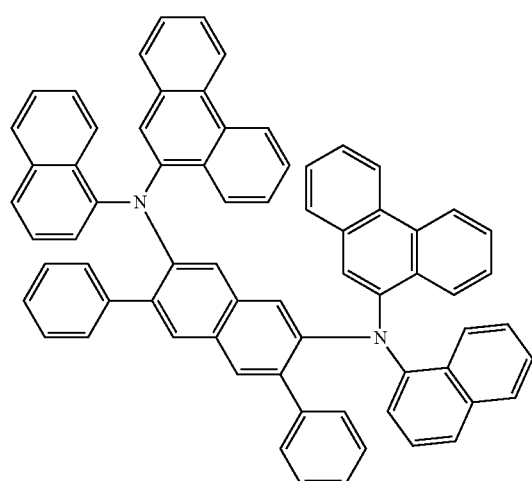
2-32
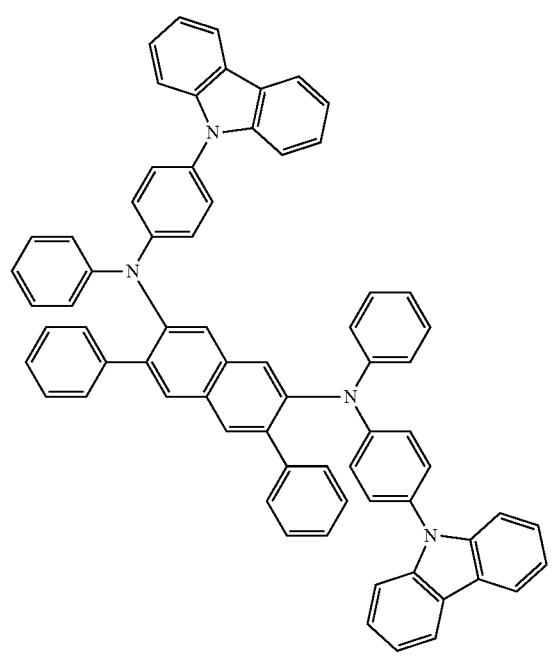

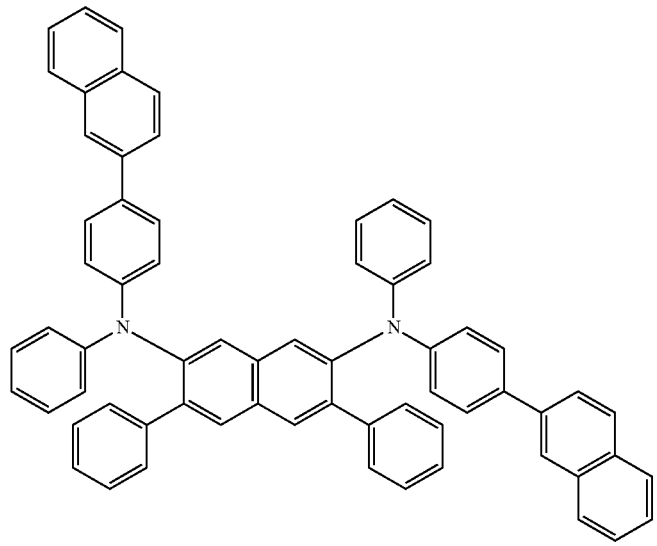
2-33
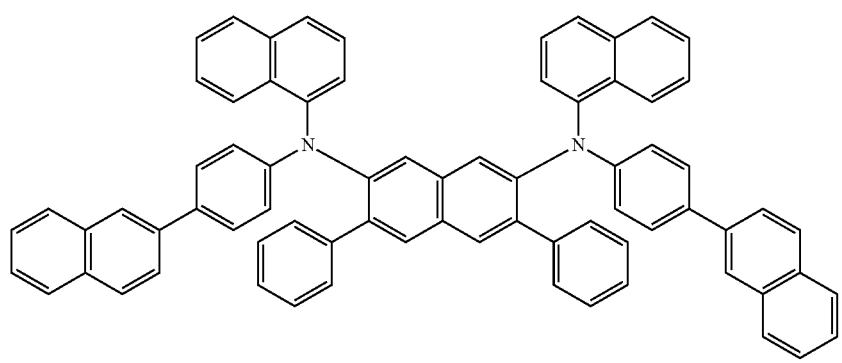
2-34
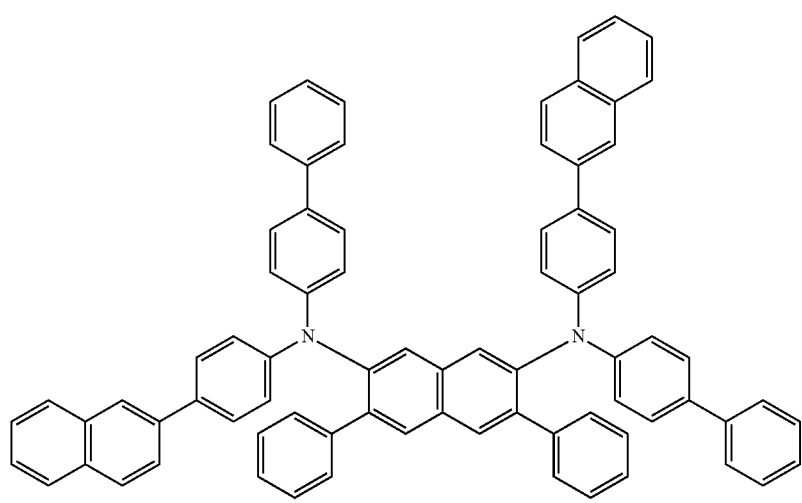
2-35

-continued
3-1
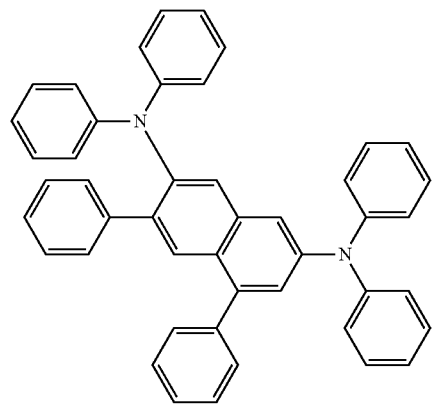
3-2
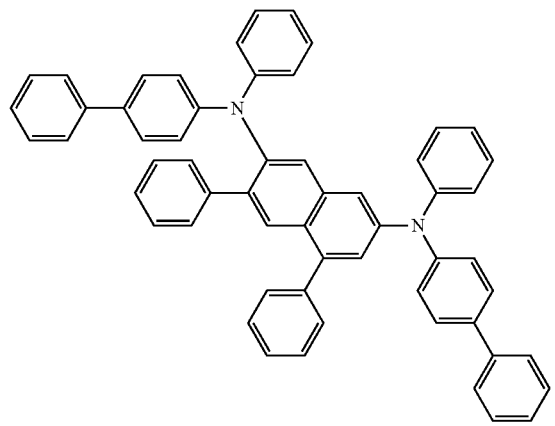
3-3
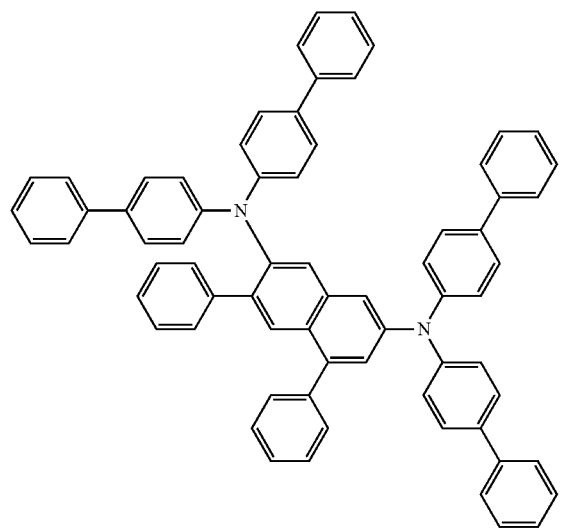
3-4
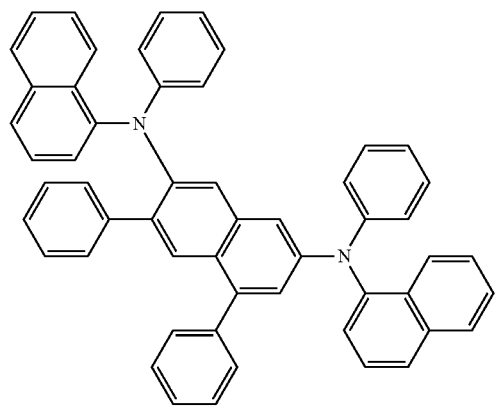
3-5
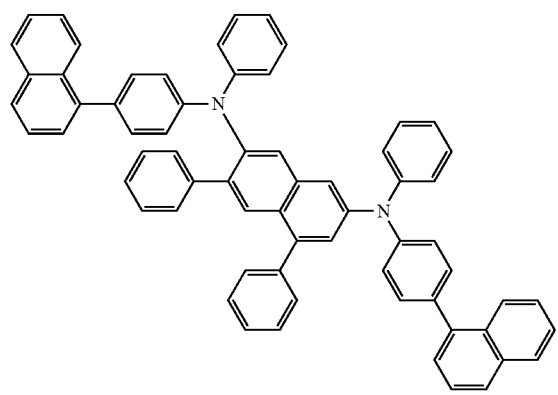
3-6
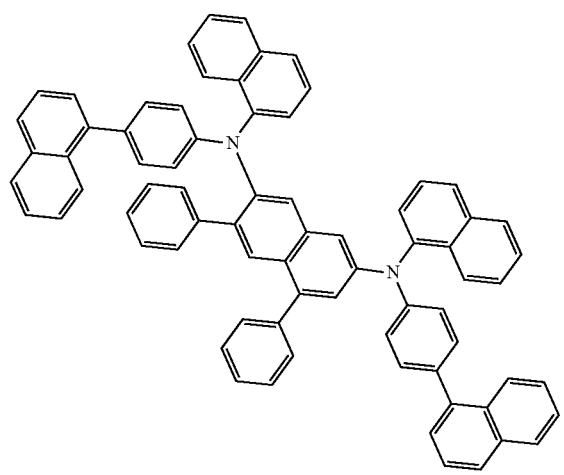

-continued
3-7
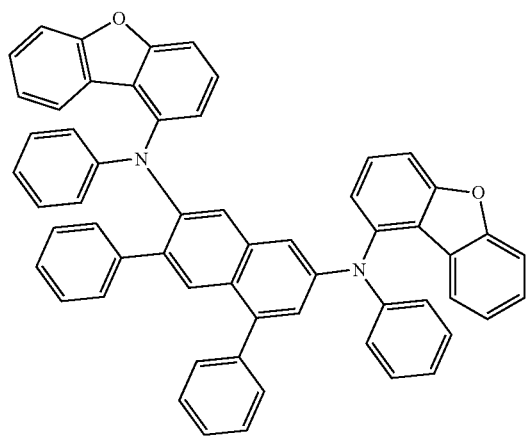
3-8
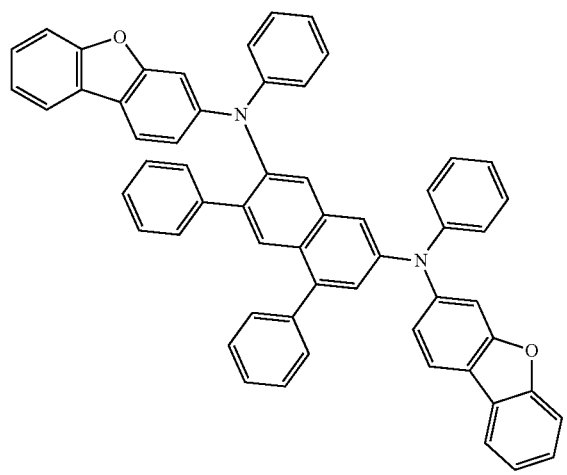
3-9
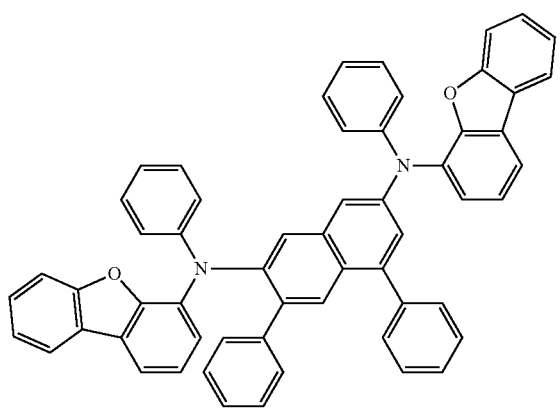
3-10
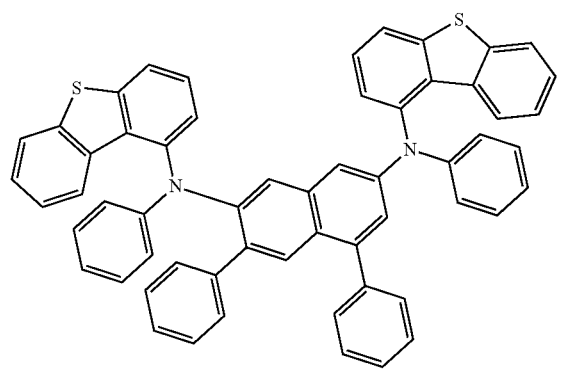
3-11
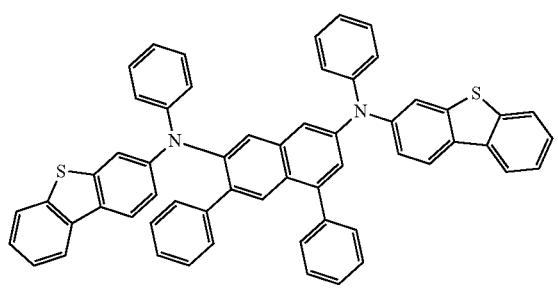
3-12
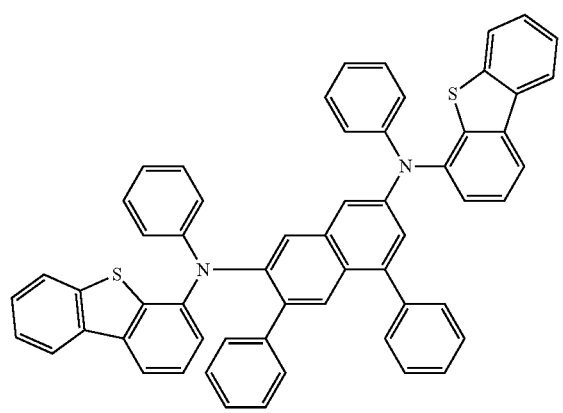

-continued
3-13
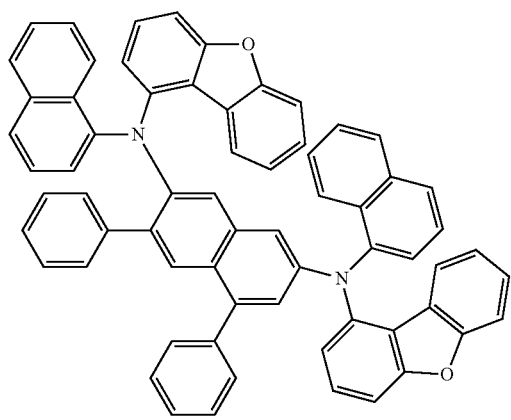
3-14
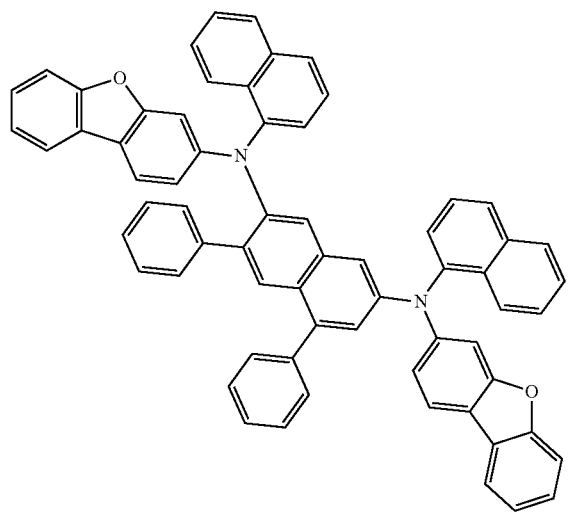
3-15
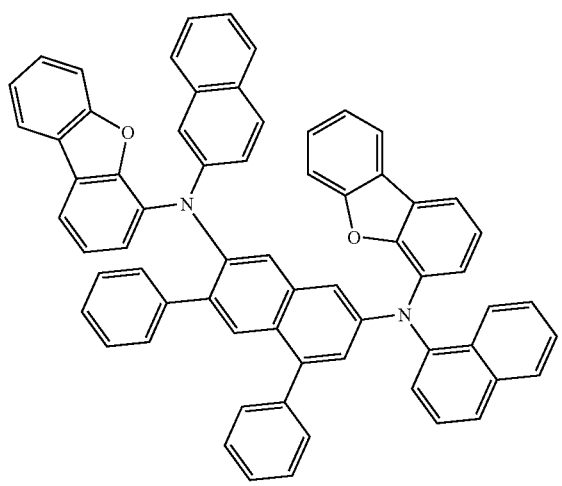
3-16
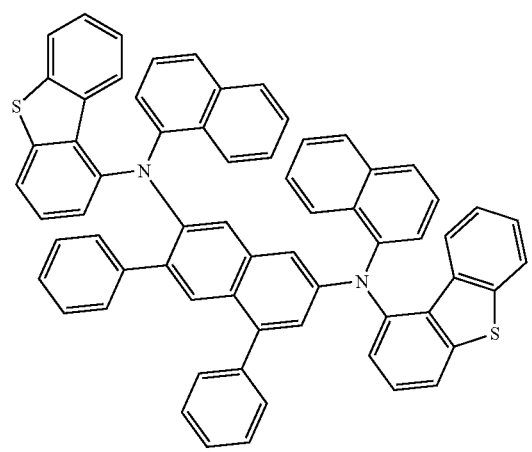
3-17
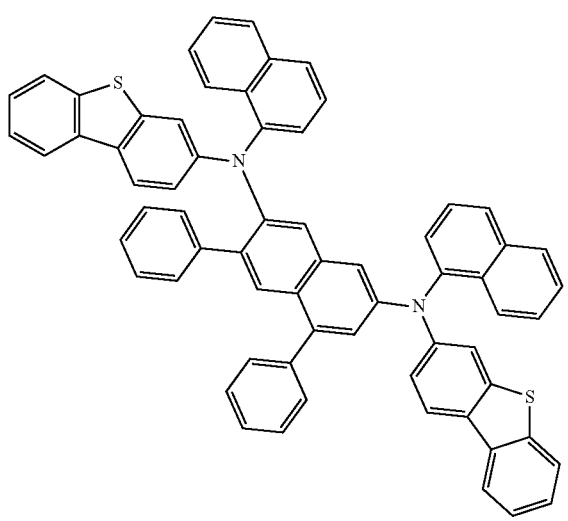
3-18
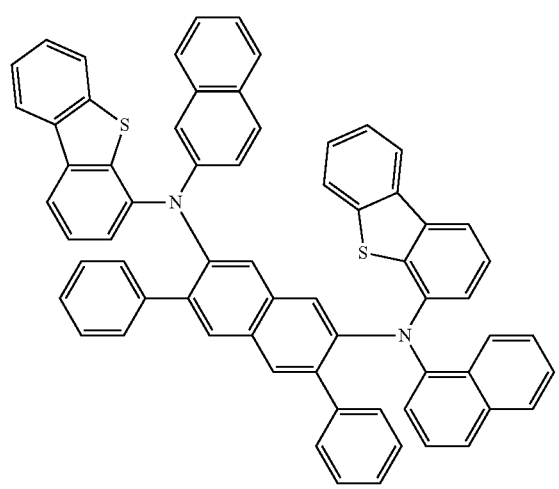

-continued
3-19
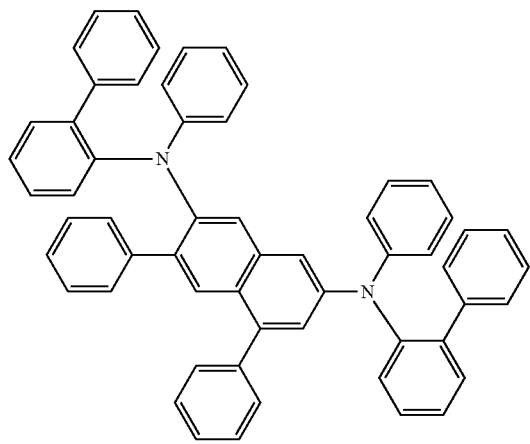
3-20
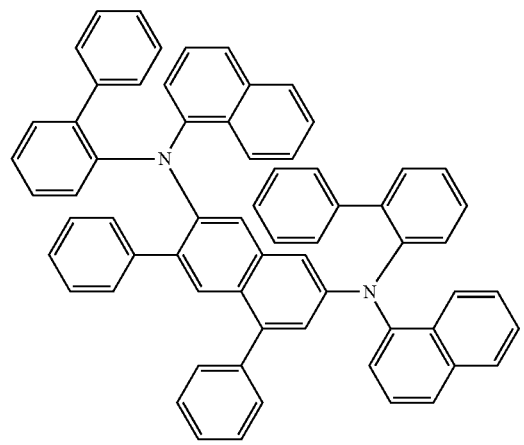
3-21
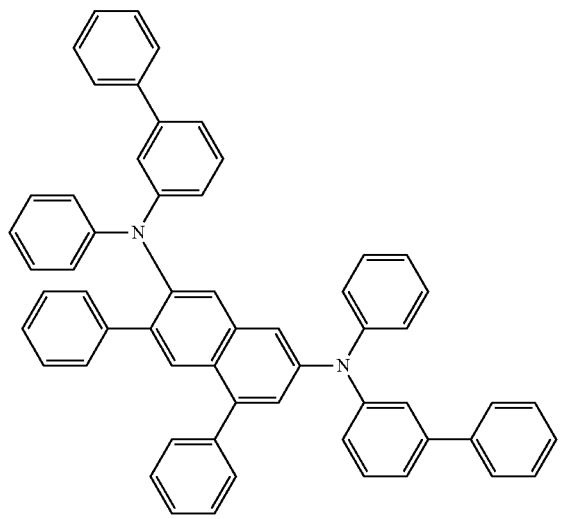
3-22
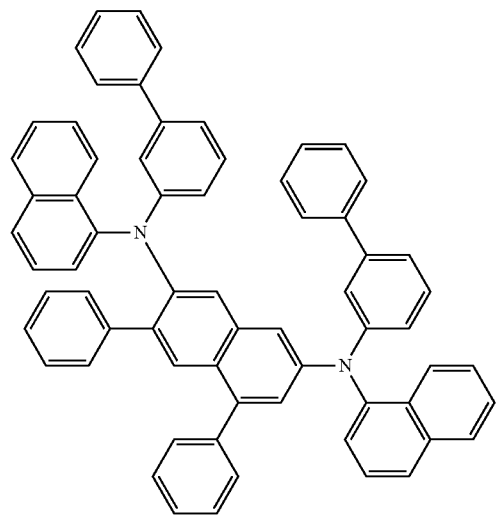
3-23
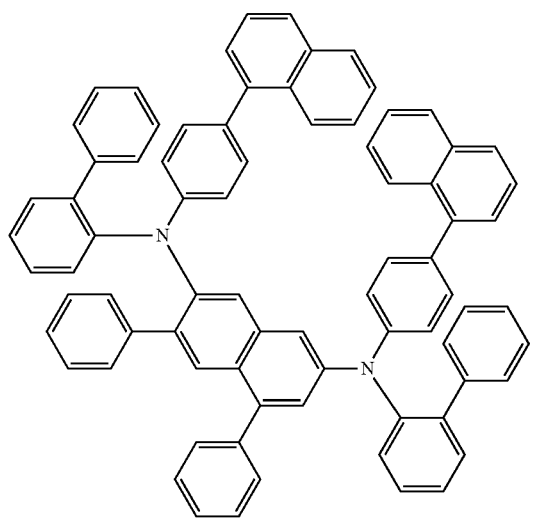
3-24
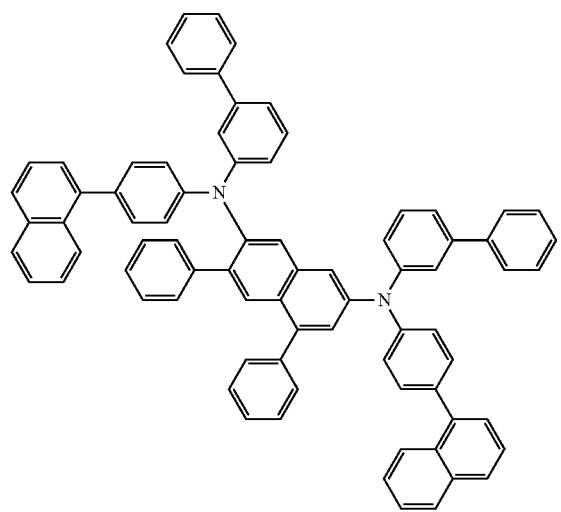

3-25
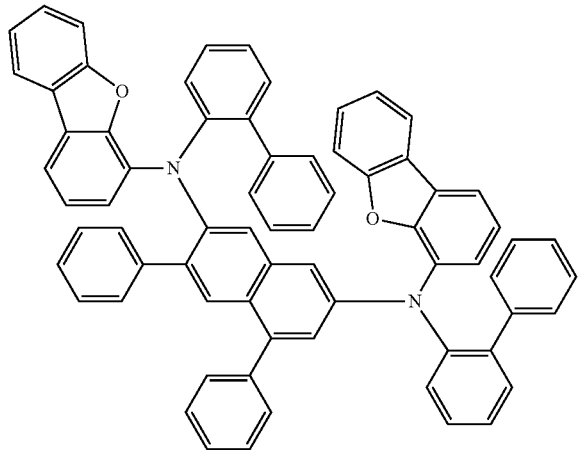
3-26
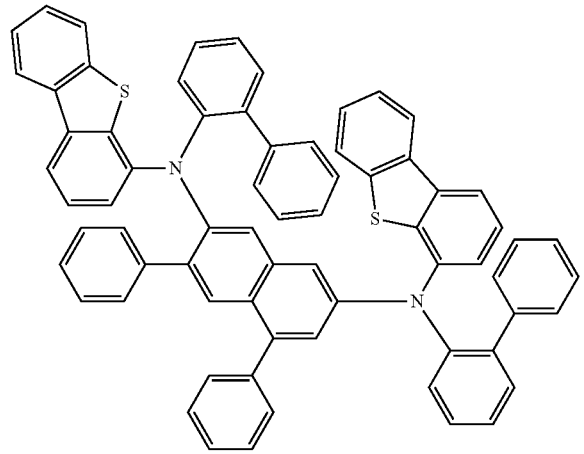
3-27
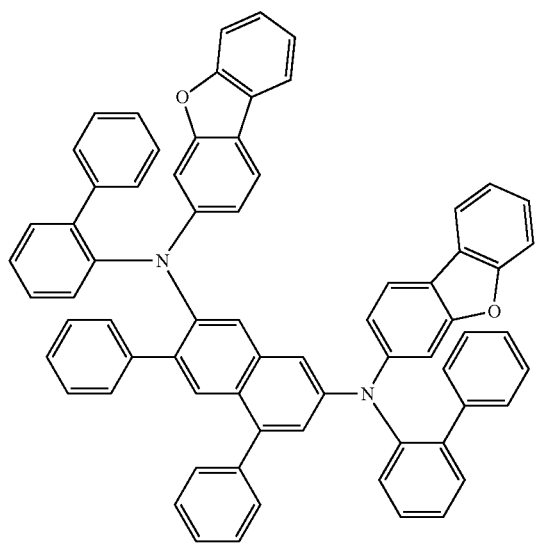
3-28
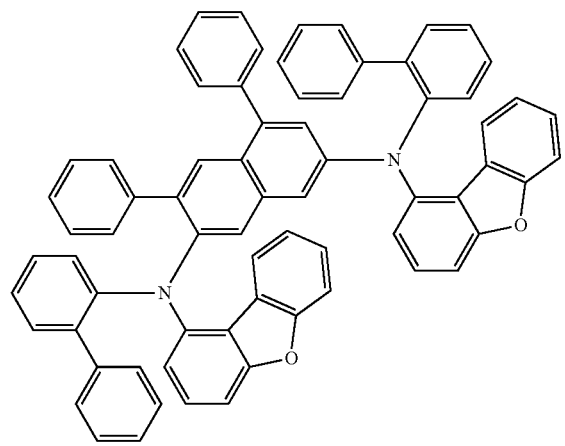
3-29
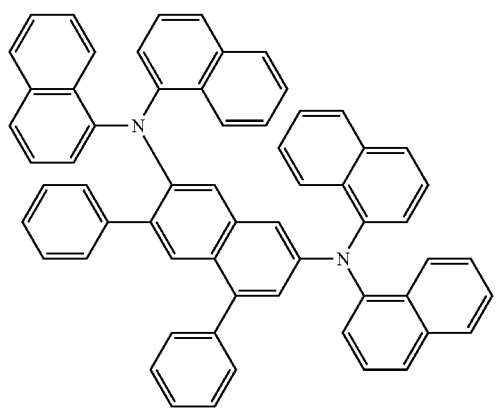
3-30
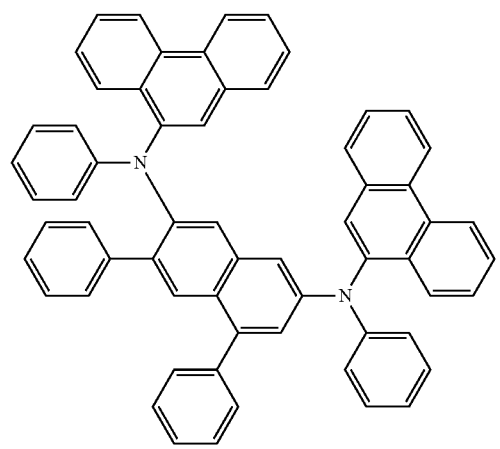

3-31
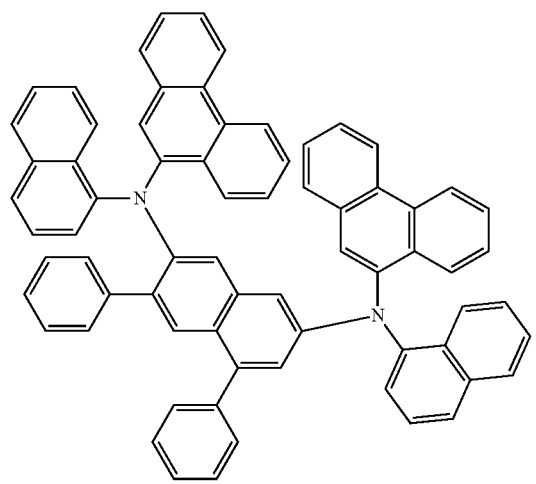
3-32
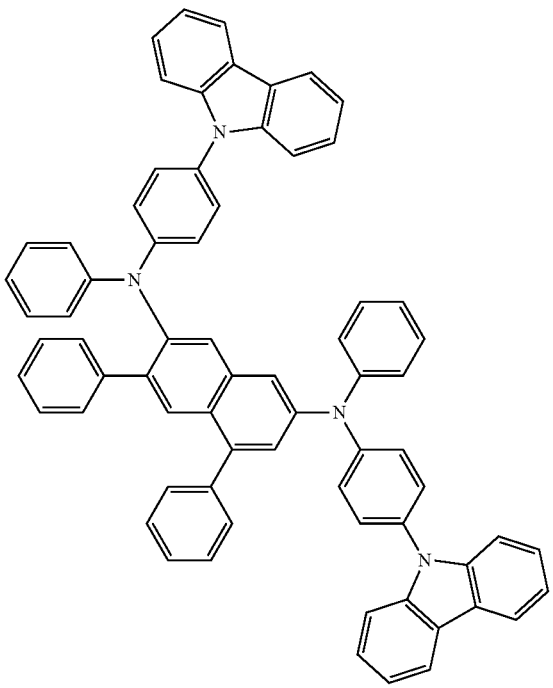
3-33
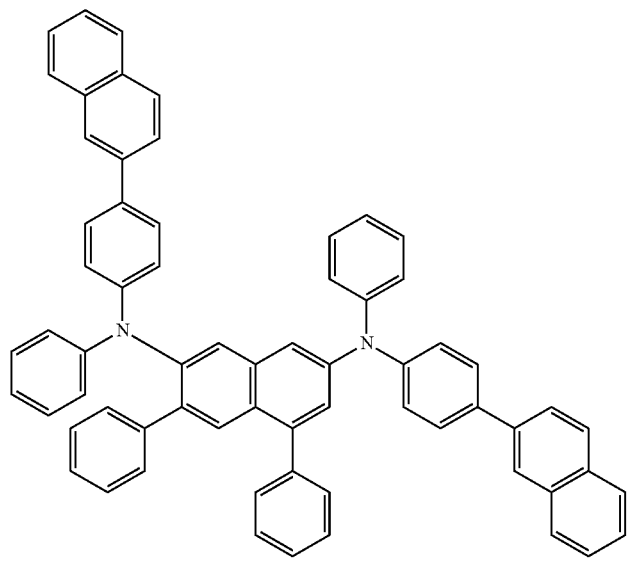
3-34
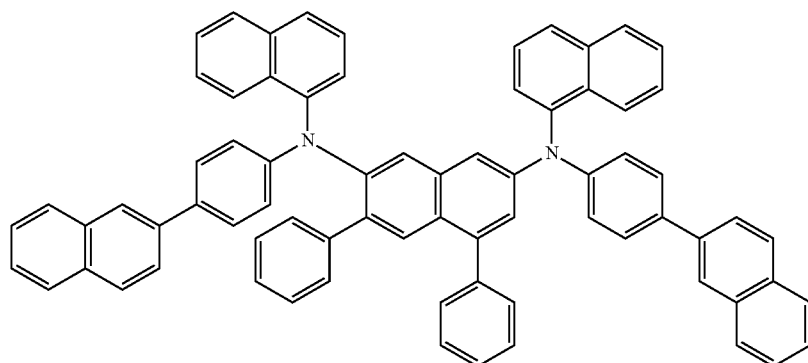

-continued
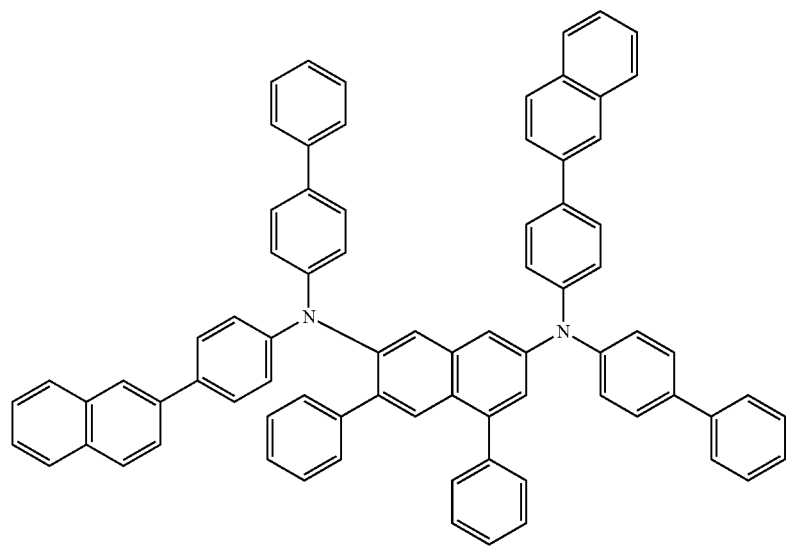
3-35
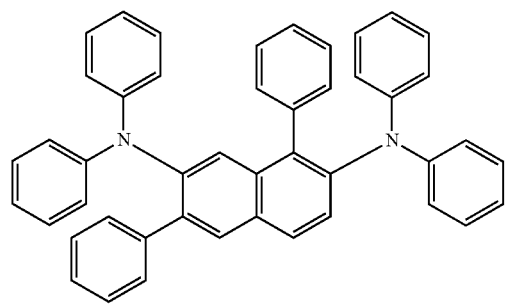
4-1
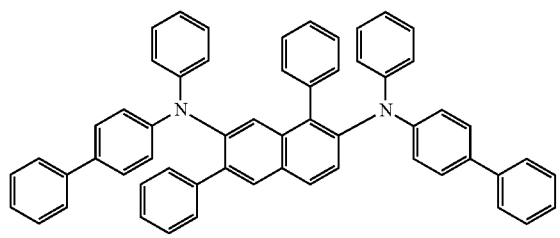
4-2
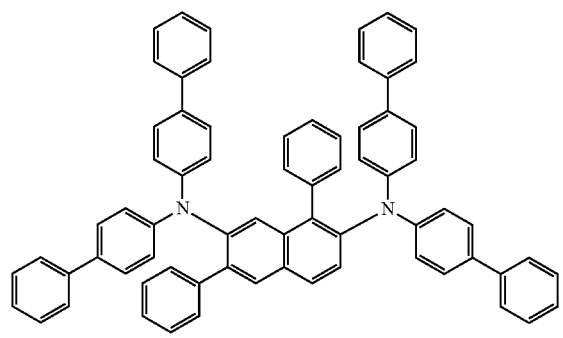
4-3
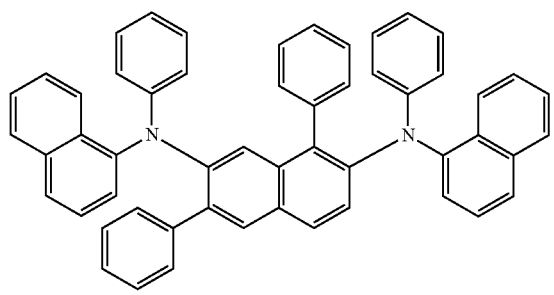
4-4

-continued
4-5
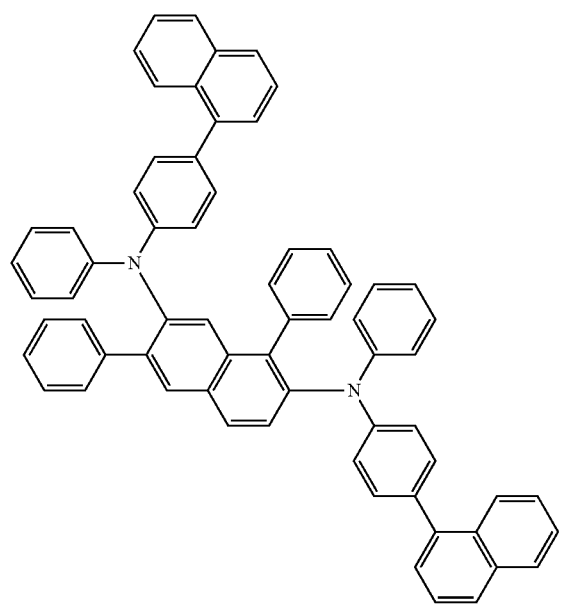
4-6
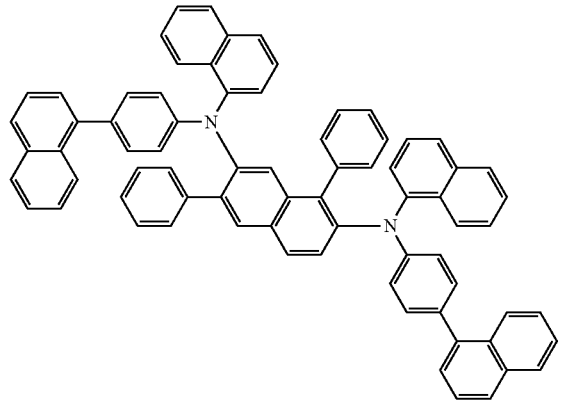
4-7
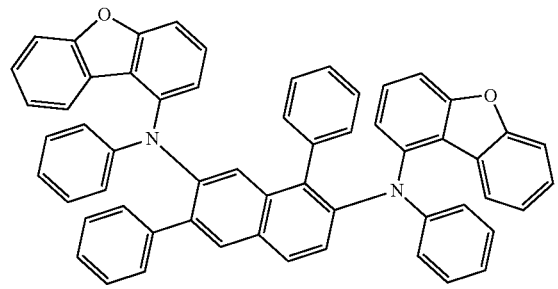
4-8
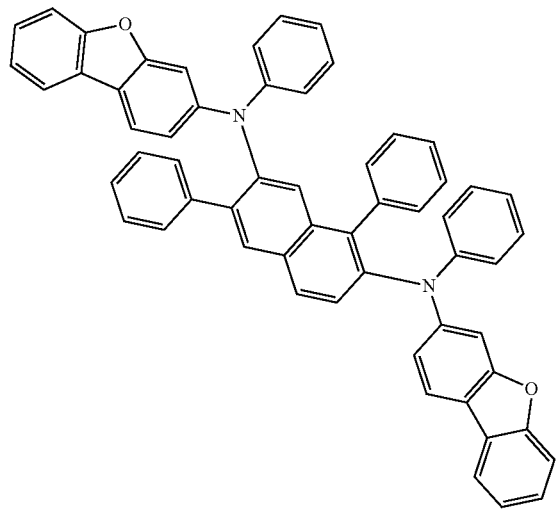
4-9
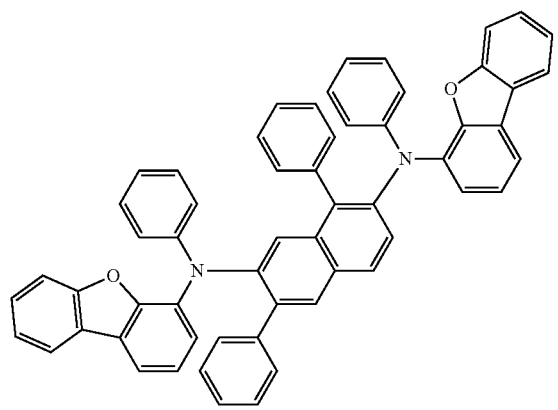
4-10
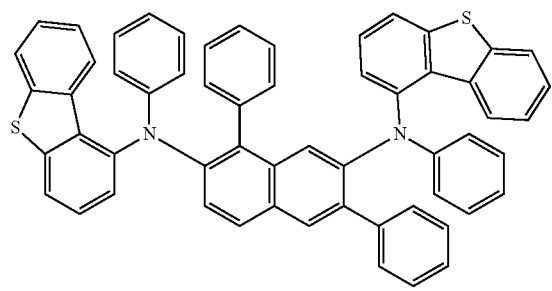

-continued
4-11
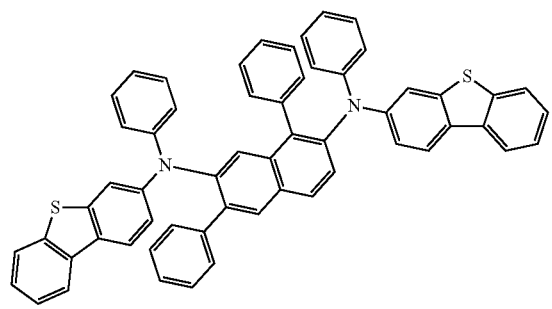
4-12
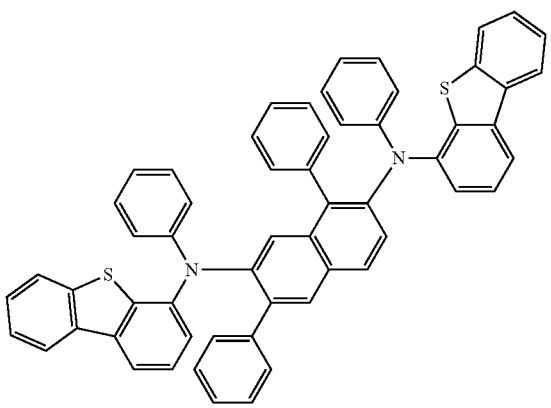
4-13
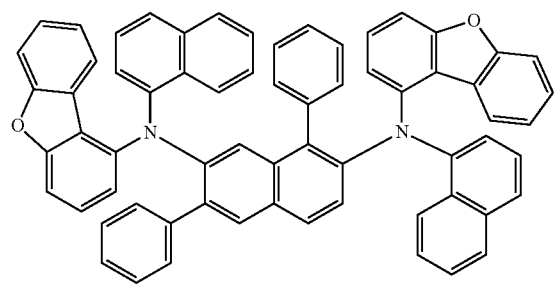
4-14
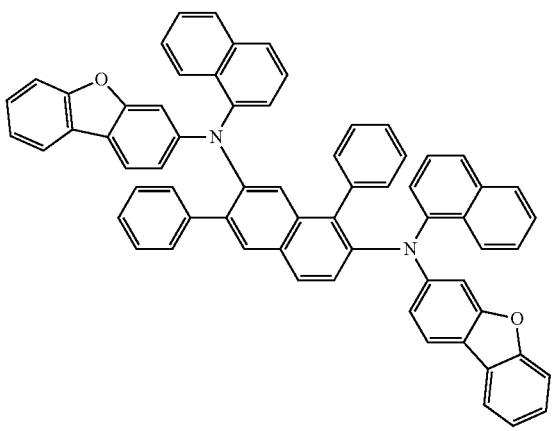
4-15
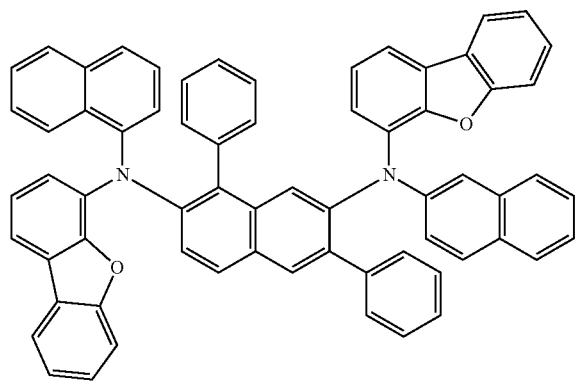
4-16
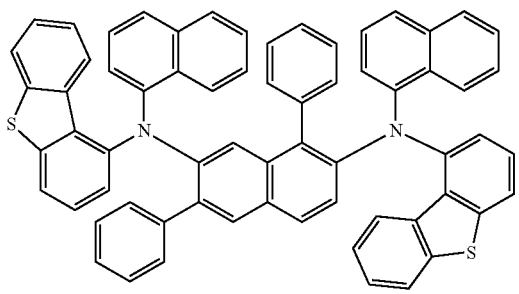

-continued
4-17
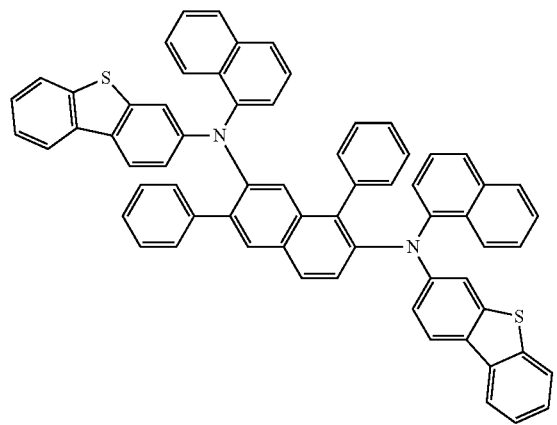
4-18
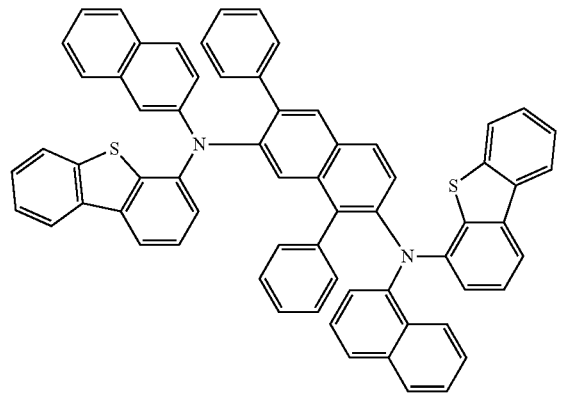
4-19
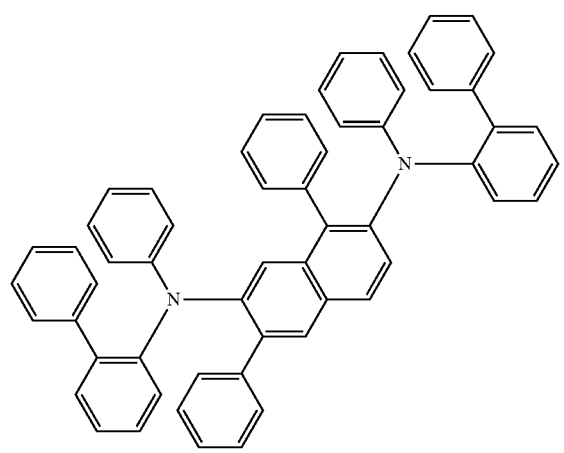
4-20
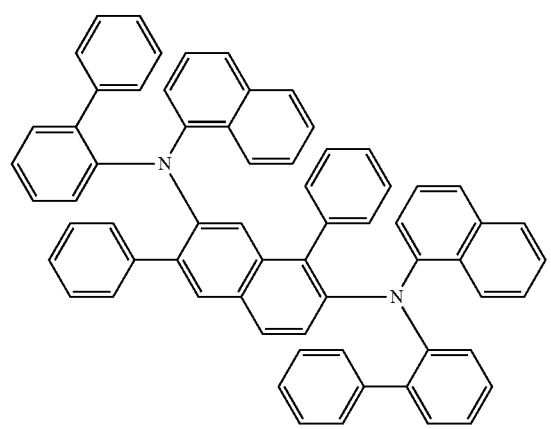
4-21
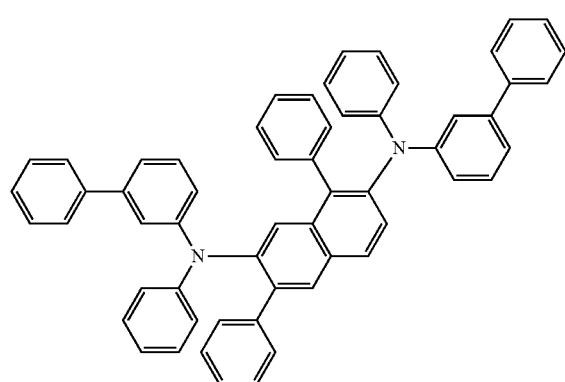
4-22
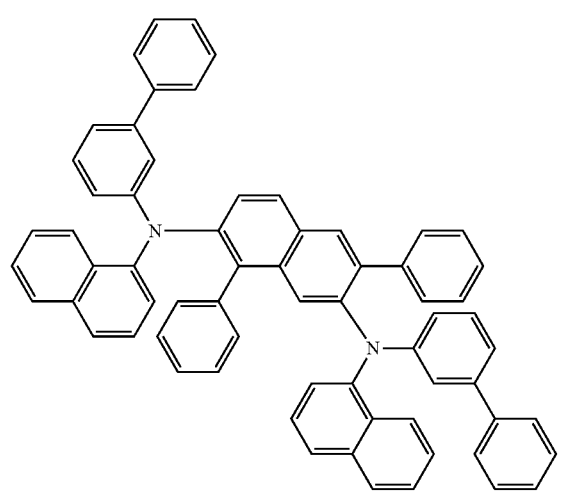

-continued
4-23
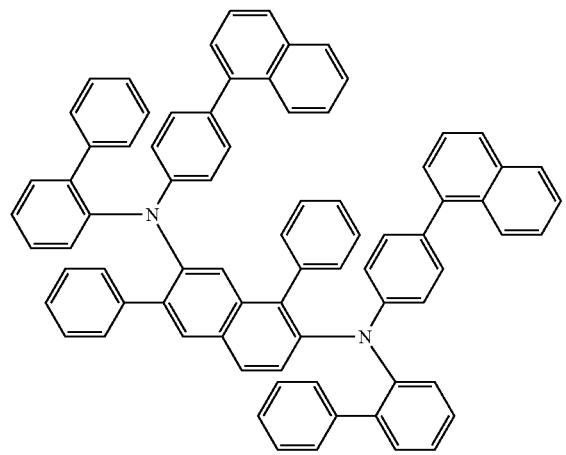
4-24
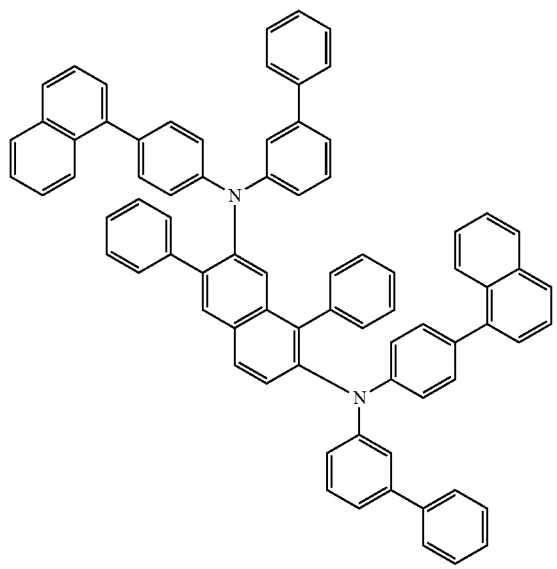
4-25
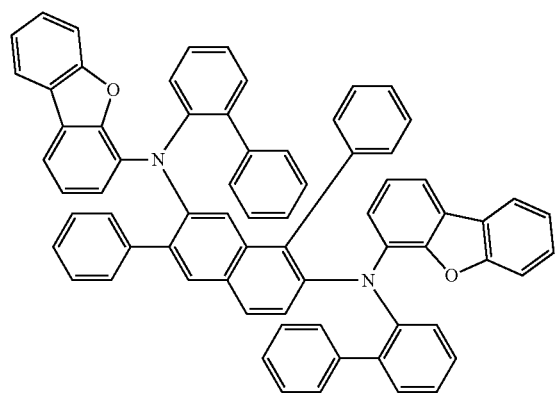
4-26
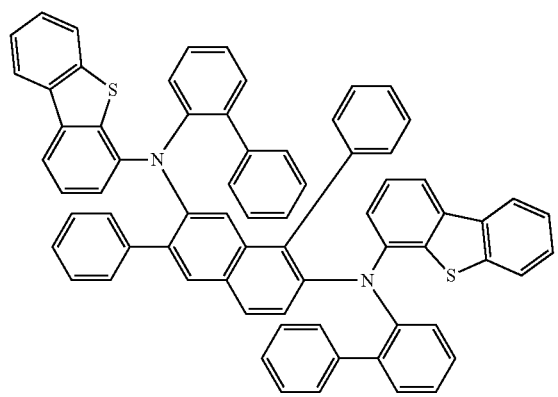
4-27
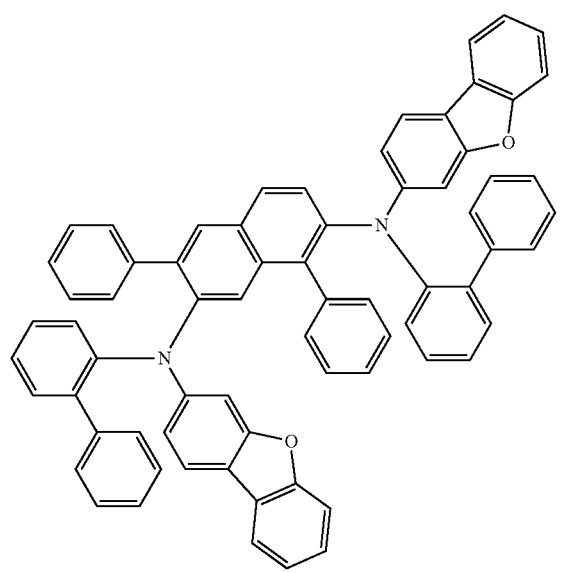
4-28
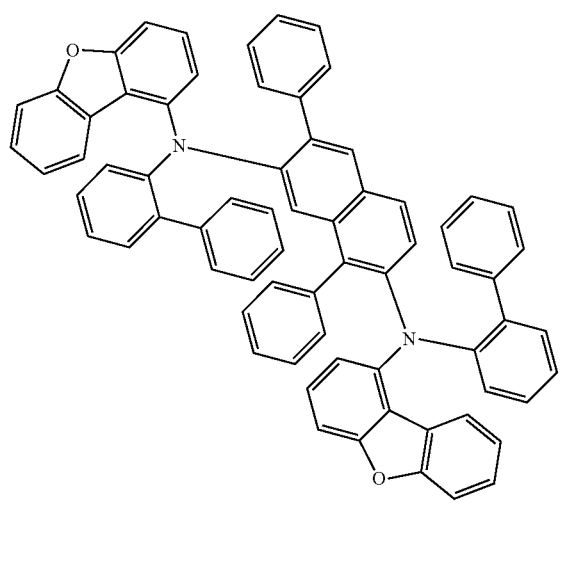

-continued
4-29
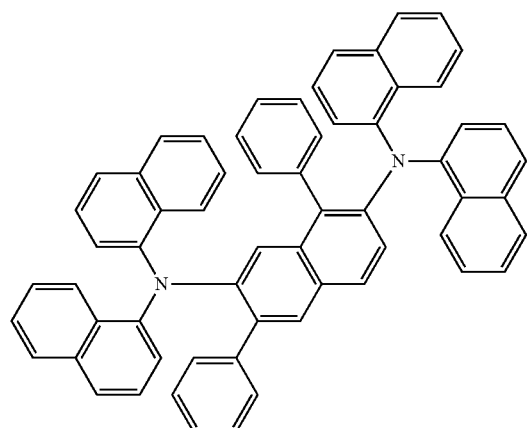
4-30
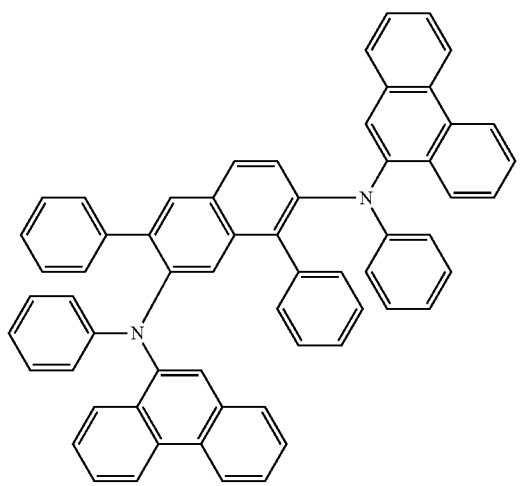
4-31
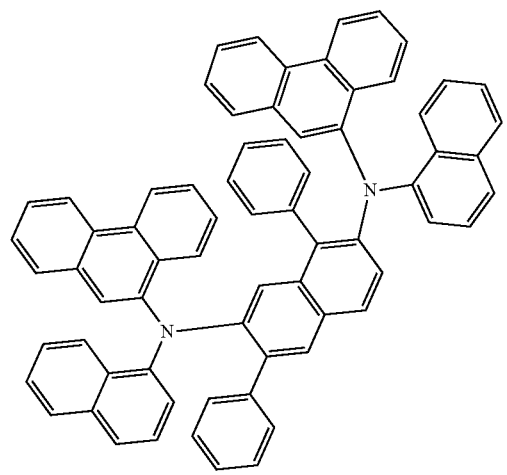
4-32
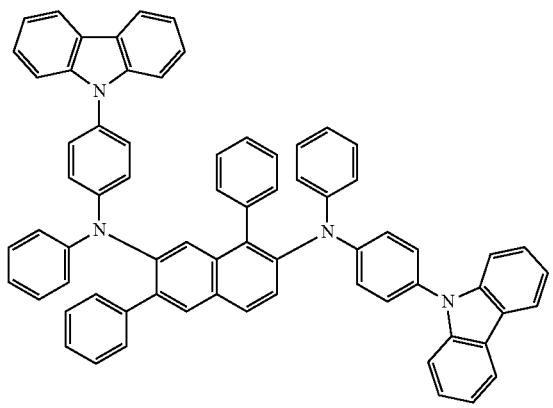
4-33
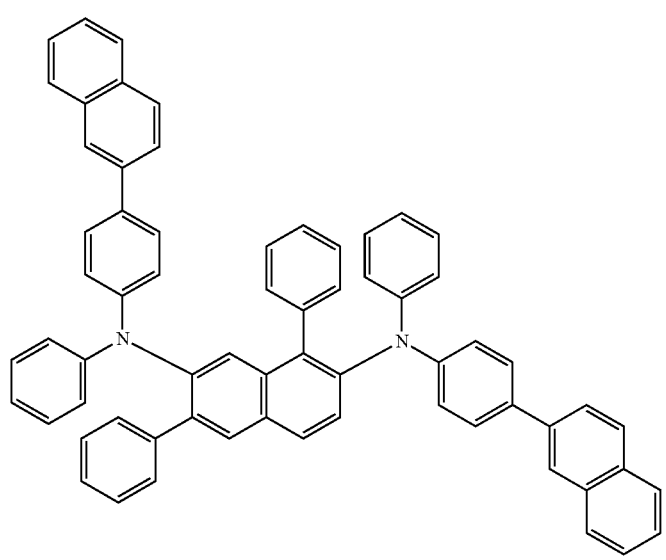

4-34
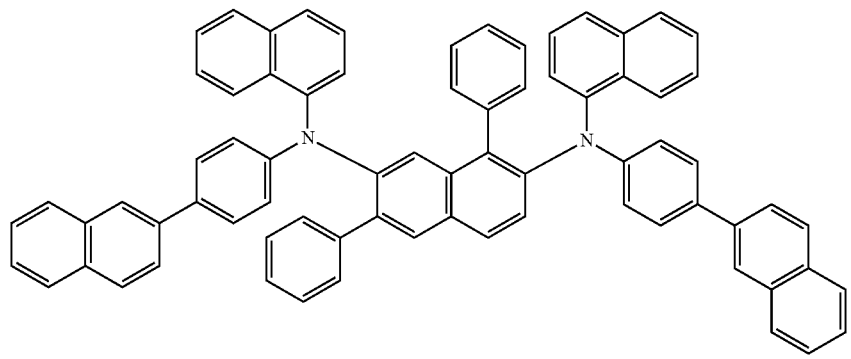
4-35
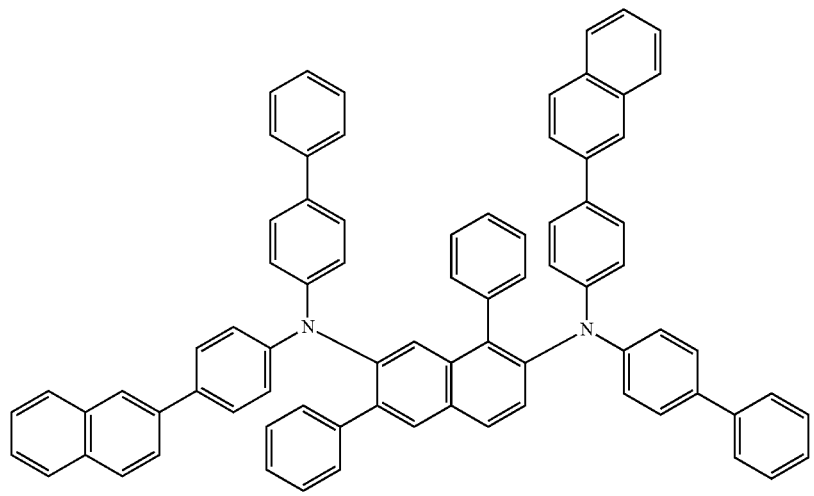
5-1
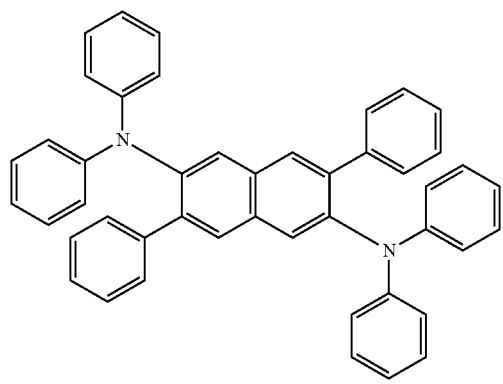
5-2
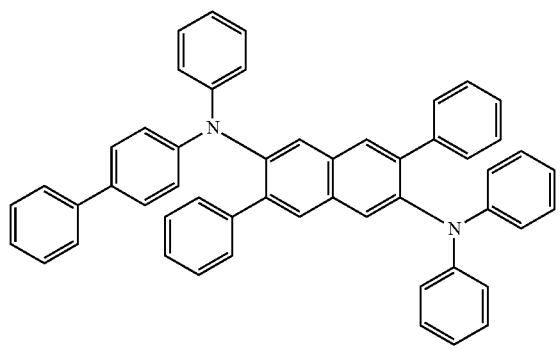

-continued
5-3
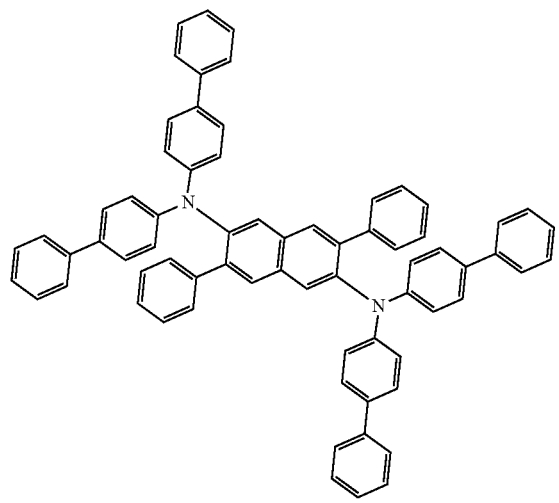
5-4
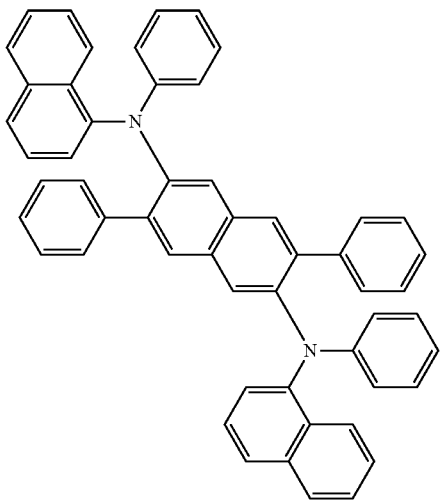
5-5
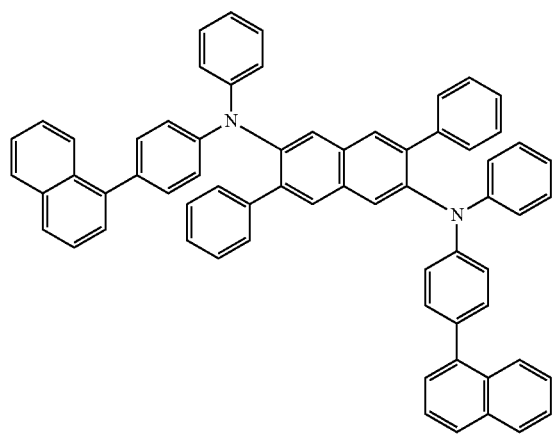
5-6
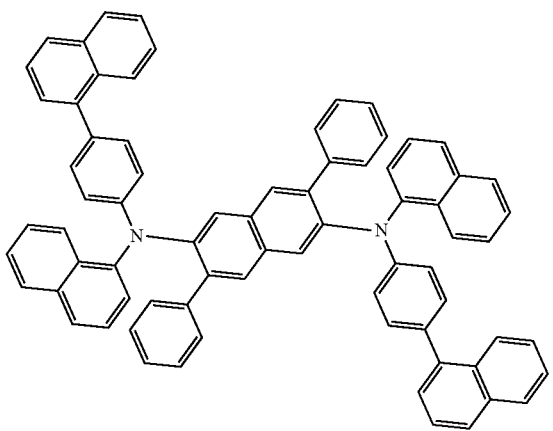
5-7
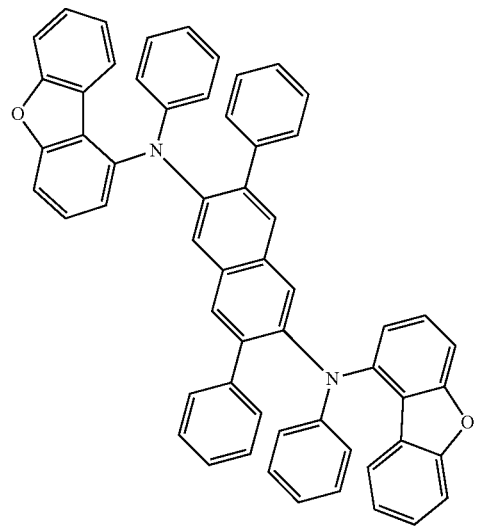
5-8
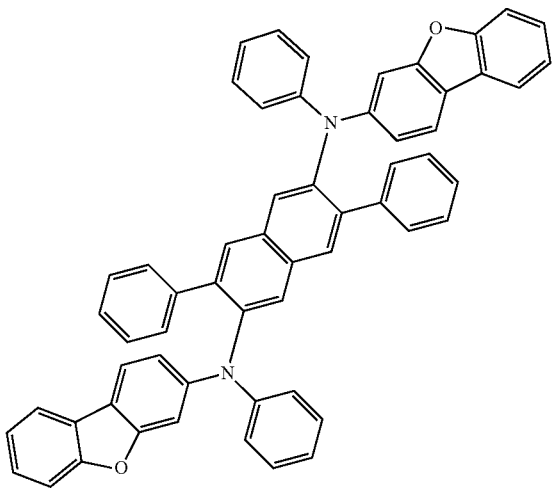

-continued
5-9
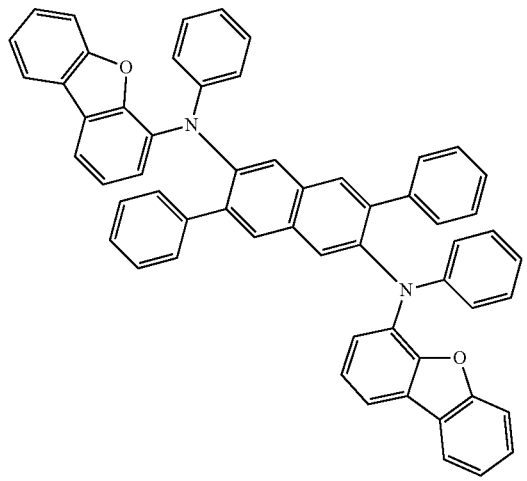
5-10
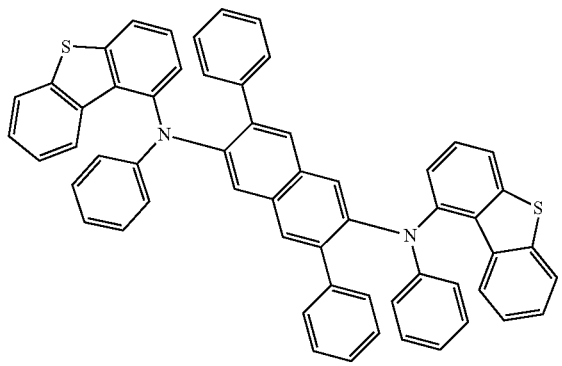
5-11
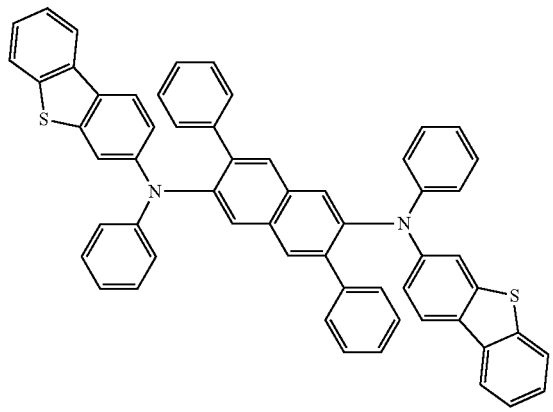
5-12
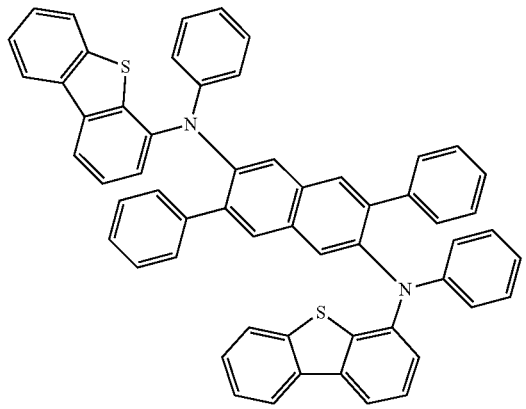
5-13
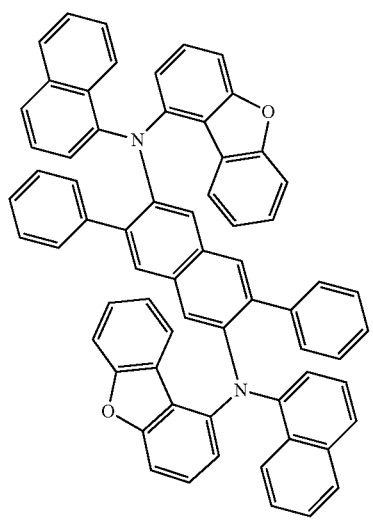
5-14
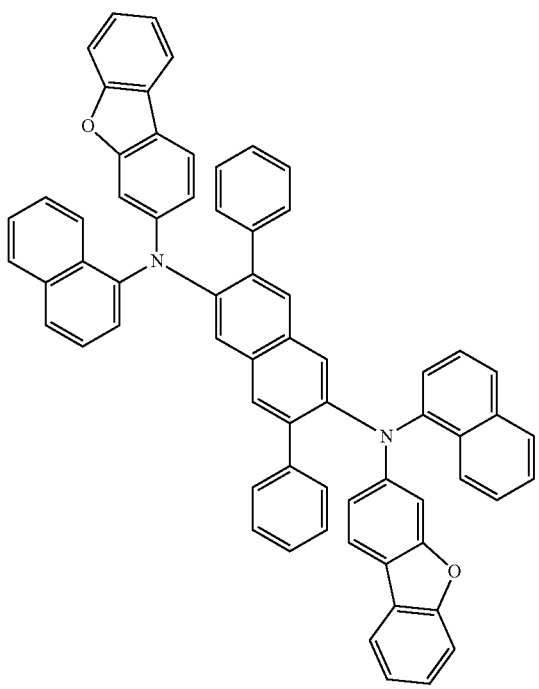

-continued
5-15
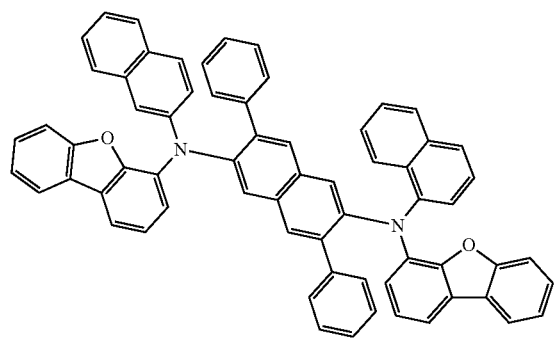
5-16
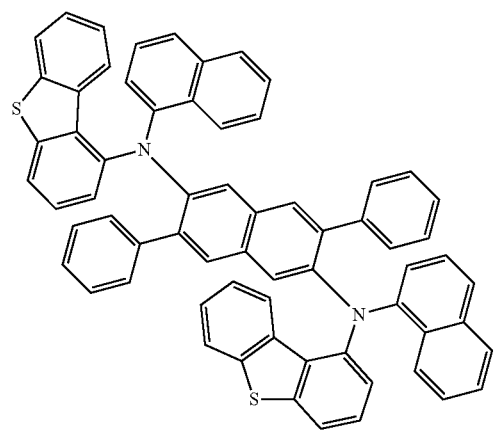
5-17
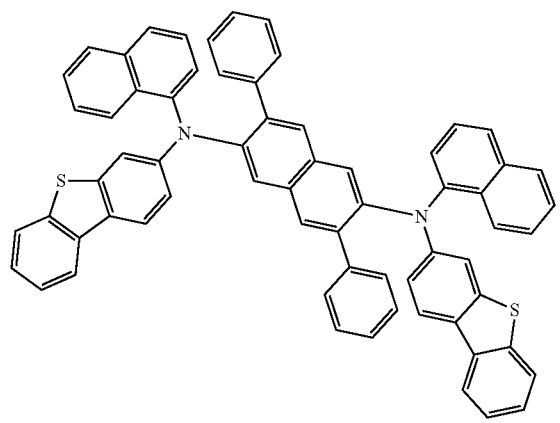
5-18
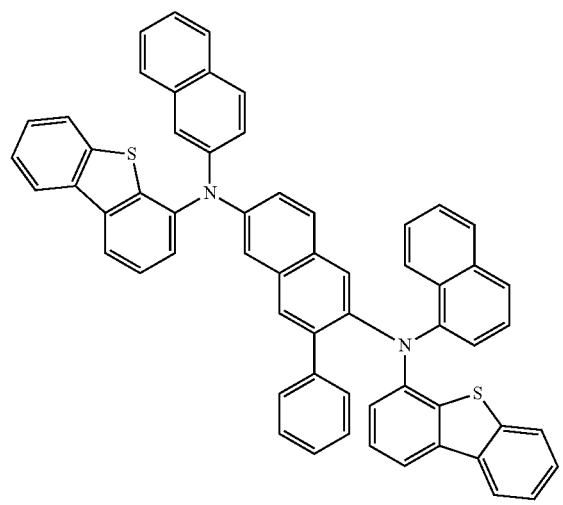
5-19
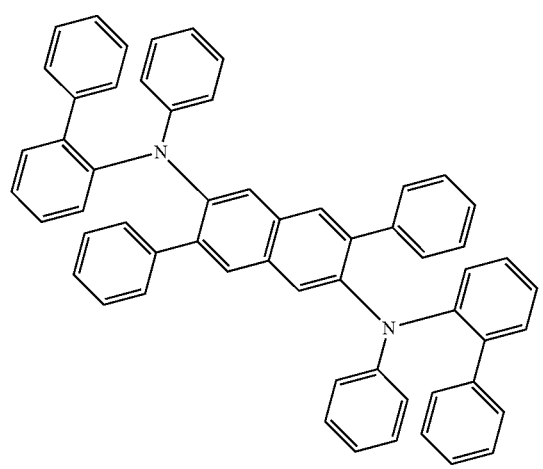
5-20
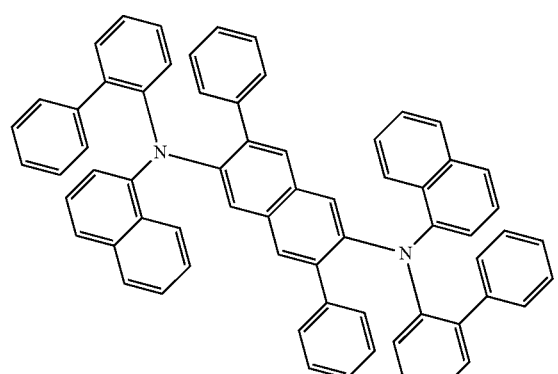

-continued
5-21
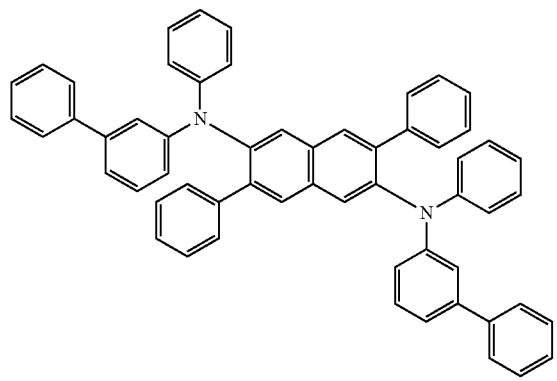
5-22
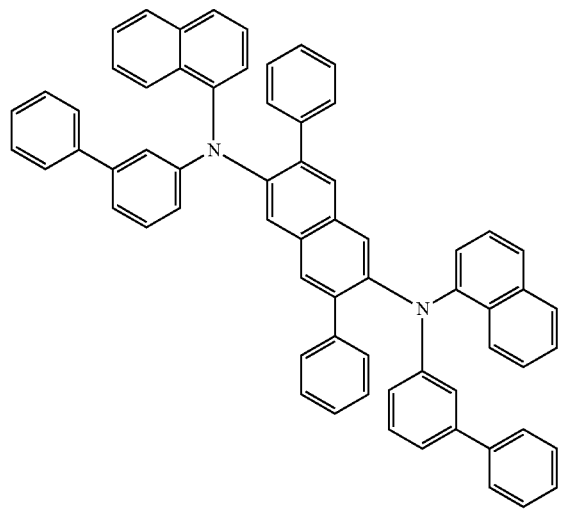
5-23
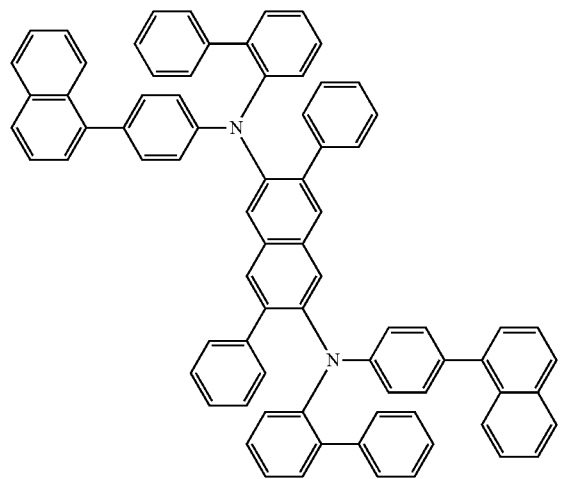
5-24
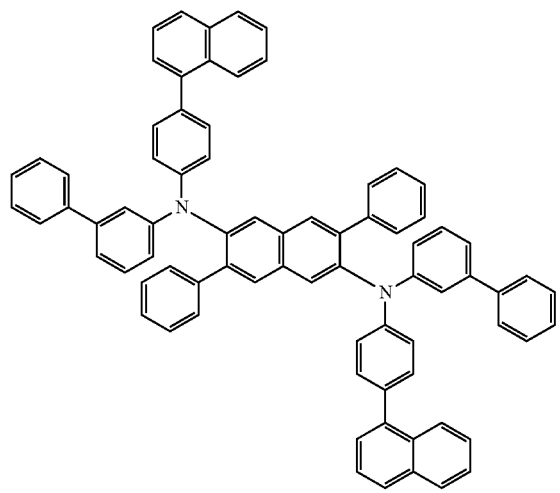
5-25
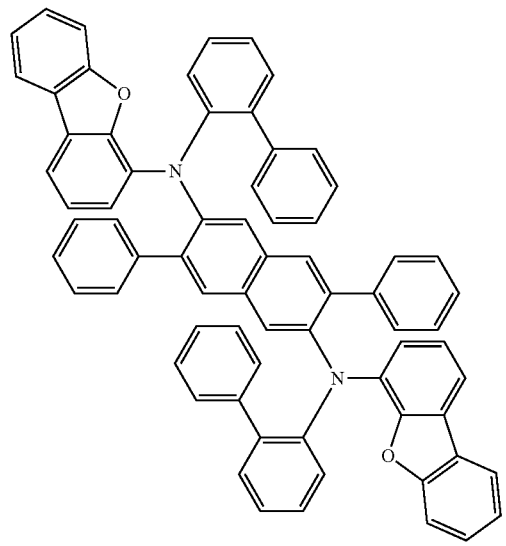
5-26
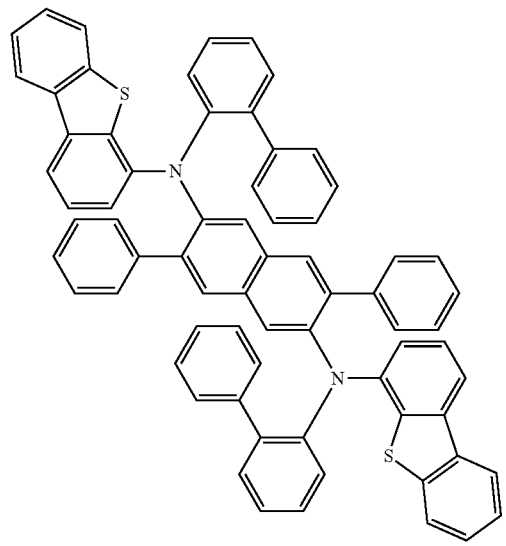

-continued
5-27
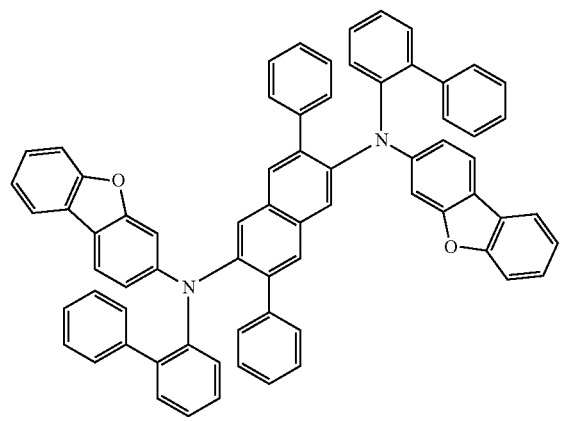
5-28
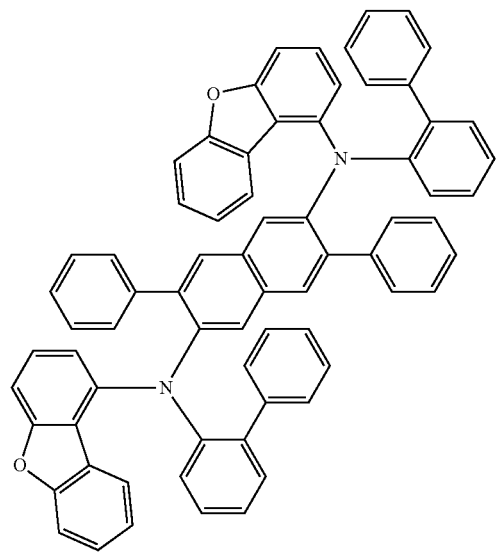
5-29
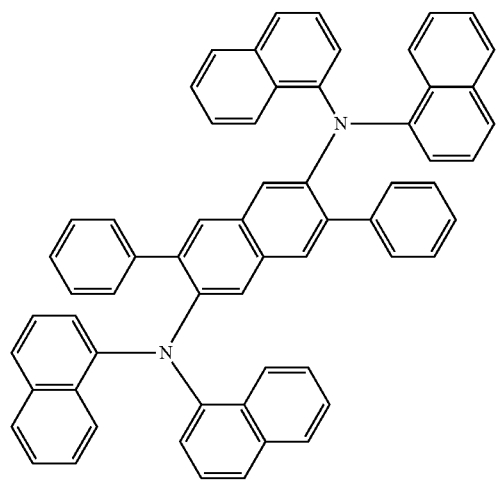
5-30
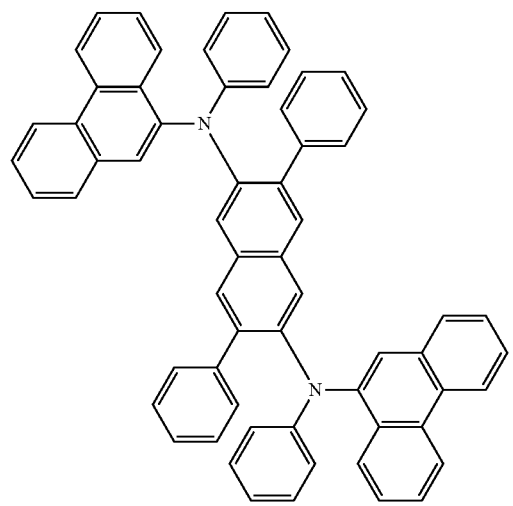
5-31
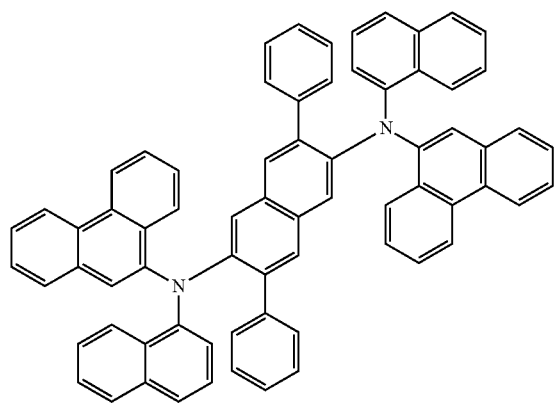
5-32
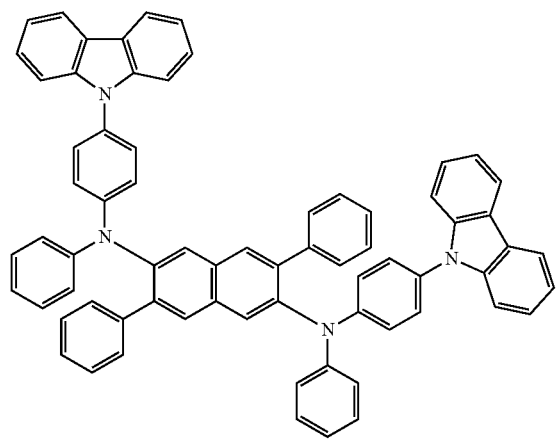

-continued
5-33
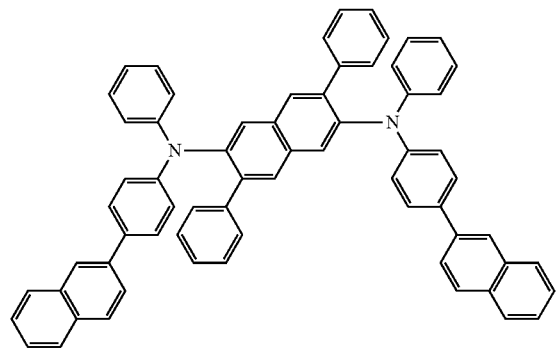
5-34
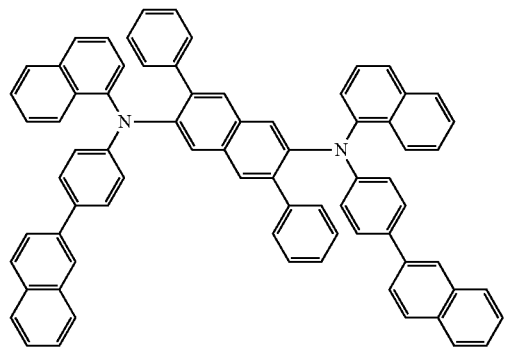
5-35
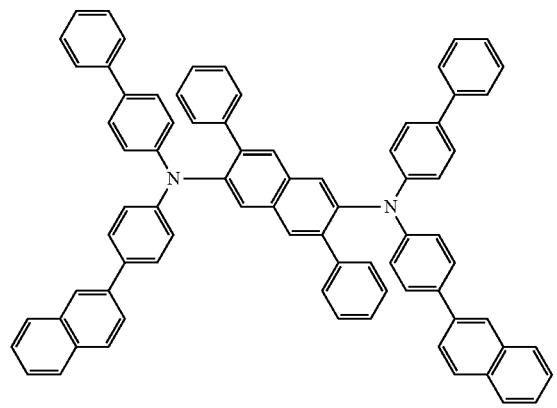
6-1
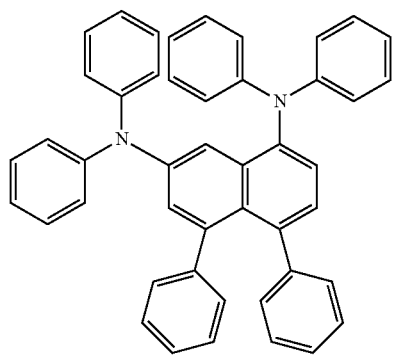
6-2
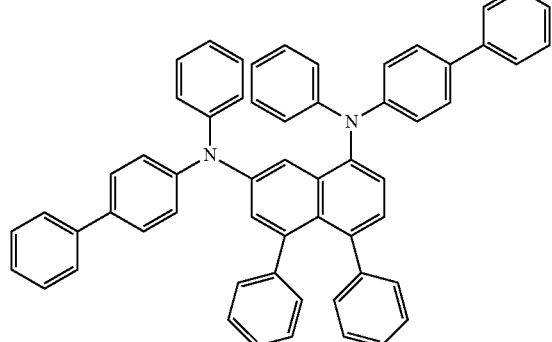
6-3
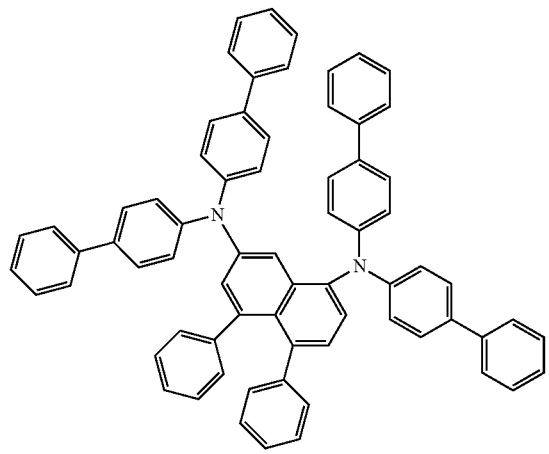
6-4
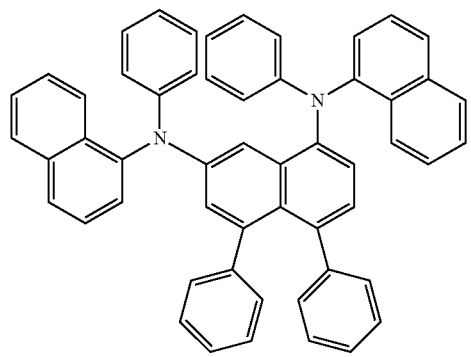
6-5
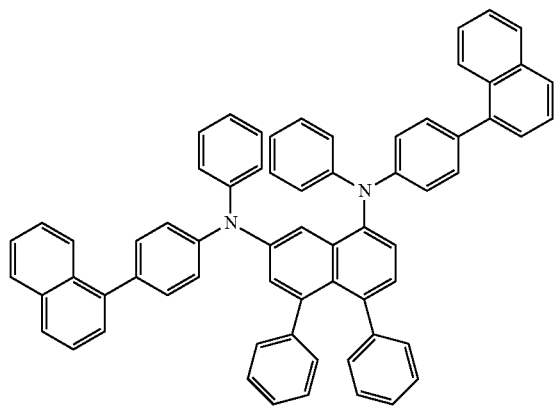

-continued
6-6
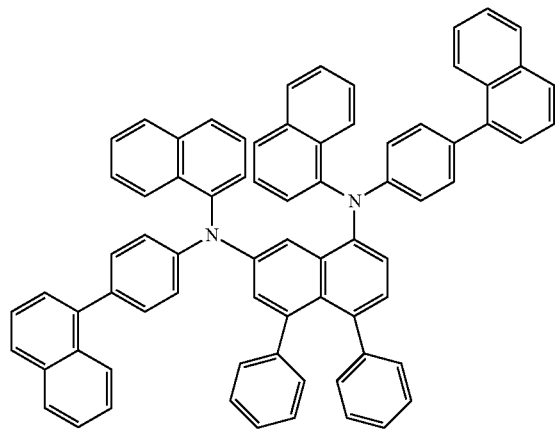
6-7
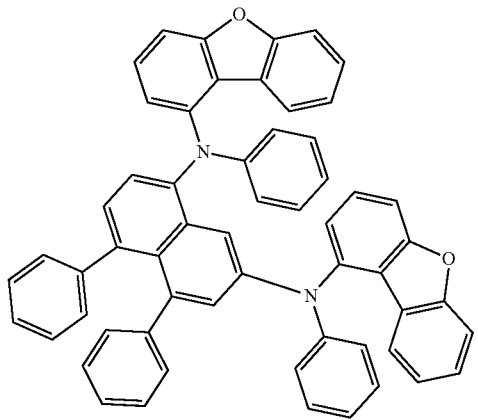
6-8
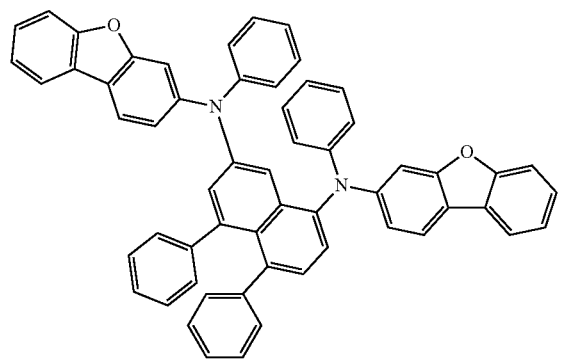
6-9
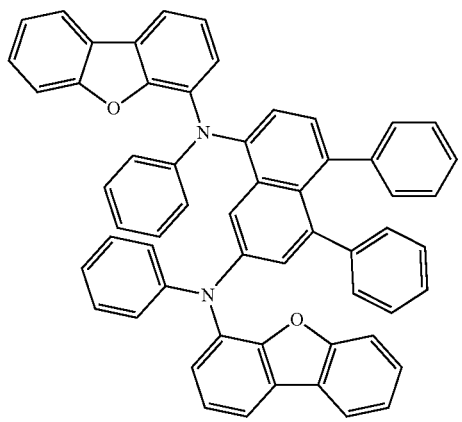
6-10
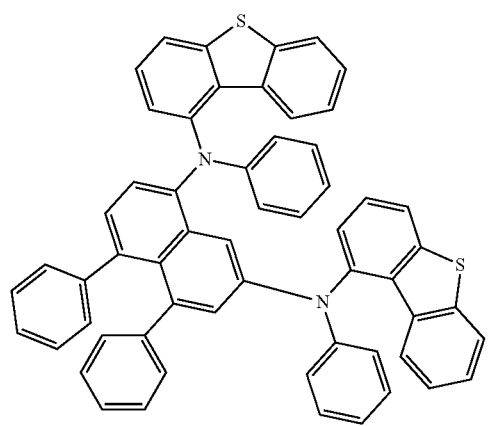
6-11
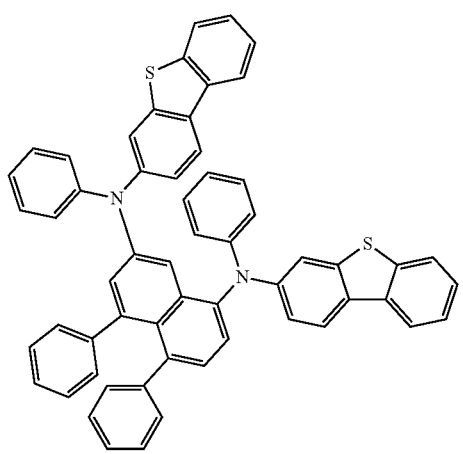

-continued
6-12
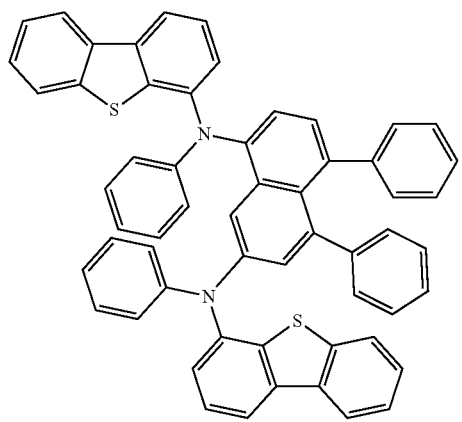
6-13
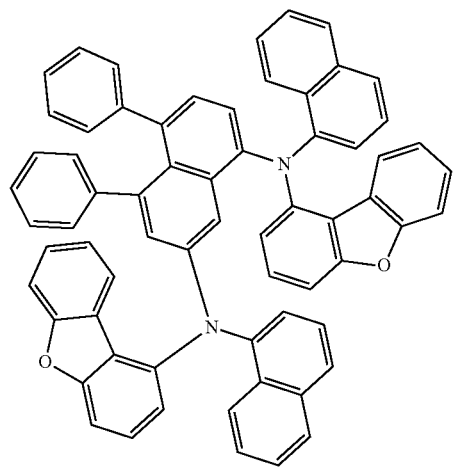
6-14
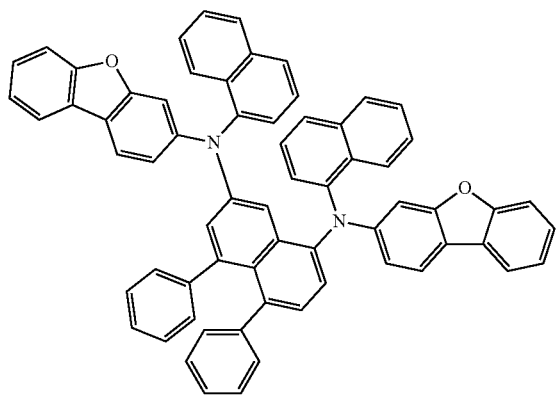
6-15
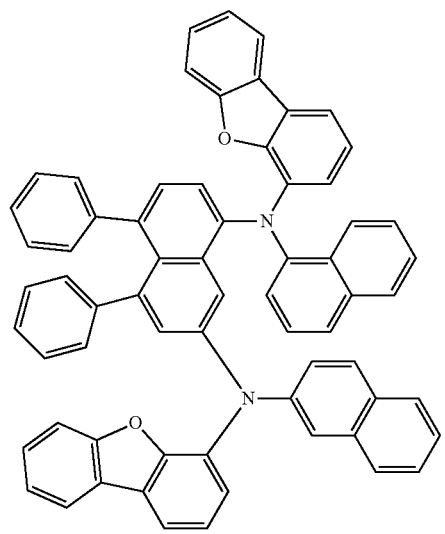
6-16
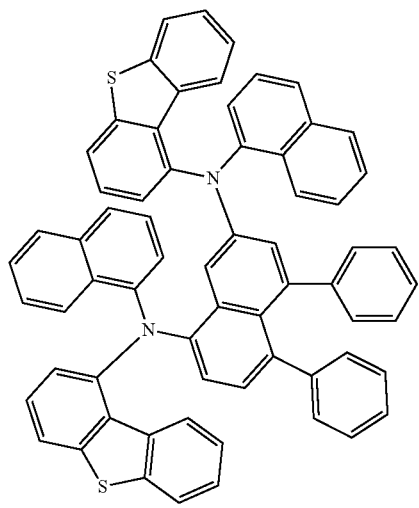
6-17
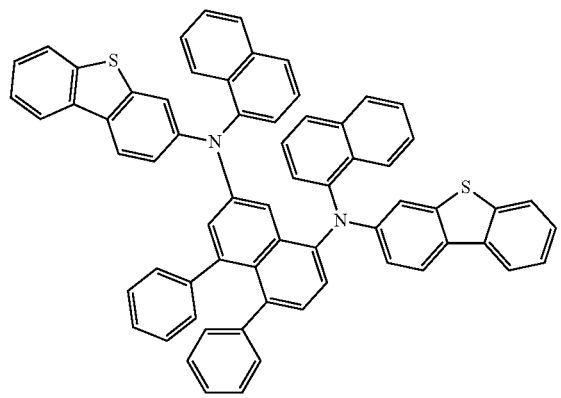

-continued
6-18
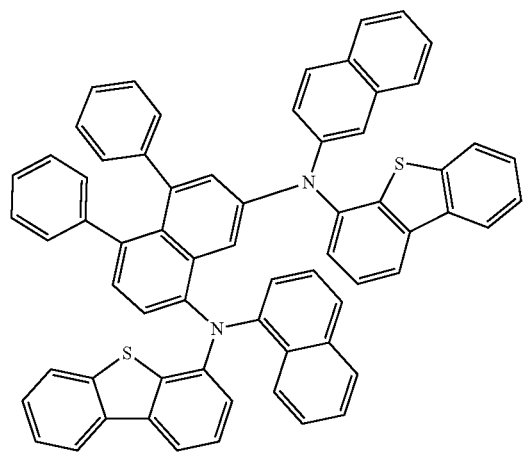
6-19
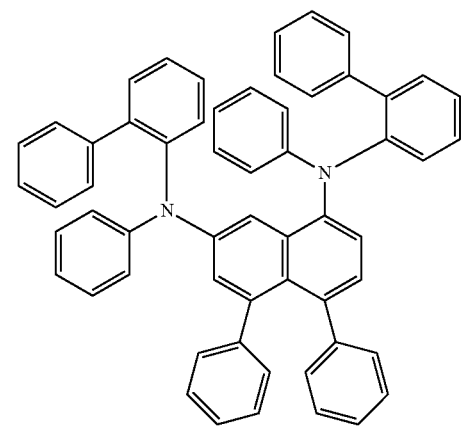
6-20
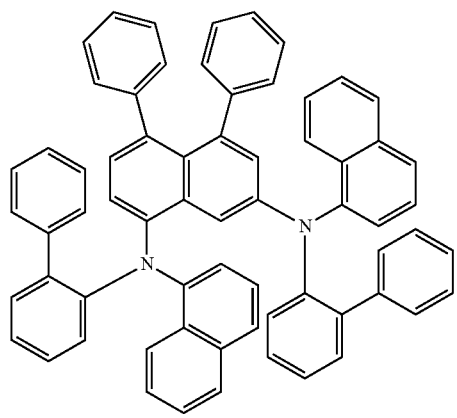
6-21
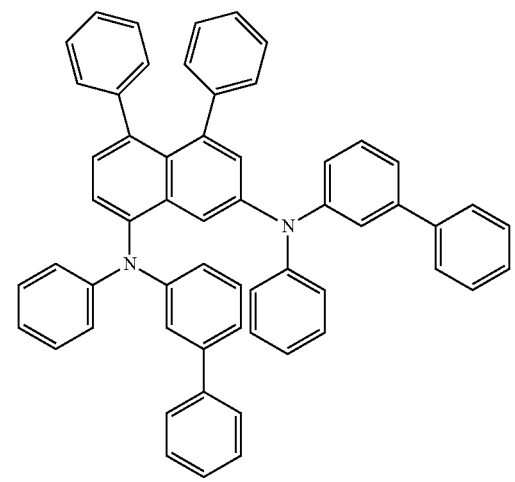
6-22
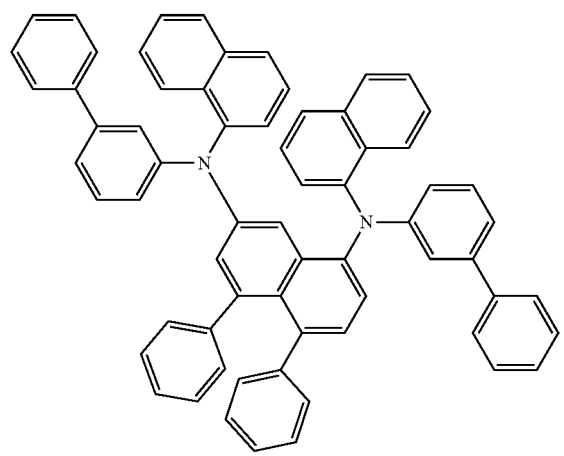
6-23
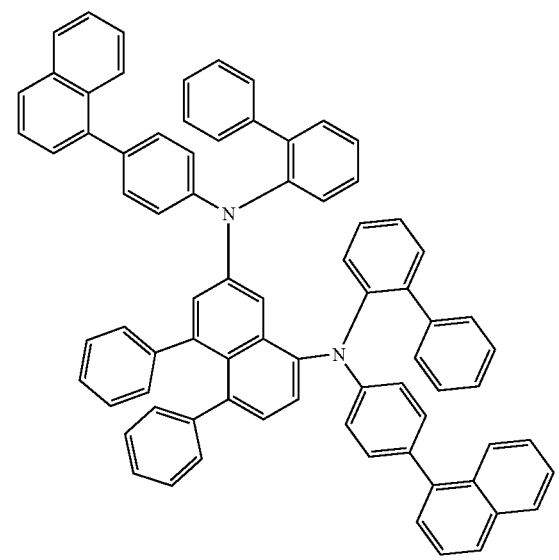

-continued
6-24
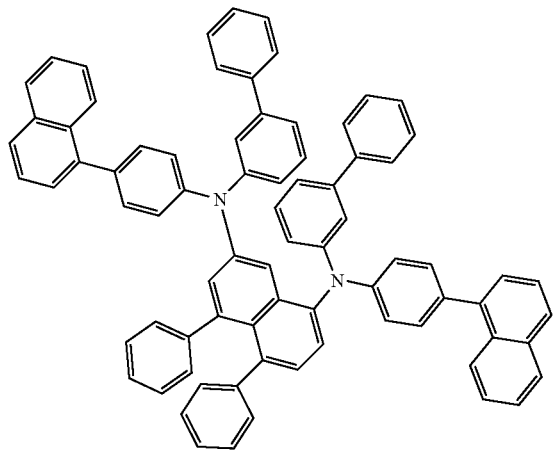
6-25
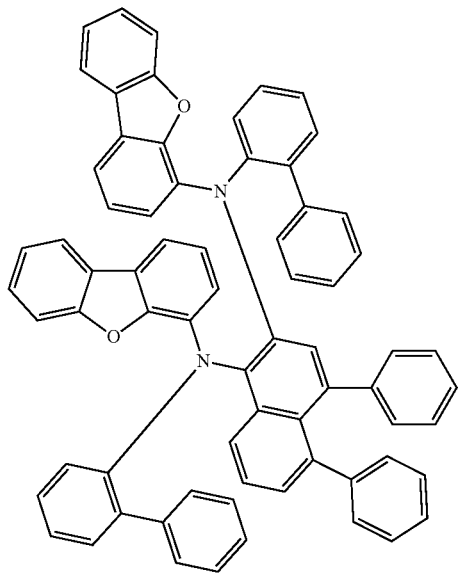
6-26
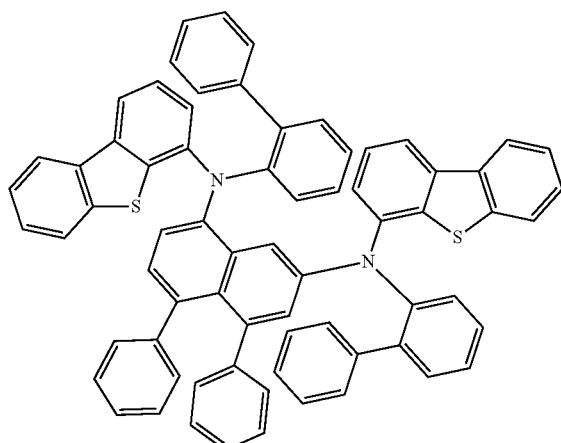
6-27
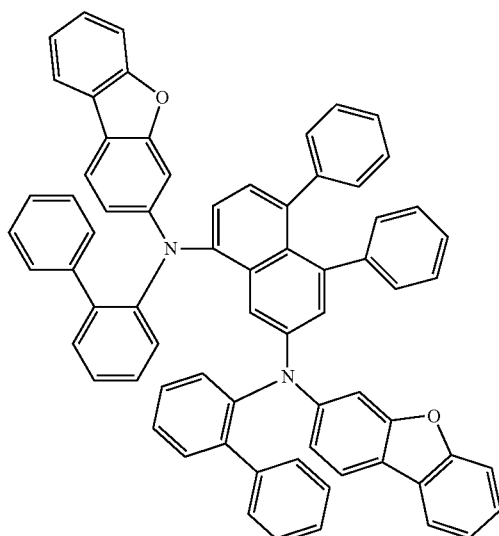
6-28
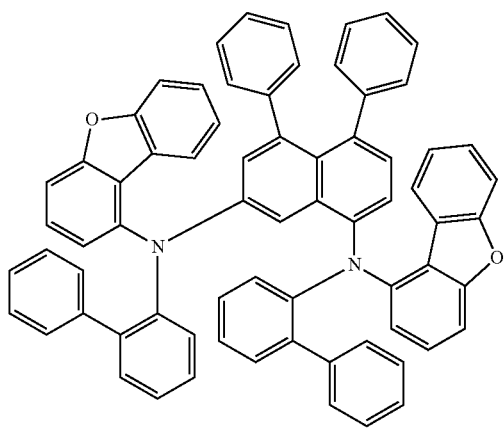
6-29
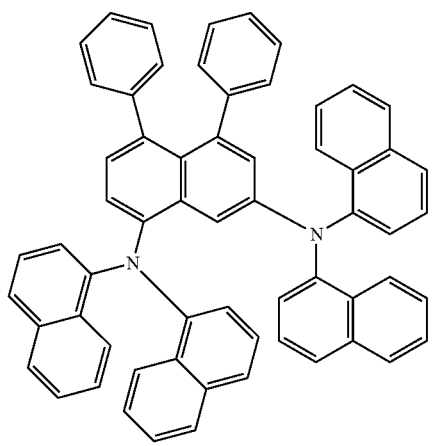

-continued
6-30
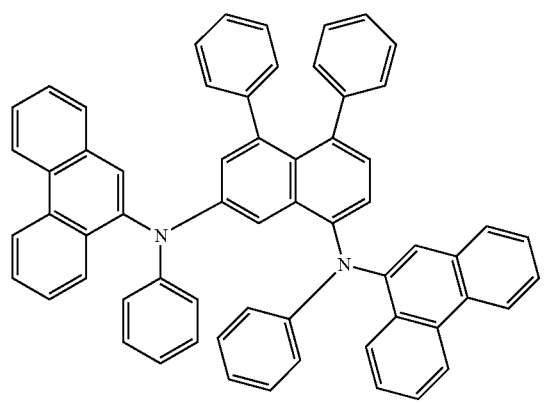
6-31
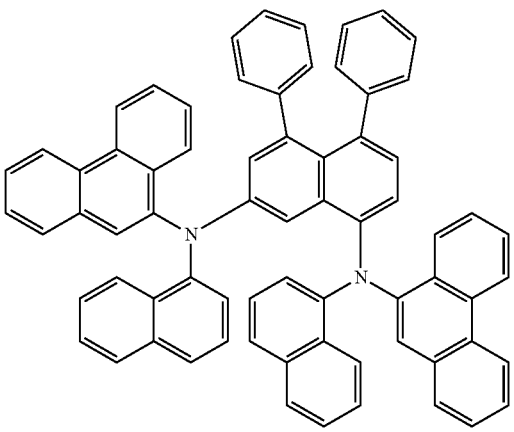
6-32
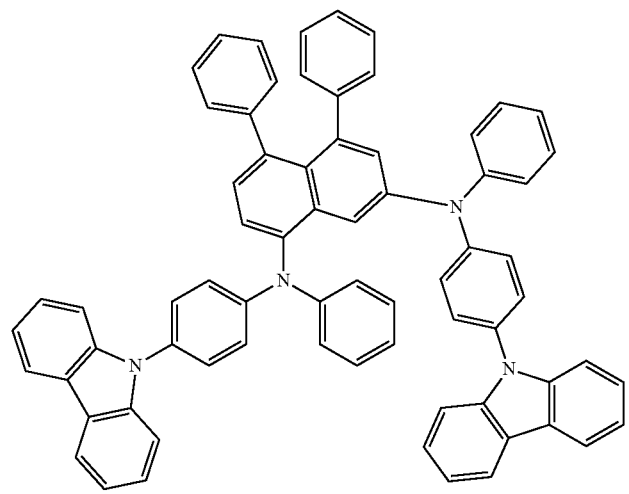
6-33
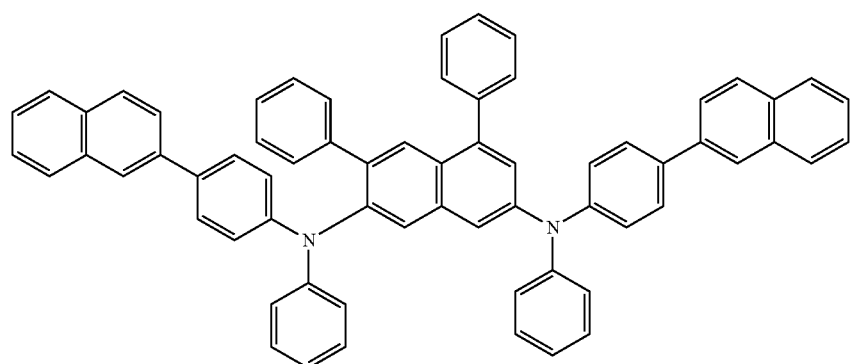

6-34
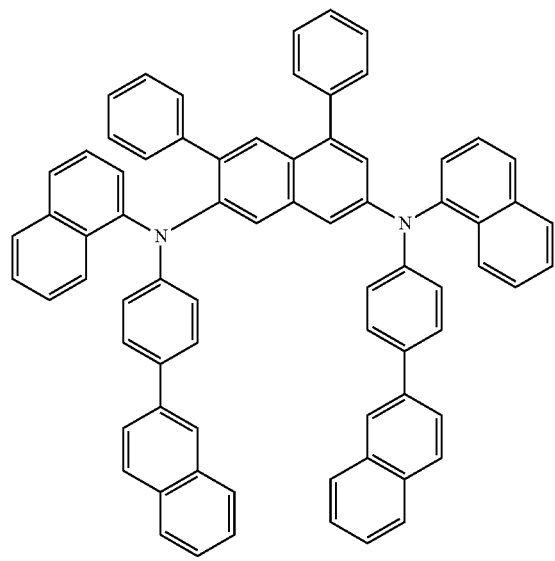
6-35
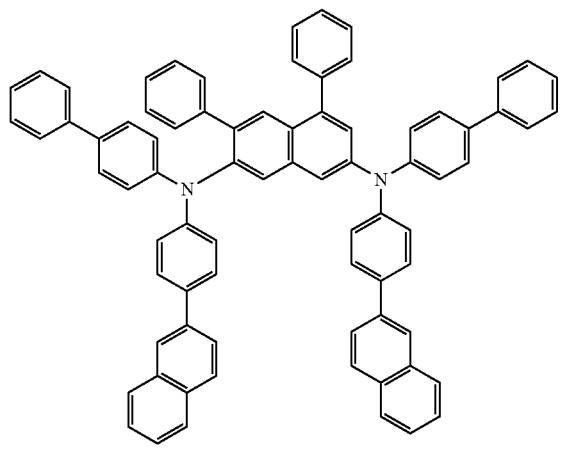
7-1
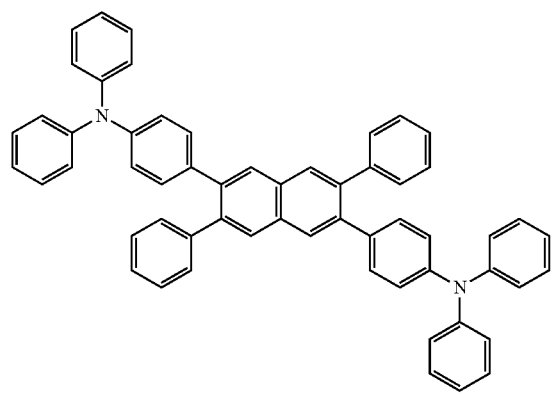
7-2
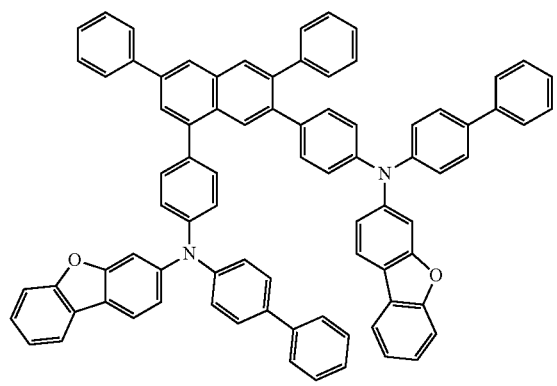
7-3
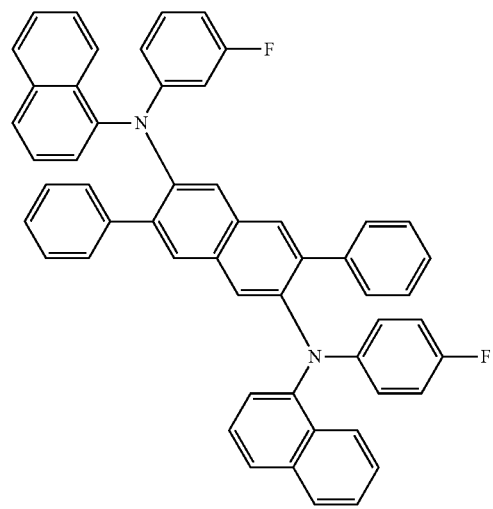
7-4
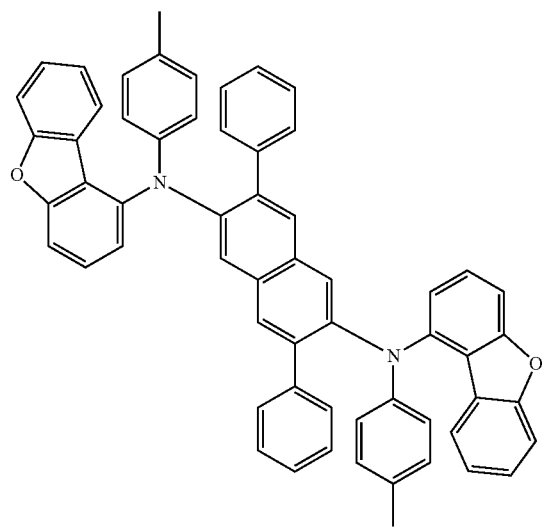

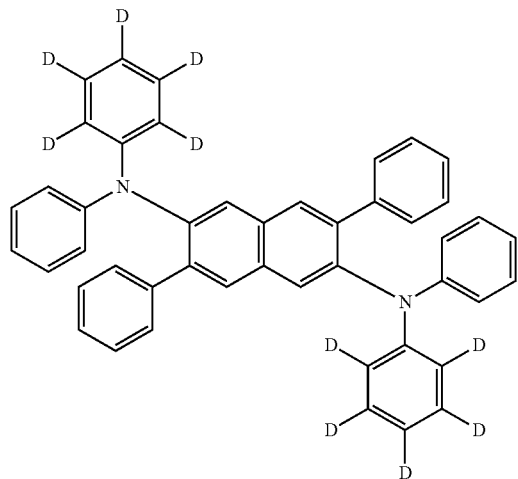

7-5

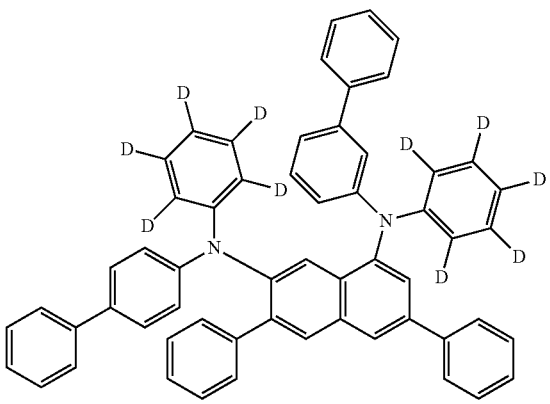

7-6

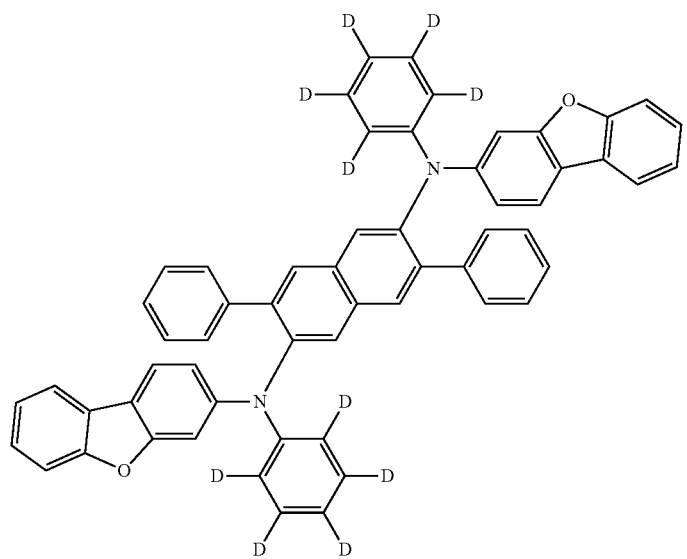

7-7

An organic electroluminescence device according to an embodiment of the inventive concept will be described with reference to FIGS. 1 to 3.

As described above, the hole transport region HTR may include a diamine compound according to an embodiment of the inventive concept as described above. For example, the hole transport region HTR may include the diamine compound represented by Formula 1.

When the hole transport region HTR is a multilayer structure having multiple layers, any one of the layers may include a diamine compound represented by Formula 1. For example, the hole transport region HTR may include the hole injection layer HIL disposed on the first electrode EL1 and the hole transport layer HTL disposed on the hole injection layer, wherein the hole transport layer HTL may include a diamine compound represented by Formula 1. However, the embodiments are not limited thereto. For example, the hole injection layer HIL may include a diamine compound represented by Formula 1.

The hole transport region HTR may include one or two or more of the diamine compounds represented by Formula 1. For example, the hole transport region HTR may include at least one selected from the compounds represented by Compound Group 1 as described above.

The hole transport region HTR may be formed using various methods such as a vacuum deposition method, a spin coating method, a cast method, a Langmuir-Blodgett (LB) method, an inkjet printing method, a laser printing method, and a laser induced thermal imaging (LITI) method.

However, the hole transport region HTR may further include materials below in each layer.

The hole injection layer HIL may include, for example, a phthalocyanine compound such as copper phthalocyanine; N,N'-diphenyl-N,N'-bis-[4-(phenyl-m-tolyl-amino)-phenyl]-biphenyl-4,4-diamine (DNTPD), 4,4,4''-[tris(3-methylphenyl)phenylamino]triphenylamine] (m-MTDATA), 4,4', 4'-tris(N,N-diphenylamino)triphenylamine (TDATA), 4,4, 4"-tris{N,-(2-naphthyl)-N-phenylamino)-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(naphthalene-1-yl)-N,N'-diphenyl-benzidine (NPD), triphenylamine-containing polyetherketone (TPAPEK), 4-isopropyl-4'-methyldiphenyliodonium tetrakis(pentafluorophenyl)borate, dipyrazino[2,3-f: 2', 3-h]quinoxaline-2,3,6,7,10,11-hexacarbonitrile (HAT-CN), etc.

The hole transport layer HTL may include general materials known in the art. The hole transport layer HTL may further include, for example, carbazole derivatives such as N-phenyl carbazole and polyvinyl carbazole, fluorene derivatives, N,N'-bis(3-methylphenyl)-N,N'-diphenyl-[1,1-biphenyl]-4,4'-diamine (TPD), triphenylamine derivatives such as 4,4',4"-tris(N-carbazolyl)triphenylamine (TCTA), N,N'-di(naphthalene-1-yl)-N,N'-diphenyl-benzidine (NPD), 4,4'-cyclohexylidene bis[N,N-bis(4-methylphenyl]benzenamine] (TAPC), 4,4'-bis[N,N'-(3-tolyl)amino]-3,3'-dimethylbiphenyl (HMTPD), 1,3-Bis(N-carbazolyl)benzene (mCP), etc.

The electron blocking layer EBL may include, for example, carbazole derivatives such as N-phenyl carbazole and polyvinyl carbazole, fluorine derivatives, N,N'-bis(3-methylphenyl)-N,N'-diphenyl-[1,1-biphenyl]-4,4'-diamine (TPD), triphenylamine derivatives such as 4,4',4"-tris(N-carbazolyl)triphenylamine (TCTA), N,N'-di(1-naphthalene-1-yl)-N,N'-diphenyl-benzidine (NPD), 4,4'-cyclohexylidene bis[N,N-bis(4-methylphenyl]benzenamine] (TAPC), 4,4'-bis[N,N'-(3-tolyl)amino]-3,3'-dimethylbiphenyl (HMTPD), mCP, etc.

The thickness of the hole transport region HTR may be in a range of about 50 Å to about 15,000 Å. For example, the thickness of the hole transport region HTR may be in a range of about 100 Å to about 5,000 Å. The thickness of the hole injection region HIL may be in a range of about 30 Å to about 1,000 Å, and the thickness of the hole transport layer HTL may be in a range of about 30 Å to about 1,000 Å. For example, the thickness of the electron blocking layer EBL may be in a range of about 10 Å to about 1,000 Å. If the thicknesses of the hole transport region HTR, the hole injection layer HIL, the hole transport layer HTL and the electron blocking layer EBL satisfy the above-described ranges, satisfactory hole transport properties may be achieved without a substantial increase in driving voltage.

The hole transport region HTR may further include, in addition to the above-described materials, a charge generating material to increase conductivity. The charge generating material may be dispersed uniformly or non-uniformly in the hole transport region HTR. The charge generating material may be, for example, a p-dopant. The p-dopant may be one of quinone derivatives, metal oxides, or cyano group-containing compounds, but is not limited thereto. For example, non-limiting examples of the p-dopant may include, but are not limited to, quinone derivatives such as tetracyanoquinodimethane (TCNQ) and 2,3,5,6-tetrafluoro-7,7,8,8-tetracyanoquinodimethane (F4-TCNQ), metal halides such as MgF$_2$, CuI, RbI, metal oxides such as tungsten oxides and molybdenum oxides.

As described above, the hole transport region HTR may further include at least one of the hole buffer layer or the electron blocking layer EBL. The hole buffer layer may compensate a resonance distance according to the wavelength of light emitted from the emission layer EML to increase light emission efficiency. Materials which may be included in the hole transport region HTR may be used as materials which may be included in the hole buffer layer. The electron blocking layer EBL may be a layer that serves to prevent electrons from being injected from the electron transport region ETR to the hole transport region HTR.

The emission layer EML may be provided on the hole transport region HTR. The thickness of the emission layer EML may be in a range of about 100 Å to about 1,000 Å. For example, the thickness of the emission layer EML may be in a range of about 100 Å to about 600 Å. The emission layer EML may have a single layer formed of a single material, a single layer formed of different materials, or a multilayer structure having multiple layers formed of different materials.

As materials of the emission layer EML, known materials may be used, and one selected among fluoranthene derivatives, pyrene derivatives, arylacetylene derivatives, anthracene derivatives, fluorene derivatives, perylene derivatives, chrysene derivatives, etc. may be used, without specific limitation. Preferably, the host materials may include pyrene derivatives, perylene derivatives, and anthracene derivatives. For example, as the host materials of the emission layer EML, anthracene derivatives represented by Formula 10 below may be used.

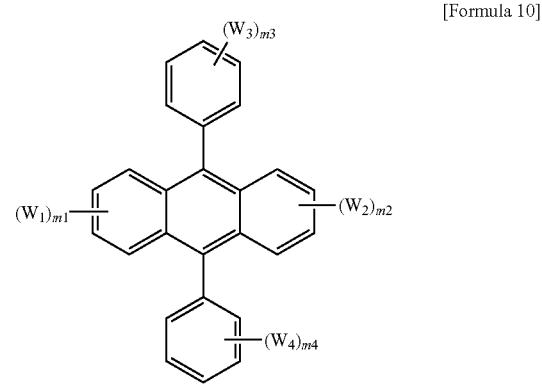

[Formula 10]

In Formula 10, $W_1$ to $W_4$ may each independently be a hydrogen atom, a deuterium atom, a halogen atom, a substituted or unsubstituted silyl group, a substituted or unsubstituted alkyl group having 1 to 20 carbon atoms, a substituted or unsubstituted aryl group having 6 to 30 ring-forming carbon atoms, a substituted or unsubstituted heteroaryl group having 2 to 30 ring-forming carbon atoms, or bonded to an adjacent group to form a ring, m1 and m2 may each independently be an integer from 0 to 4, and m3 and m4 may each independently be an integer from 0 to 5.

If m1 is 1, $W_1$ may not be a hydrogen atom, if m2 is 1, $W_2$ may not be a hydrogen atom, if m3 is 1, $W_3$ may not be a hydrogen atom, and if m4 is 1, $W_4$ may not be a hydrogen atom.

If m1 is 2 or more, then the $W_1$'s may be the same or different. If m2 is 2 or more, then the $W_2$'s may be the same or different. If m3 is 2 or more, then the $W_3$'s may be the same or different. If m4 is 2 or more, then the $W_4$'s may be the same or different.

The compound represented by Formula 10 may include, for example, a compound represented by the following structures. However, the compound represented by Formula 10 is not limited thereto.

a-1
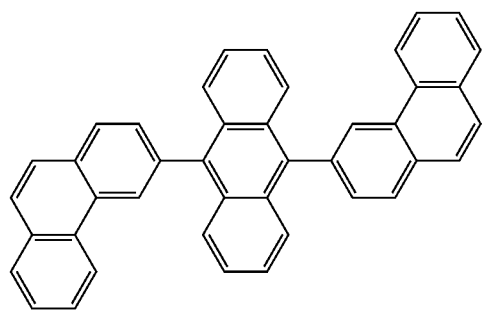
a-2
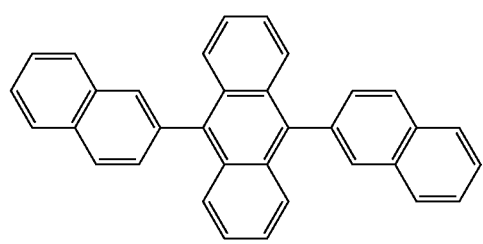
a-3
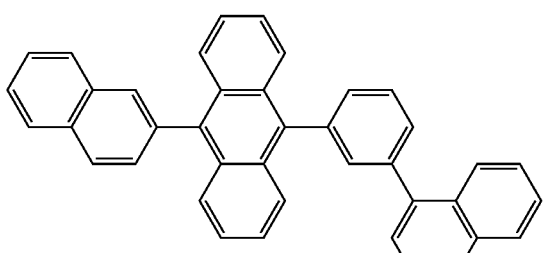
a-4
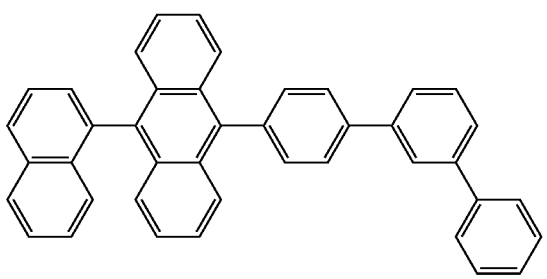
a-5
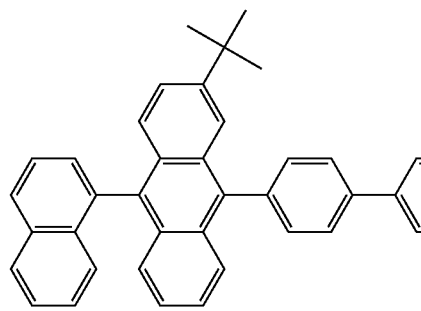
-continued
a-6
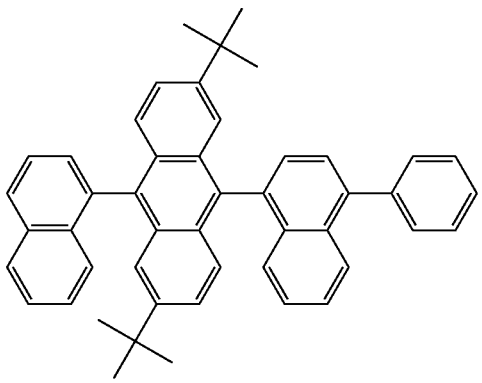
a-7
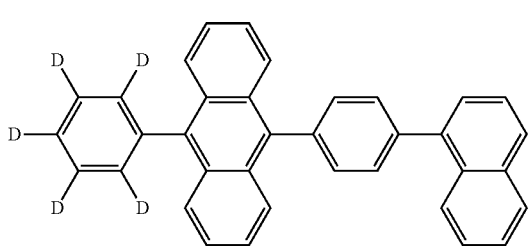
a-8
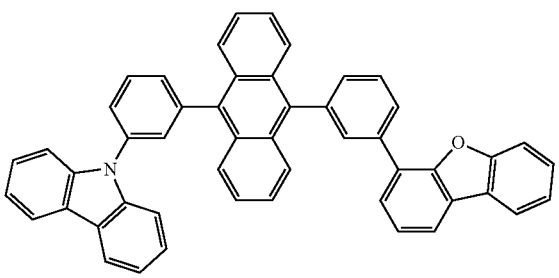
a-9
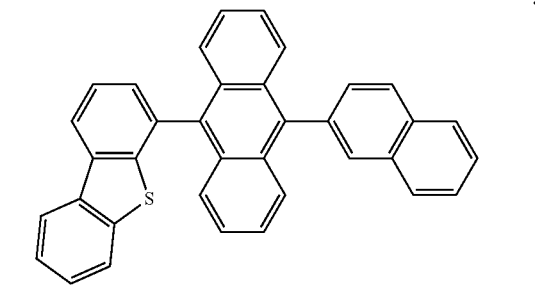
a-10
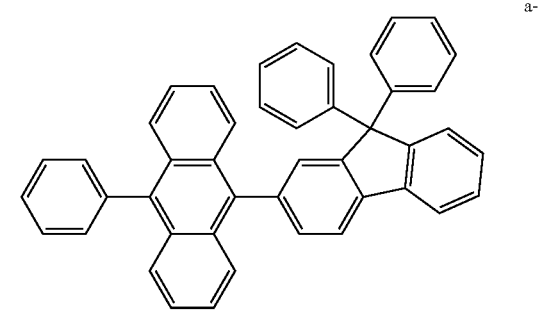

-continued a-11
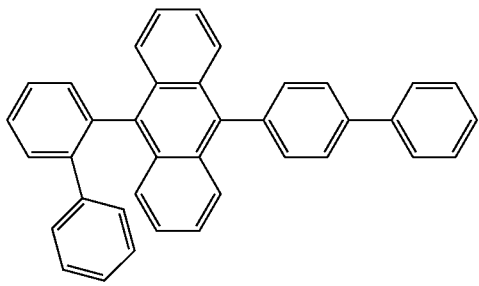

a-12
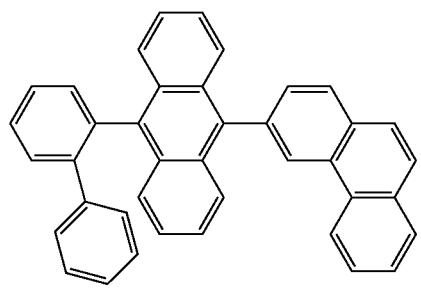

a-13
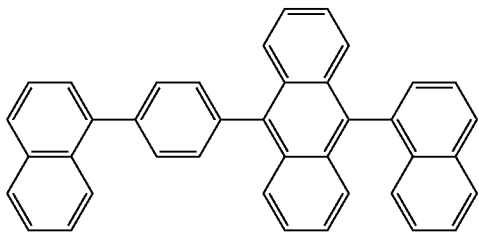

a-14
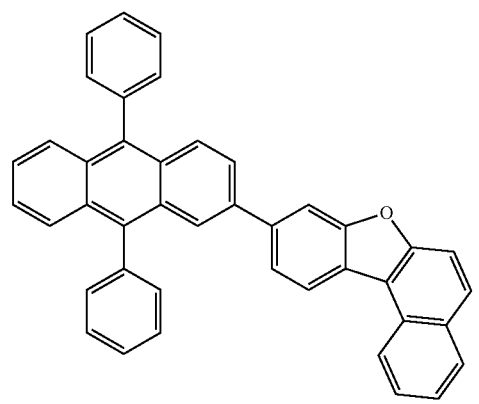

-continued a-15
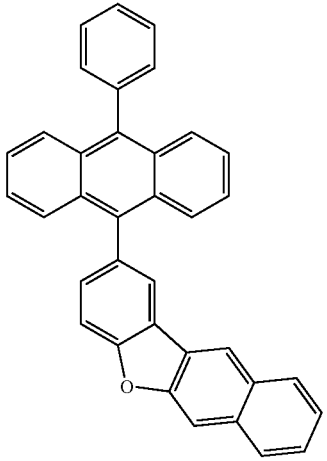

a-16
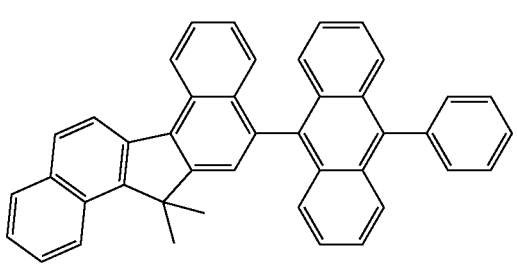

The emission layer EML may include a dopant, know materials may be used as the dopant. For example, at least any one of styryl derivatives (for example, 1,4-bis[2-(3-N-ethylcarbazoryl)vinyl]benzene (BCzVB), 4-(di-p-tolylamino)-4"-[(di-p-tolylamino)styryl]stilbene (DPAVB), and N-(4-((E)-2-(6-((E)-4-(diphenylamino)styryl)naphthalen-2-yl)vinyl)phenyl)-N-phenylbenzenamine (N-BDAVBi), perylene and the derivatives thereof (for example, 2,5,8,11-tetra-t-butylperylene (TBPe)), pyrene and the derivatives thereof (for example, 1,1-dipyrene, 1,4-dipyrenylbenzene, 1,4-bis(N,N-diphenylamino)pyrene, and 1,6-bis(N,N-diphenylamino)pyrene), 2,5,8,11-tetra-t-butylperylene (TBP), or 1,3,5-tris(N-phenylbenzimidazole-2-yl)benzene (TPBi) may be used as a dopant, but is not limited thereto.

The emission layer EML may include a host material. For example, the emission layer EML may include, but is not limited to, as a host material, at least one of tris(8-hydroxyquinolino)aluminum ($Alq_3$), bis[2-(diphenylphosphino)phenyl] ether oxide (DPEPO), 4,4'-bis(carbazol-9-yl)biphenyl (CBP), 1,3-bis(carbazol-9-yl)benzene (mCP), 2,8-bis(diphenylphosphoryl)dibenzo[b,d]furan (PPF), 4,4',4"-tris(carbazol-9-yl)-triphenylamine (TCTA), poly(n-vinylcabazole (PVK), 9,10-di(naphthalene-2-yl)anthracene (ADN), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), hexaphenyl cyclotriphosphazene (CPI), 1,4-bis(triphenylsilyl)benzene (UGH-2), hexaphenylcyclotrisiloxane ($DPSiO_3$), octaphenylcyclotetra siloxane ($DPSiO_4$), 2,8-bis(diphenylphosphoryl)dibenzofuran (PPF), or 1,3,5-tris(1-phenyl-1H-benzo[d]imidazole-2-yl)benzene (TPBi).

When the emission layer EML emits red light, the emission layer EML may further include, for example, a fluorescent material including tris(dibenzoylmethanato) phenanthoroline europium ($PBD:Eu(DBM)_3(Phen)$) or perylene. When the emission layer EML emits red light, a dopant included in the emission layer EML may be, for example, a metal complex such as bis(1-phenylisoquinoline) acetylacetonate iridium (PIQIr(acac)), bis(1-phenylquinoline) acetylacetonate iridium (PQIr(acac)), tris(1-phenylquinoline) iridium (PQIr) and octaethylporphyrin platinum (PtOEP), or an organometallic complex, rubrene and derivatives thereof, and 4-dicyanomethylene-2-(p-dimethylaminostyryl)-6-methyl-4H-pyran (DCM) and derivatives thereof.

When the emission layer EML emits green light, the emission layer EML may further include, for example, a fluorescent material including tris(8-hydroxyquinolino)aluminum ($Alq_3$). When the emission layer EML emits green light, a dopant included in the emission layer EML may be, for example, selected from among a metal complex such as fac-tris(2-phenylpyridine) iridium (Ir(ppy)3) or an organometallic complex, and coumarins and derivatives thereof.

When the emission layer EML emits blue light, the emission layer EML may further include, for example, a fluorescent material including any one selected from the group consisting of spiro-DPVBi, spiro-6P, distyryl-benzene (DSB), distyryl-arylene (DSA), polyfluorene (PFO)-based polymer and poly(p-phenylene vinylene (PPV)-based polymer. When the emission layer EML emits blue light, a dopant included in the emission layer EML may be, for example, selected from among a metal complex such as (4,6-F2ppy) 2Irpic or an organometallic complex, perylene and derivatives thereof.

The electron transport region ETR is disposed on the emission layer EML. The electron transport region ETR may include, but is not limited to, at least one of the hole blocking layer HBL, the electron transport layer ETL, or the electron injection layer EIL.

The electron transport region ETR may have a single layer formed of a single material, a single layer formed of different materials, or a multilayer structure including multiple layers formed of different materials.

For example, the electron transport region ETR may have a single layer structure of an electron injection layer EIL or an electron transport layer ETL, and may have a single layer structure formed of an electron injection material and an electron transport material. The electron transport region ETR may have a single layer structure formed of different materials, or may have a structure in which an electron transport layer ETL/electron injection layer EIL and a hole blocking layer HBL/electron transport layer ETL/electron injection layer EIL may be stacked in order from the emission layer EML, but is not limited thereto. The thickness of the electron transport region ETR may be, for example, in a range of about 100 Å to about 1,500 Å.

The electron transport region ETR may be formed using various methods such as a vacuum deposition method, a spin coating method, a cast method, a Langmuir-Blodgett (LB) method, an inkjet printing method, a laser printing method, a laser induced thermal imaging (LITI) method, etc.

When the electron transport region ETR includes the electron transport layer ETL, the electron transport region ETR may include an anthracene-based compound. However, the inventive concept is not limited thereto, and the electron transport region may include, for example, tris(8-hydroxyquinolinato)aluminum (Alq3), 1,3,5-tri[(3-pyridyl)-phen-3-yl]benzene, 2,4,6-tris(3'-(pyridin-3-yl)biphenyl-3-yl)-1,3,5-triazine, bis[2-(diphenylphosphino)phenyl]ether oxide (DPEPO), 2-(4-(N-phenylbenzoimidazolyl-1-ylphenyl)-9,10-dinaphthylanthracene, 1,3,5-tri(1-phenyl-1H-benzo[d]imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato) aluminum (BAlq), berylliumbis(benzoquinolin-10-olate (Bebq2), 9,10-di(naphthalene-2-yl)anthracene (ADN), or a mixture thereof. The thickness of the electron transport layers ETL may be in a range of about 100 Å to about 1,000 Å. For example, the thickness of the electron transport layers ETL may be in a range of about 150 Å to about 500 Å. If the thickness of the electron transport layers ETL satisfies the above-described range, satisfactory electron transport characteristics may be obtained without a substantial increase in driving voltage.

If the electron transport region ETR includes the electron injection layer EIL, the electron transport region ETR may be formed using a metal halide such as LiF, NaCl, CsF, RbCl, and RbI, a lanthanide metal such as Yb, a metal oxide such as $Li_2O$ and BaO, or lithium quinolate (LiQ), etc., but the inventive concept is not limited thereto. The electron injection layer EIL may also be formed of a mixture material of an electron transport material and an insulating organo-metal salt. The organo-metal salt may be a material having an energy band gap of about 4 eV or more. Specifically, the organo-metal salt may include, for example, metal acetates, metal benzoates, metal acetoacetates, metal acetylacetonates or metal stearates.

The thickness of the electron injection layers EIL may be in a range of about 1 Å to about 100 Å. For example, the thickness of the electron injection layers EIL may be in a range of about 3 Å to about 90 Å. If the thickness of the electron injection layers EIL satisfies the above-described range, satisfactory electron injection properties may be obtained without a substantial increase in driving voltage.

The electron transport region ETR may include a hole blocking layer HBL as described above. The hole blocking layer HBL may include, but is not limited to, for example, at least one of 2,9-dimethyl-4,7-diphenyl-1,10-phenanthroline (BCP), bis[2-(diphenylphosphino)phenyl]ether oxide (DPEPO), or 4,7-diphenyl-1,10-phenanthroline (Bphen).

The second electrode EL2 may be provided on the electron transport region ETR. The second electrode EL2 may be a common electrode or a negative electrode. The second electrode EL2 may be a transmissive electrode, a transflective electrode, or a reflective electrode. When the second electrode EL2 is a transmissive electrode, the second electrode EL2 may be formed of transparent metal oxides, for example, ITO, IZO, ZnO, ITZO, etc.

When the second electrode EL2 is a transflective electrode or a reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, or a compound thereof or a mixture thereof (for example, a mixture of Ag and Mg). The second electrode EL2 may have a multilayer structure including a reflective layer or a transflective layer formed of the above-described materials, and a transparent conductive layer formed of ITO, IZO, ZnO, ITZO, etc.

Although not shown, the second electrode EL2 may be connected with an auxiliary electrode. If the second electrode EL2 is connected with the auxiliary electrode, the resistance of the second electrode EL2 may decrease.

Referring to FIG. 4, the organic electroluminescence device 10 according to an embodiment may further include a capping layer CPL on the second electrode EL2. The capping layer CPL may include, for example, α-NPD, NPB, TPD, m-MTDATA, Alq$_3$, CuPc, N4,N4,N4',N4'-tetra (biphenyl-4-yl) biphenyl-4,4'-diamine (TPD15), 4,4',4"-Tris (carbazol sol-9-yl) triphenylamine (TCTA), N, N'-bis (naphthalen-1-yl), etc.

In the organic electroluminescence device 10, as a voltage is applied to the first electrode EL1 and the second electrode EL2, respectively, the holes injected from the first electrode EL1 may move through the hole transport region HTR to the emission layer EML, and the electrons injected from the second electrode EL2 may move through the electron transport region ETR to the emission layer EML. The electrons and holes may recombine in the emission layer EML to generate excitons and emit light when the excitons return to a ground state from an excited state.

When the organic electroluminescence device 10 is a front emission type, the first electrode EL1 may be a reflective electrode, and the second electrode EL2 may be a transmissive electrode or transflective electrode. When the organic electroluminescence device 10 is a rear emission type, the first electrode EL1 may be a transmissive electrode or transflective electrode, and the second electrode EL2 may be a reflective electrode.

The organic electroluminescence device 10 according to an embodiment of the inventive concept includes the diamine compound represented by Formula 1, and thereby achieving high efficiency, a long service life, and a low driving voltage.

Hereinafter, the disclosure will be described in more detail with reference to Examples and Comparative Examples. The embodiments are only illustrations for assisting the understanding of the inventive concept, and the scope of the inventive concept is not limited thereto.

SYNTHETIC EXAMPLES

A diamine compound according to an embodiment of the inventive concept may be synthesized, for example, as follows. However, a synthetic method of the diamine compound according to an embodiment of the inventive concept is not limited thereto.

1. Synthesis of Compound 1-1

Synthesis of Intermediates A-1 and A-2

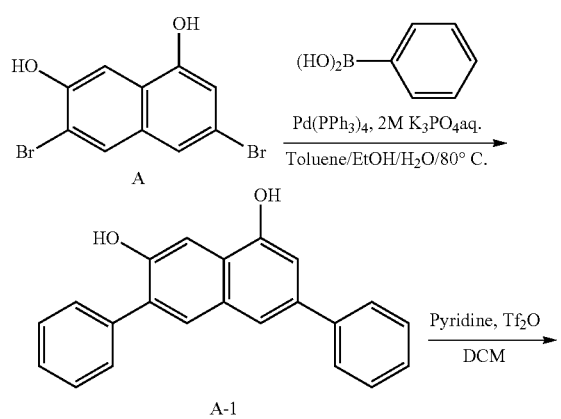

Synthesis of Intermediate A-1

In a three-neck flask, Compound A (15.9 g, 50 mmol), boronic acid (12.19 g, 120.0 mmol), K$_3$PO$_4$ (47.58 g, 3.0 mmol), and toluene/EtOH/H$_2$O (v/v/v=4/2/1, 785 ml) were added and degassed. In an Ar atmosphere, Pd(PPh$_3$)$_4$ (3.5 g, 150 mmol) were added thereto and stirred at 80° C. for 6 hours. The reaction solution was standing to cool to room temperature, extracted with toluene, washed with H$_2$O, dried with MgSO$_4$, and concentrated. The resulting crude product was purified by a silica gel column chromatography to obtain Compound which is a white solid (14.8 g, yield 95%).

By measuring FAB-MS, a mass number of m/z=312 was observed by molecular ion peak, thereby identifying Compound A-1.

Synthesis of Intermediate A-2

In an Ar atmosphere, in three-neck flask, Compound A-1 (14.5 g, 46.4 mm) and 90 ml of pyridine were added. After the reaction solution was cooled to 0° C., Tf$_2$O (31.4 g, 111.4 mmol) was dropped for 1 hour. The reactant was stirred at room temperature for 12 hours. H$_2$O was added to the reaction solution, and the reaction solution was extracted with CH$_2$Cl$_2$, washed with an NaHCO$_3$ aqueous solution, H$_2$O, and brine, and dried with MgSO$_4$. The resulted solution was concentrated, purified by a silica gel column chromatography to obtain Compound (25.4 g, yield 95%).

By measuring FAB-MS, a mass number of m/z=576 was observed by molecular ion peak, thereby identifying Compound A-2.

Synthesis of Compound 1-2

-continued

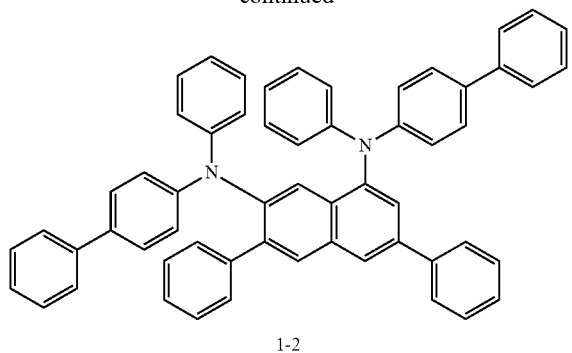

1-2

In an Ar atmosphere, in a 300 mL three-neck flask, Compound A-2 (7.1 g, 12.0 mmol), Pd(dba)$_2$ (0.43 g, 0.1 equiv, 1.2 mmol), NaOtBu (1.44 g, 2 equiv, 24 mmol), Ruphos (0.43 g, 0.2 equiv, 2.40 mmol), and 120 mL of xylene were sequentially added and heated and stirred under reflux for 6 hours. After air cooling to room temperature, the organic layer was fractionated by adding water to the reaction solvent. The organic layer was further extracted by adding toluene to a water layer, and the combined organic layers were washed with saline and dried with MgSO$_4$. MgSO$_4$ was filtered off and the organic layer was concentrated, and the resulting crude product was purified by a silica gel column chromatography to obtain Compound 1-2 which is a white solid (7.4 g, yield 80%).

By measuring FAB-MS, a mass number of m/z=767 was observed by molecular ion peak, thereby identifying Compound 1-2.

2. Synthesis of Compound 1-12

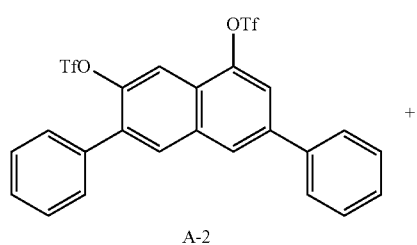

A-2

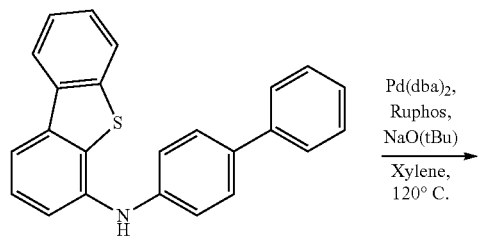

-continued

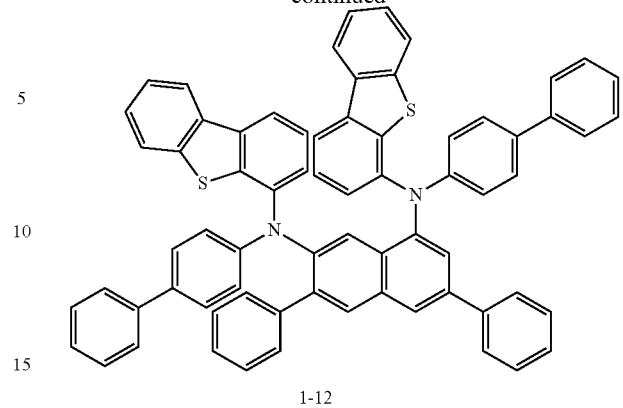

1-12

Compound 1-12 was synthesized using N,N-[(4-biphenyl)-(4-dibenzofuan)]amine in the same manner as the synthesis of Compound 1-2.

By measuring FAB-MS, a mass number of m/z=979 was observed by molecular ion peak, thereby identifying Compound 1-12.

3. Synthesis of Compound 1-14

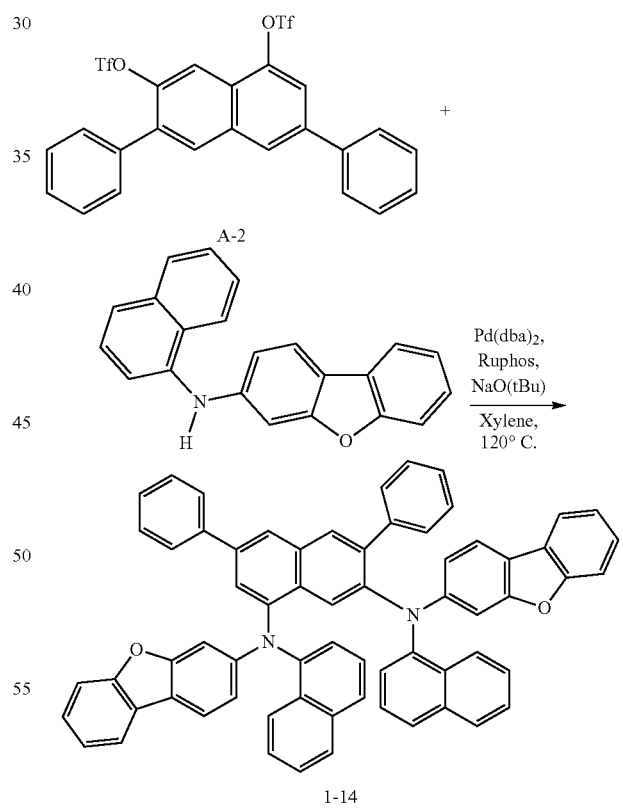

1-14

Compound 1-14 was synthesized using N,N-[(1-naphthalenyl)-3-dibenzofuran]amine in the same manner as the synthesis of Compound 1-2.

By measuring FAB-MS, a mass number of m/z=895 was observed by molecular ion peak, thereby identifying Compound 1-14.

4. Synthesis of Compound 2-3

Synthesis of Intermediates B-1 and B-2

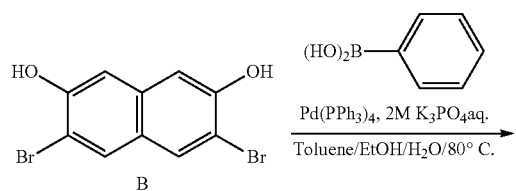

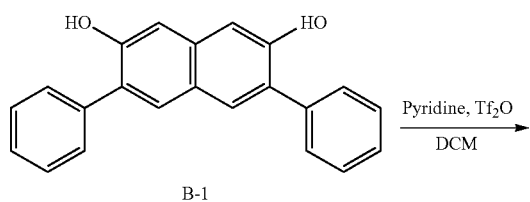

Intermediates B-1 and B-2 were synthesized in the same manner as the synthesis of Intermediates A-1 and A-2.

By measuring FAB-MS, a mass number of m/z=312 and a mass number of m/z=576 were observed by molecular ion peak, thereby identifying Compound B-1 and B-2.

Synthesis of Compound 2-3

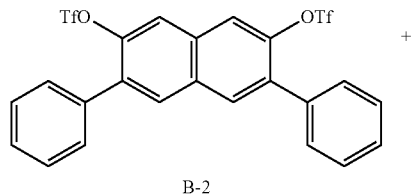

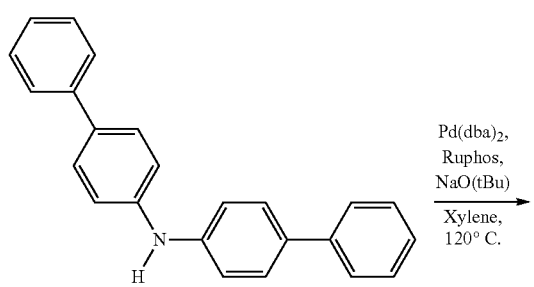

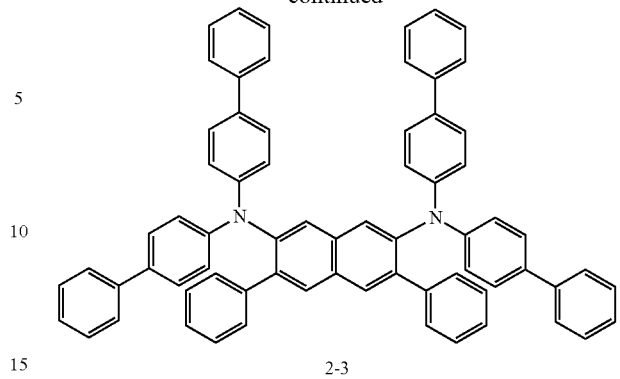

Compound 2-3 was synthesized using Compound B-2 and N,N-bis(4-biphenylnaphthalenyl)amine in the same manner as the synthesis of Compound 1-2.

By measuring FAB-MS, a mass number of m/z=919 was observed by molecular ion peak, thereby identifying Compound 2-3.

5. Synthesis of Compound 1-6

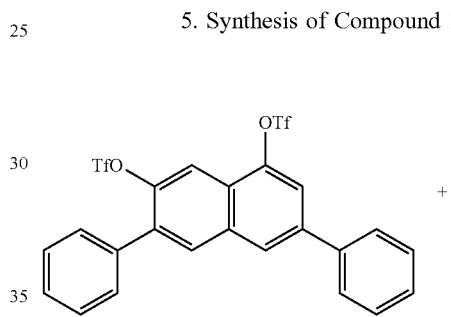

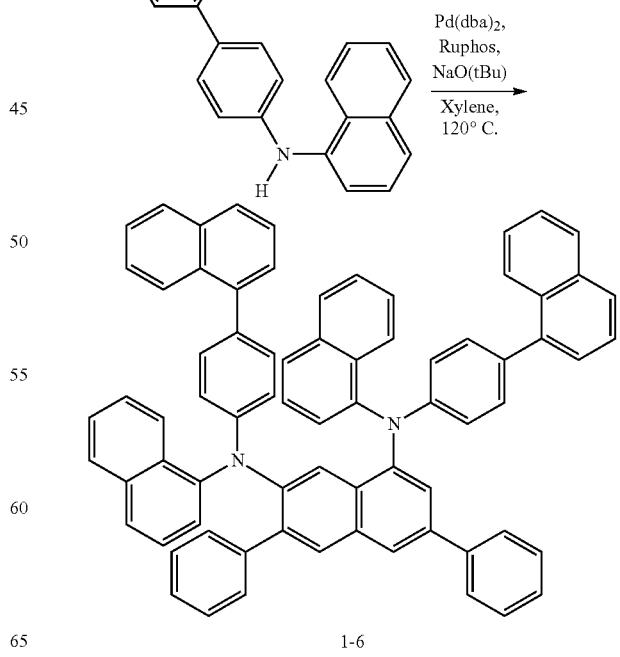

Compound 1-6 was synthesized using Compound A-2 and N,N-[(4-naphthylphenylyl)-1-naphthyl]amine in the same manner as the synthesis of Compound 1-2.

By measuring FAB-MS, a mass number of m/z=967 was observed by molecular ion peak, thereby identifying Compound 1-6.

6. Synthesis of Compound 4-12

Synthesis of Intermediates C-1 and C-2

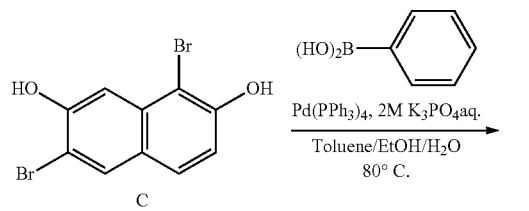

C

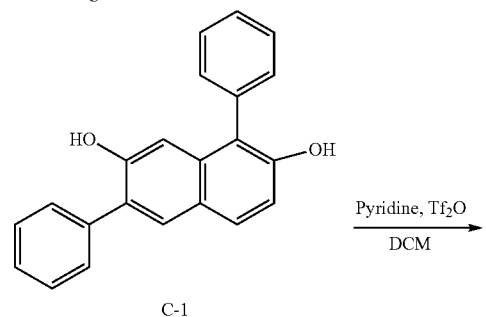

C-1

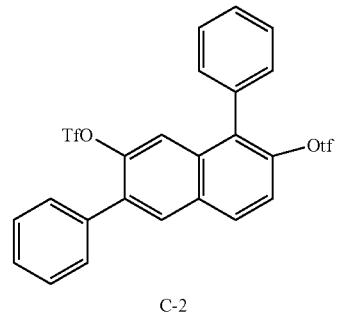

C-2

Intermediates C-1 and C-2 were synthesized in the same manner as the synthesis of Intermediates A-1 and A-2.

By measuring FAB-MS, a mass number of m/z=312 and a mass number of m/z=576 were observed by molecular ion peak, thereby identifying Compound C-1 and C-2.

Synthesis of Compound 4-12

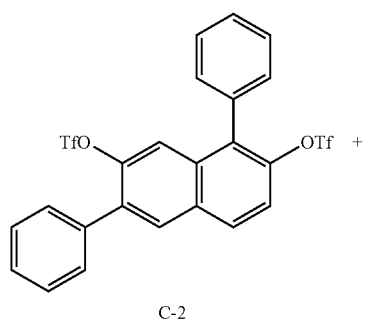

C-2

-continued

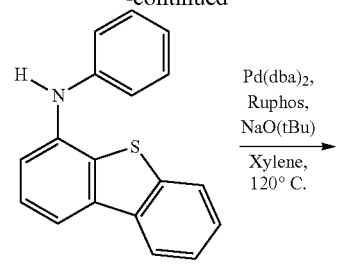

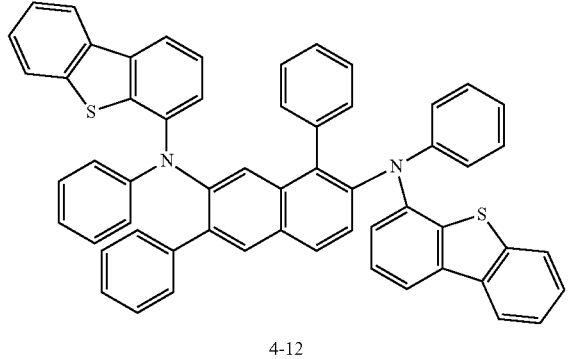

4-12

Compound 4-12 was synthesized using Compound C-2 and N,N-(4-dibenzothiophene)aniline in the same manner as the synthesis of Compound 1-2.

By measuring FAB-MS, a mass number of m/z=827 was observed by molecular ion peak, thereby identifying Compound 4-12.

7. Synthesis of Compound 5-8

Synthesis of Intermediates D-1 and D-2

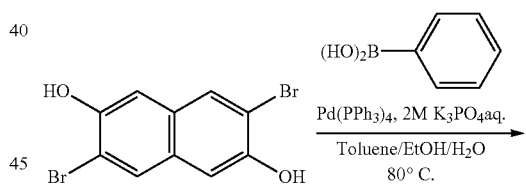

D

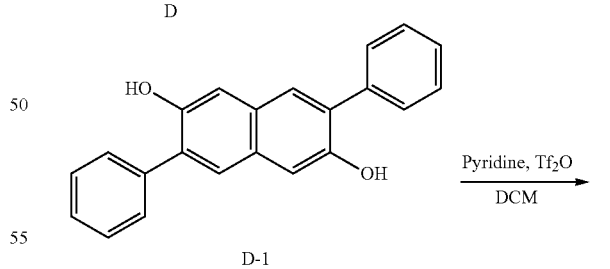

D-1

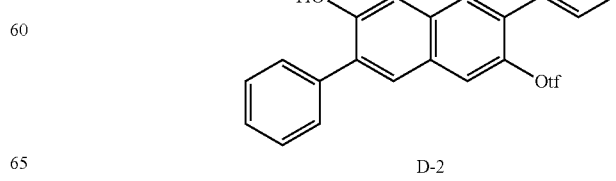

D-2

Intermediates C-1 and C-2 were synthesized in the same manner as the synthesis of Intermediates A-1 and A-2.

By measuring FAB-MS, a mass number of m/z=312 and a mass number of m/z=576 were observed by molecular ion peak, thereby identifying Compound D-1 and D-2.

Synthesis of Compound 5-8

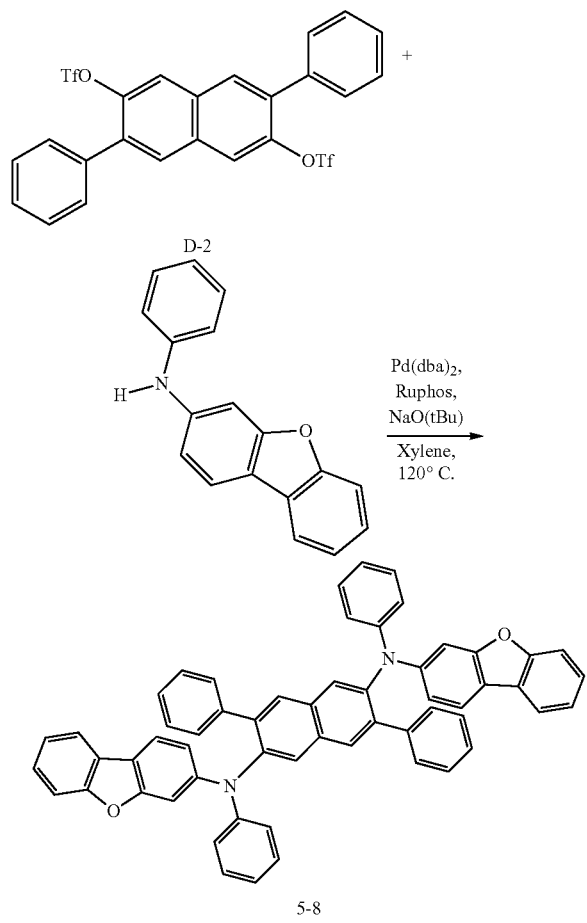

Compound 5-8 was synthesized using Compound D-2 and N,N-(4-dibenzothiophene)aniline in the same manner as the synthesis of Compound 1-2.

By measuring FAB-MS, a mass number of m/z=794 was observed by molecular ion peak, thereby identifying Compound 5-8.

8. Synthesis of Compound 5-12

Compound 5-12 was synthesized using Compound D-2 and N,N-(4-dibenzothiophene)aniline in the same manner as the synthesis of Compound 1-2.

By measuring FAB-MS, a mass number of m/z=827 was observed by molecular ion peak, thereby identifying Compound 5-12.

(Device Manufactured Examples)

Organic electroluminescence devices were manufactured using Example Compounds and Comparative Example Compounds below as a hole transport region material:

[Example Compounds]

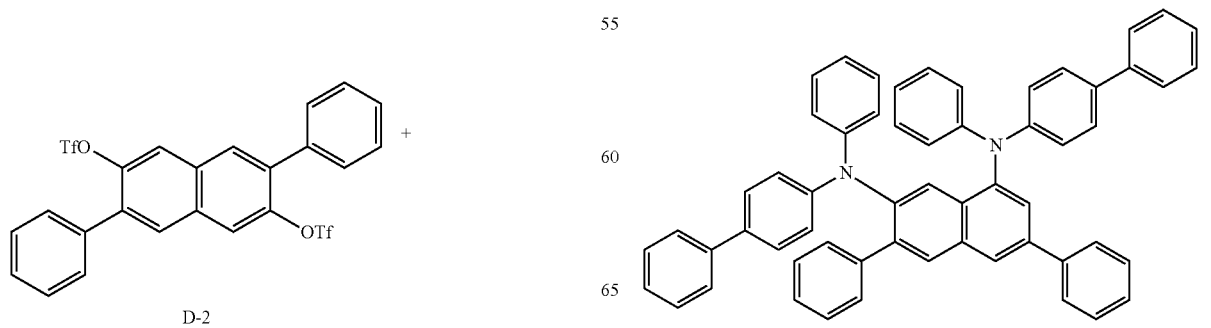

1-12
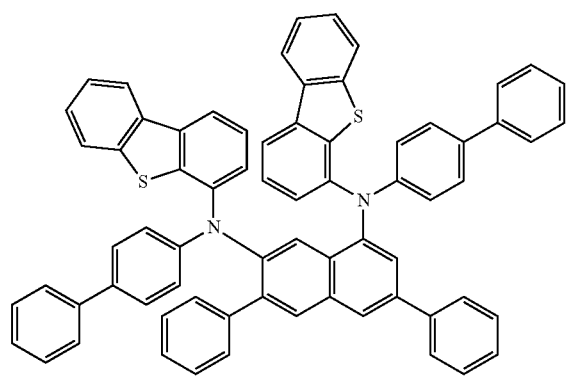
4-12
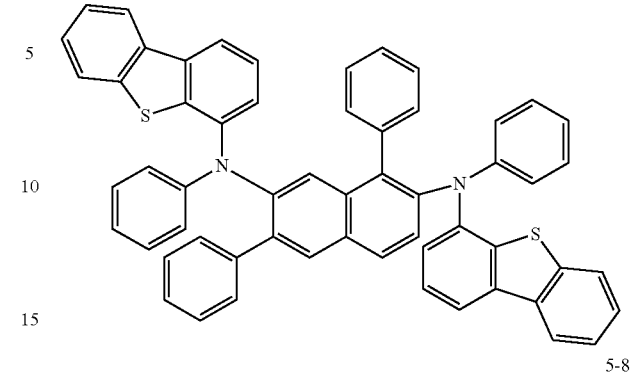
1-14
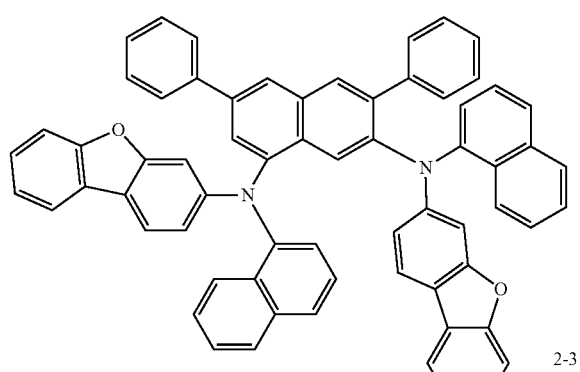
5-8
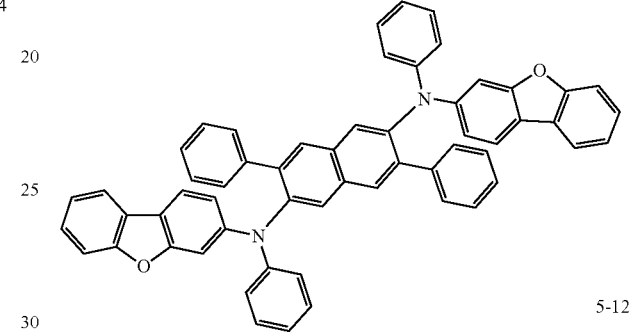
2-3
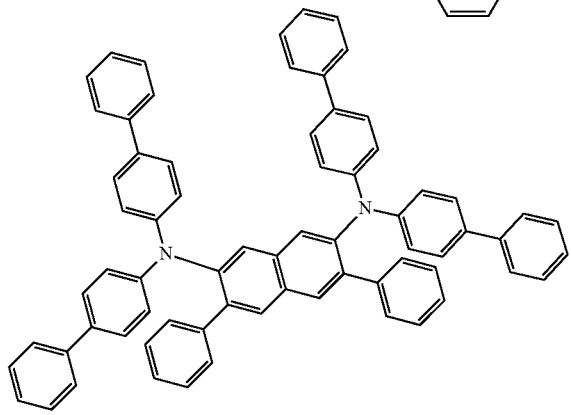
5-12
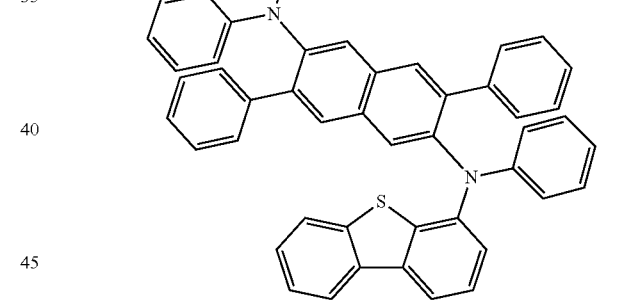
[Comparative Example Compounds]
1-6
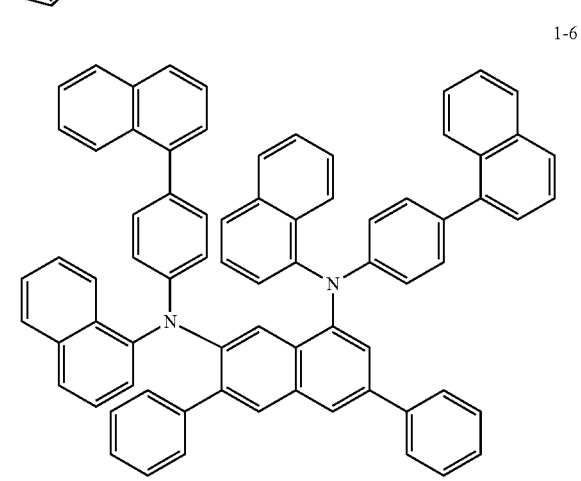
R1
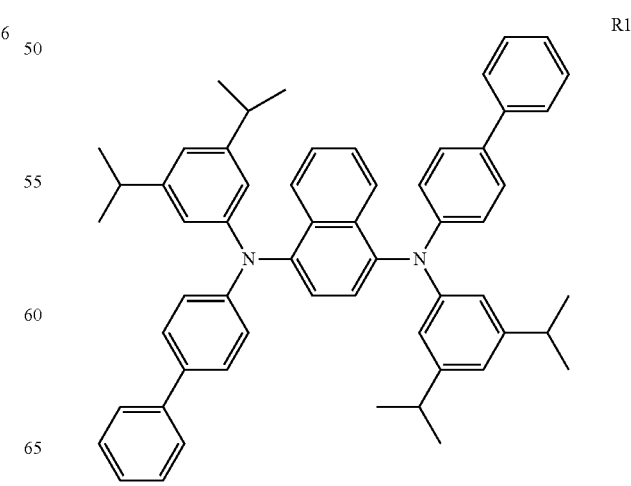

R2

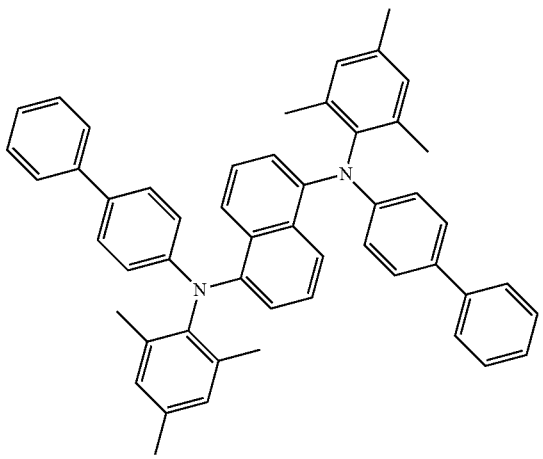

R3

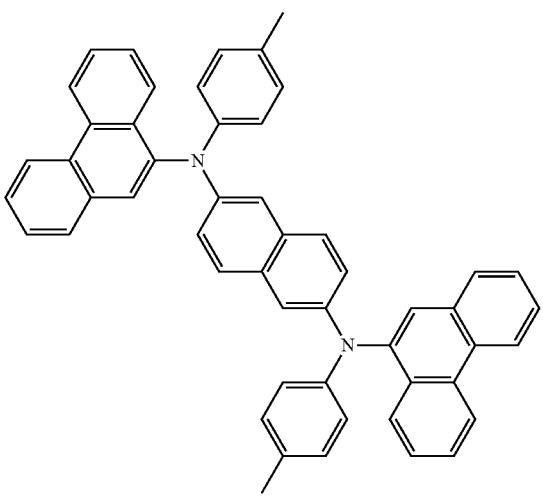

R4

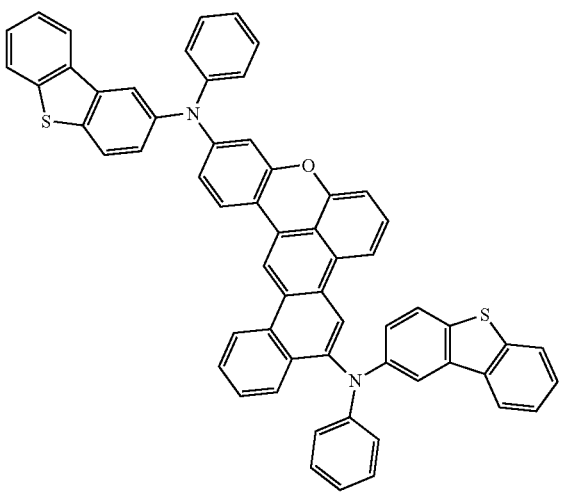

R5

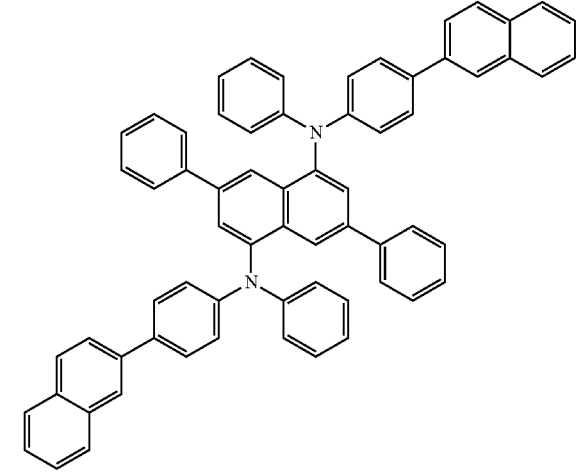

The organic electroluminescence devices of Examples and Comparative Examples were manufactured by the following method. A 150 nm-thick ITO was patterned on a glass substrate, and the glass substrate was washed with ultrapure water and treated with UV and ozone for about 10 minutes to form a first electrode. 2-TNATA was deposited thereon to a thickness of about 60 nm, and Example Compounds or Comparative Example Compounds were used to form a hole transport layer having a thickness of about 30 nm. TBP was doped to ADN by 3% to form an emission layer having a thickness of about 25 nm, a layer having a thickness of about 25 nm was formed with $Alq_3$ on the emission layer, and a layer having a thickness of about 1 nm was formed with LiF to form an electron transport region. A second electrode having a thickness of about 100 nm was formed with aluminum (Al). Each layer was formed by a vacuum deposition method.

The light emission efficiencies of the organic electroluminescence devices according to Examples 1 to 8 and Comparative Examples 1 to 5 are shown in Table 1 below. Current efficiency was measured at 10 $mA/cm^2$, and a half service life represents a time taken to reduce the brightness to about 50% with respect to an initial brightness of 1,000 $cd/m^2$.

TABLE 1

| | Hole transport layer | Voltage (V) | Efficiency (cd/A) | Service life (LT50(h)) |
|---|---|---|---|---|
| Example 1 | Example Compound 1-2 | 5.2 | 9.4 | 2100 |
| Example 2 | Example Compound 1-12 | 5.4 | 9.6 | 2400 |
| Example 3 | Example Compound 1-14 | 5.4 | 9.1 | 2600 |
| Example 4 | Example Compound 2-3 | 5.3 | 9.2 | 2200 |
| Example 5 | Example Compound 1-6 | 5.5 | 94 | 2000 |
| Example 6 | Example Compound 4-12 | 5.6 | 9.5 | 2150 |
| Example 7 | Example Compound 5-8 | 5.3 | 9.0 | 2500 |
| Example 8 | Example Compound 5-12 | 5.1 | 9.7 | 2000 |
| Comparative Example 1 | Comparative Example Compound R1 | 6.0 | 8.0 | 1400 |

TABLE 1-continued

|  | Hole transport layer | Voltage (V) | Efficiency (cd/A) | Service life (LT50(h)) |
|---|---|---|---|---|
| Comparative Example 2 | Comparative Example Compound R2 | 6.0 | 8.5 | 1300 |
| Comparative Example 3 | Comparative Example Compound R3 | 5.8 | 8.7 | 1600 |
| Comparative Example 4 | Comparative Example Compound R4 | 6.3 | 7.2 | 900 |
| Comparative Example 5 | Comparative Example Compound R5 | 6.2 | 8.4 | 1200 |

Referring to Table 1 above, it is confirmed that Examples 1 to 8 have achieved all of a low voltage, a long service life, and high efficiency compared to Comparative Examples 1 to 5.

A diamine compound according to examples of the inventive concept is used in the hole transport region to contribute to a low voltage, a long service life, and high efficiency of organic electroluminescence devices.

The Compounds of Examples 1 to 8 are diamine compounds having a naphthalene skeleton, wherein orientation characteristics by stereoscopic factors and electronic characteristics by delocalisation may be improved. Therefore, it is determined that the Compounds of Examples 1 to 8 improve electron resistance, film quality, and thermal stability of a material, as well as, improve characteristics in charge injection and charge transport processes, thereby realizing high light emission efficiency and a long service life at the same time. As in Examples 7 and 8, a heterocycle may be introduced to the amine group to reduce symmetry of the compound, and delocalisation effect of a charge may be increased to improve both efficiency and a service life of the device.

In Comparative Example 1, two amino groups are substituted in one benzene ring of the naphthalene skeleton, and thus it is determined that a service life is particularly low due to stereoscopic and electronic factors.

In Comparative Examples 2 and 3, an amino group is introduced to both sides of the naphthalene skeleton, but an aryl group is not substituted in the naphthalene skeleton. Thus, it was confirmed that Comparative Examples 2 and 3 has a service life shorter than that of Examples in which an aryl group is introduced to the naphthalene skeleton. This is because in Examples, the conjugation is extended by the introduction of the aryl group, thereby improving electronic characteristics.

In Comparative Example 4, charges were concentrated on a linker based on chrysene, and thus, both efficiency and a service life of the device were greatly reduced compared to Examples.

Comparative Example 5 has high structural symmetry, and thus, as the film quality is deteriorated, the voltage is increased, and both efficiency and a service life of the device are reduced.

The diamine compound according to examples of the inventive concept is used in the hole transport region to contribute to a low driving voltage, high efficiency, and a long service life of organic electroluminescence devices.

The organic electroluminescence device according to an embodiment of the inventive concept may have excellent efficiency.

The diamine compound according to an embodiment of the inventive concept may be used as a material of the hole transport region of the organic electroluminescence device, and thereby the organic electroluminescence device may have improved efficiency.

Although the embodiments of the inventive concept are described, those with ordinary skill in the technical field to which the inventive concept pertains will understood that the disclosure may be carried out in other specific forms without changing the technical idea or essential features. Therefore, the above-disclosed embodiments are to be considered illustrative and not restrictive.

What is claimed is:

1. An organic electroluminescence device comprising:

a first electrode;

a hole transport region disposed on the first electrode;

an emission layer disposed on the hole transport region;

an electron transport region disposed on the emission layer; and a second electrode disposed on the electron transport region, wherein the hole transport region comprises a diamine compound represented by one of Formulas 3-1, 3-2, 5 to 8, 9-1, 10, and 11:

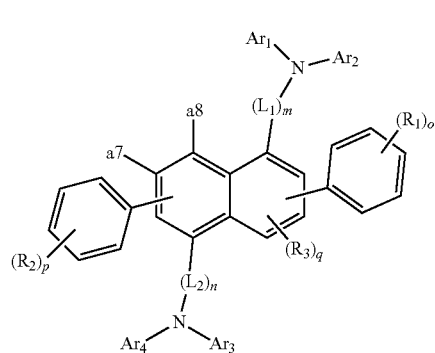

[Formula 3-1]

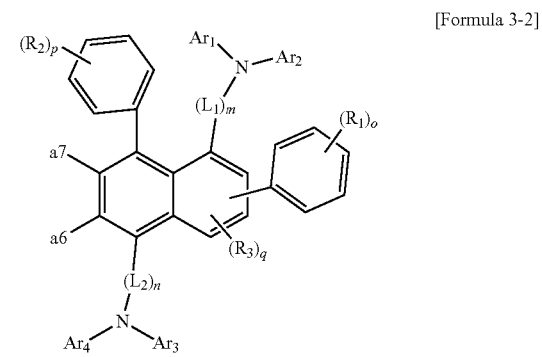

[Formula 3-2]

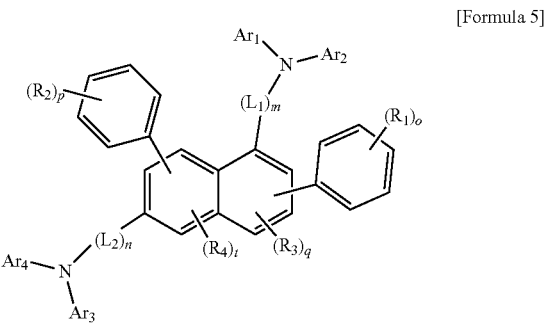

[Formula 5]

-continued

[Formula 6]
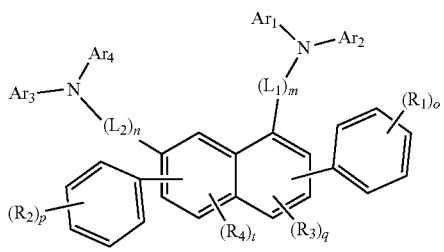

[Formula 7]
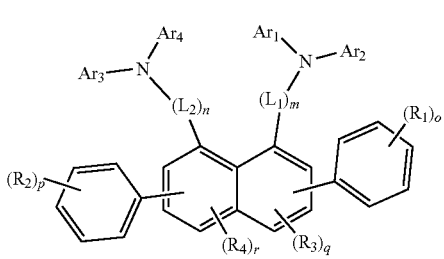

[Formula 8]
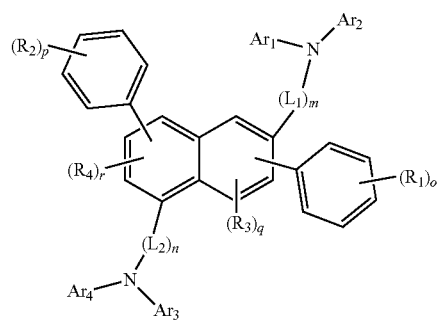

[Formula 9-1]
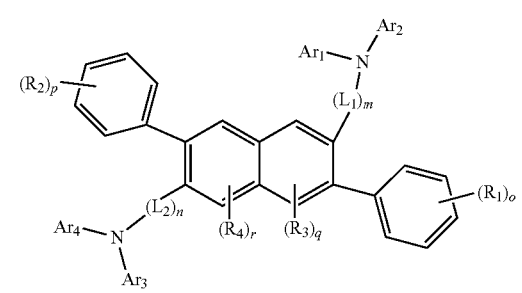

[Formula 10]
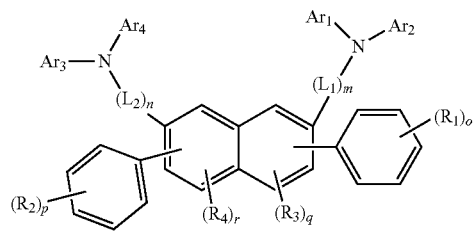

[Formula 11]
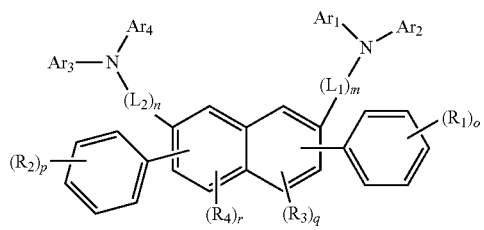

wherein in Formulas 3-1, 3-2, 5 to 8, 9-1, 10, and 11,
a6 to a8 are each independently a hydrogen atom or a deuterium atom,
$L_1$ and $L_2$ are each independently a direct linkage, a substituted or unsubstituted arylene group having 6 to 30 ring-forming carbon atoms, or a substituted or unsubstituted heteroarylene group having 2 to 30 ring-forming carbon atoms,
m and n are each independently an integer from 0 to 4,
$Ar_1$ to $Ar_4$ are each independently a substituted or unsubstituted aryl group having 6 to 30 ring-forming carbon atoms, or a substituted or unsubstituted heteroaryl group having 2 to 30 ring-forming carbon atoms; except that in Formula 4, at least one of $Ar_1$ to $Ar_4$ is a substituted or unsubstituted heteroaryl group having 2 to 30 ring-forming carbon atoms,
$R_1$ and $R_2$ are each independently a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, a substituted or unsubstituted heteroaryl group having 2 to 30 ring-forming carbon atoms, or bonded to an adjacent group to form a ring,
and p are each independently an integer from 0 to 5,
$R_3$ and $R_4$ are each independently a hydrogen atom or a deuterium atom, and
q and r are each independently an integer from 0 to 2.

2. The organic electroluminescence device of claim 1, wherein $L_1$ and $L_2$ are each independently a direct linkage, a substituted or unsubstituted phenylene group, or a substituted or unsubstituted biphenylene group.

3. The organic electroluminescence device of claim 1, wherein the hole transport region comprises:
a hole injection layer disposed on the first electrode; and
a hole transport layer disposed on the hole injection layer, wherein the hole transport layer comprises the diamine compound.

4. The organic electroluminescence device of claim 1, wherein Formula 6 is represented by Formula 6-1 or Formula 6-2:

[Formula 6-1]
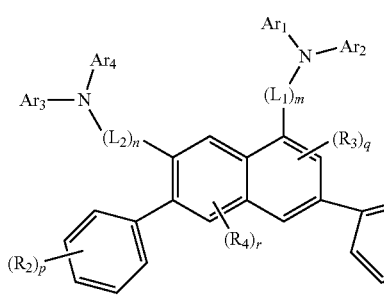

[Formula 6-2]

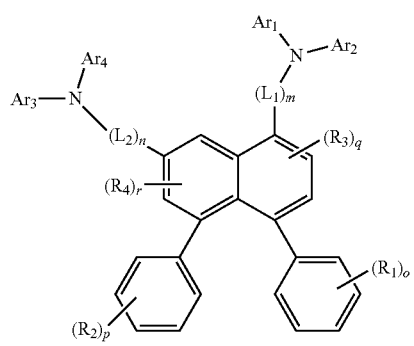

wherein in Formula 6-1 and Formula 6-2,
Ar$_1$ to Ar$_4$, L$_1$, L$_2$, R$_1$ to R$_4$, and m tor are the same as defined in Formula 6.

5. The organic electroluminescence device of claim 1, wherein Formula 10 is represented by one of Formula 10-1 to Formula 10-3:

[Formula 10-1]

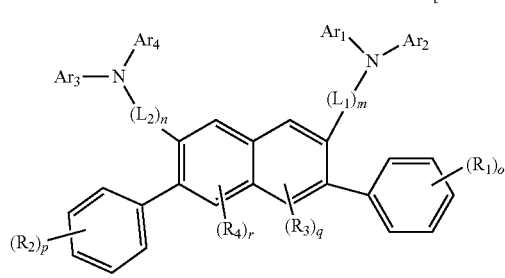

[Formula 10-2]

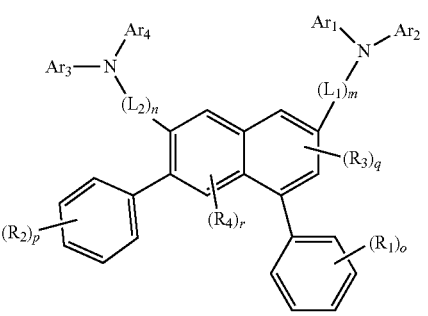

[Formula 10-3]

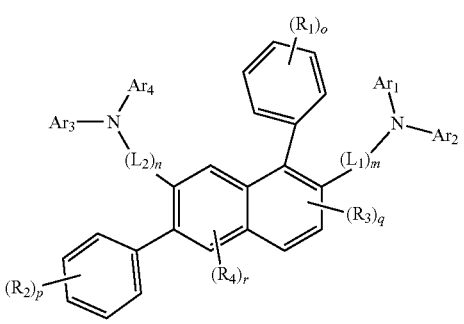

wherein in Formula 10-1 to Formula 10-3,
Ar$_1$ to Ar$_4$, L$_1$, L$_2$, R$_1$ to R$_4$, and m tor are the same as defined in Formula 10.

6. The organic electroluminescence device of claim 1, wherein the diamine compound is selected from Compound Group 1:

[Compound Group 1]

1-1

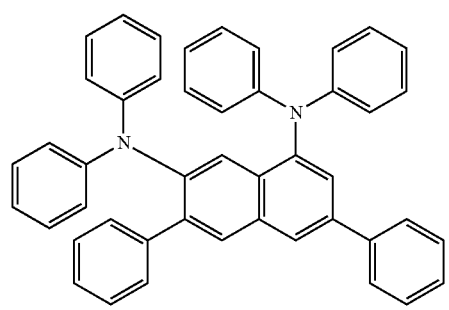

1-2

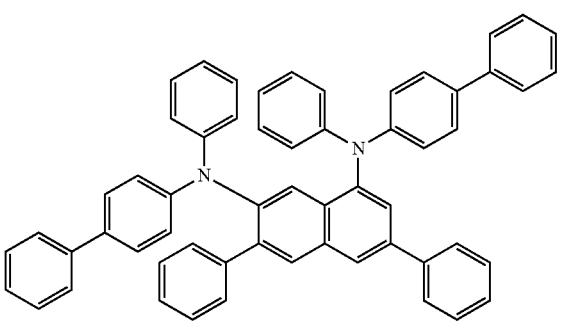

-continued
1-3
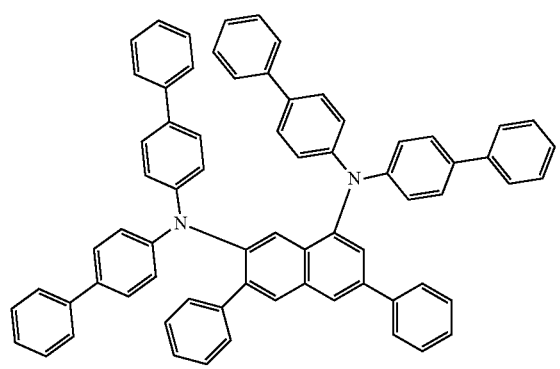
1-4
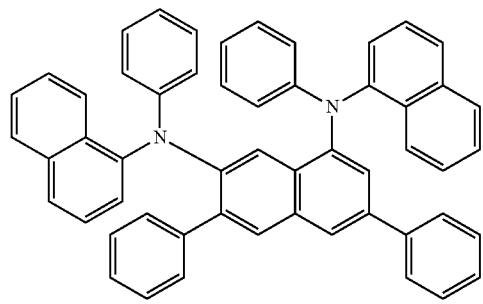
1-5
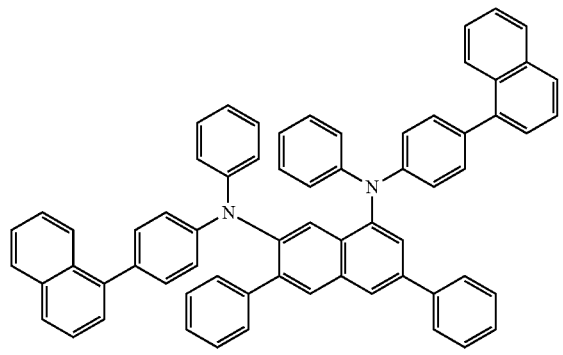
1-6
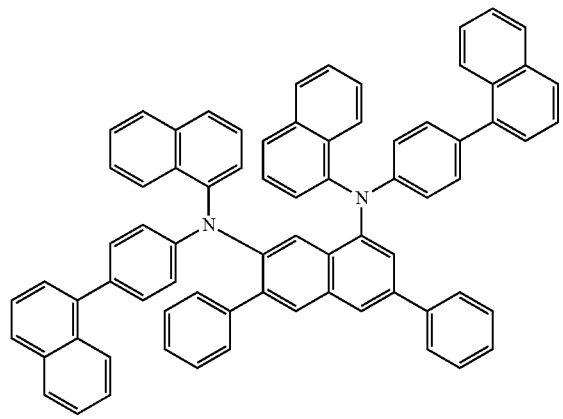
1-7
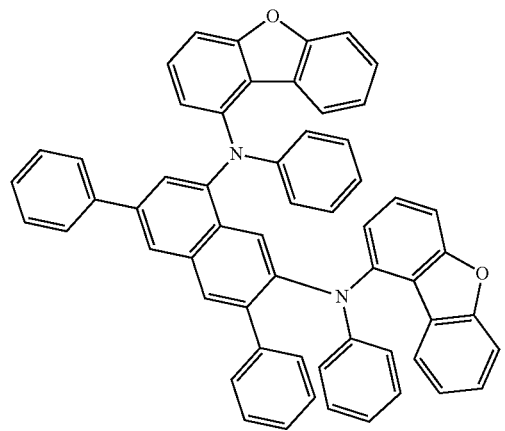
1-8
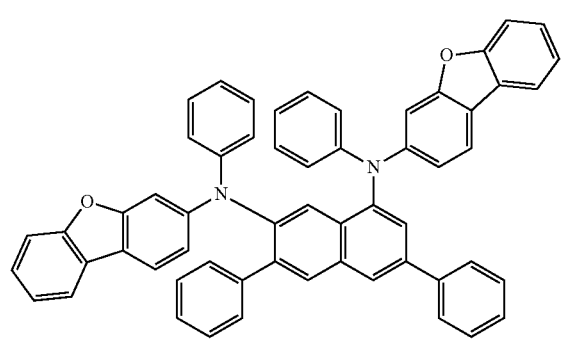

-continued
1-9
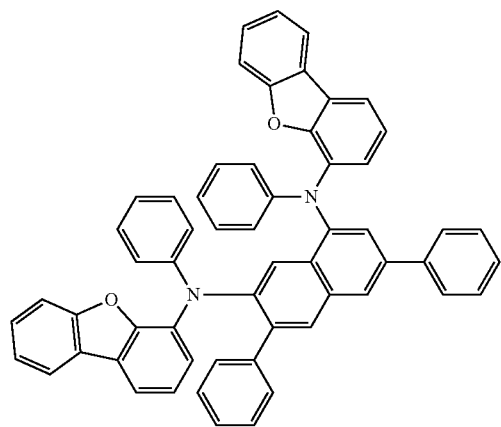
1-10
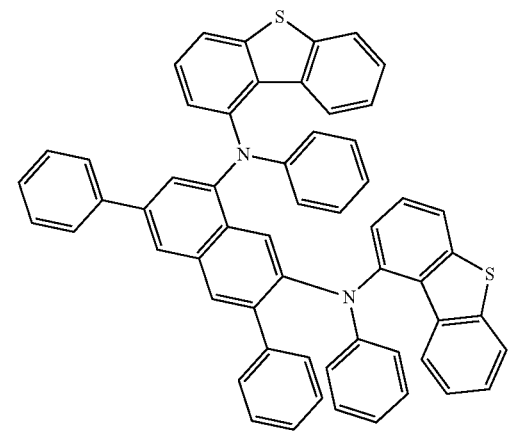
1-11
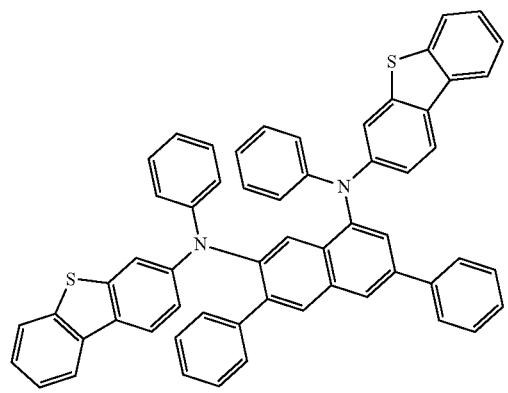
1-12
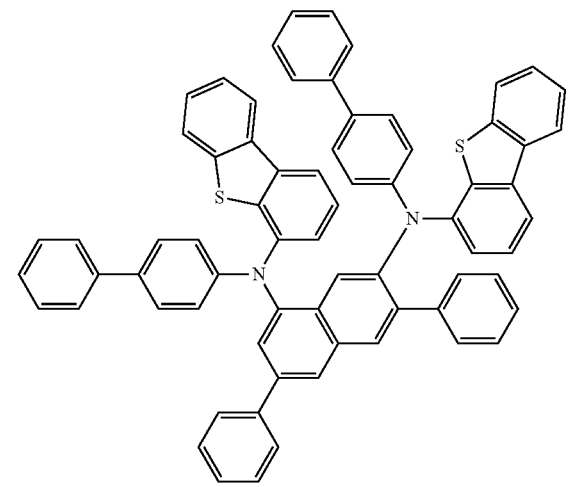
1-13
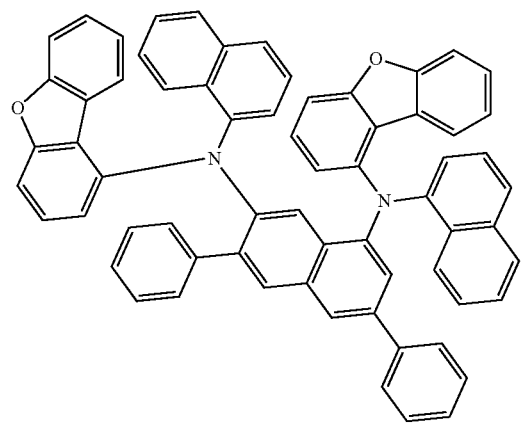
1-14
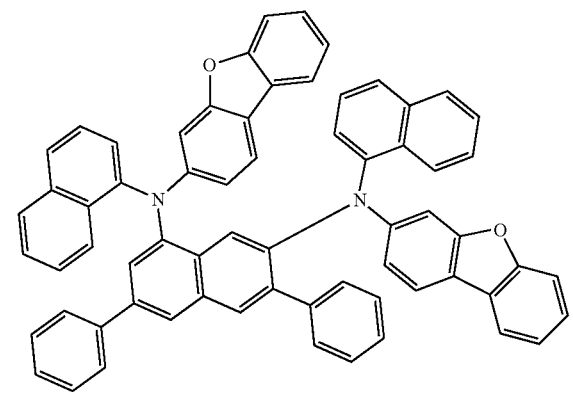

-continued
1-15
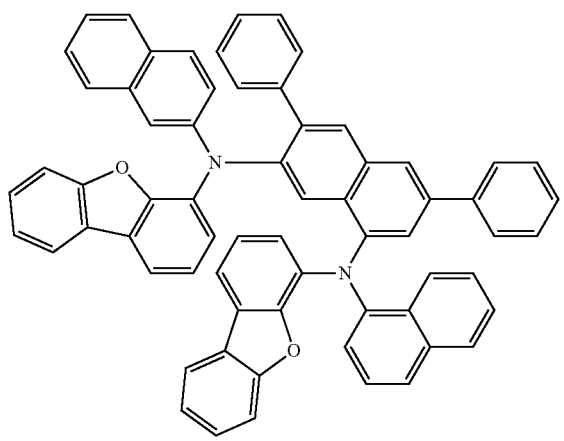
1-16
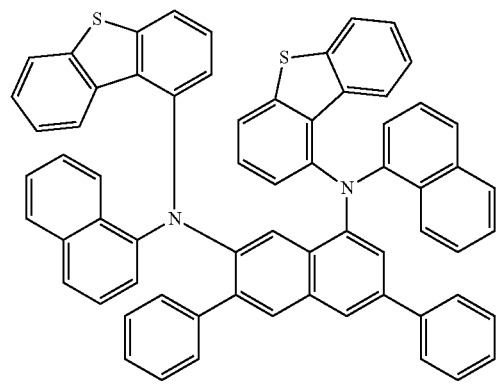
1-17
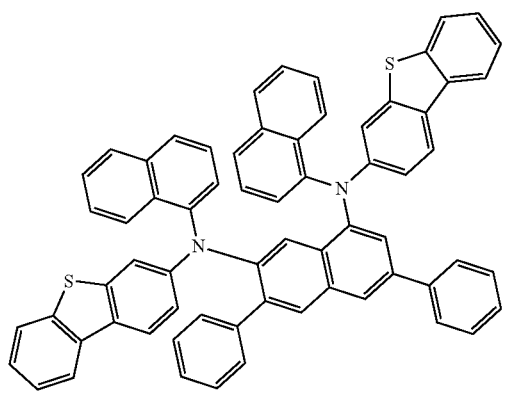
1-18
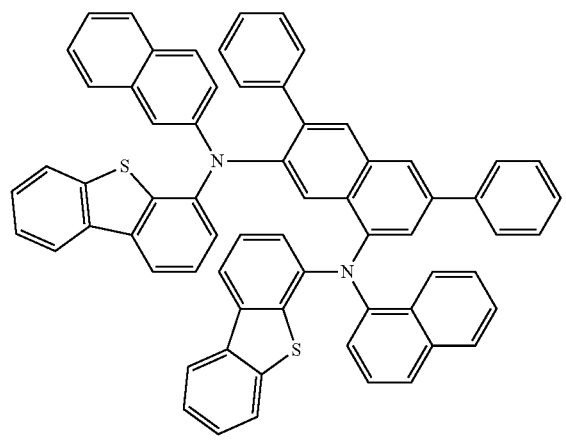
1-19
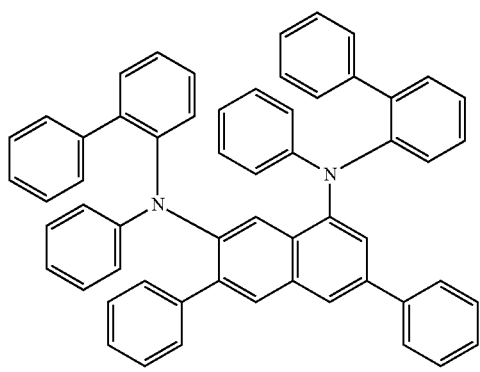
1-20
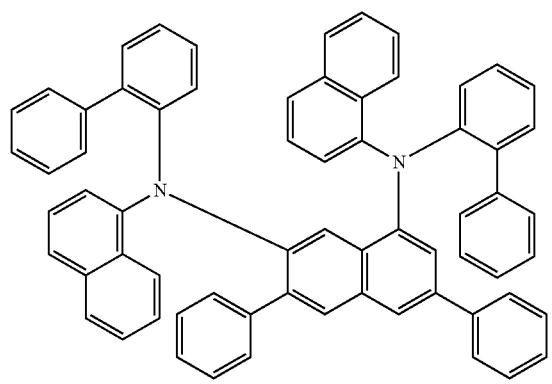

-continued
1-21
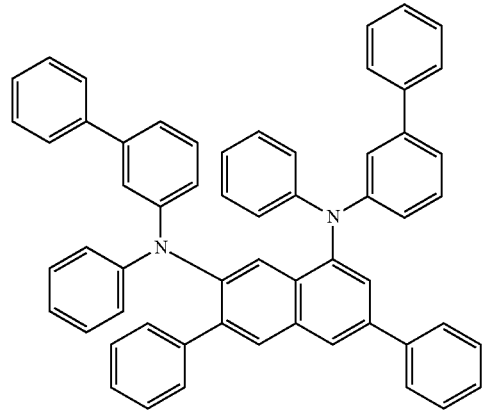
1-22
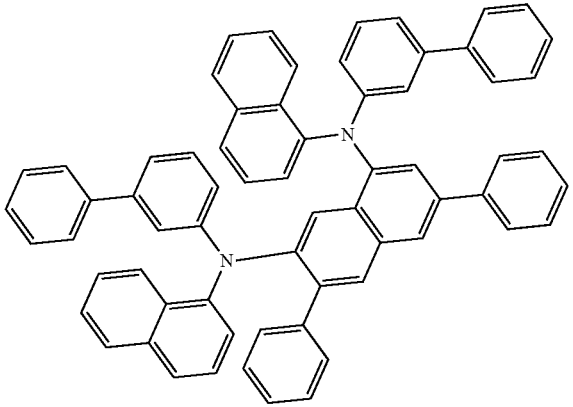
1-23
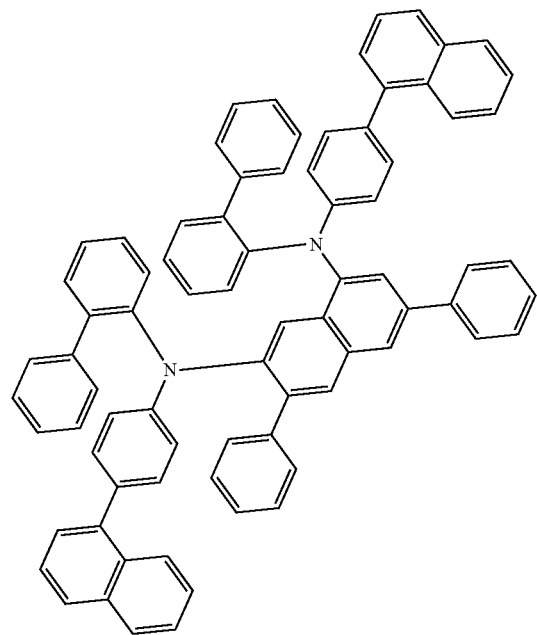
1-24
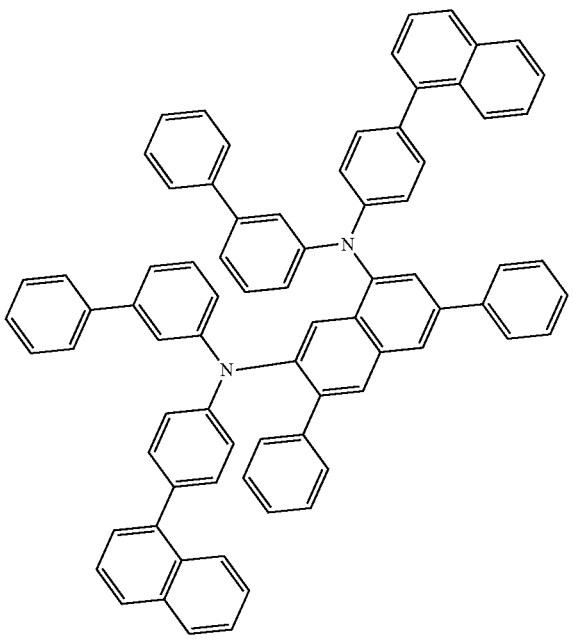
1-25
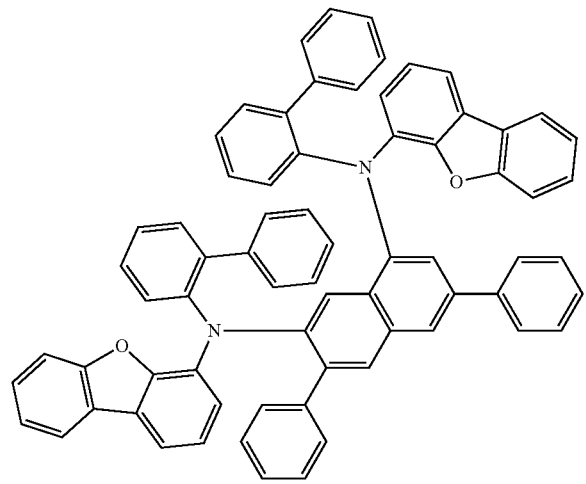
1-26
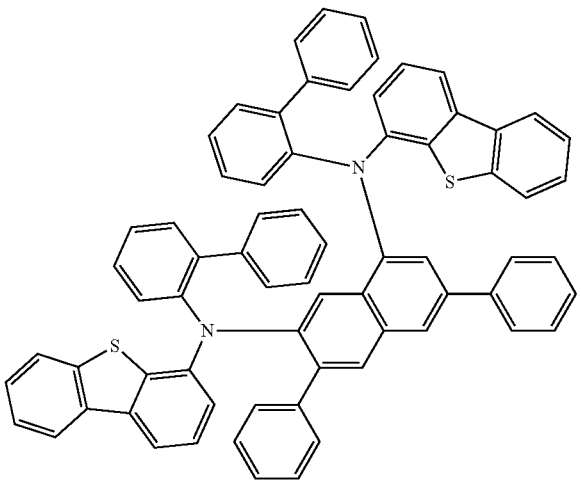

-continued
1-27
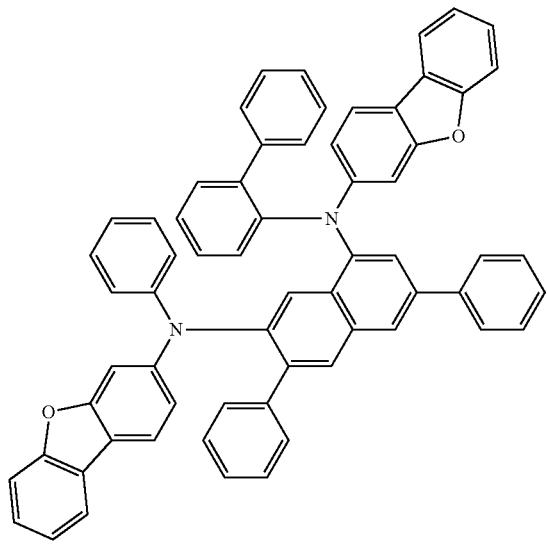
1-28
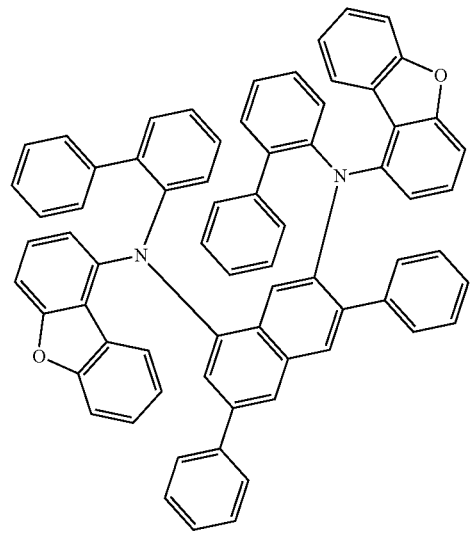
1-29
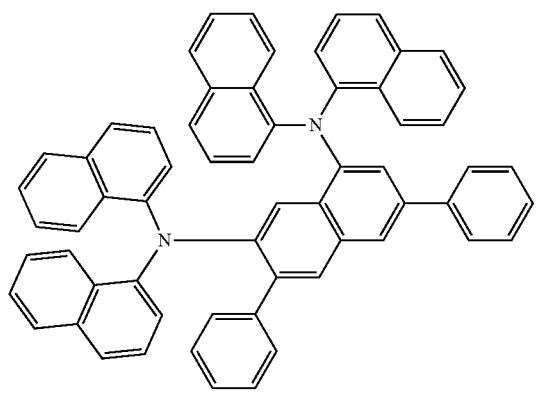
1-30
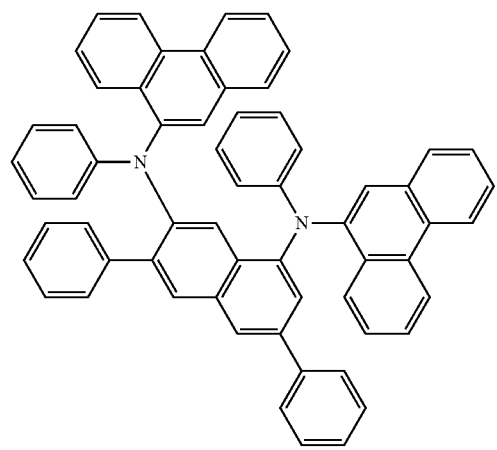
1-31
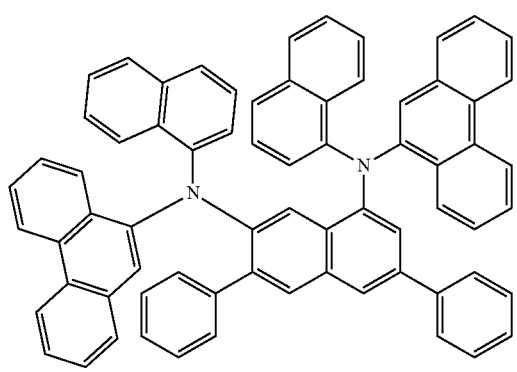
1-32
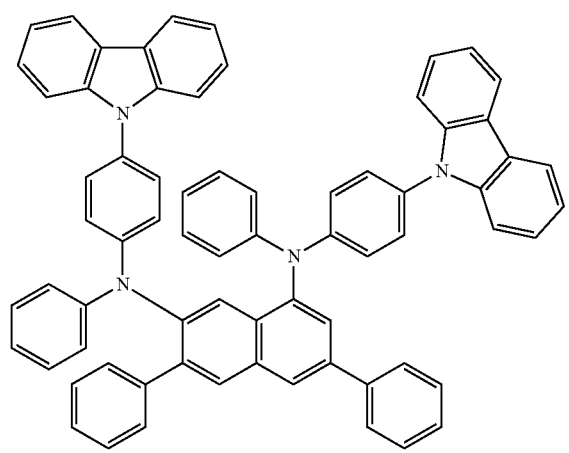

1-33
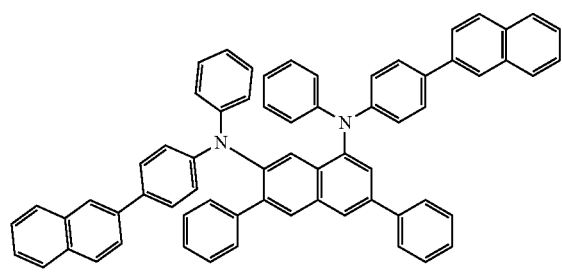
1-34
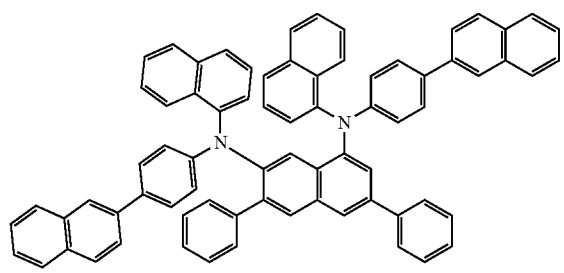
1-35
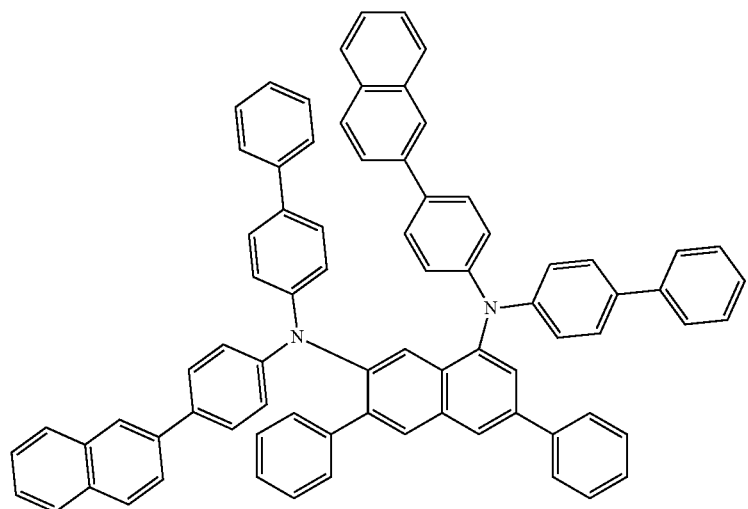
2-1
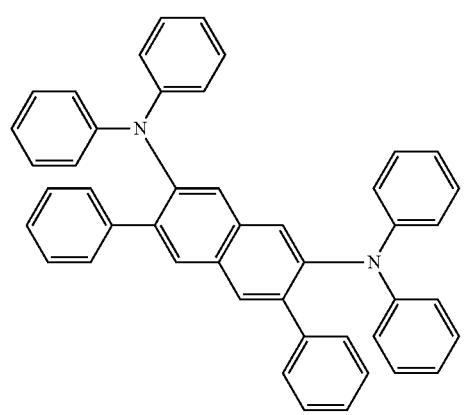
2-2
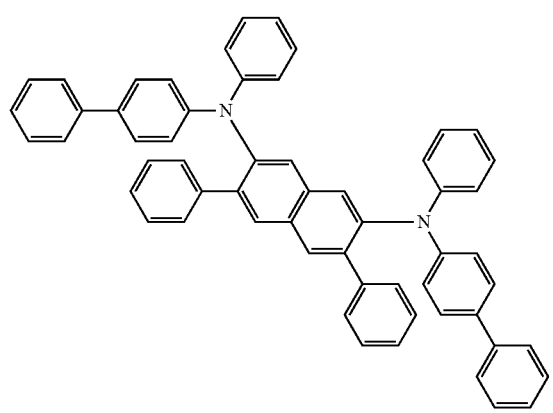

-continued
2-3
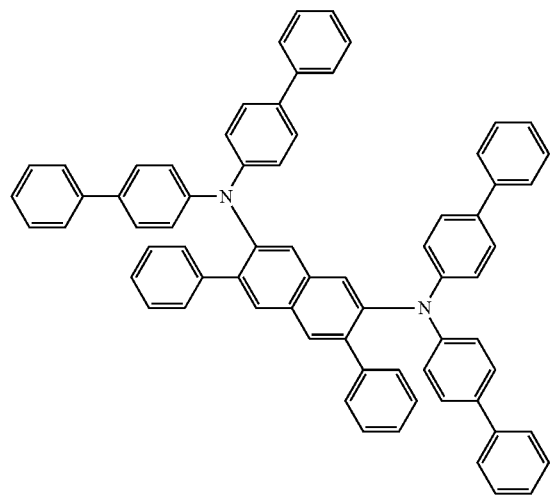
2-4
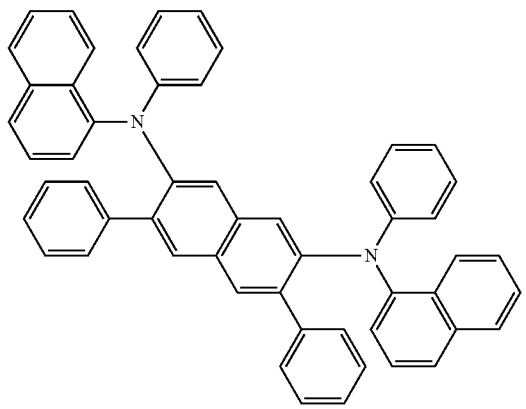
2-5
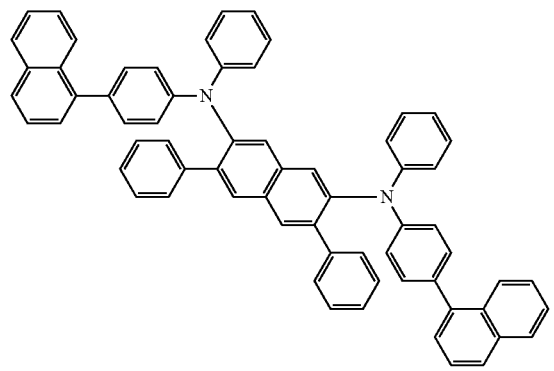
2-6
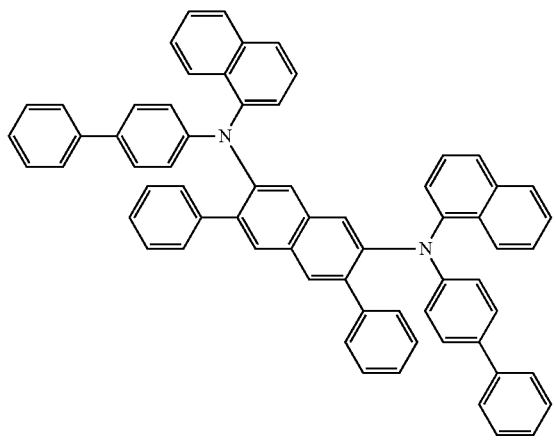
2-7
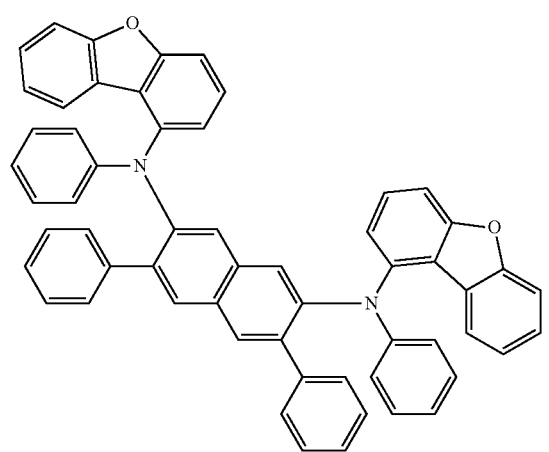
2-8
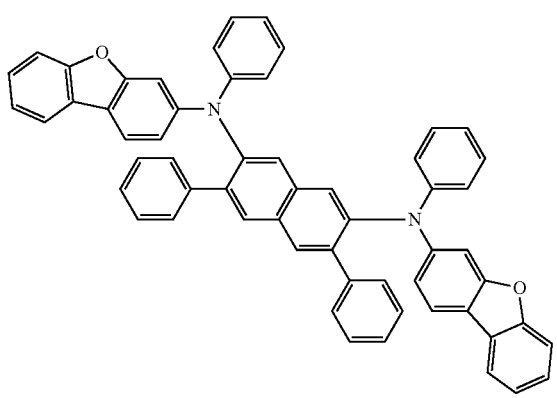

-continued
2-9
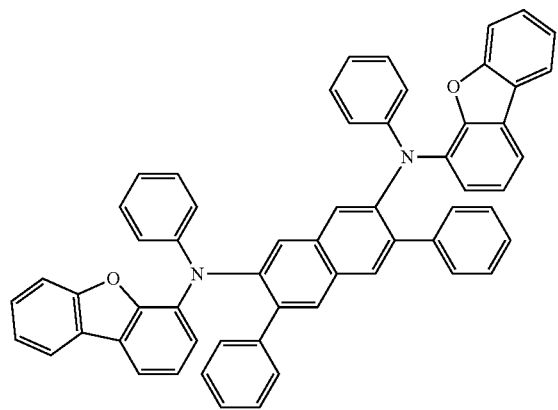
2-10
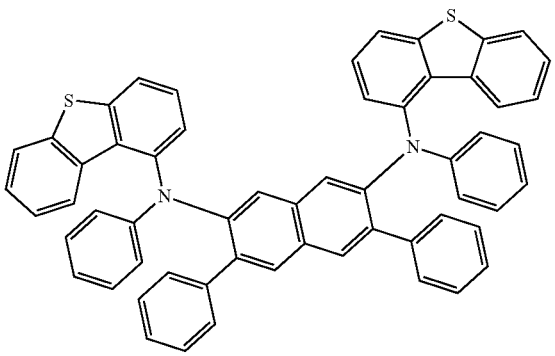
2-11
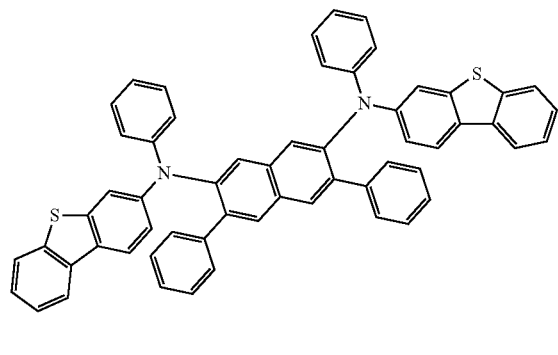
2-12
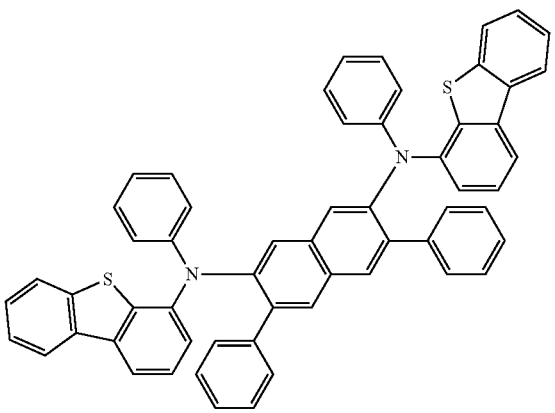
2-13
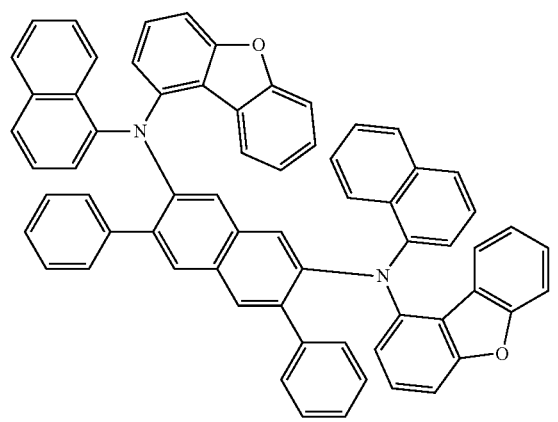
2-14
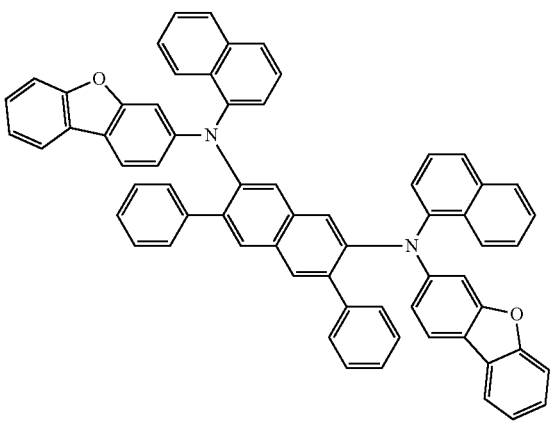

-continued
2-15
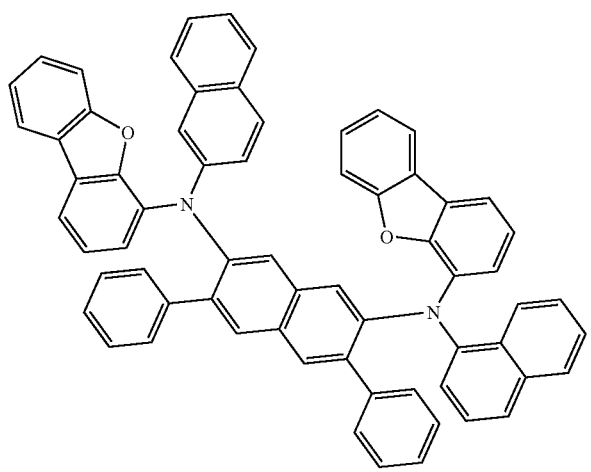
2-16
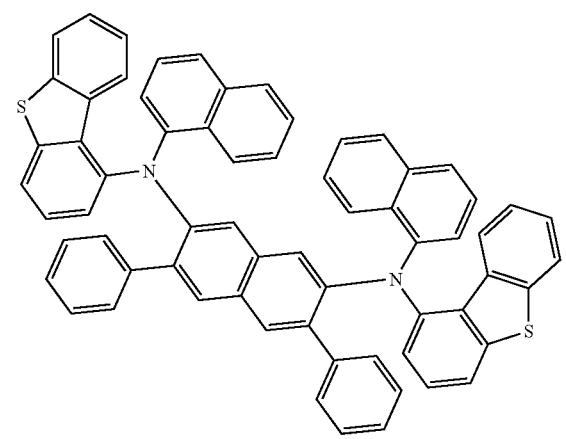
2-17
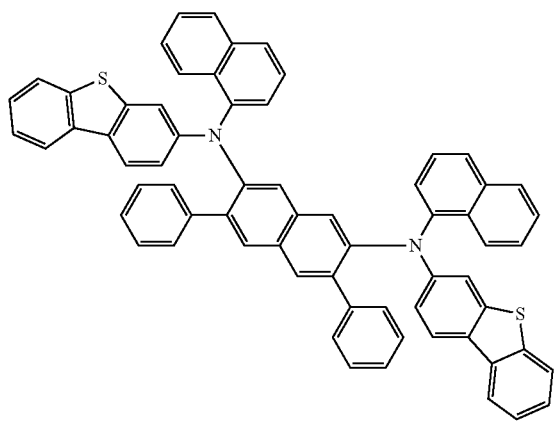
2-18
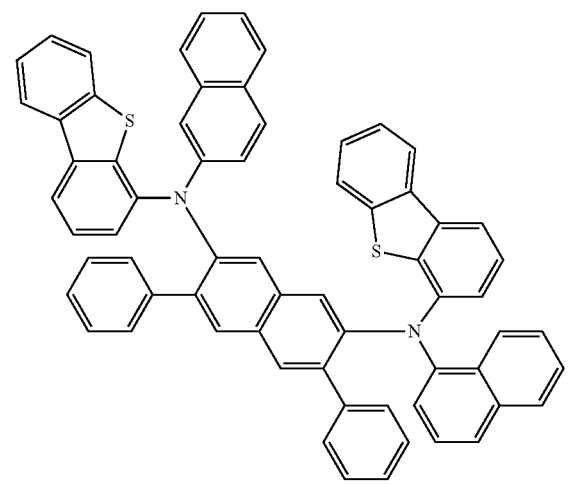
2-19
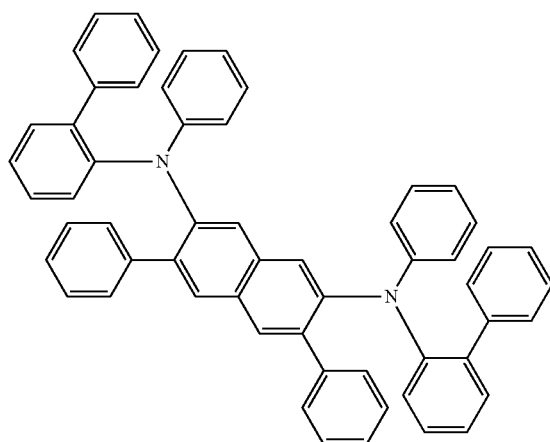
2-20
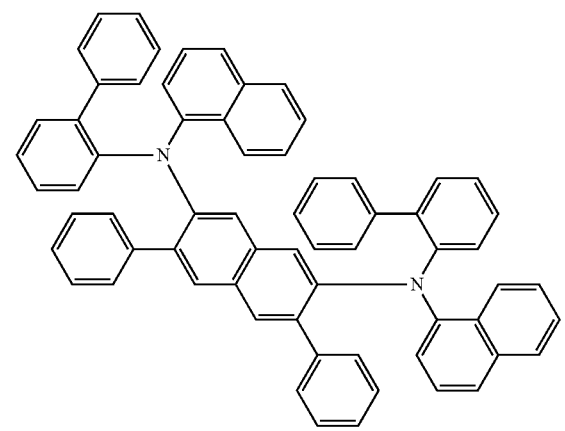

-continued
2-21
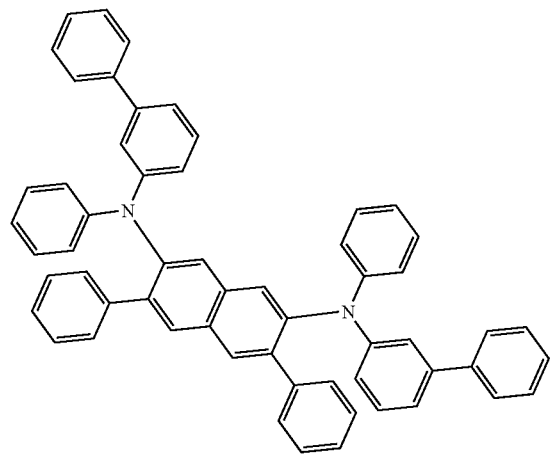
2-22
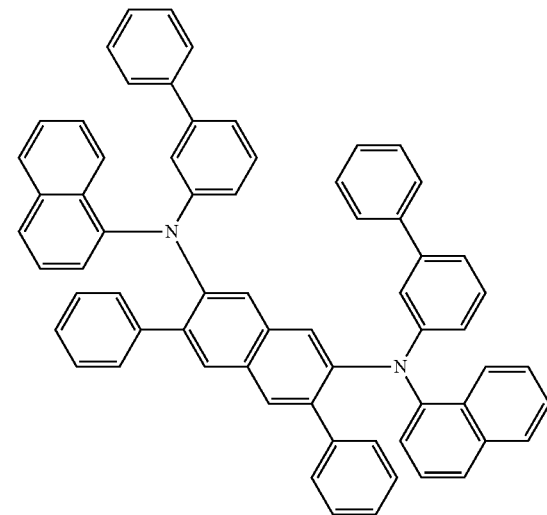
2-23
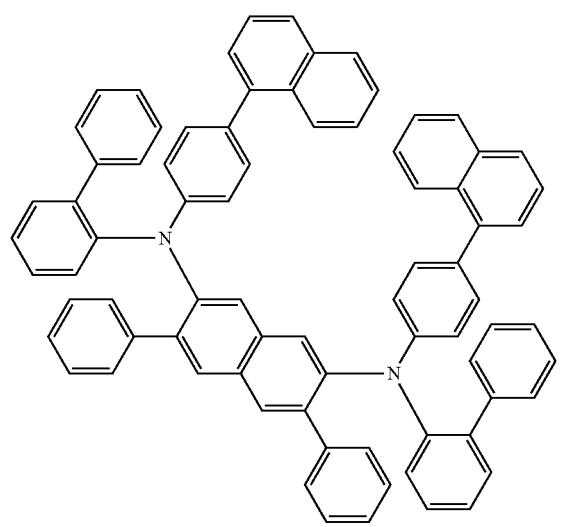
2-24
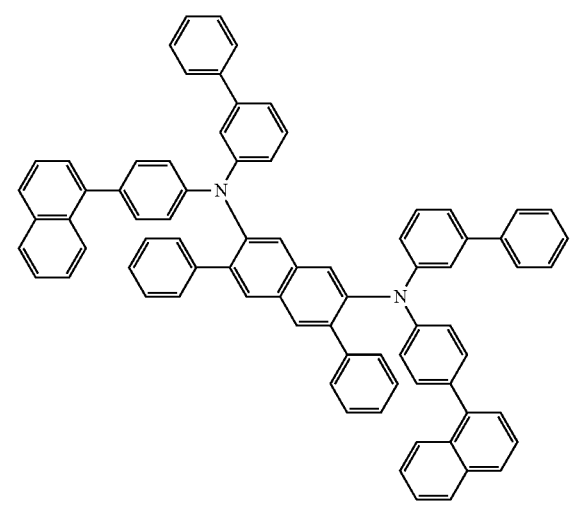
2-25
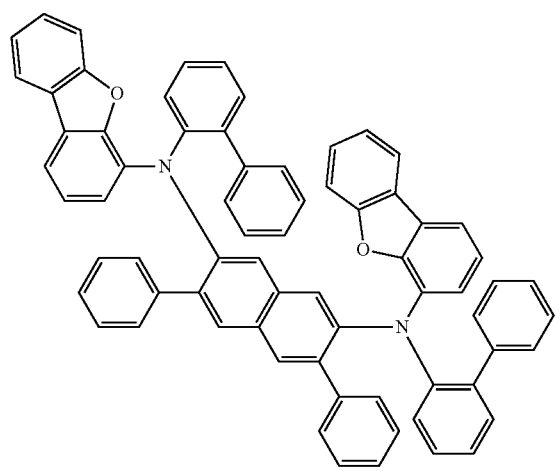
2-26
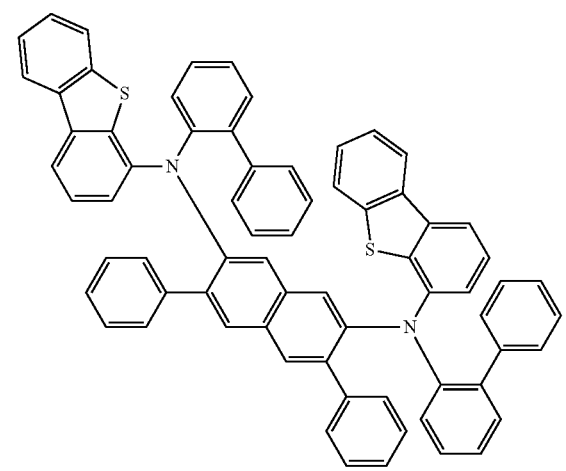

-continued
2-27
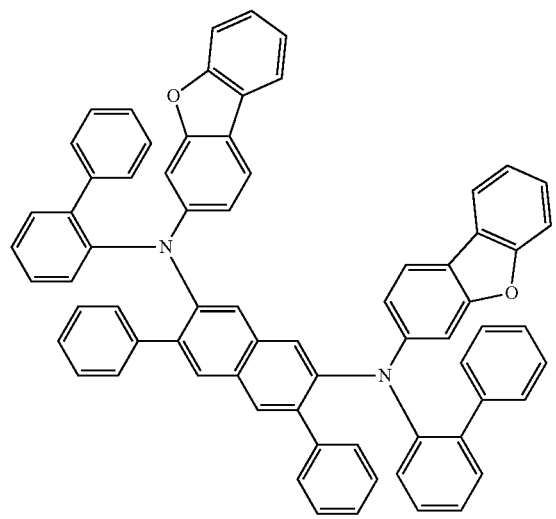
2-28
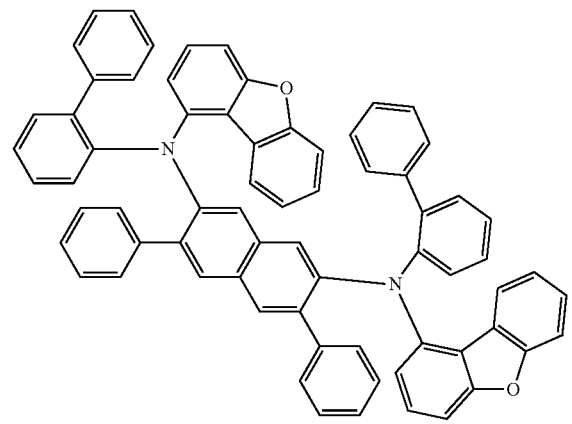
2-29
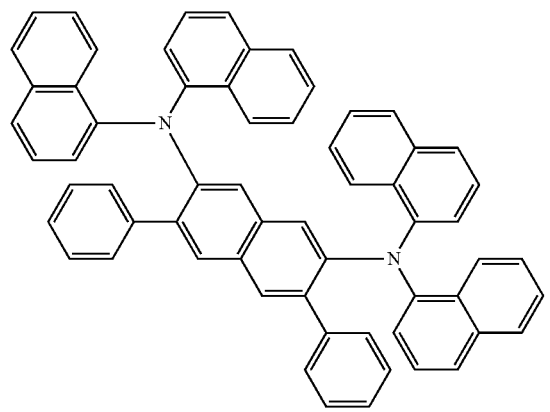
2-30
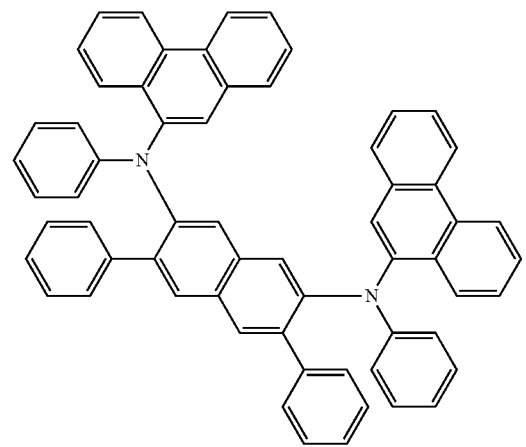
2-31
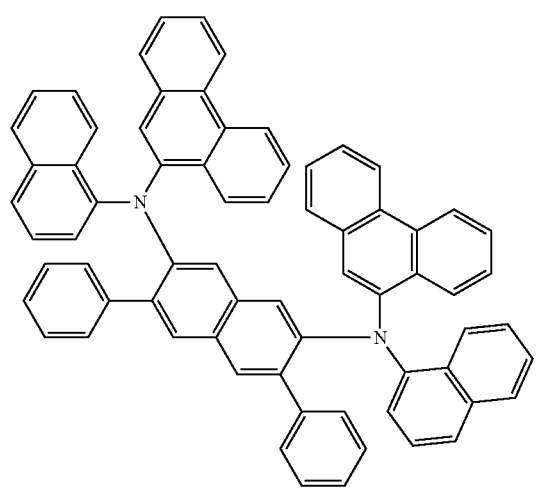
2-32
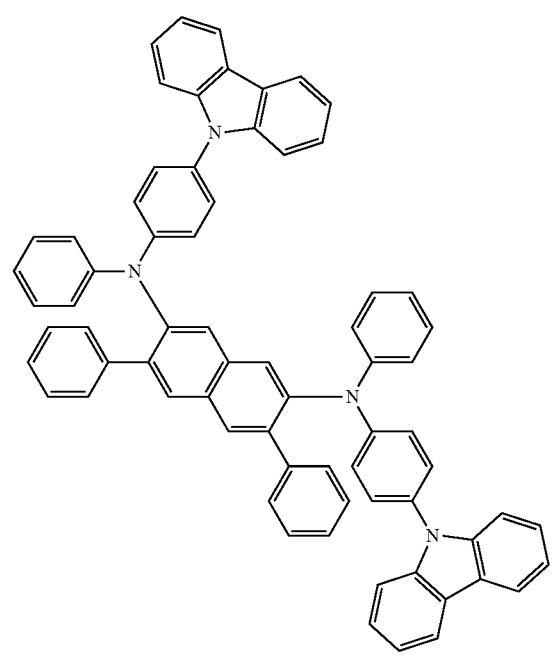

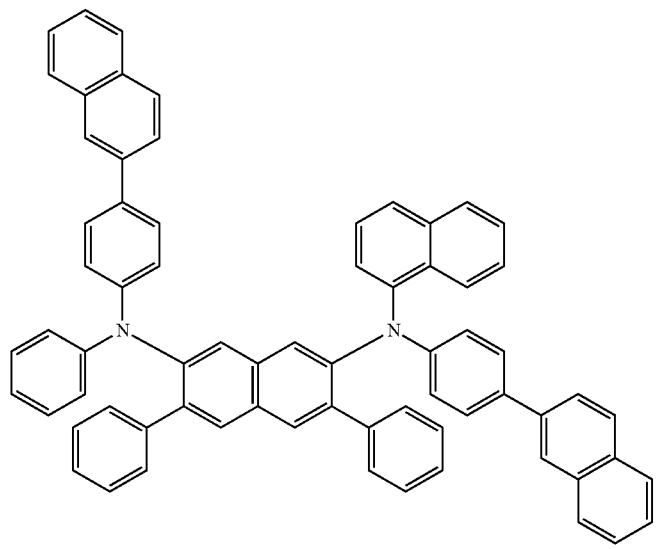
2-33
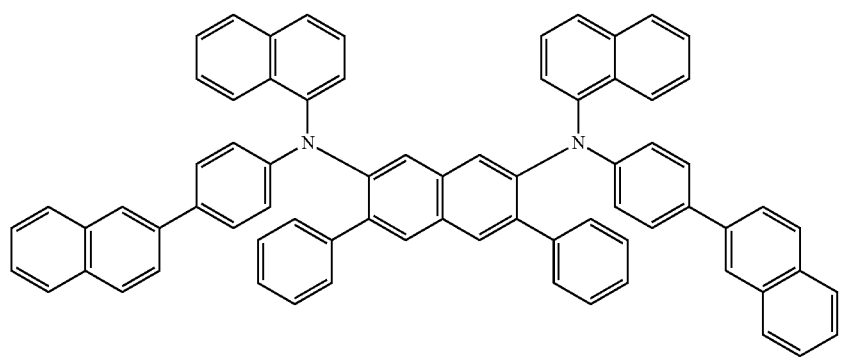
2-34
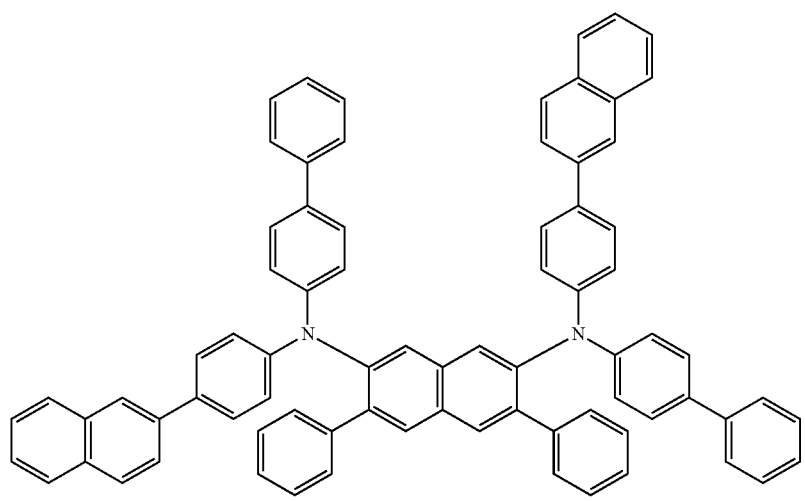
2-35

-continued
3-1
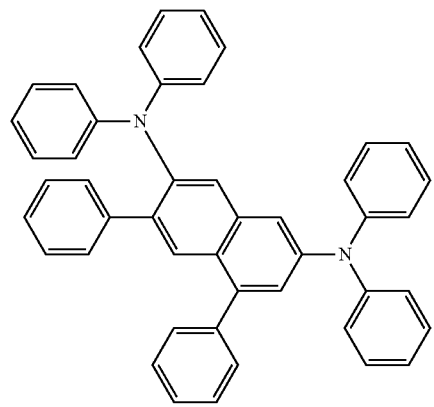
3-2
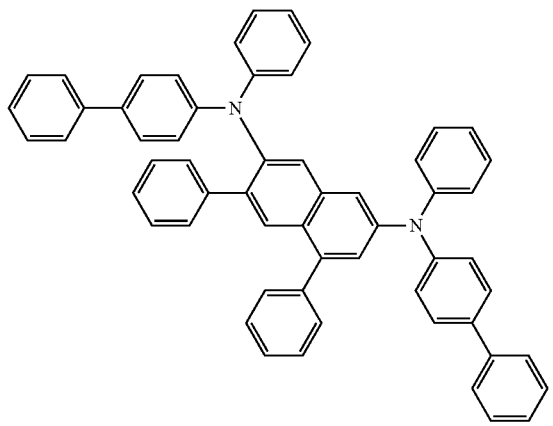
3-3
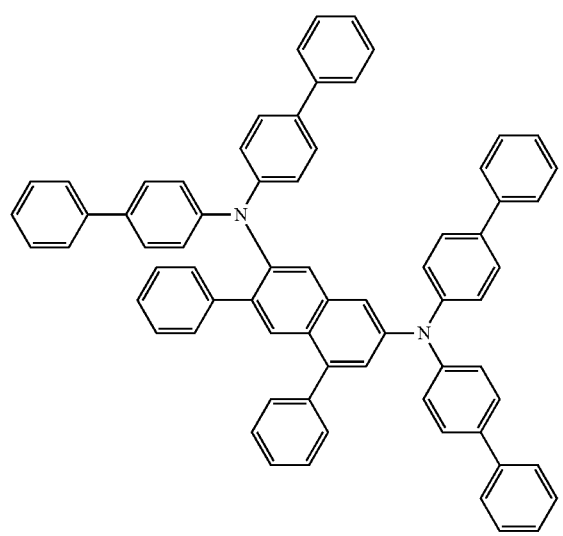
3-4
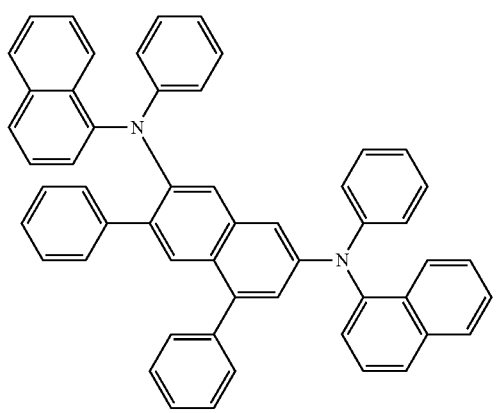
3-5
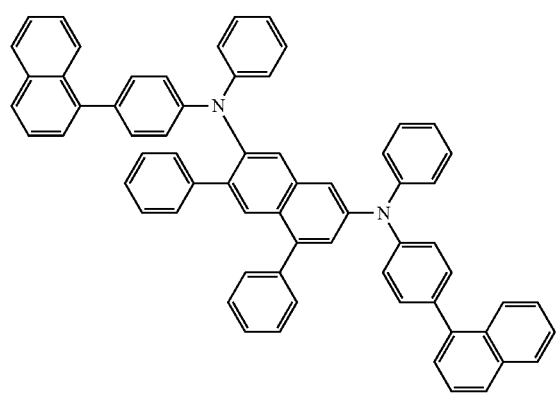
3-6
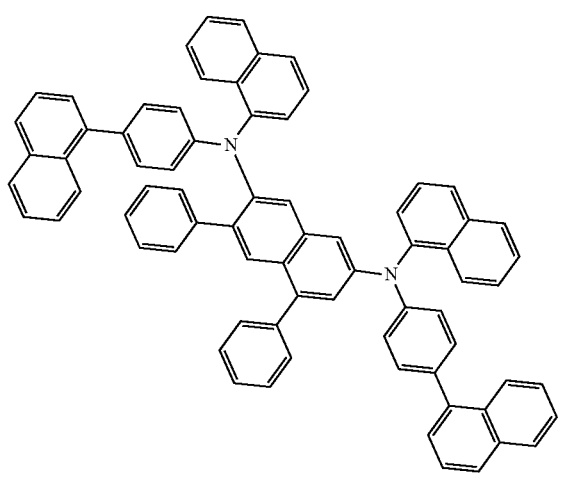

-continued
3-7
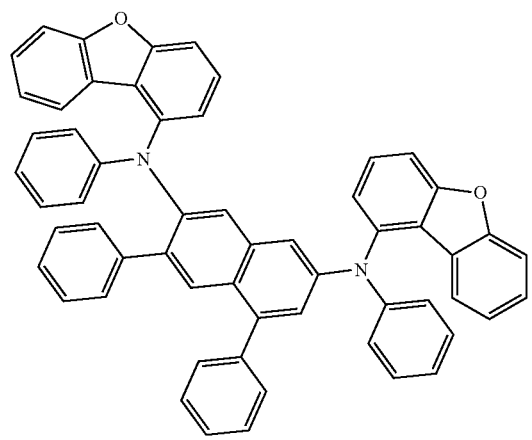
3-8
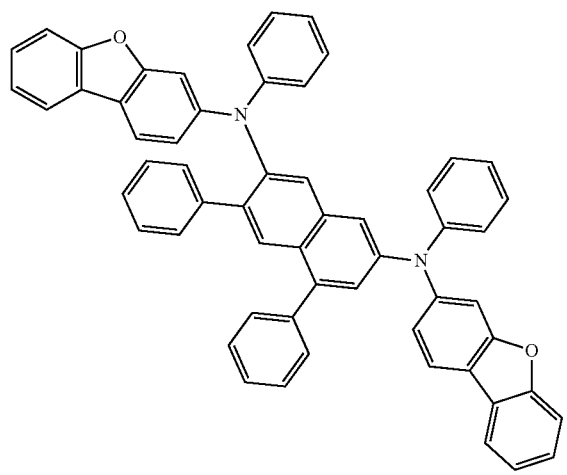
3-9
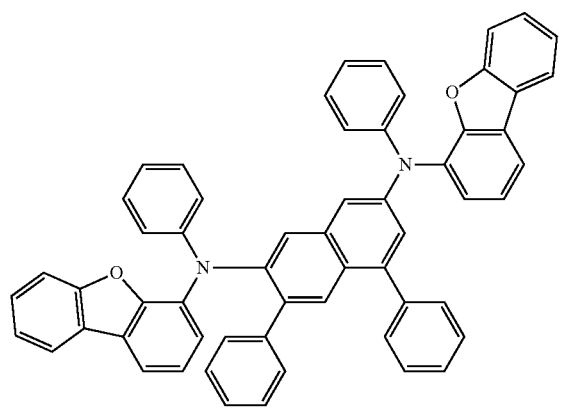
3-10
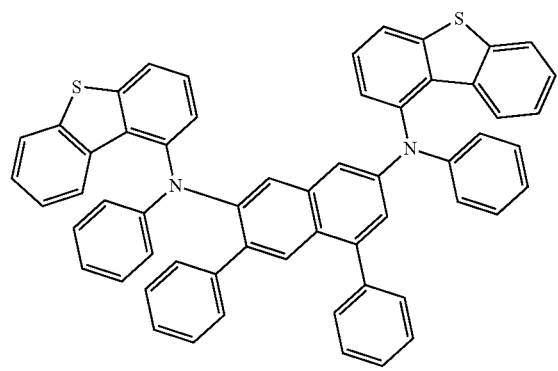
3-11
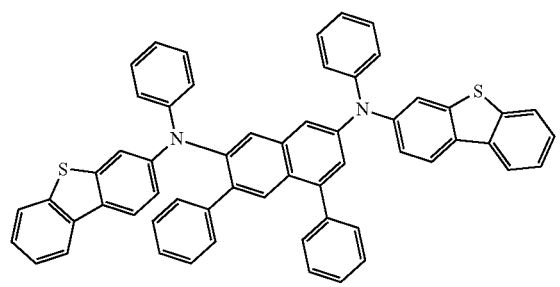
3-12
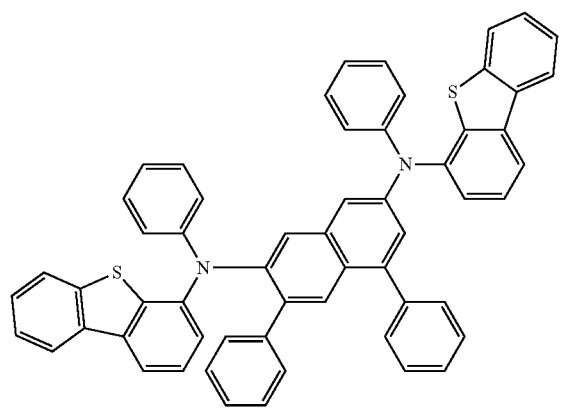

-continued
3-13
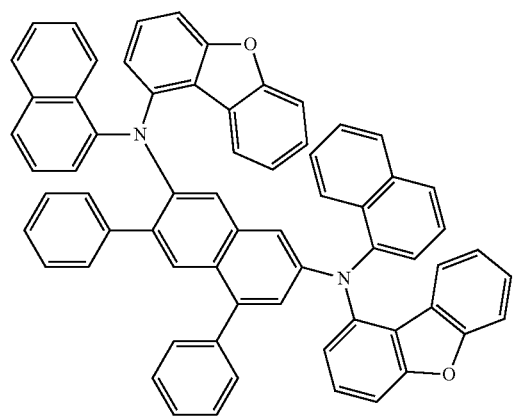
3-14
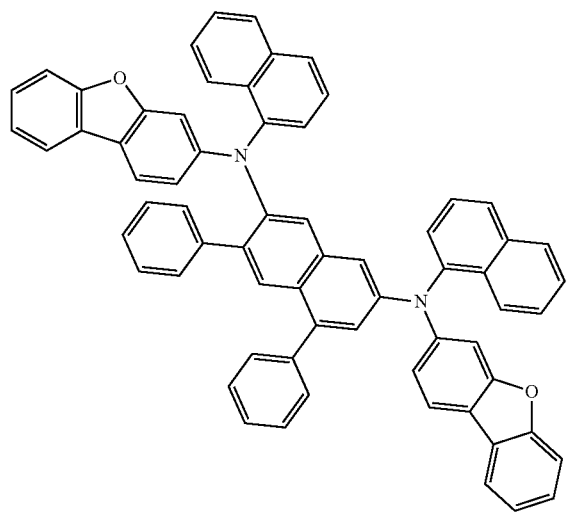
3-15
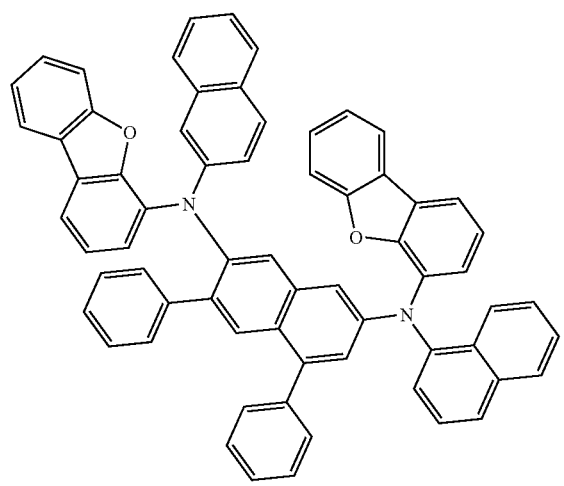
3-16
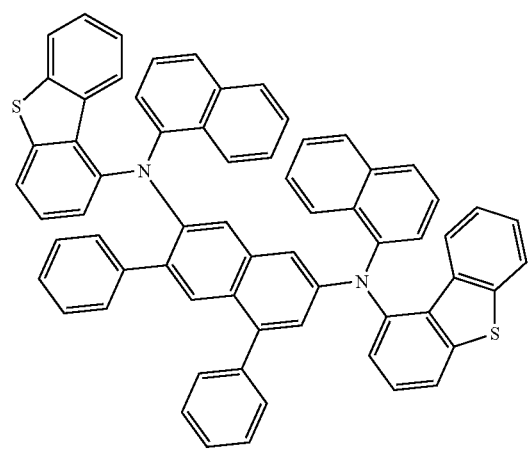
3-17
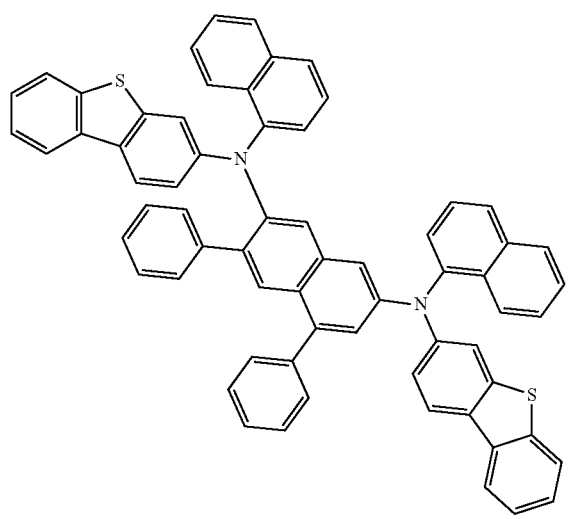
3-18
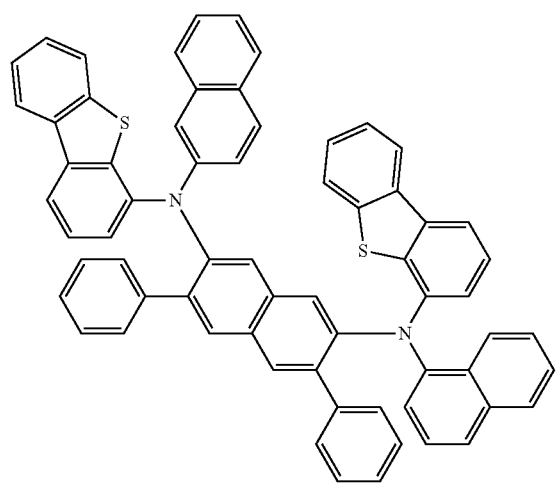

-continued
3-19
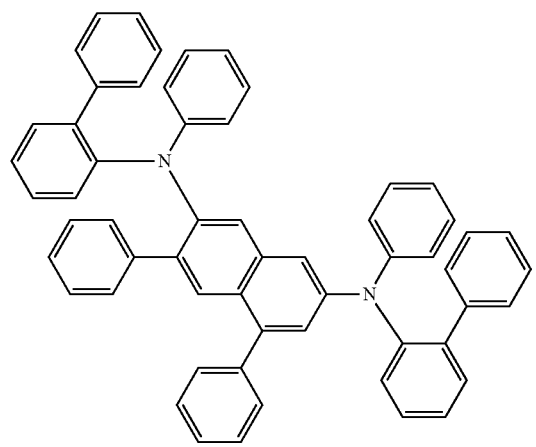
3-20
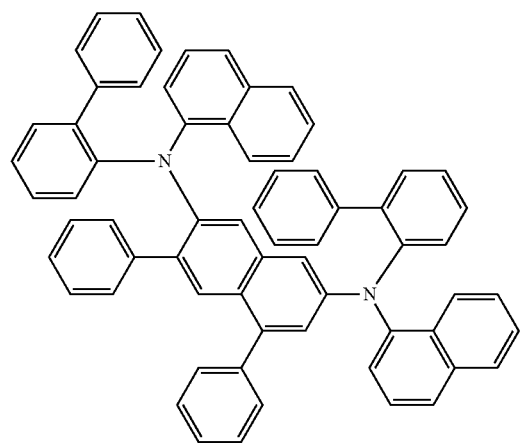
3-21
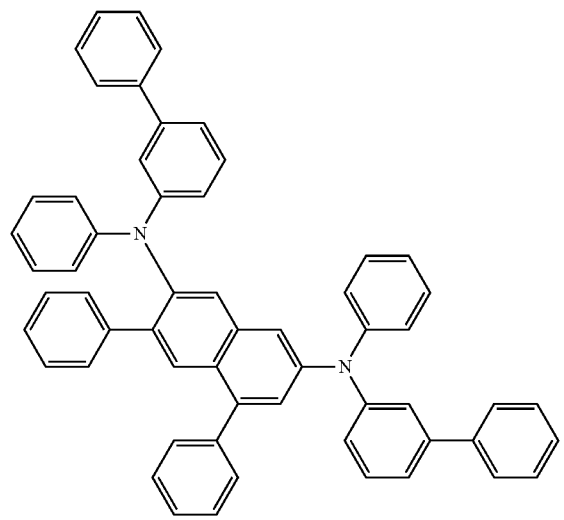
3-22
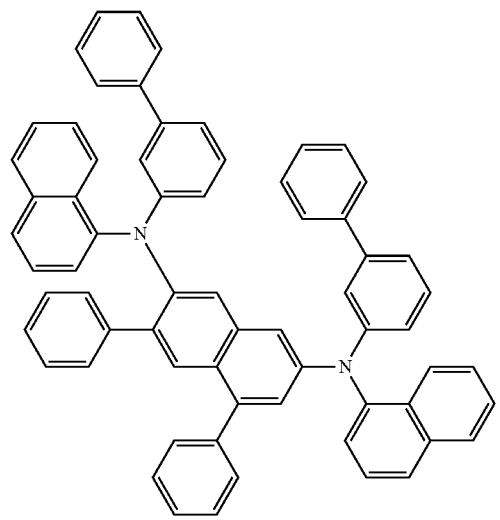
3-23
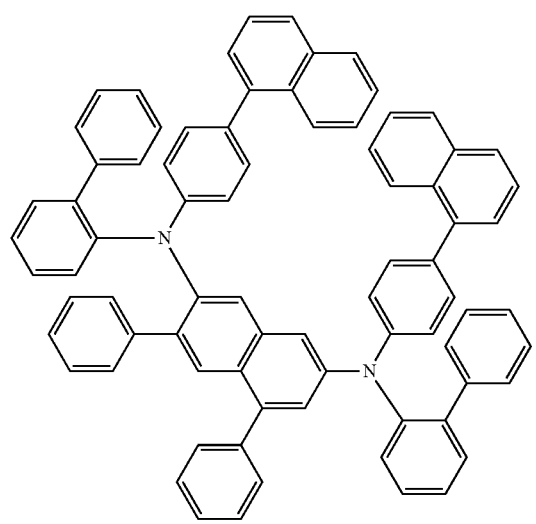
3-24
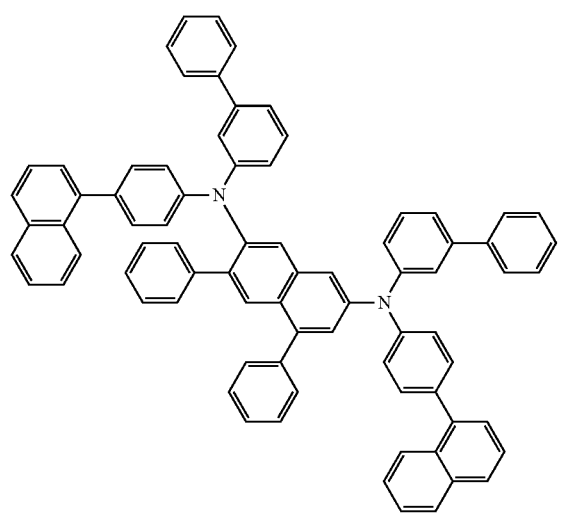

-continued
3-25
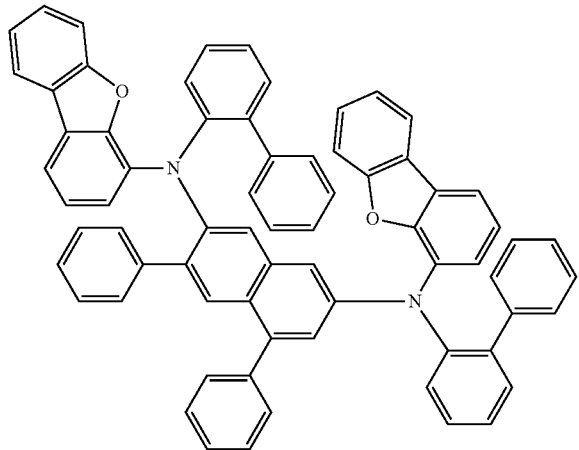
3-26
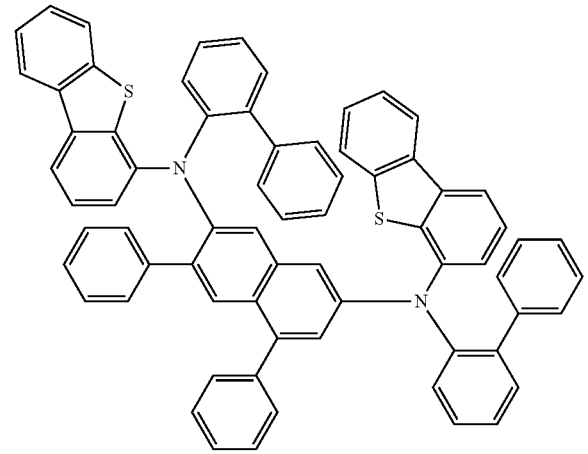
3-27
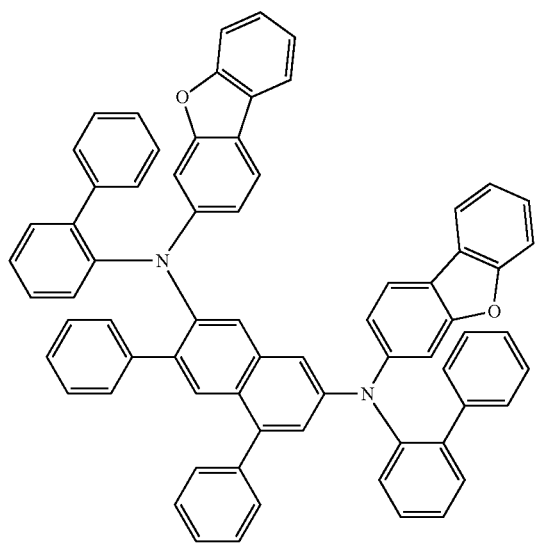
3-28
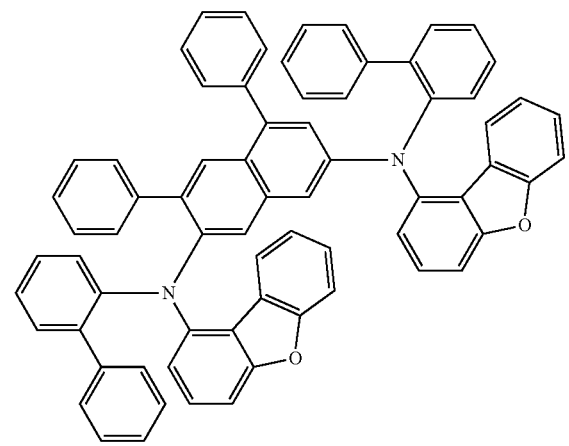
3-29
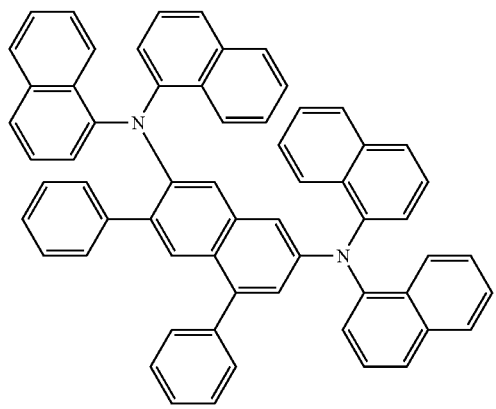
3-30
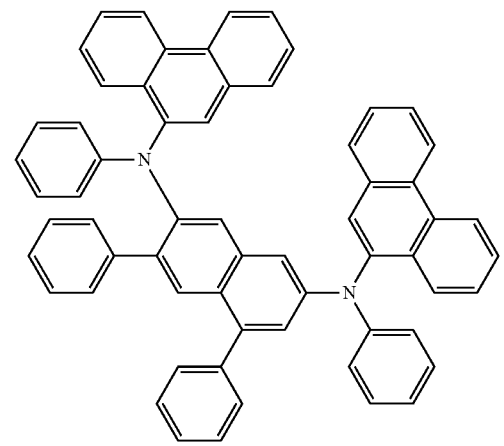

-continued
3-31
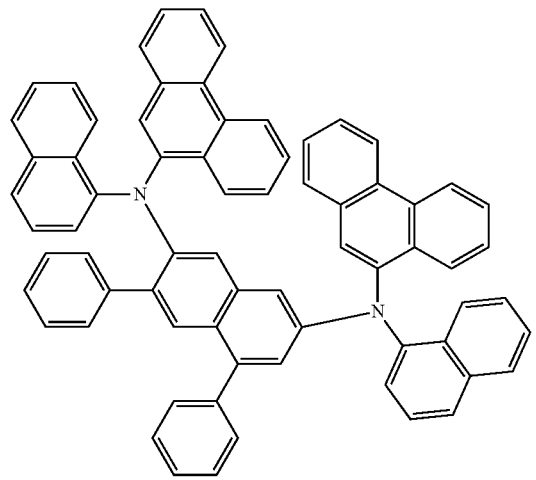
3-32
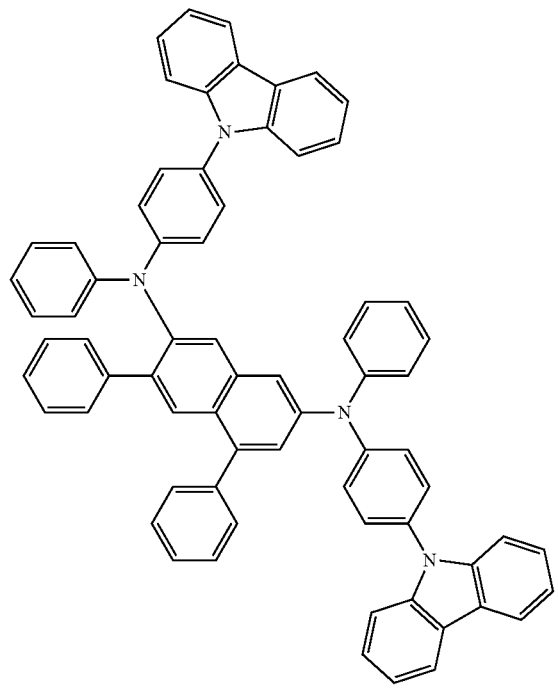
3-33
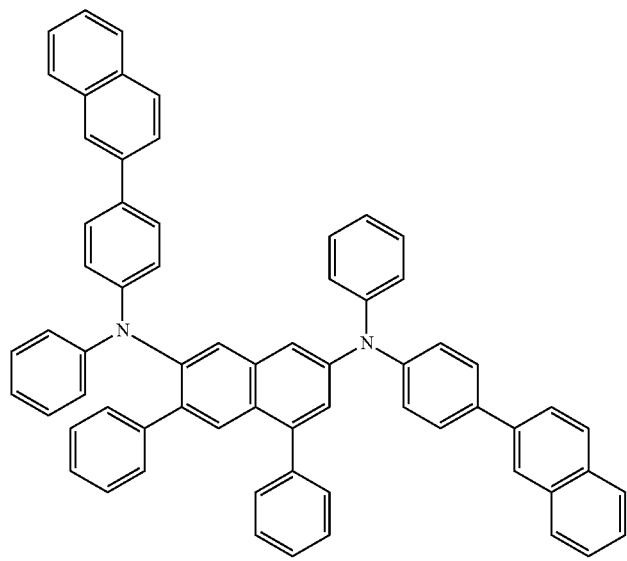
3-34
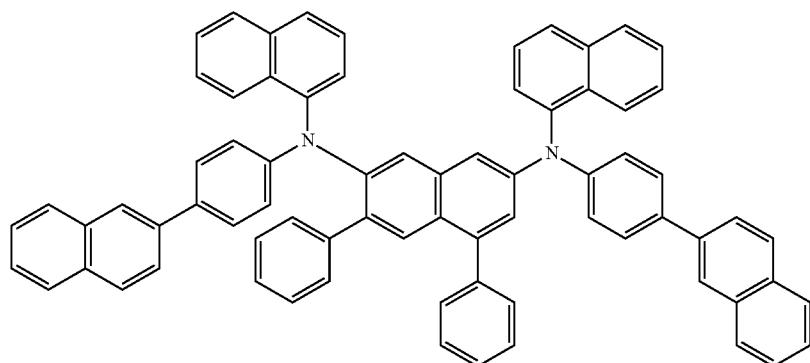

3-35
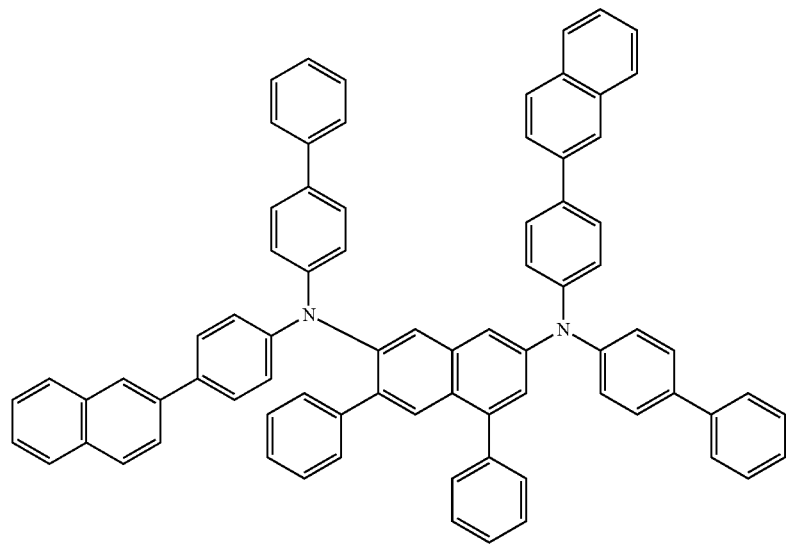
4-1
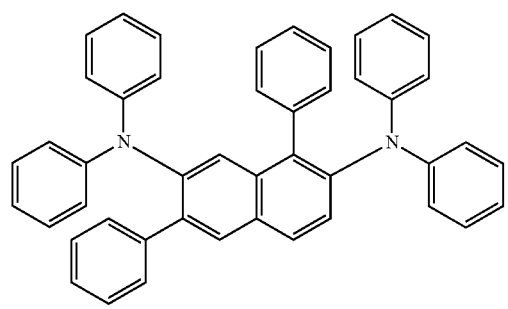
4-2
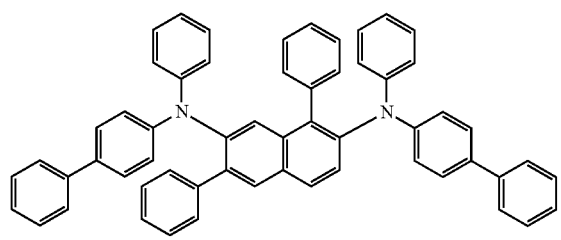
4-3
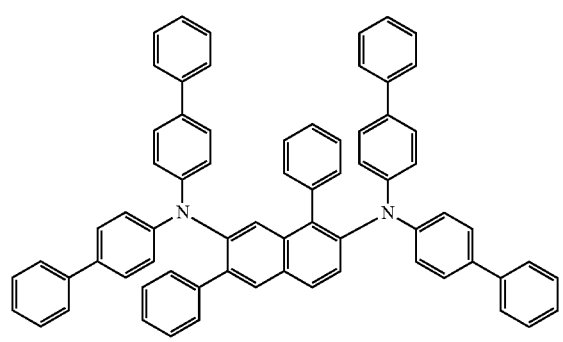
4-4
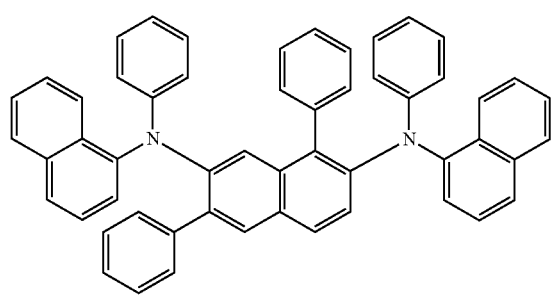

-continued
4-5
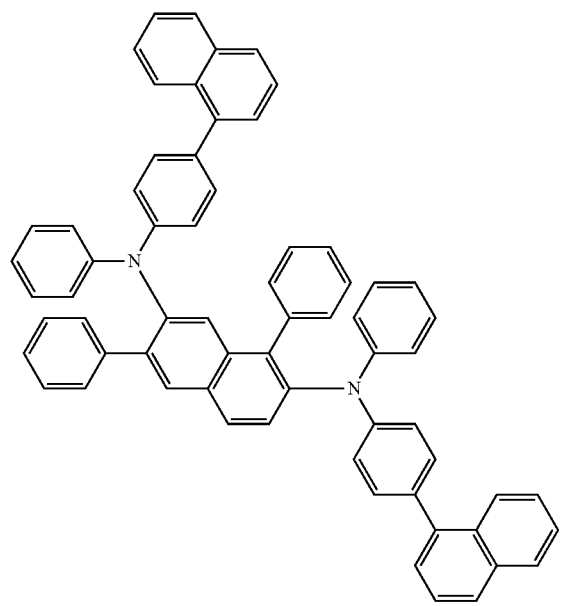
4-6
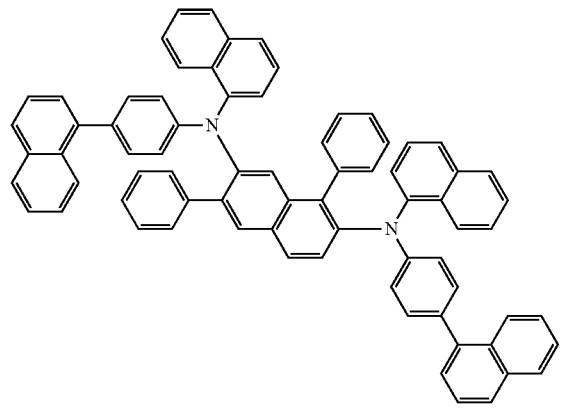
4-7
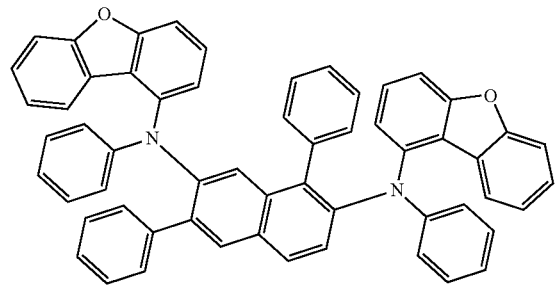
4-8
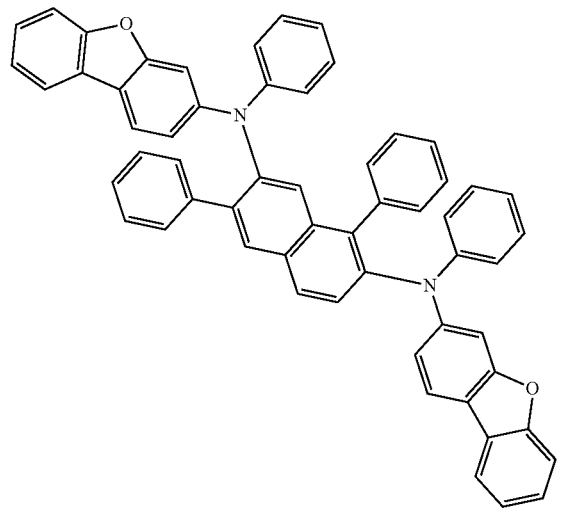
4-9
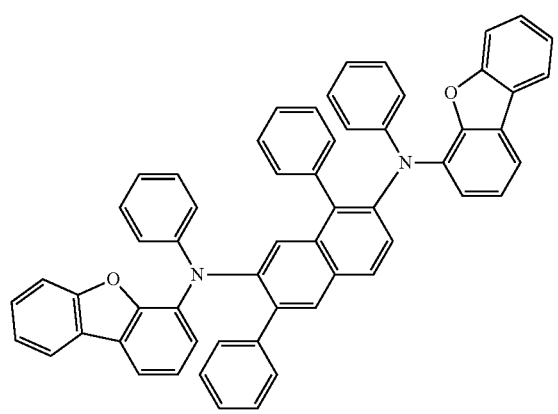
4-10
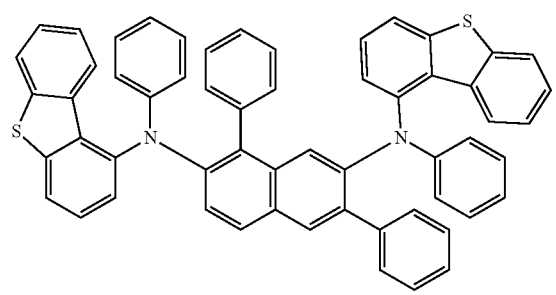

-continued
4-11
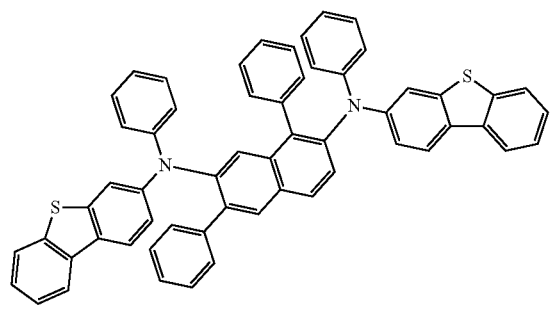
4-12
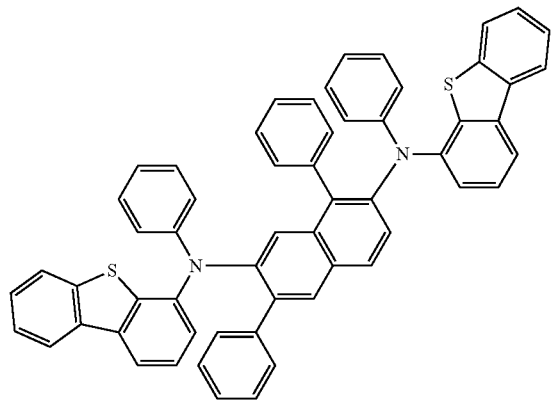
4-13
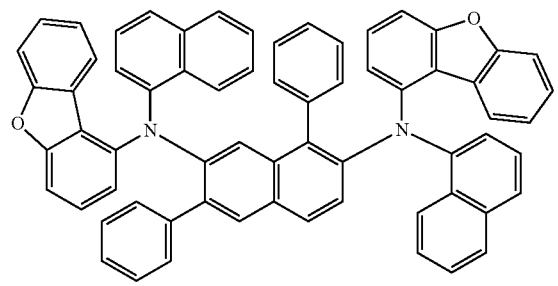
4-14
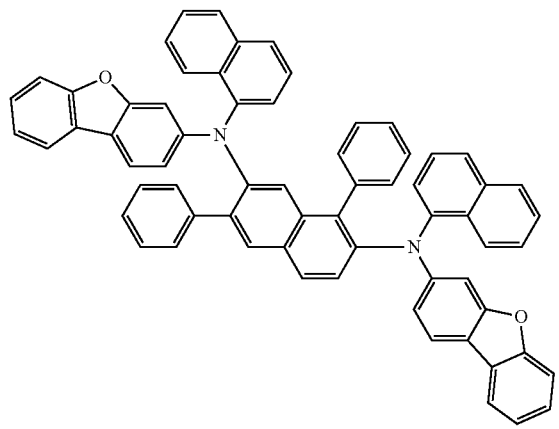
4-15
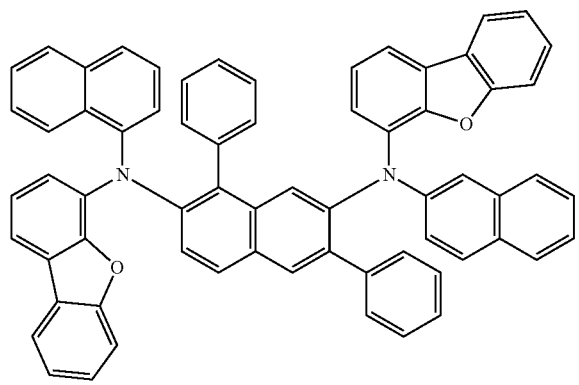
4-16
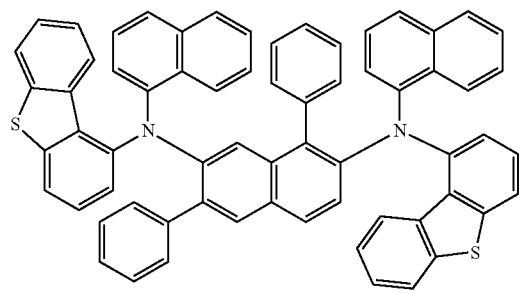

-continued
4-17
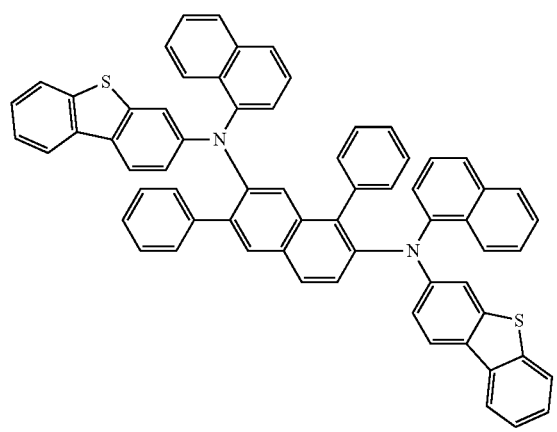
4-18
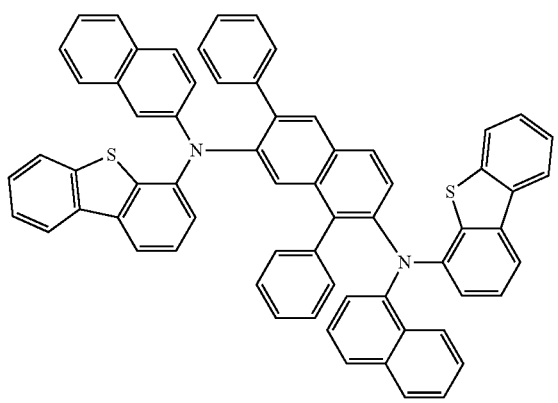
4-19
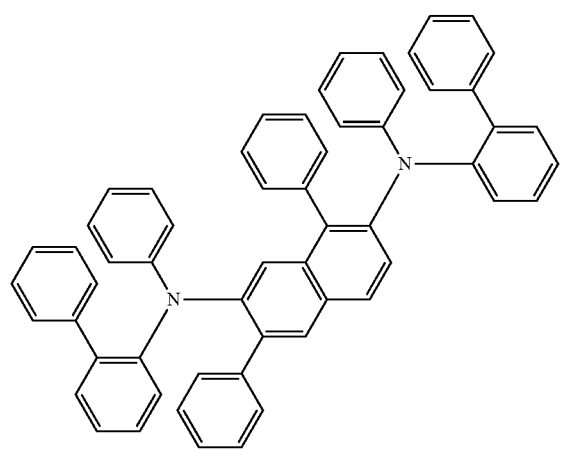
4-20
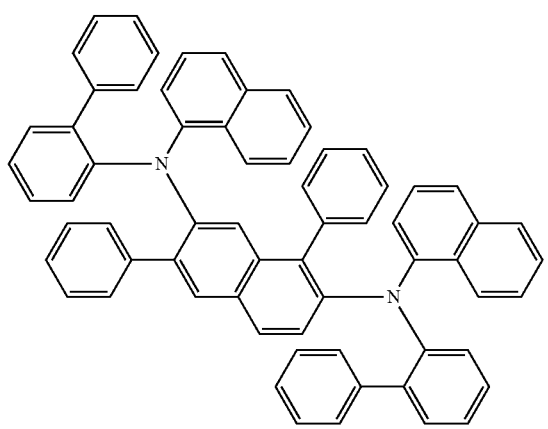
4-21
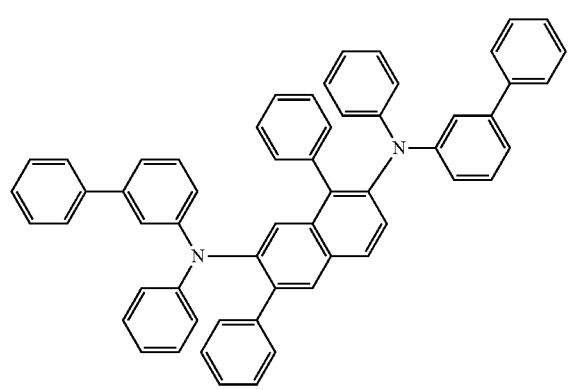
4-22
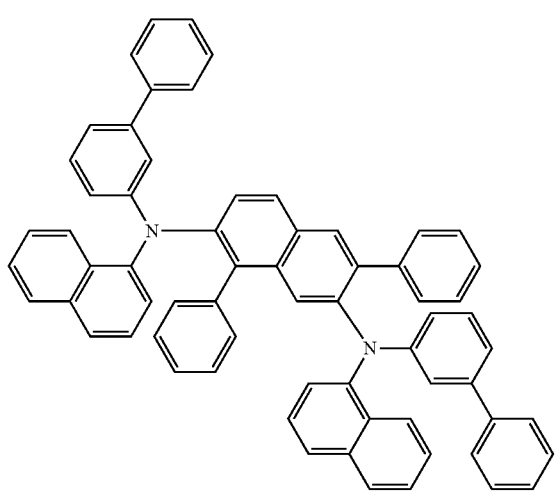

-continued
4-23
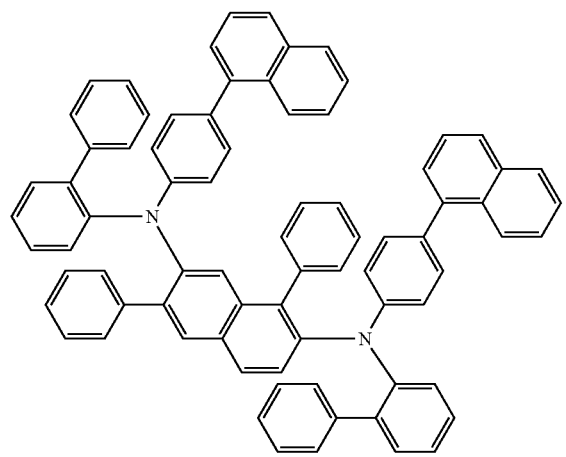
4-24
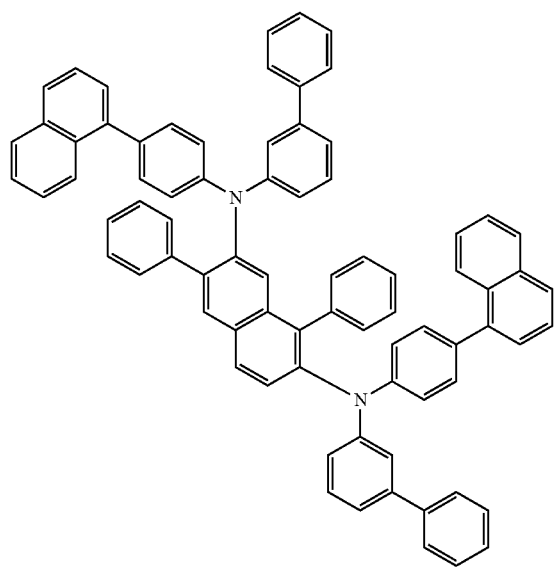
4-25
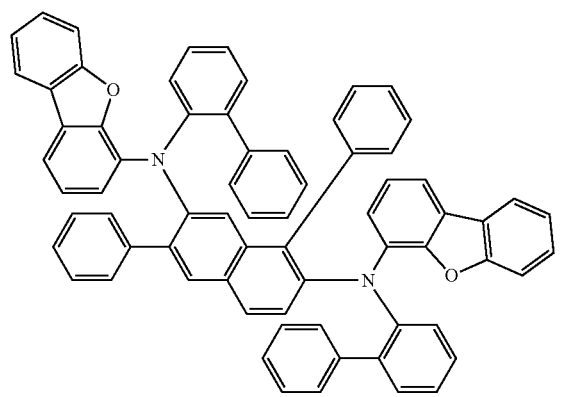
4-26
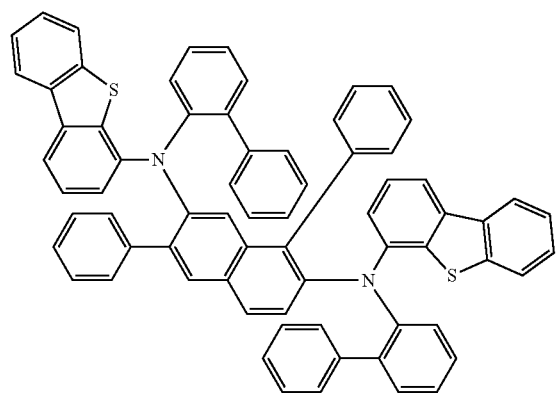
4-27
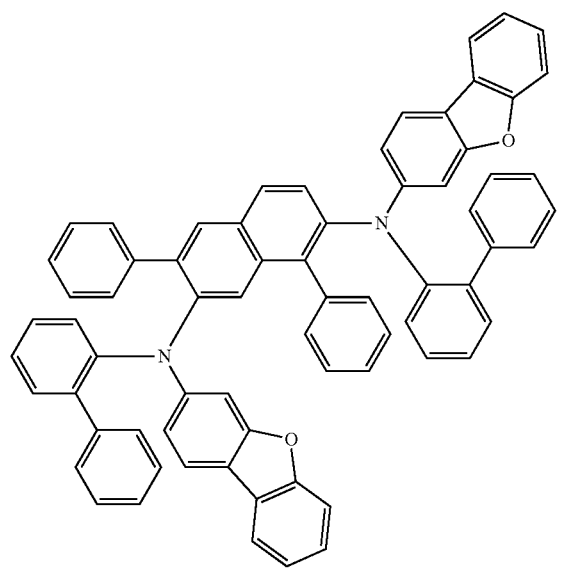
4-28
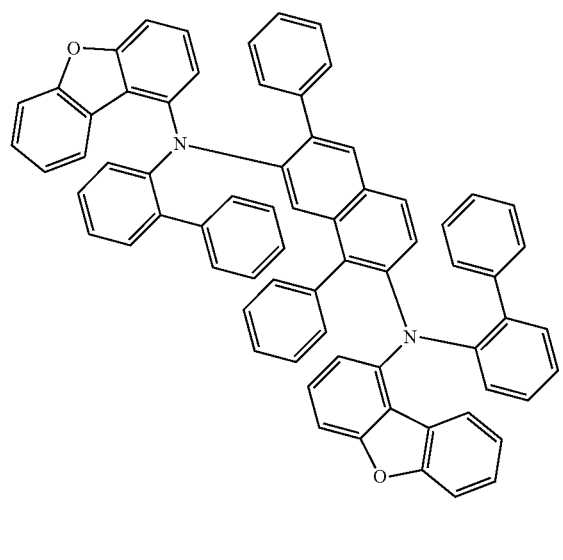

-continued
4-29
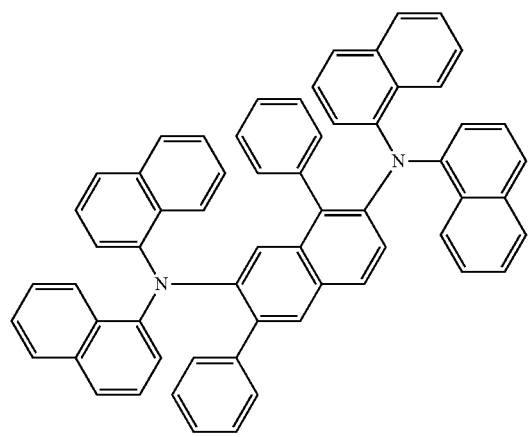
4-30
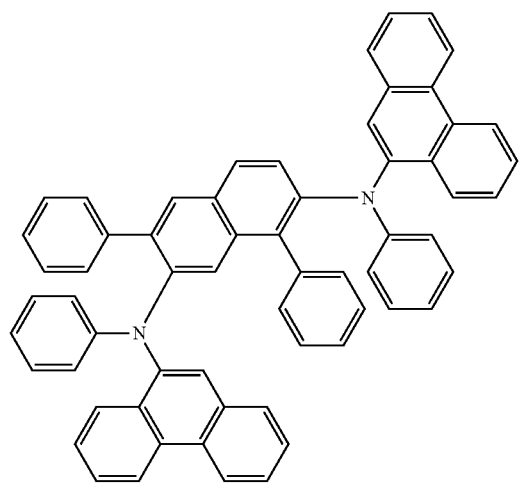
4-31
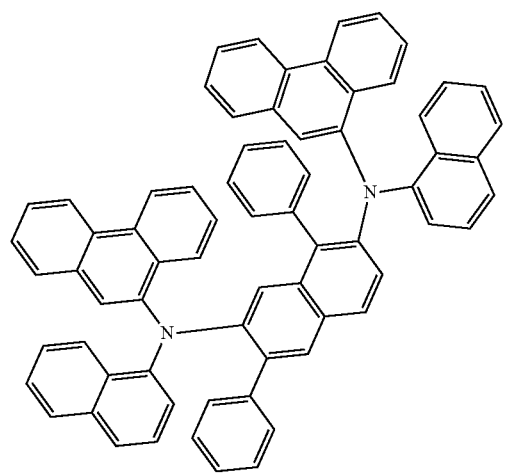
4-32
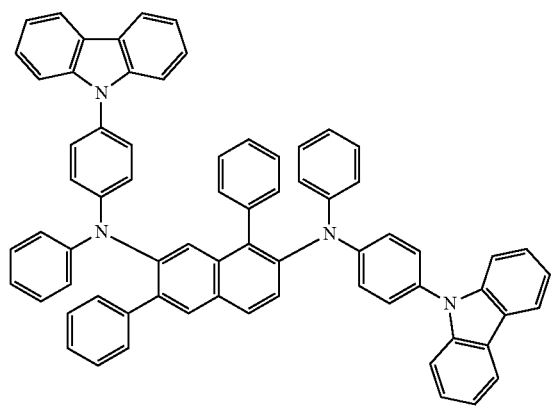
4-33
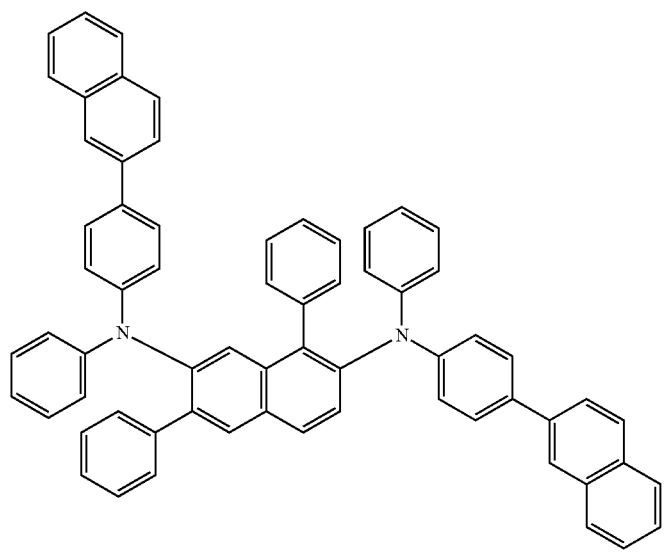

4-34
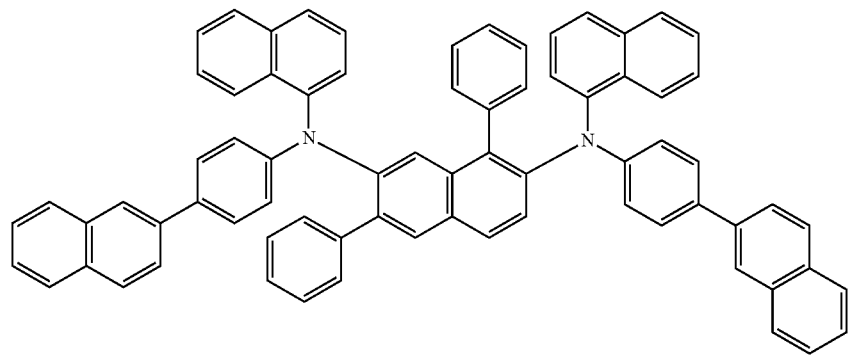
4-35
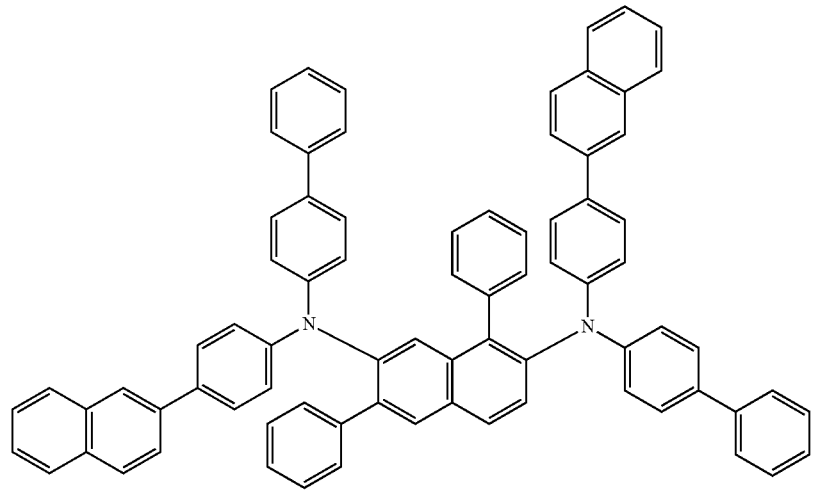
5-1
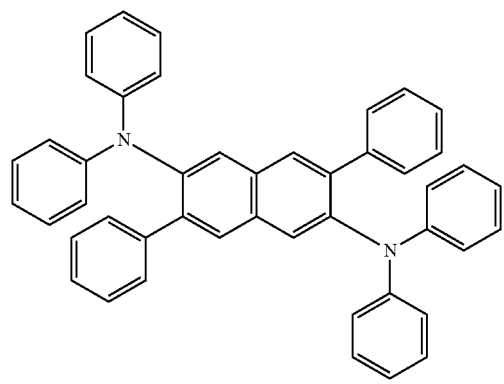
5-2
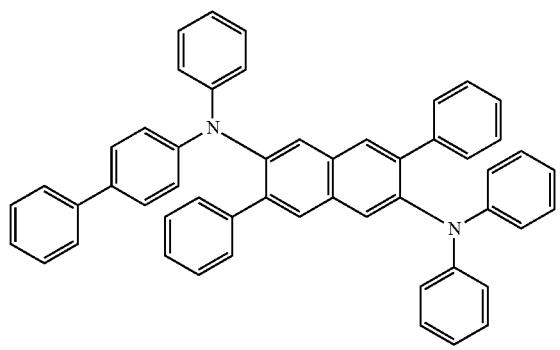

-continued
5-3
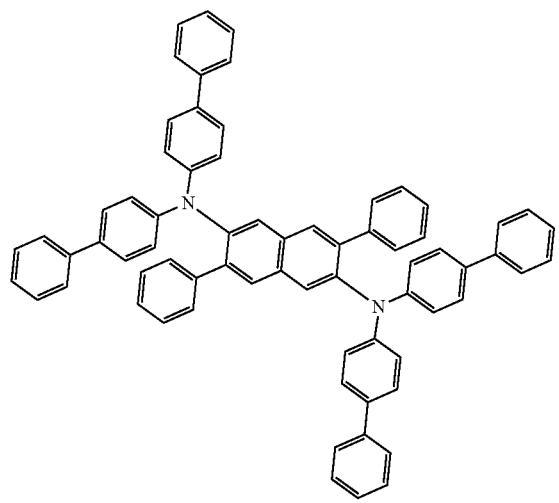
5-4
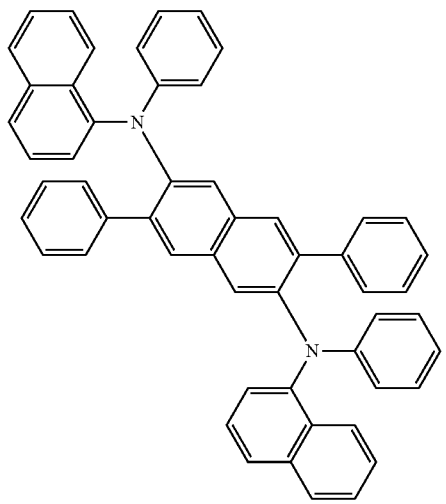
5-5
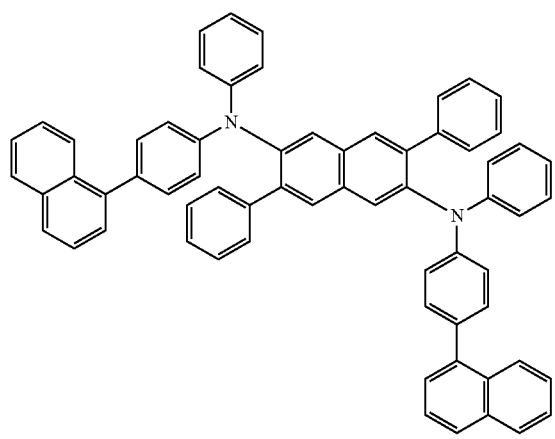
5-6
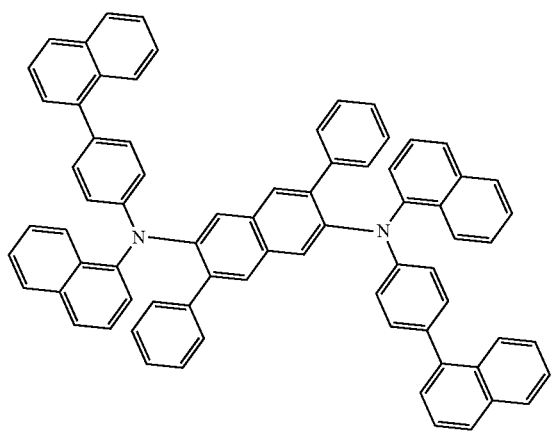
5-7
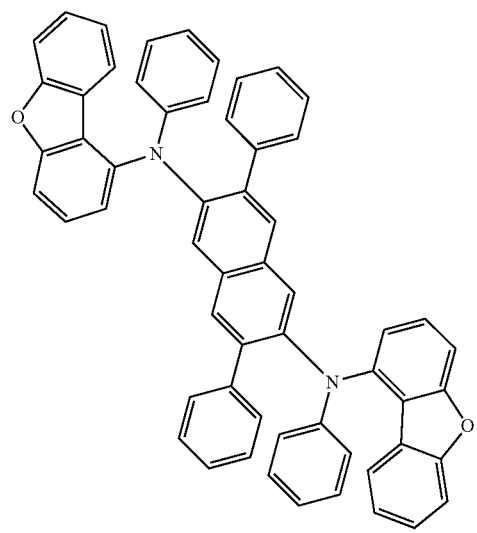
5-8
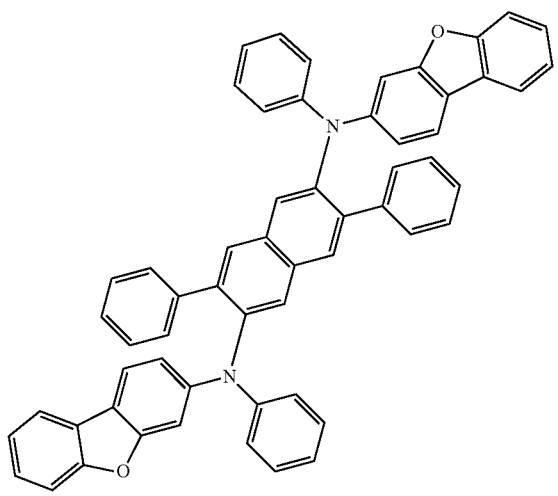

-continued
5-9
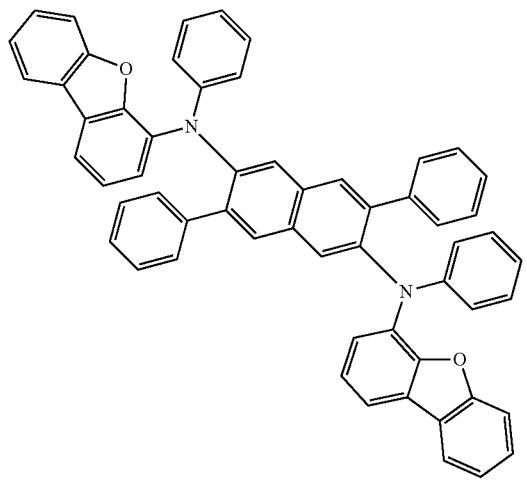
5-10
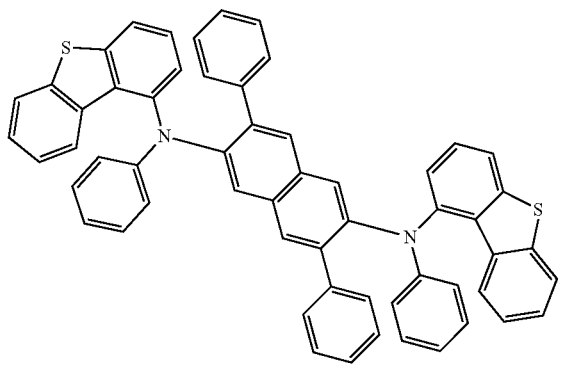
5-11
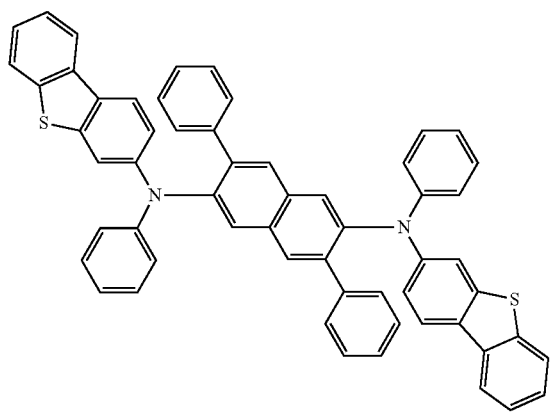
5-12
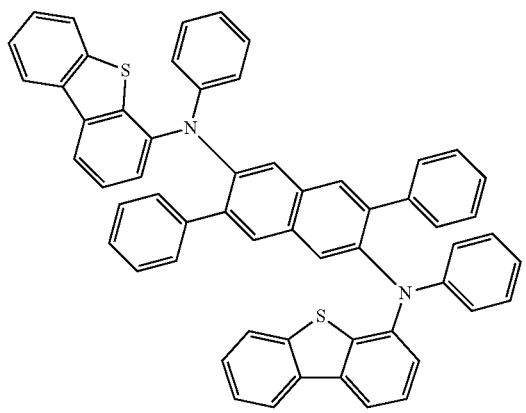
5-13
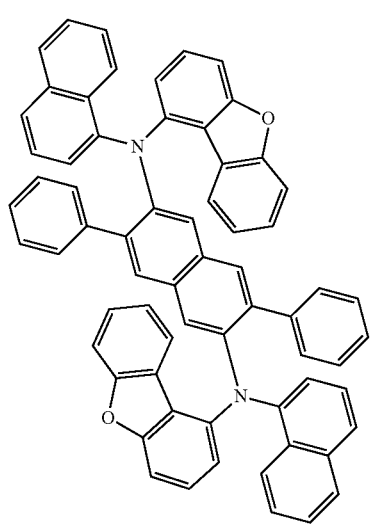
5-14
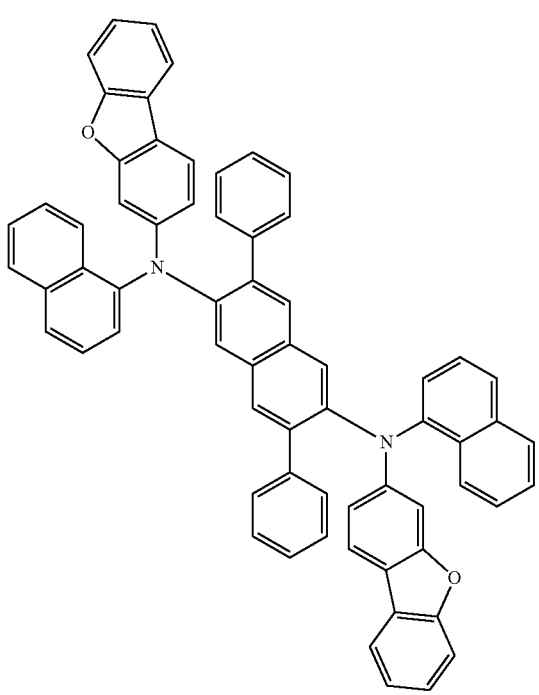

-continued
5-15
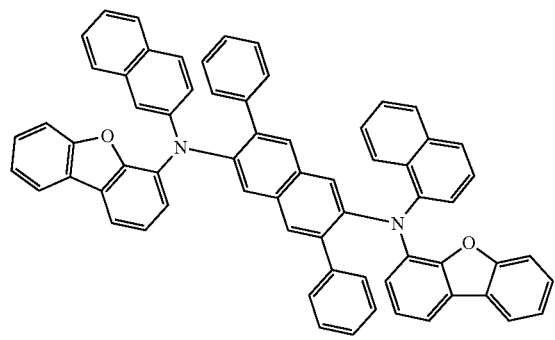
5-16
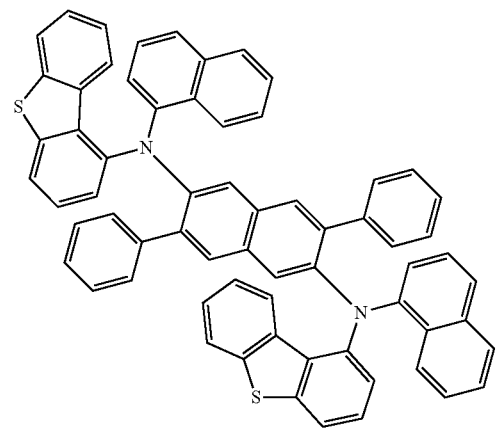
5-17
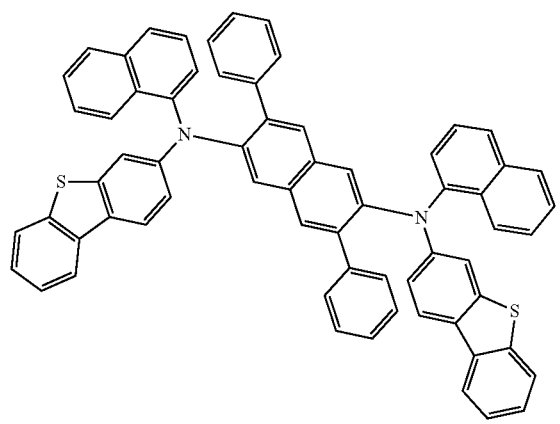
5-18
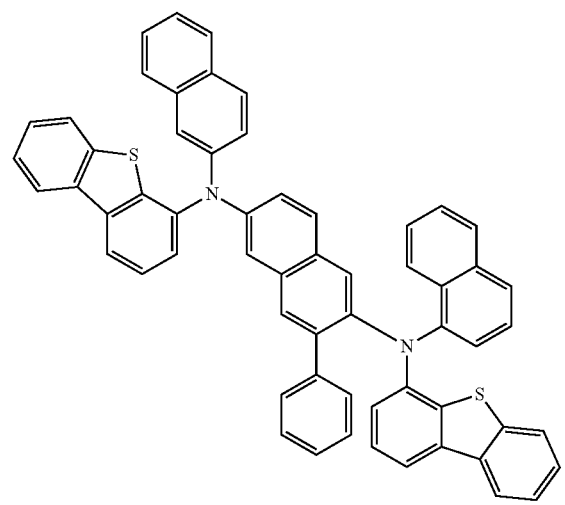
5-19
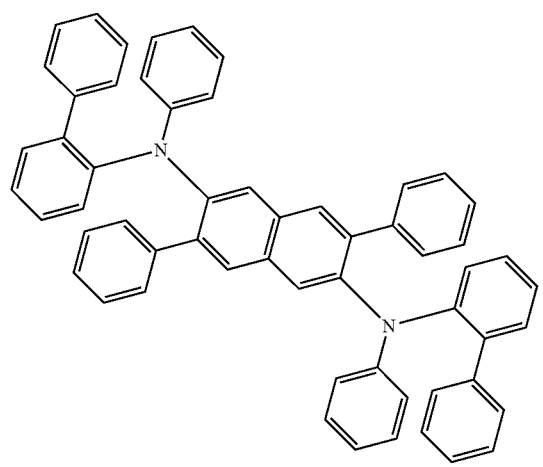
5-20
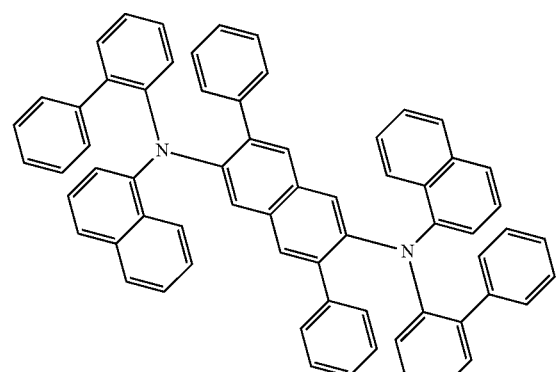

-continued
5-21
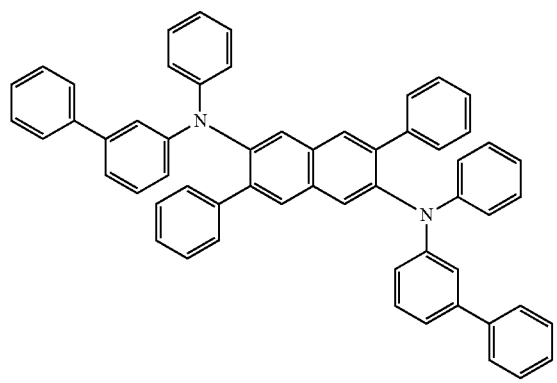
5-22
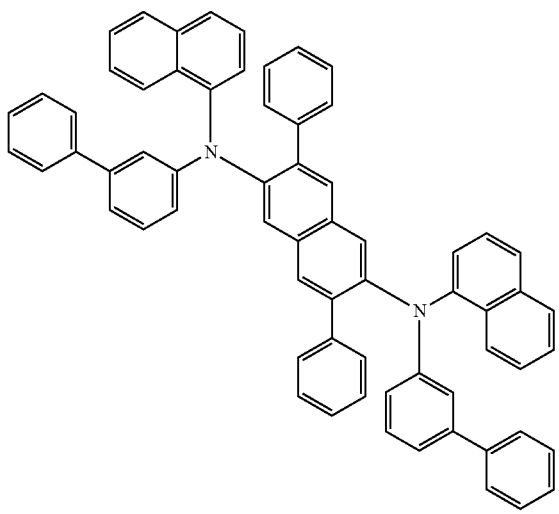
5-23
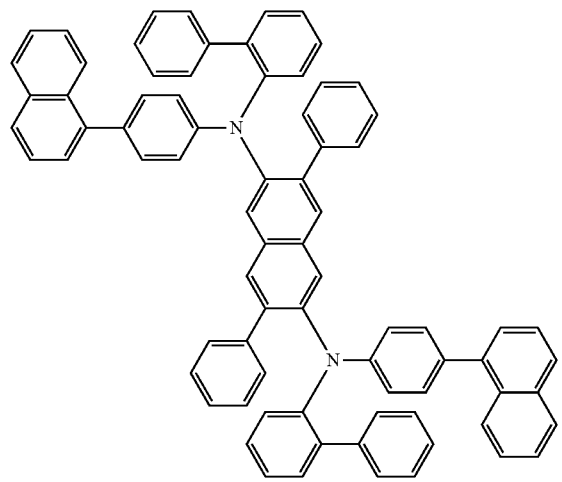
5-24
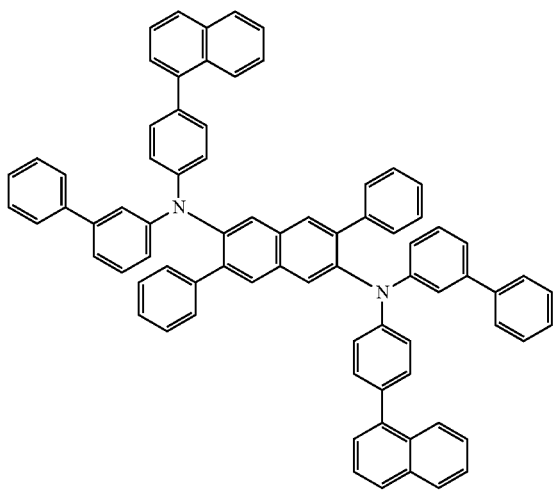
5-25
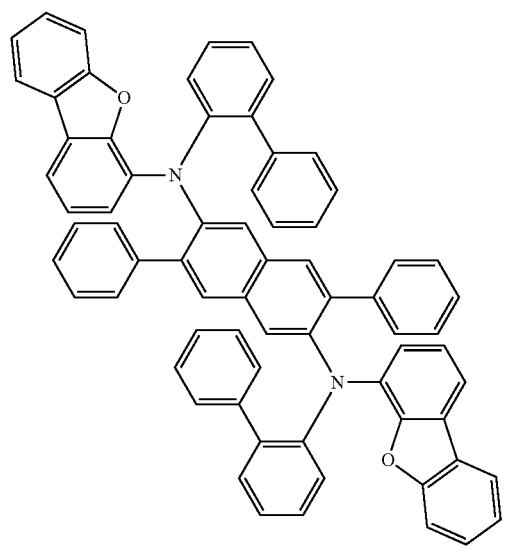
5-26
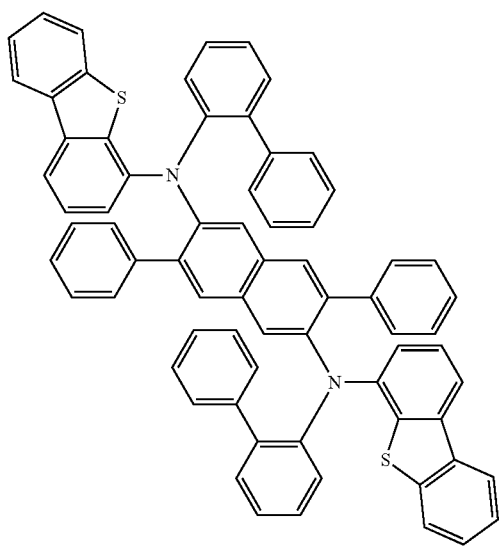

-continued
5-27
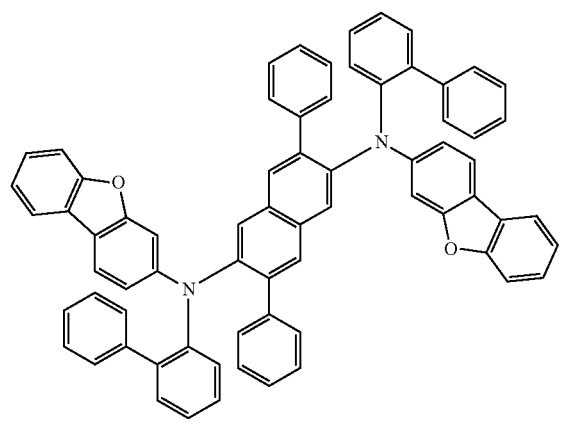
5-28
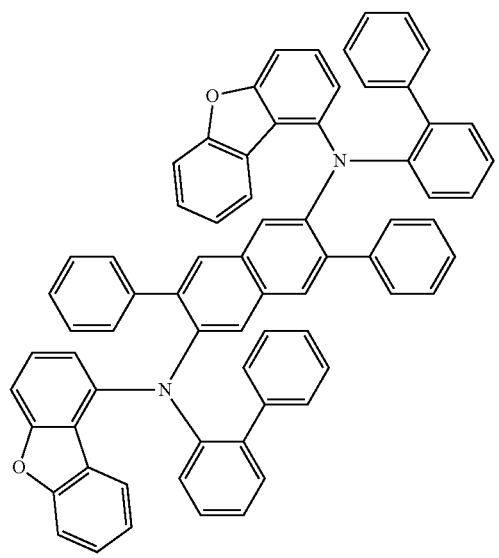
5-29
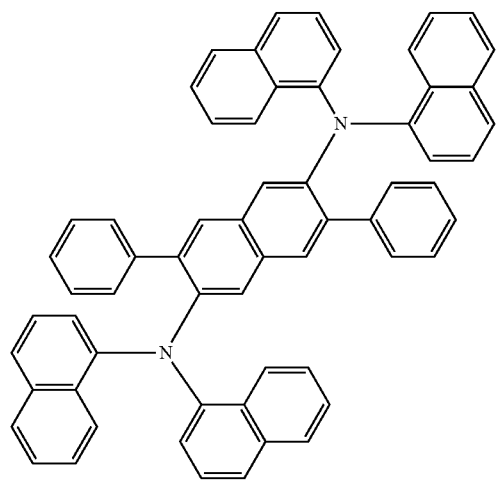
5-30
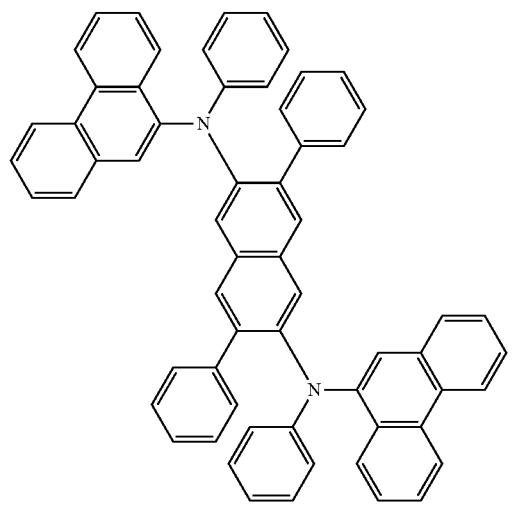
5-31
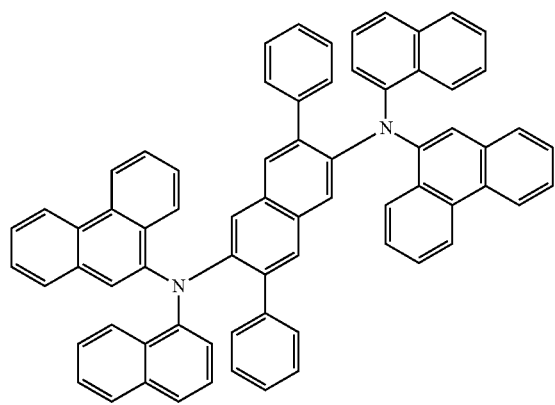
5-32
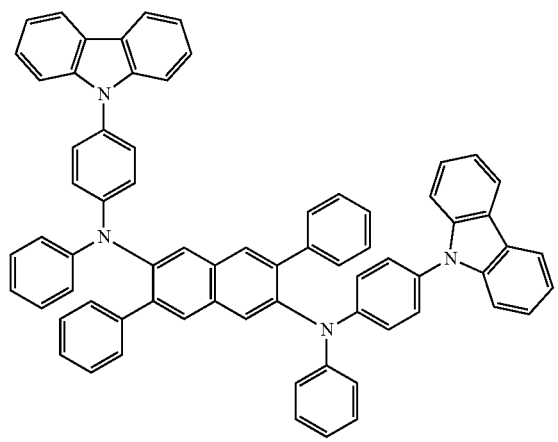

-continued
5-33
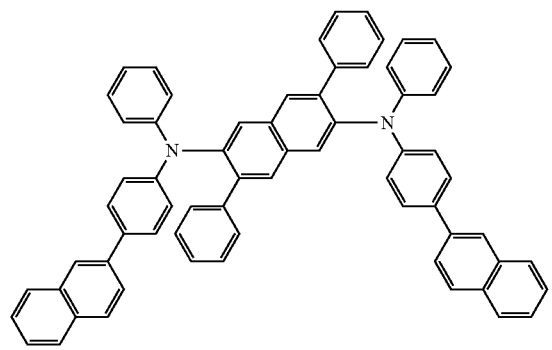
5-34
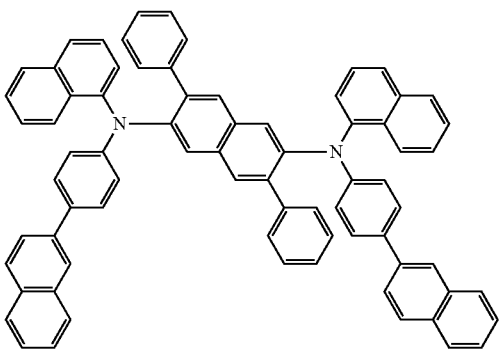
5-35
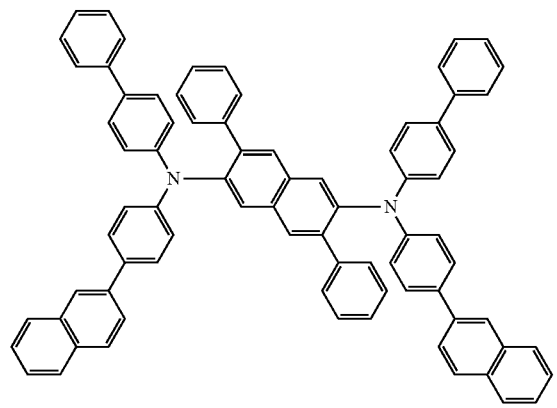
6-1
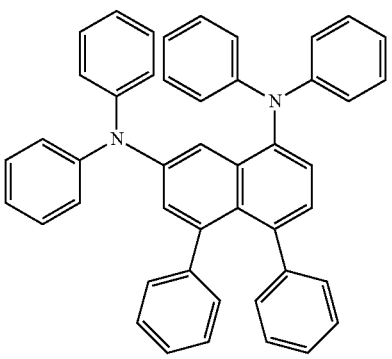
6-2
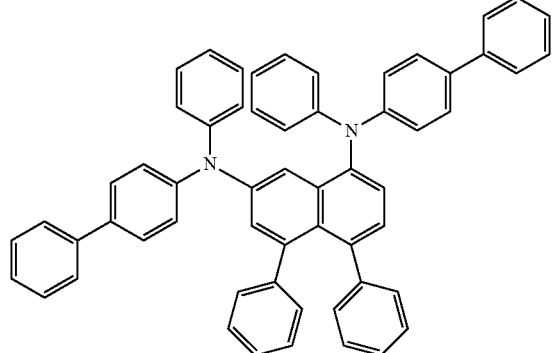
6-3
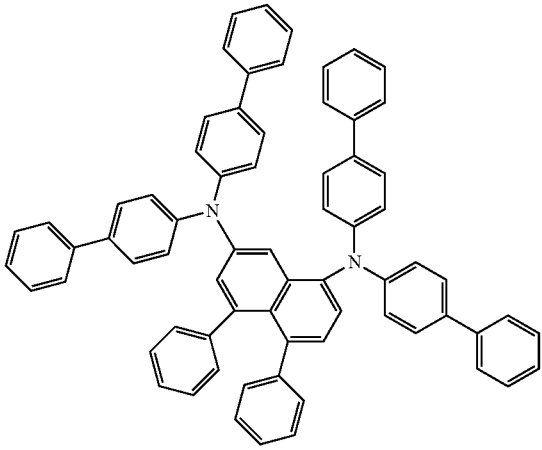
6-4
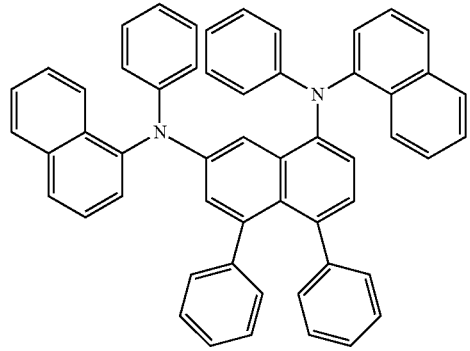
6-5
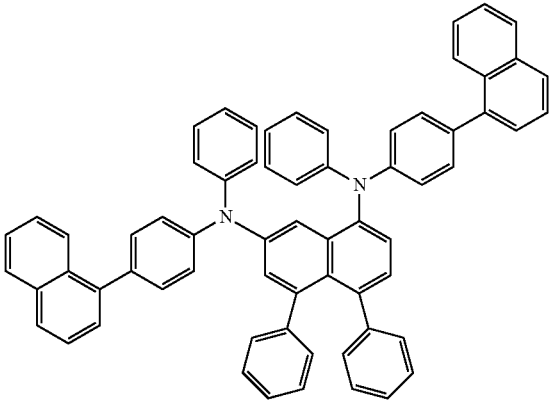

-continued
6-6
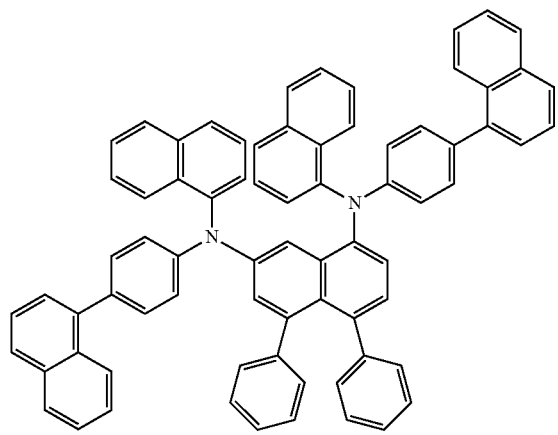
6-7
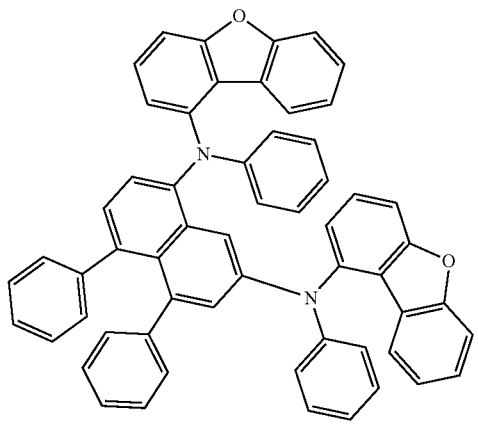
6-8
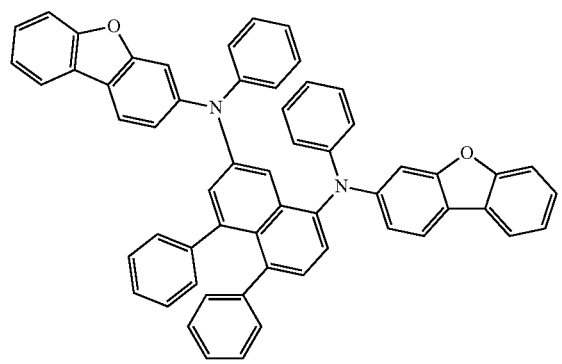
6-9
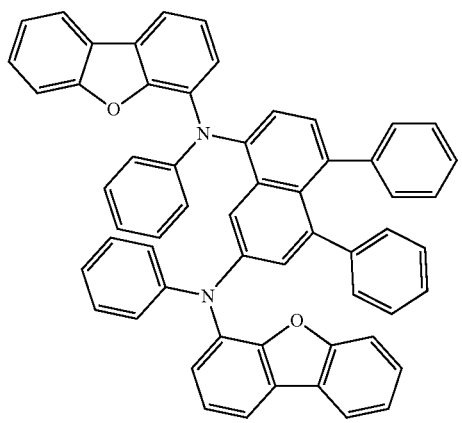
6-10
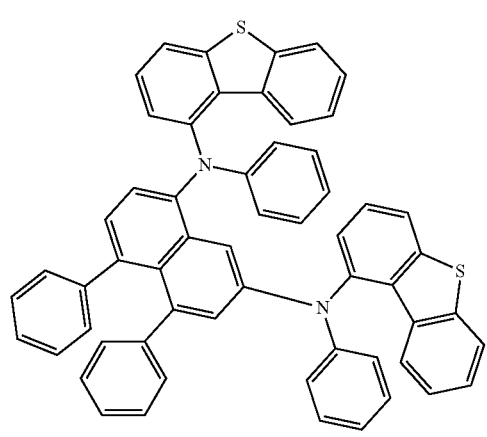
6-11
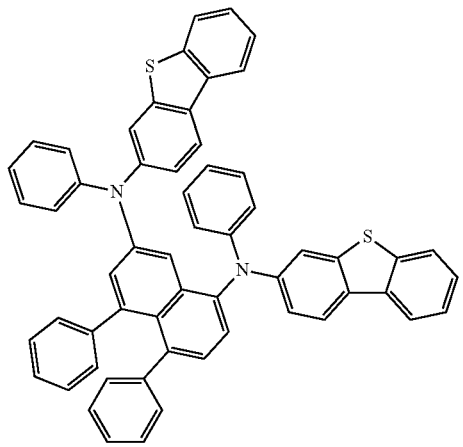

-continued
6-12
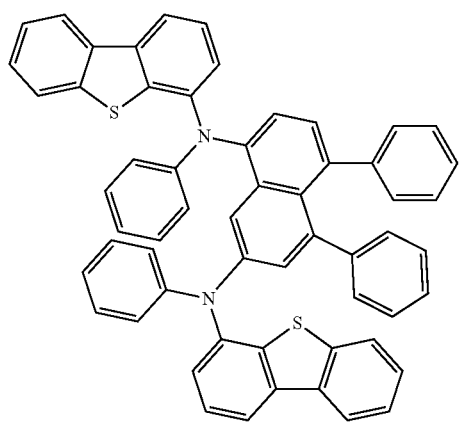
6-13
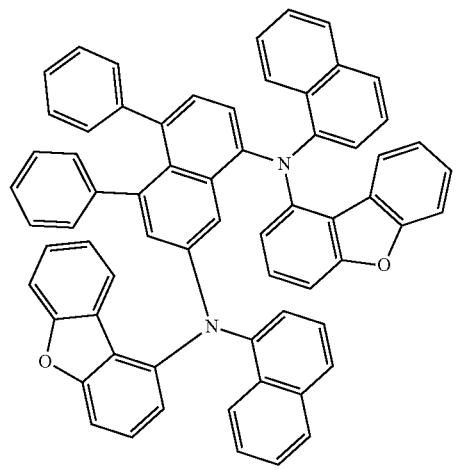
6-14
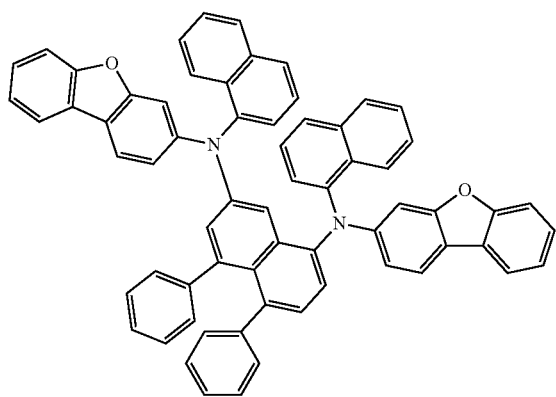
6-15
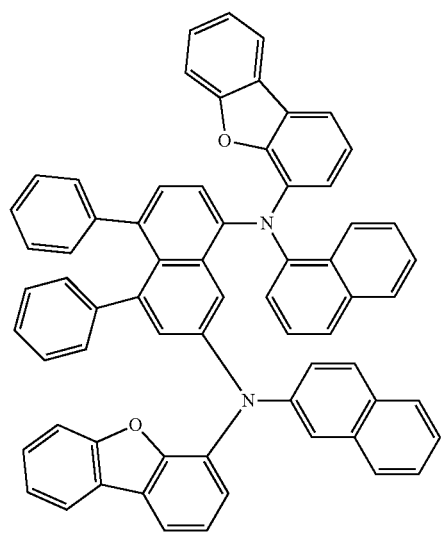
6-16
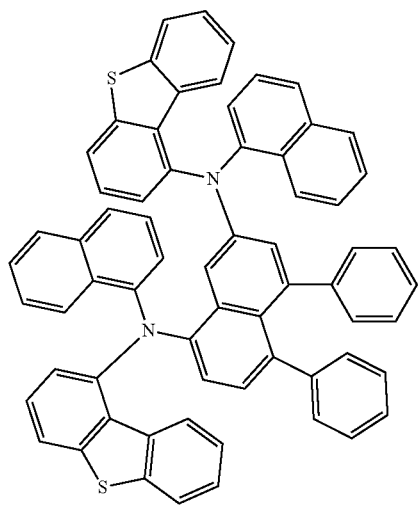
6-17
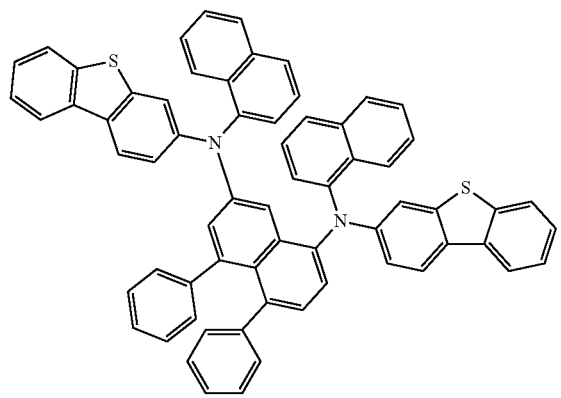

-continued
6-18
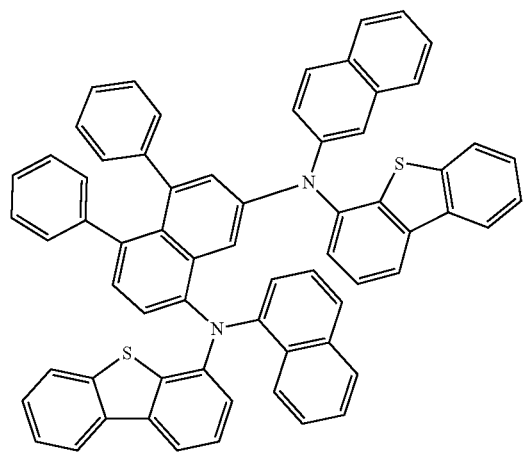
6-19
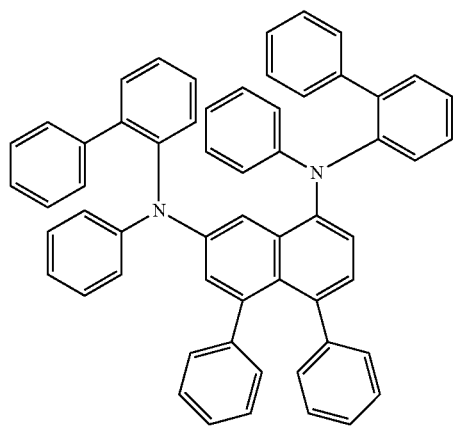
6-20
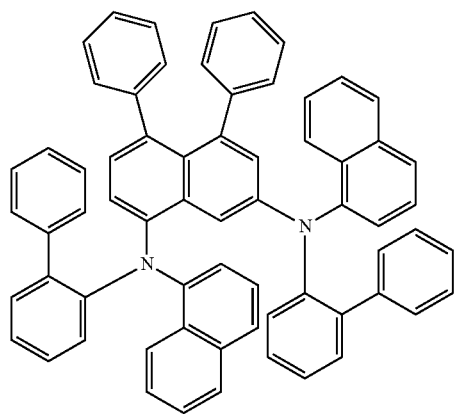
6-21
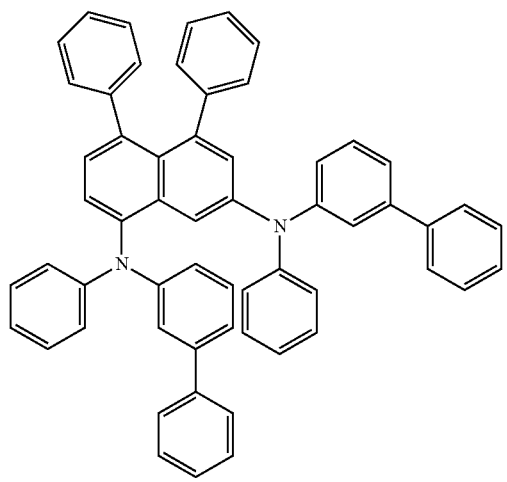
6-22
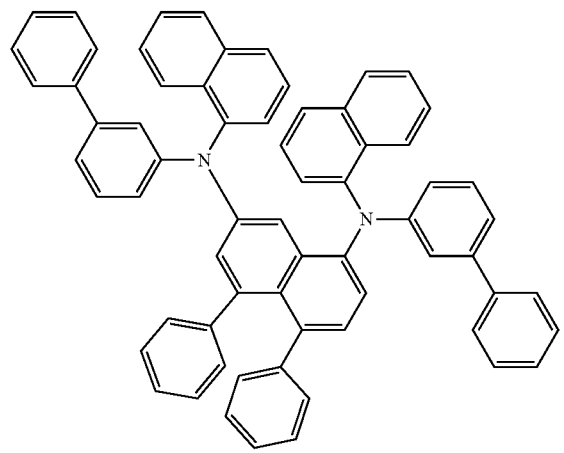
6-23
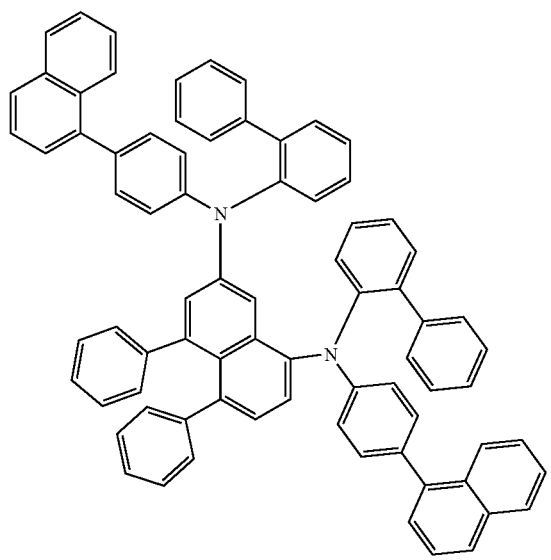

-continued
6-24
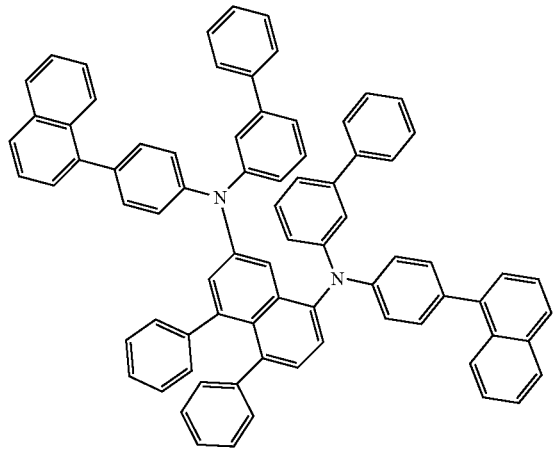
6-25
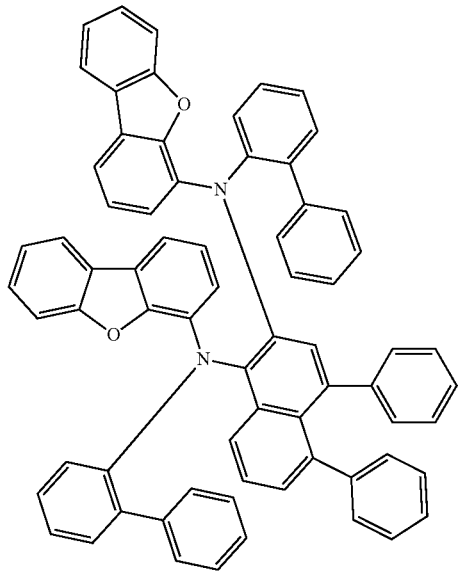
6-26
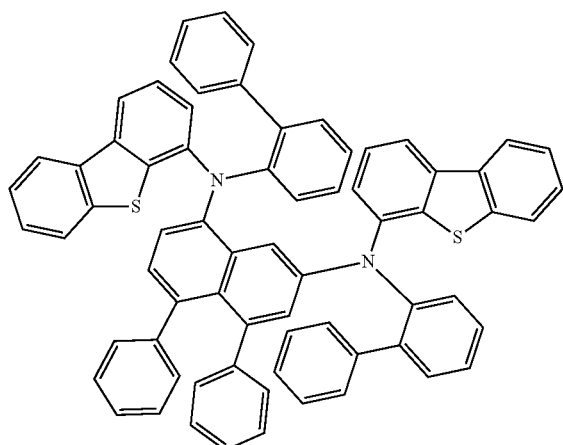
6-27
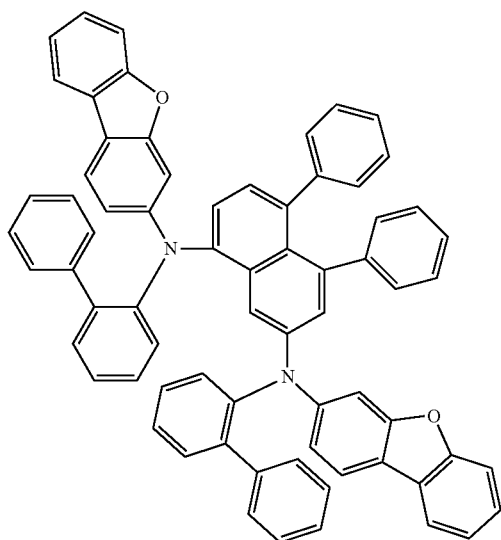
6-28
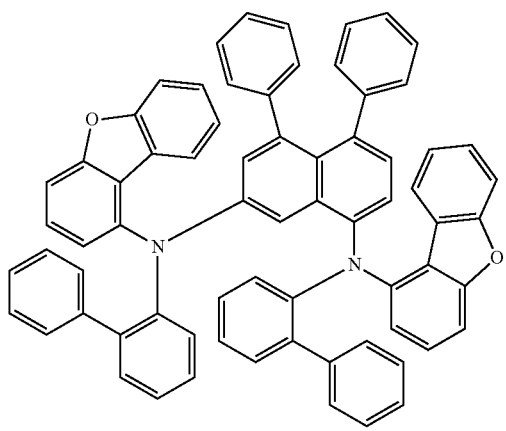
6-29
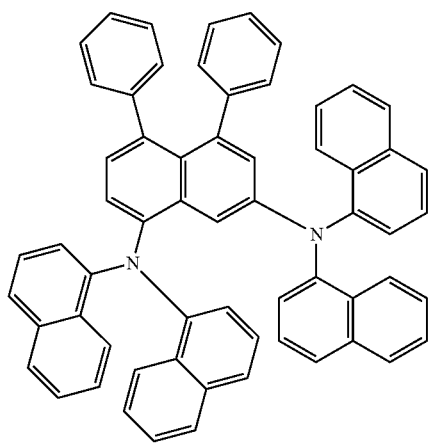

-continued
6-30
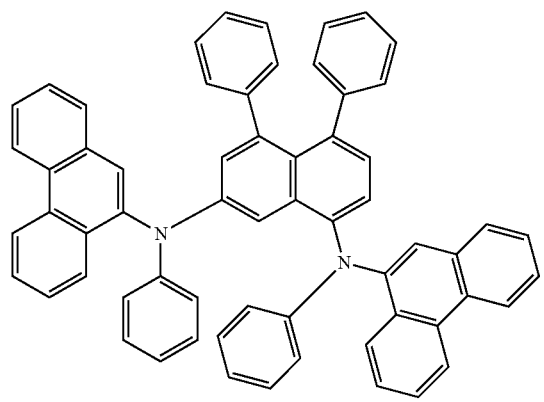
6-31
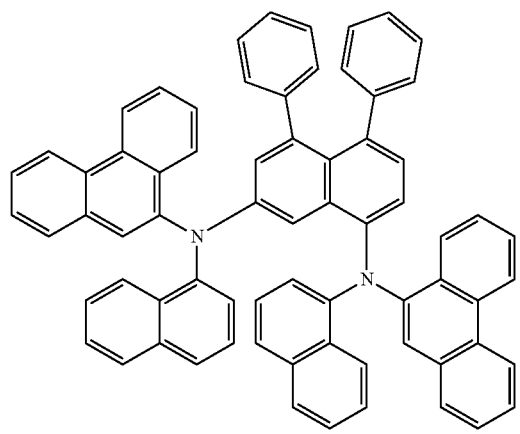
6-32
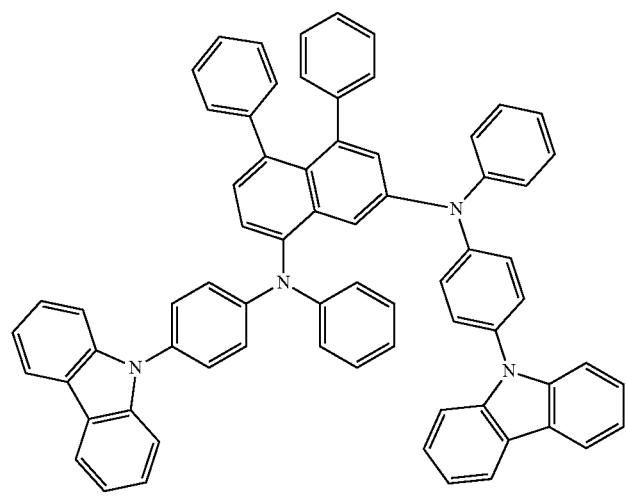
6-33
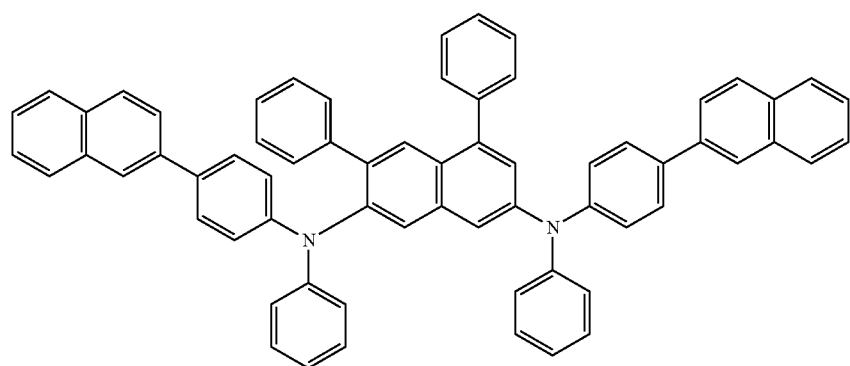

-continued
6-34
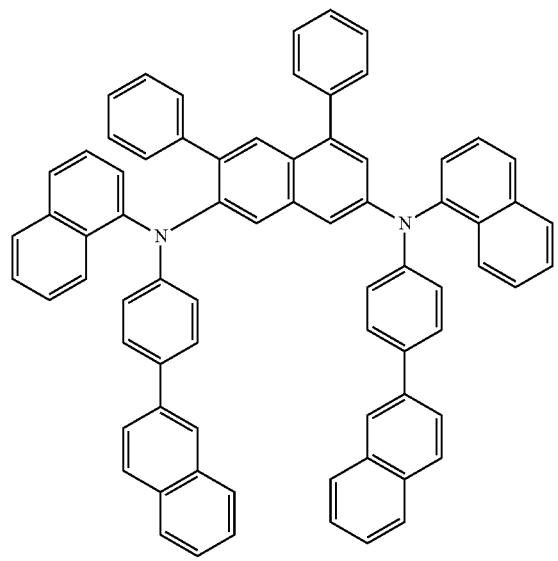
6-35
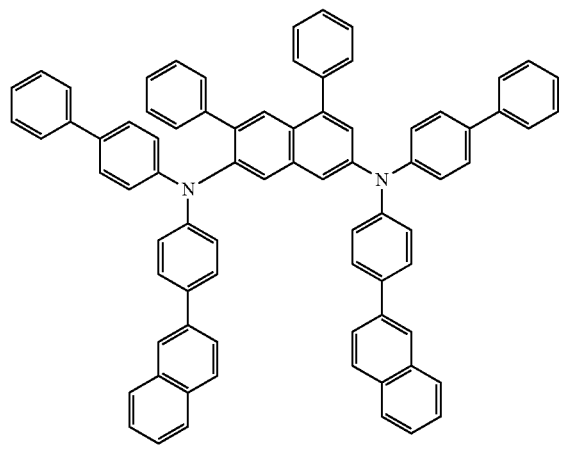
7-1
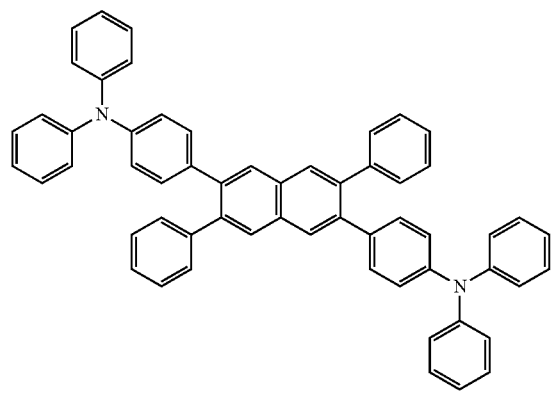
7-2
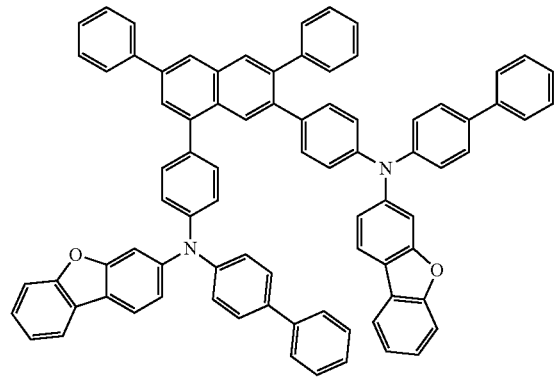
7-3
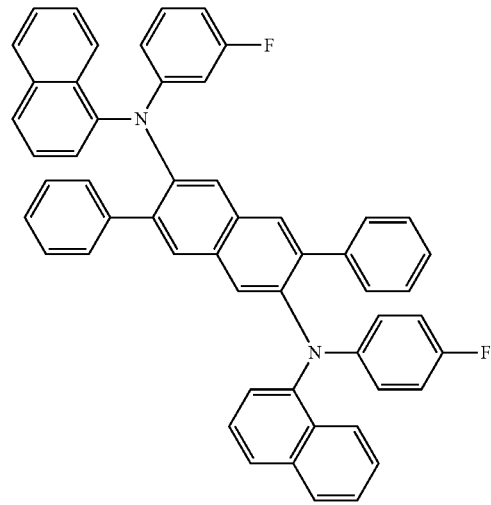
7-4
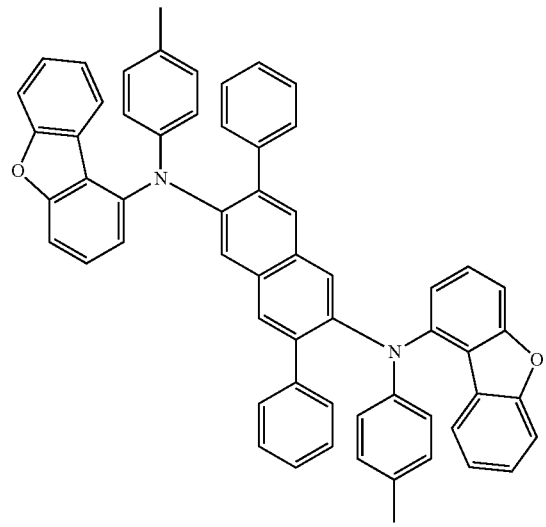

199
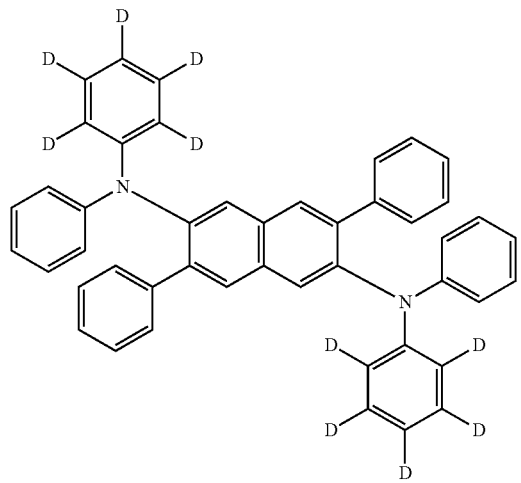
7-5
-continued
200
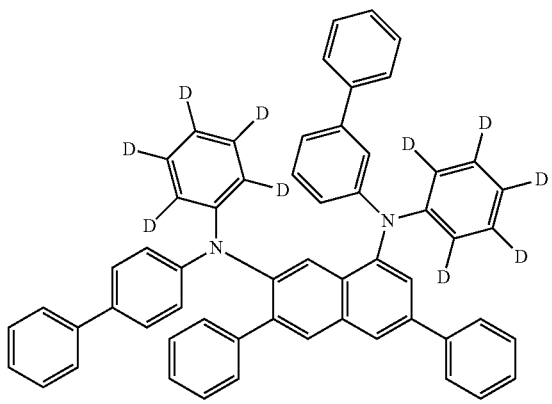
7-6
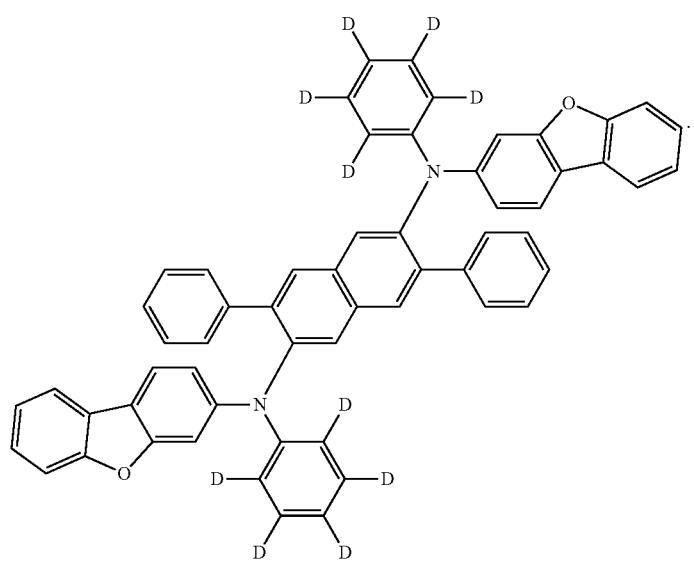
7-7
7. A diamine compound represented by one of Formulas 3-1, 3-2, 5 to 8, 9-1, 10, and 11:
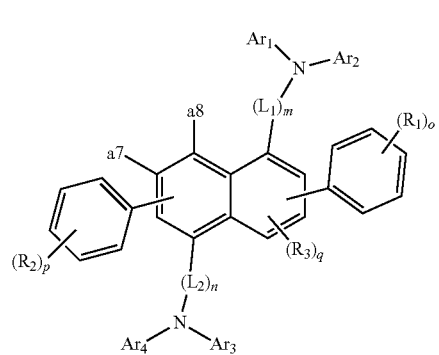
[Formula 3-1]
-continued
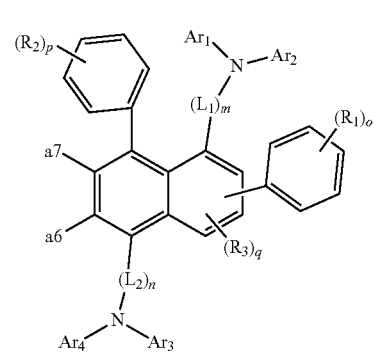
[Formula 3-2]

-continued

[Formula 5]

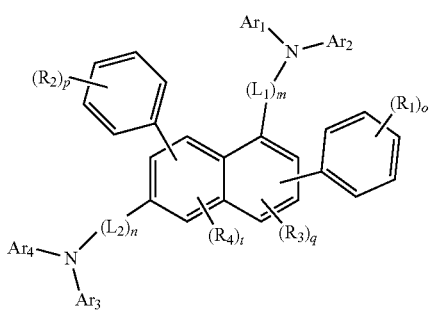

[Formula 6]

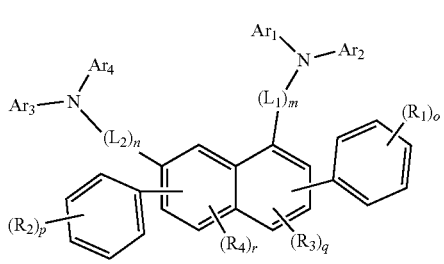

[Formula 7]

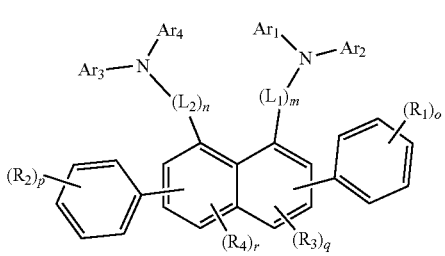

[Formula 8]

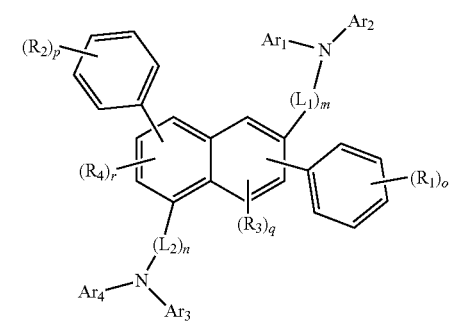

[Formula 9-1]

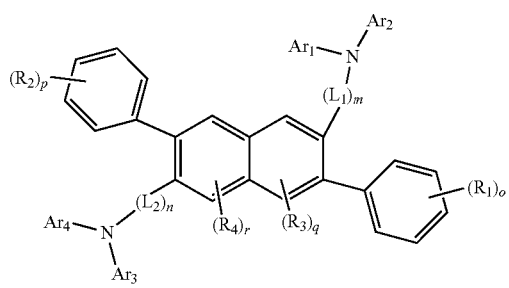

-continued

[Formula 10]

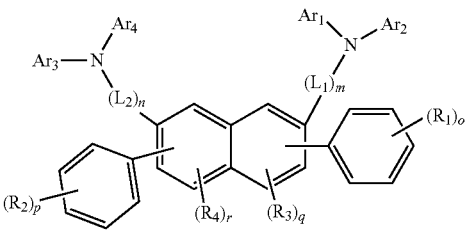

[Formula 11]

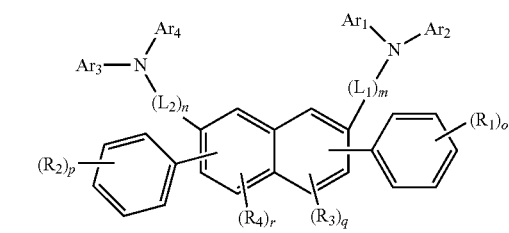

wherein in Formulas 3-1, 3-2, 5 to 8, 9-1, 10, and 11, a6 to a8 are each independently a hydrogen atom or a deuterium atom, $L_1$ and $L_2$ are each independently a direct linkage, a substituted or unsubstituted arylene group having 6 to 30 ring-forming carbon atoms, or a substituted or unsubstituted heteroarylene group having 2 to 30 ring-forming carbon atoms, m and n are each independently an integer from 0 to 4, $Ar_1$ to $Ar_4$ are each independently a substituted or unsubstituted aryl group having 6 to 30 ring-forming carbon atoms, or a substituted or unsubstituted heteroaryl group having 2 to 30 ring-forming carbon atoms; except that in Formula 4, at least one of $Ar_1$ to $Ar_4$ is a substituted or unsubstituted heteroaryl group having 2 to 30 ring-forming carbon atoms, $R_1$ and $R_2$ are each independently a hydrogen atom, a deuterium atom, a halogen atom, a substituted or unsubstituted alkyl group having 1 to 20 carbon atoms, a substituted or unsubstituted aryl group having 6 to 30 ring-forming carbon atoms, a substituted or unsubstituted heteroaryl group having 2 to 30 ring-forming carbon atoms, or bonded to an adjacent group to form a ring, and p are each independently an integer from 0 to 5, $R_3$ and $R_4$ are each independently a hydrogen atom or a deuterium atom, and q and r are each independently an integer from 0 to 2.

8. The diamine compound of claim 7, wherein $L_1$ and $L_2$ are each independently a direct linkage, a substituted or unsubstituted phenylene group, or a substituted or unsubstituted biphenylene group.

9. The diamine compound of claim 7, wherein the diamine compound is selected from Compound Group 1:

[Compound Group 1]
1-1
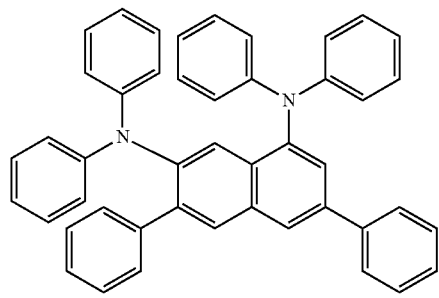
1-2
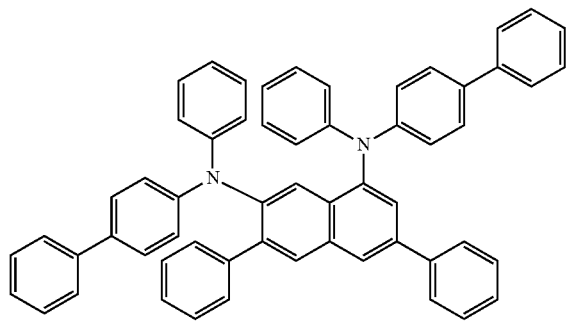
1-3
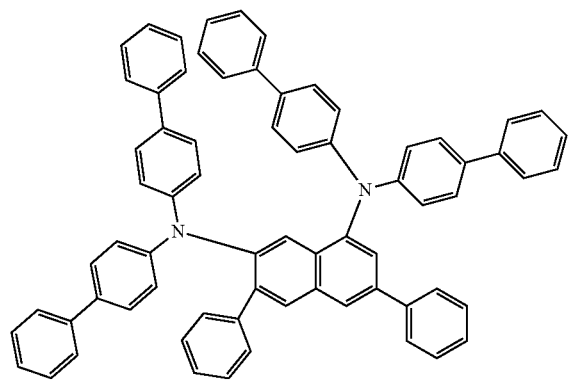
1-4
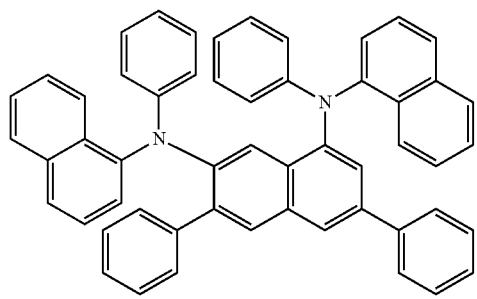
1-5
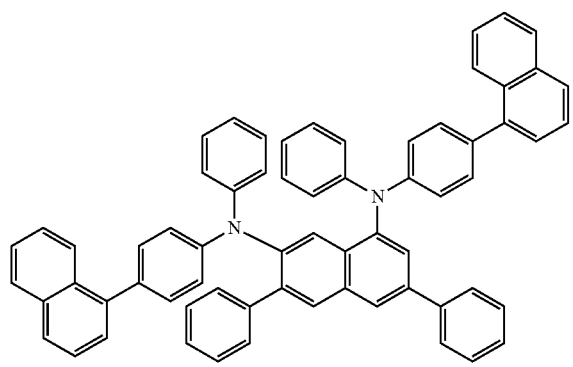
1-6
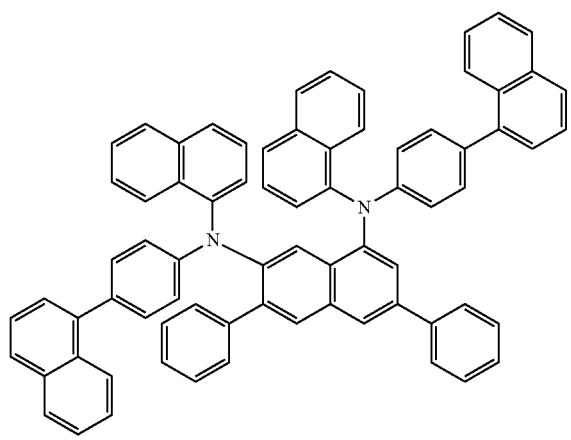

-continued
1-7
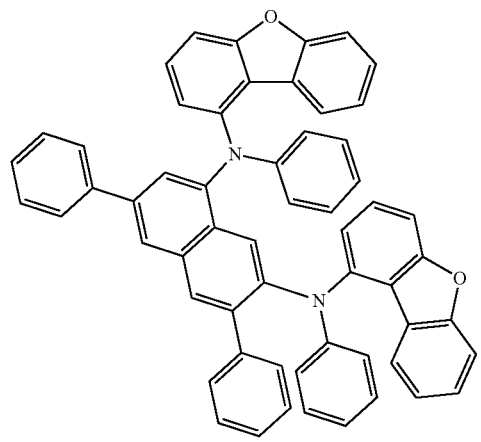
1-8
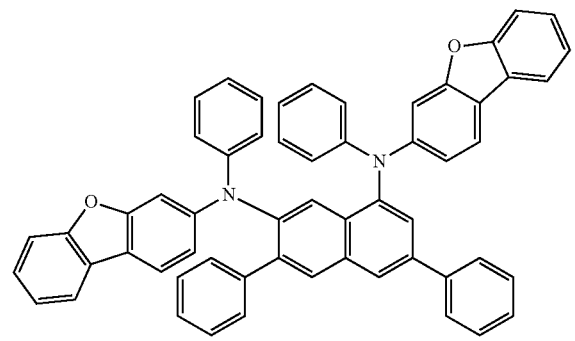
1-9
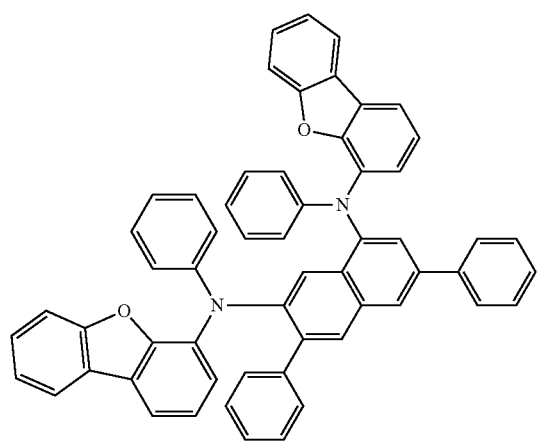
1-10
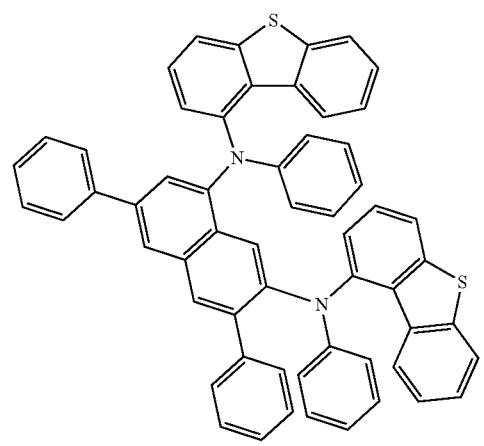
1-11
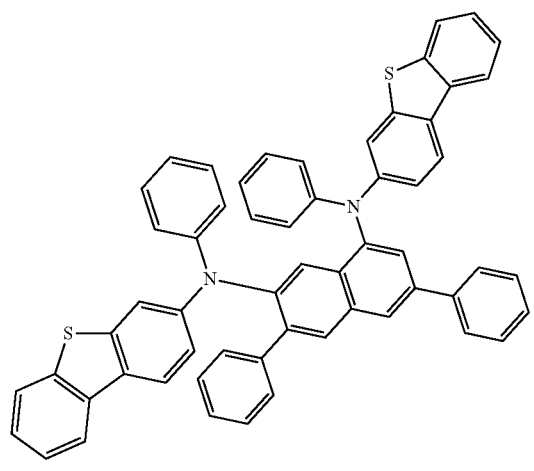
1-12
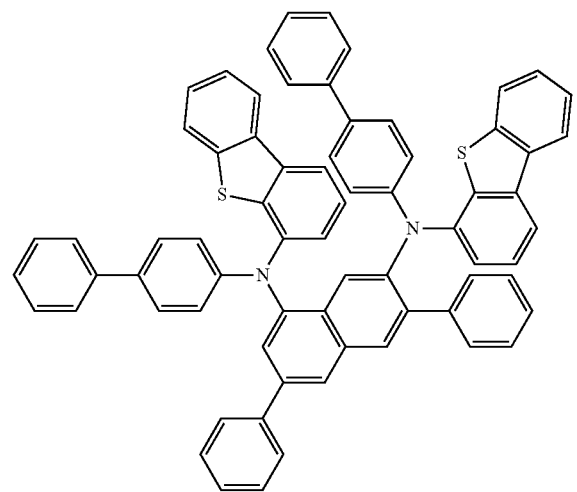

-continued
1-13
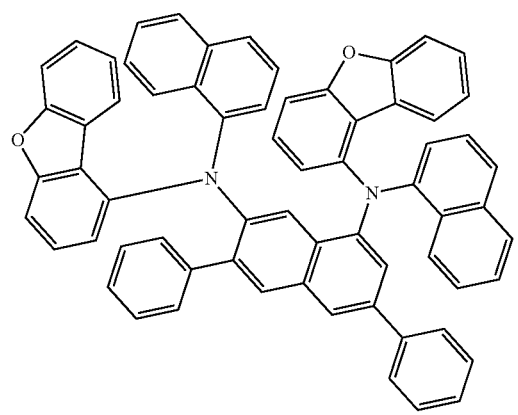
1-14
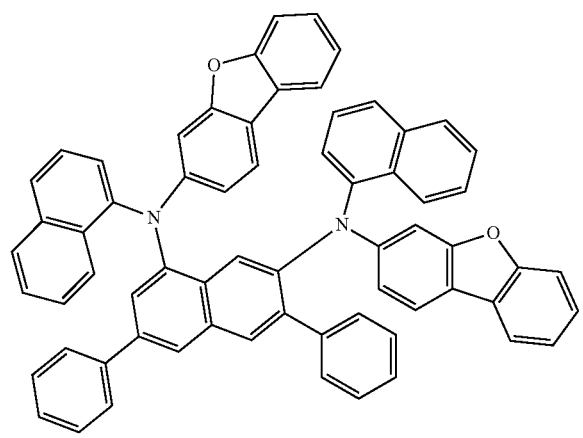
1-15
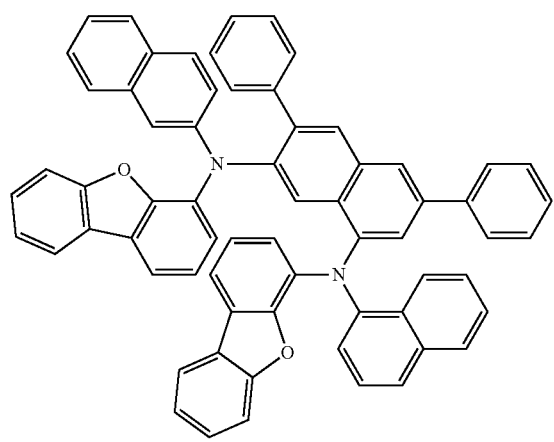
1-16
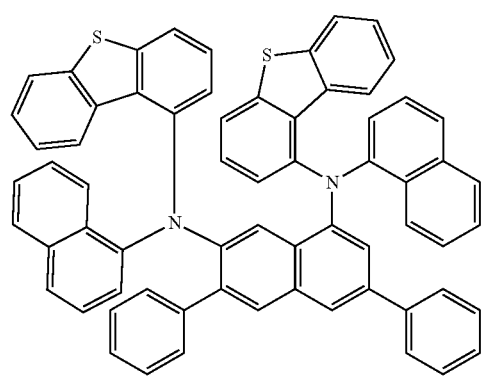
1-17
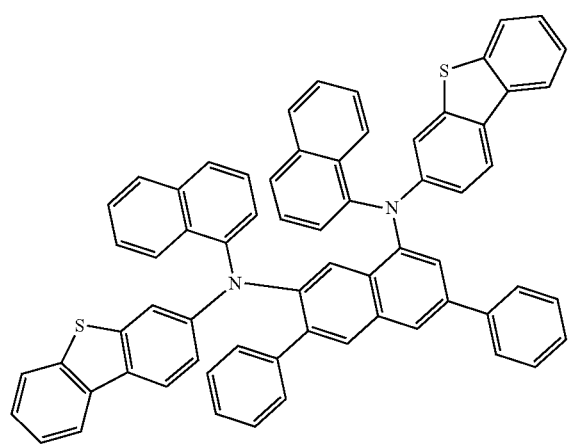
1-18
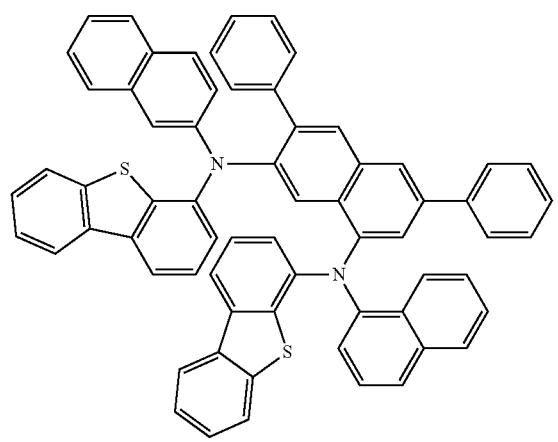

-continued
1-19
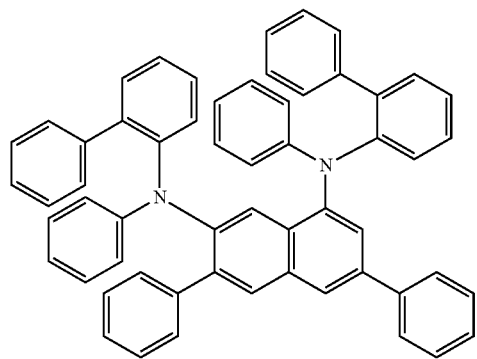
1-20
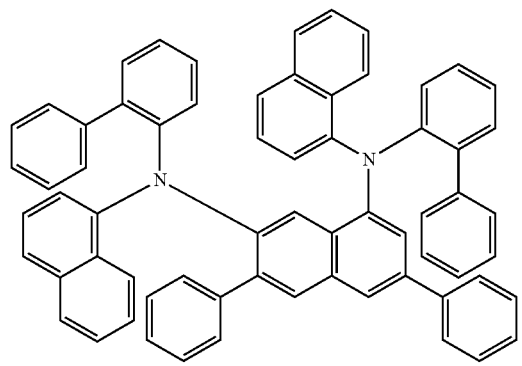
1-21
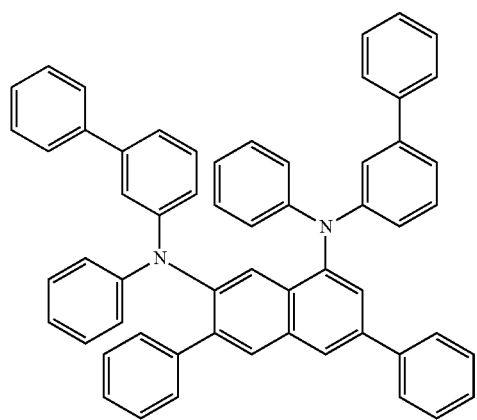
1-22
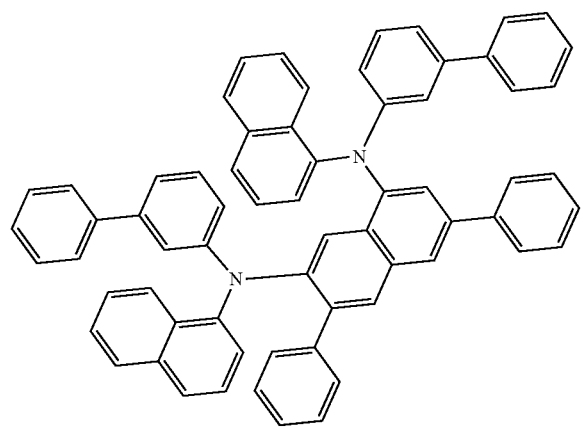
1-23
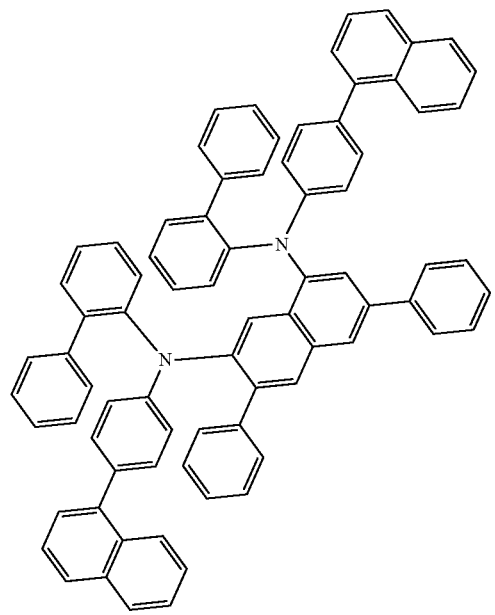
1-24
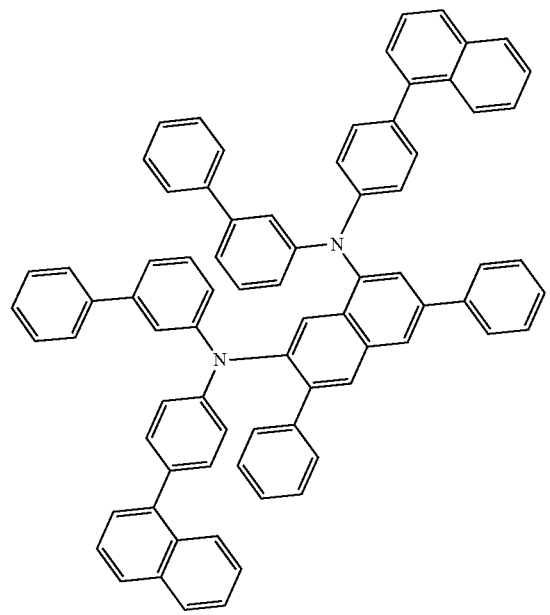

-continued
1-25
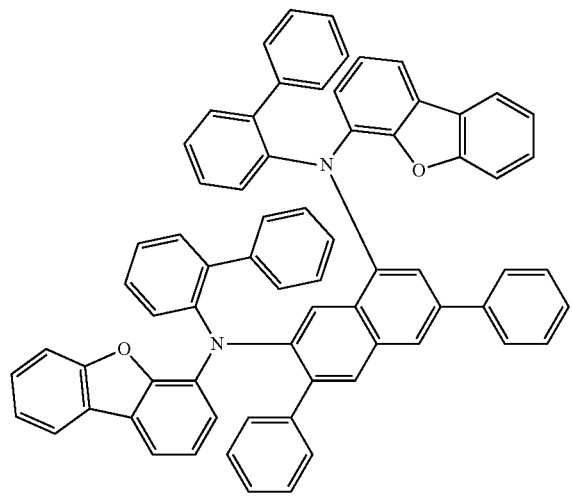
1-26
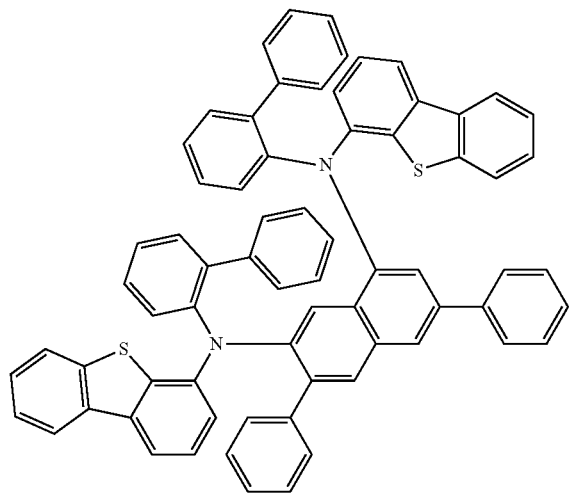
1-27
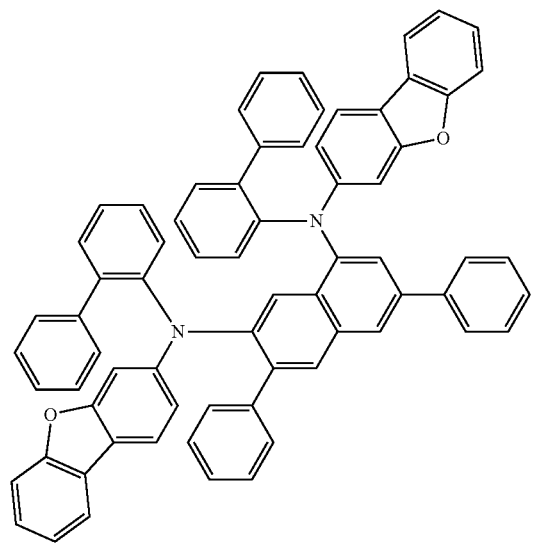
1-28
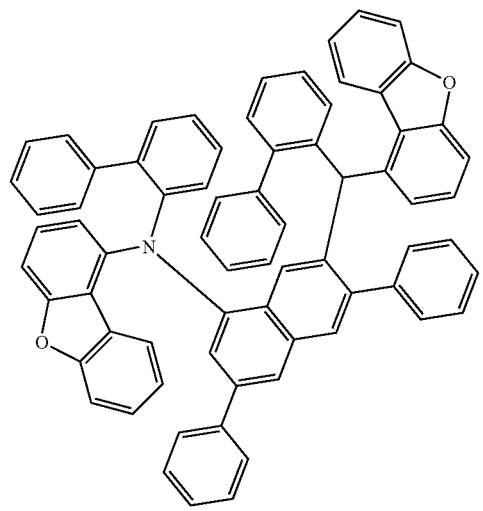
1-29
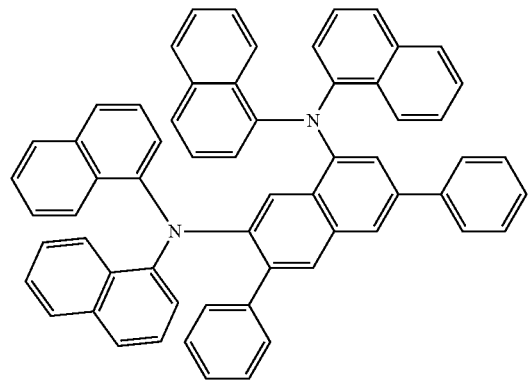
1-30
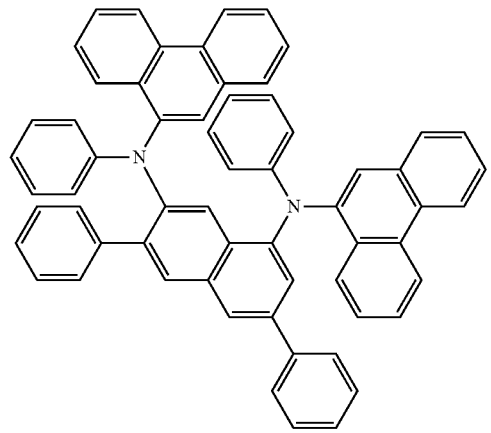

-continued
1-31
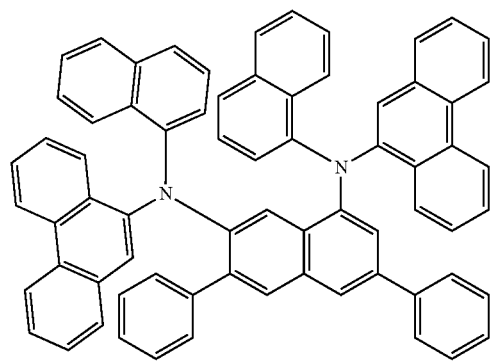
1-32
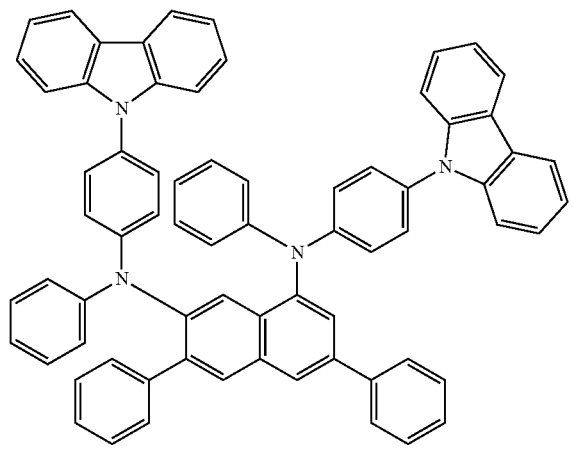
1-33
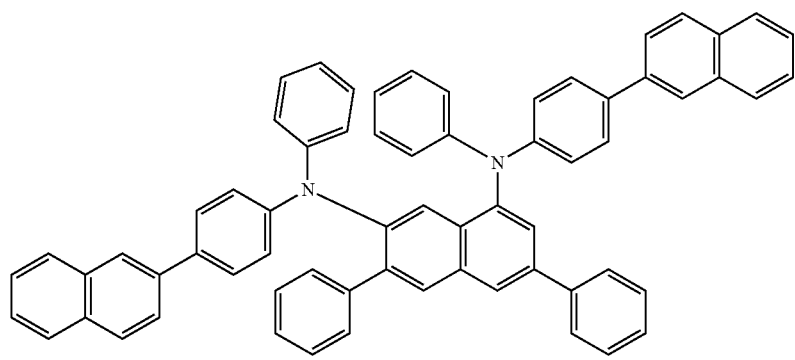
1-34
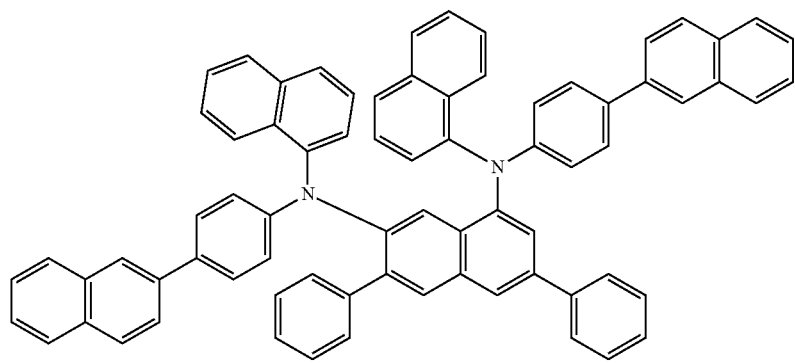
1-35
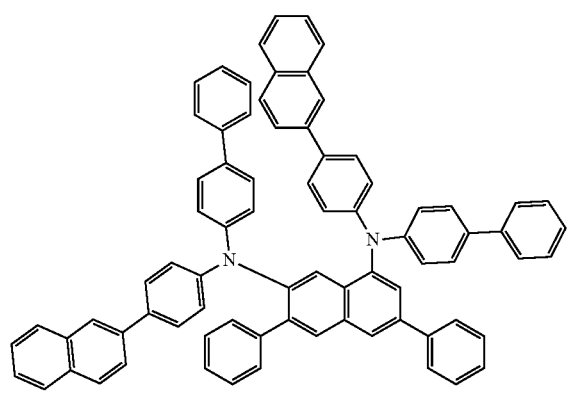
2-1
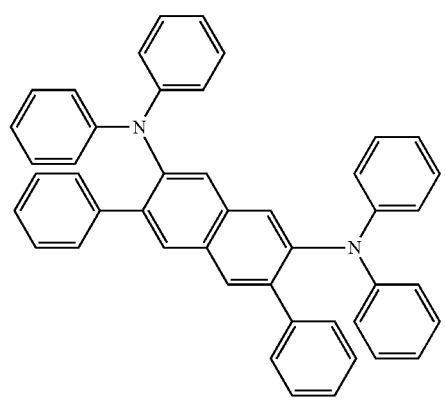

-continued
2-2
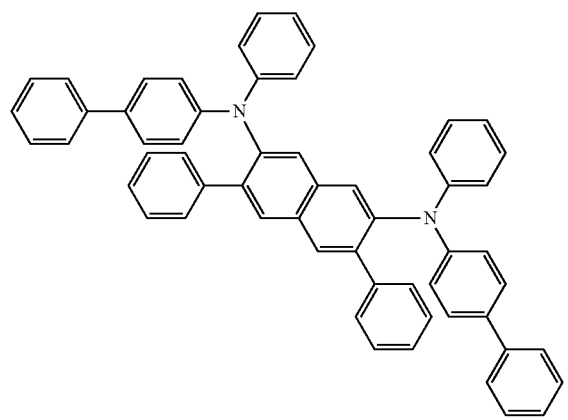
2-3
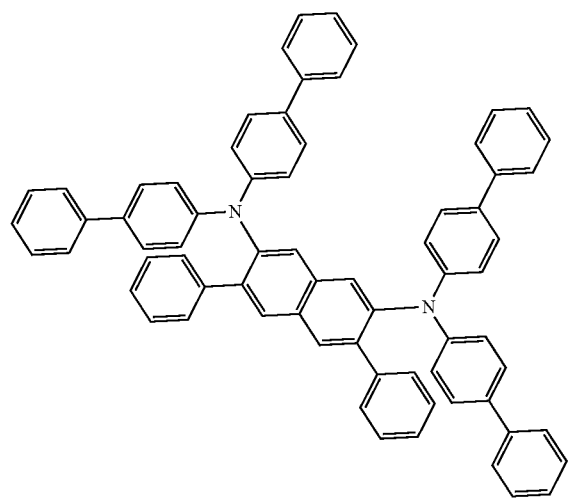
2-4
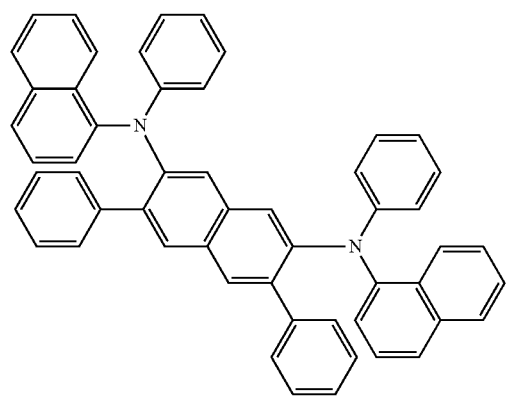
2-5
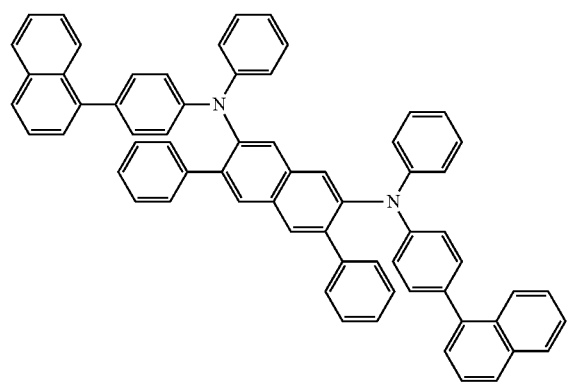
2-6
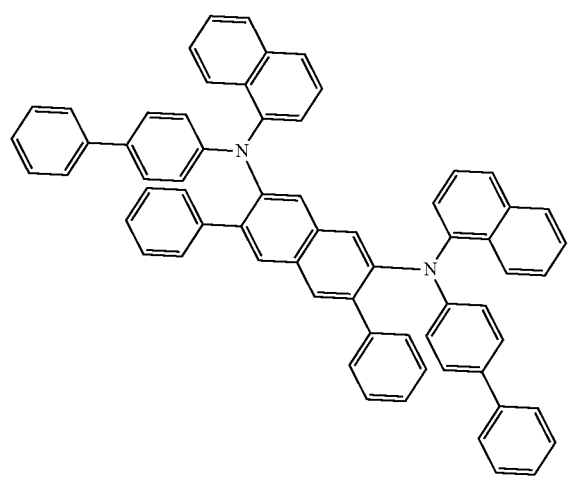
2-7
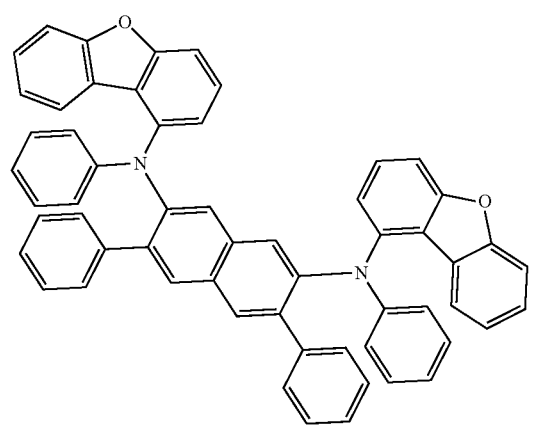

2-8
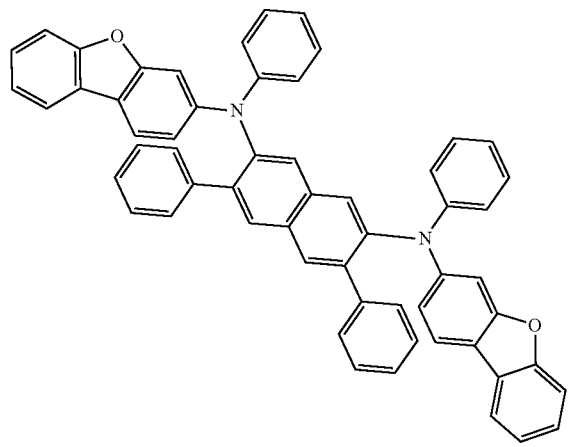
2-9
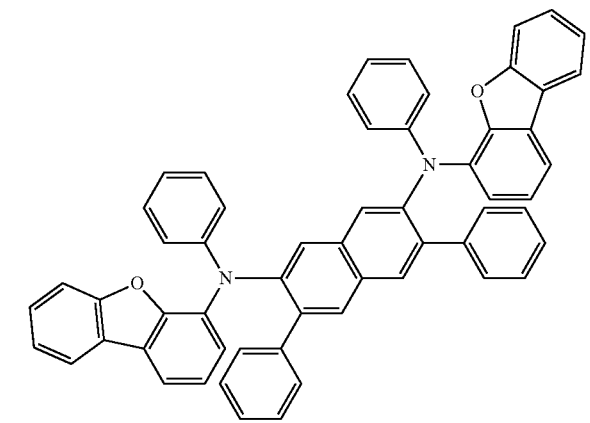
2-10
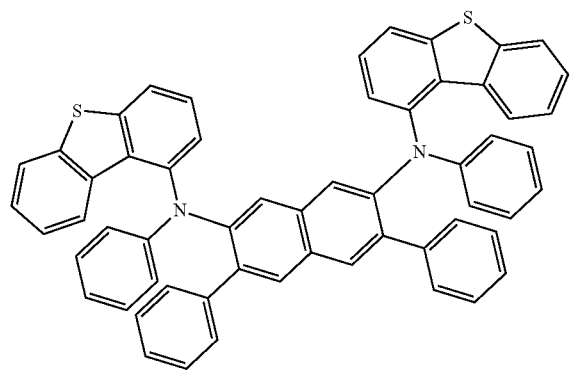
2-11
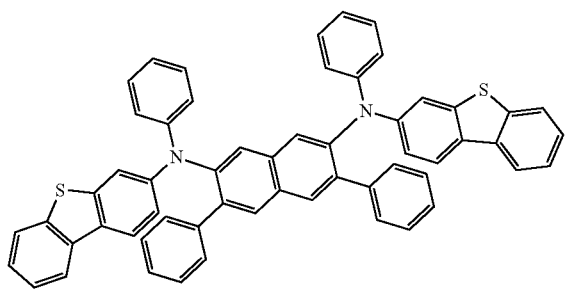
2-12
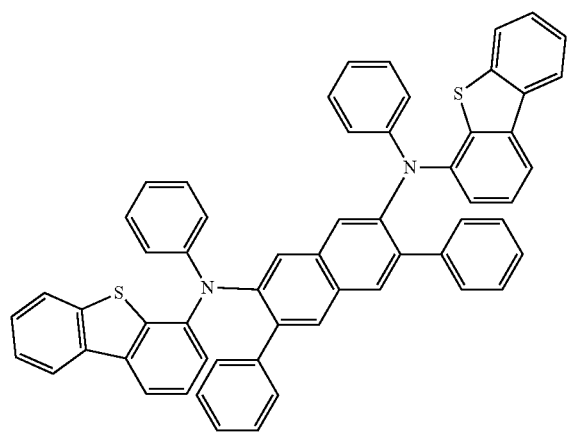
2-13
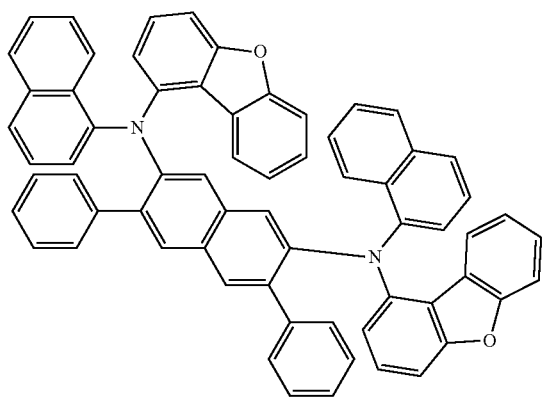

-continued
2-14
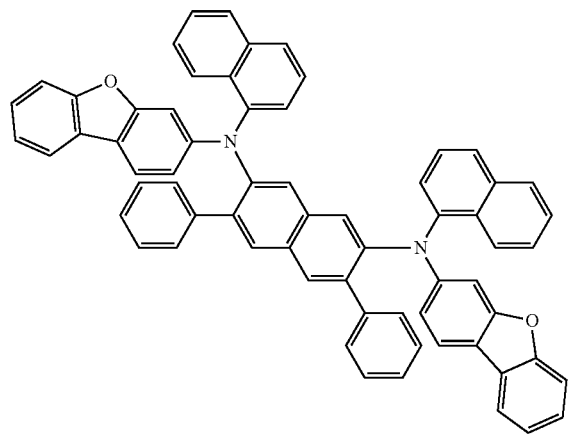
2-15
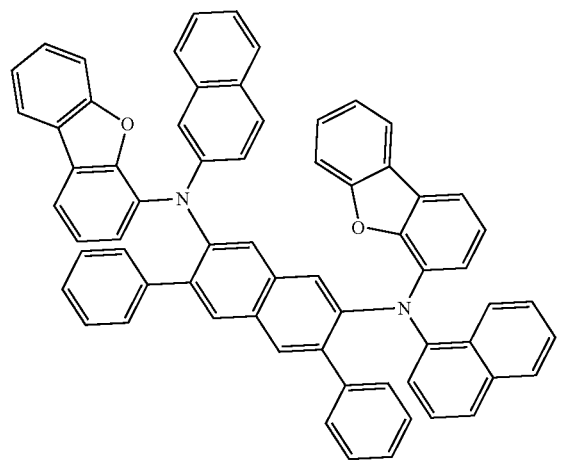
2-16
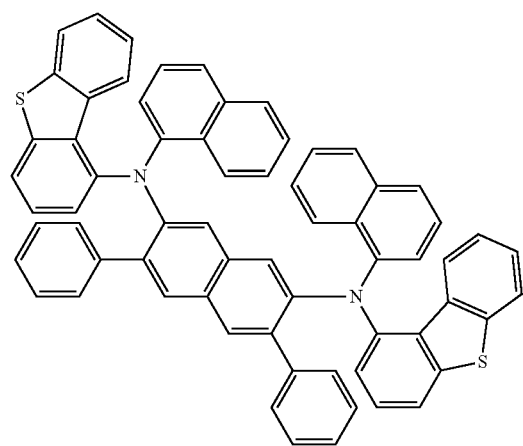
2-17
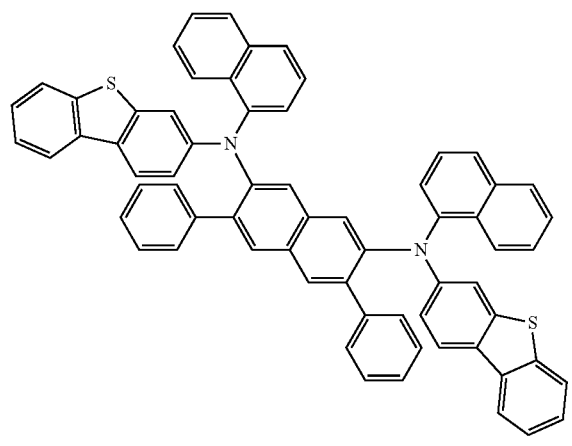
2-18
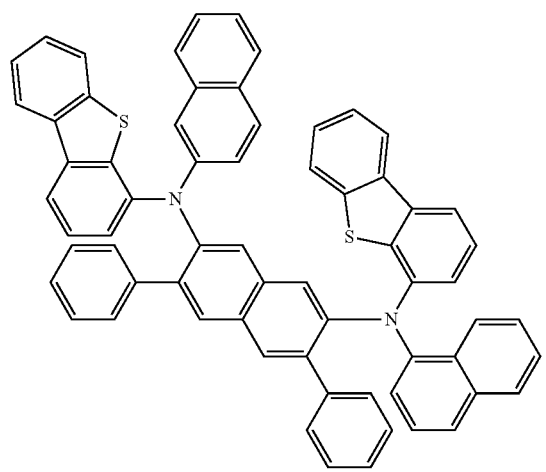
2-19
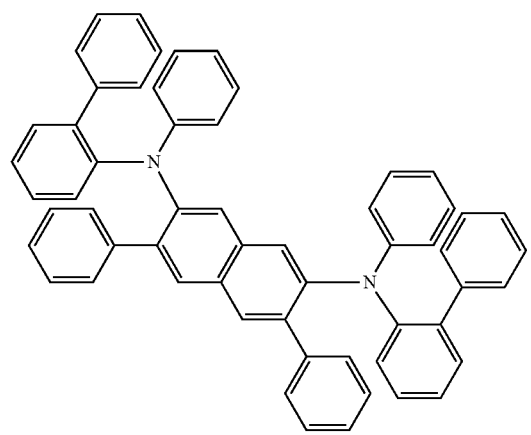

-continued
2-20
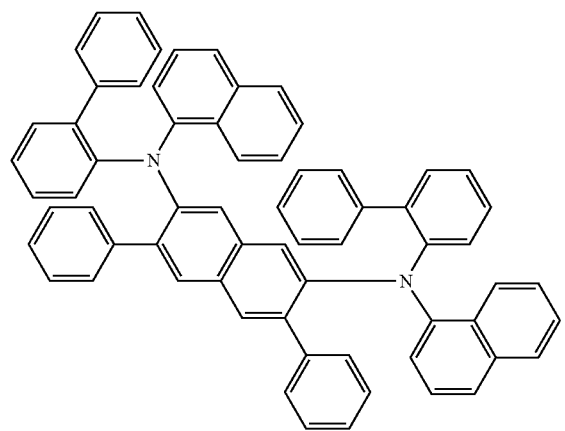
2-21
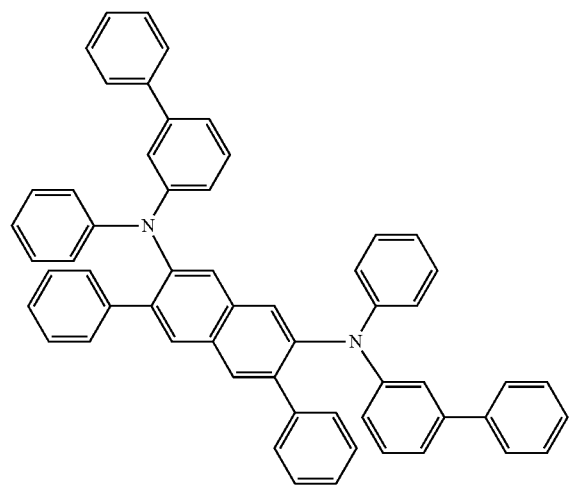
2-22
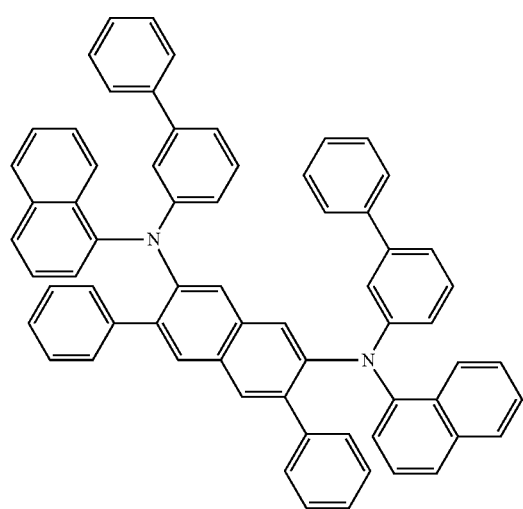
2-23
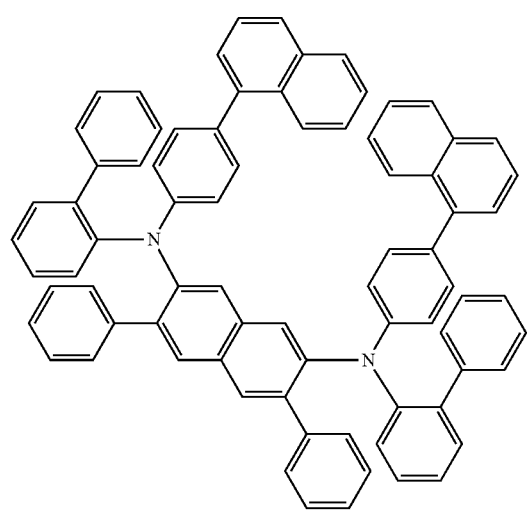
2-24
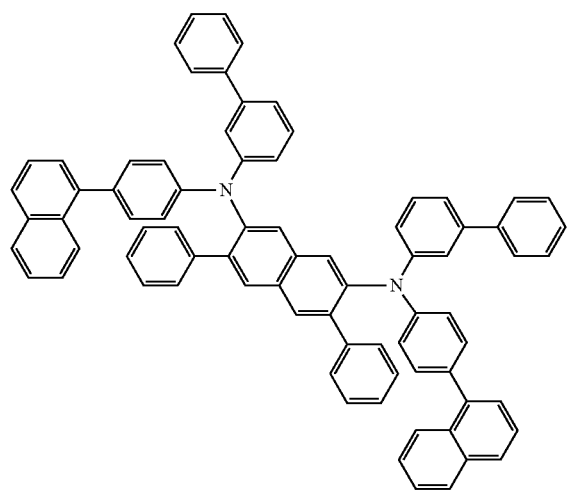
2-25
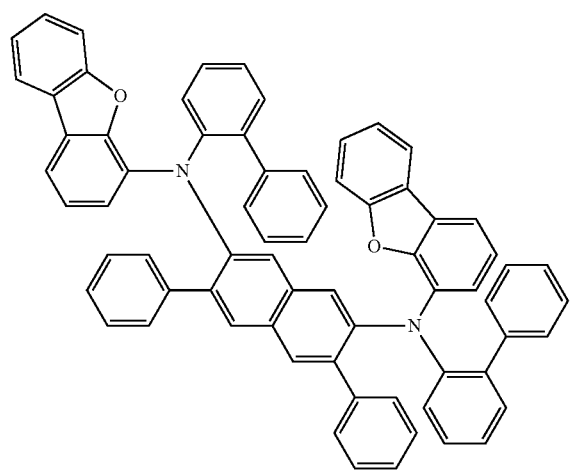

-continued
2-26
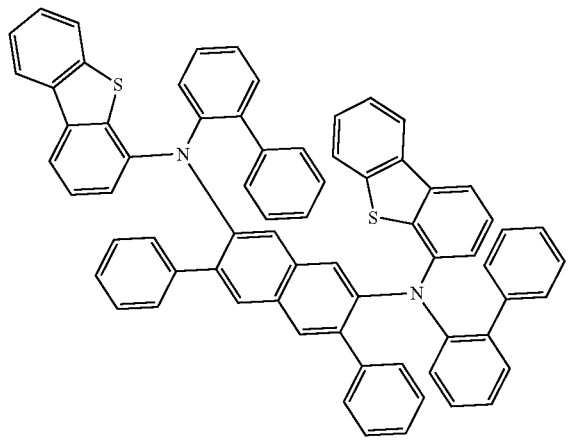
2-27
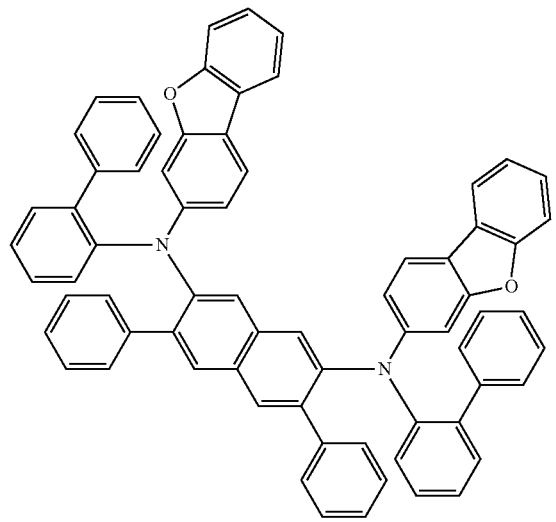
2-28
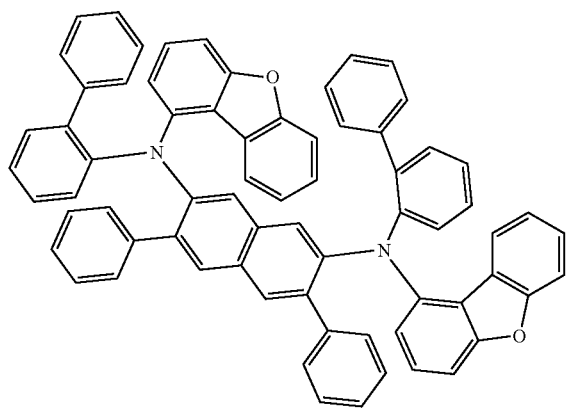
2-29
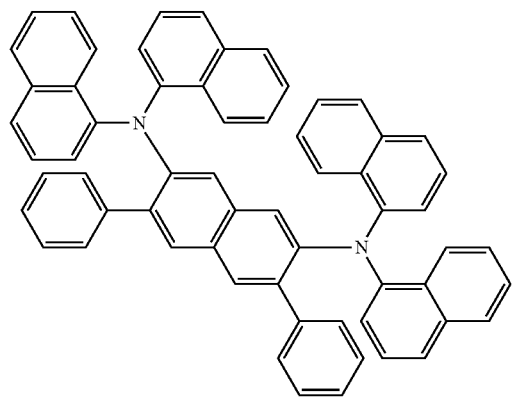
2-30
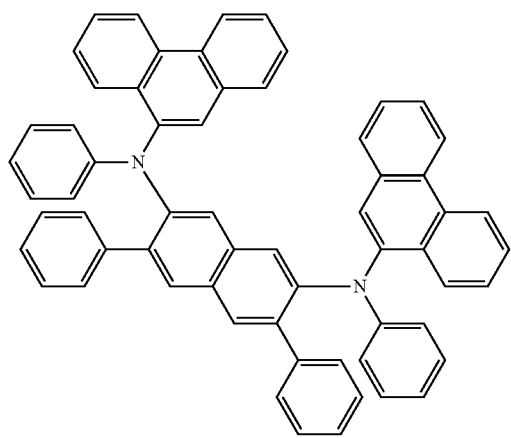
2-31
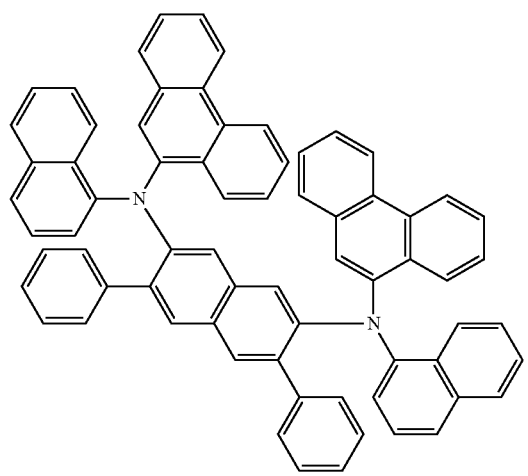

2-32
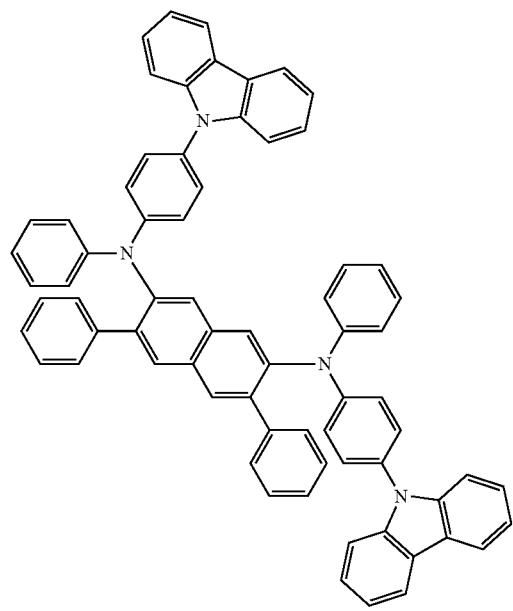
2-33
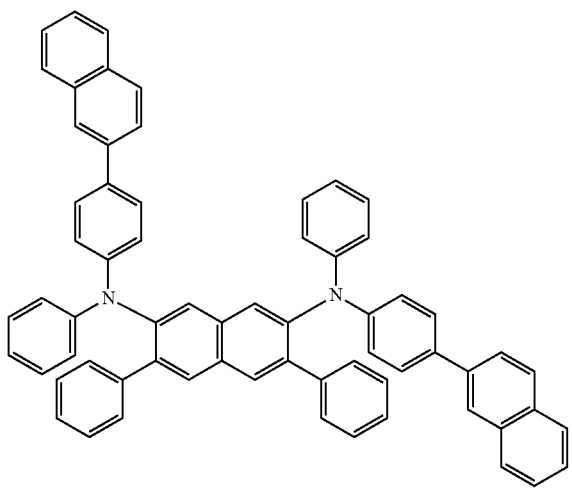
2-34
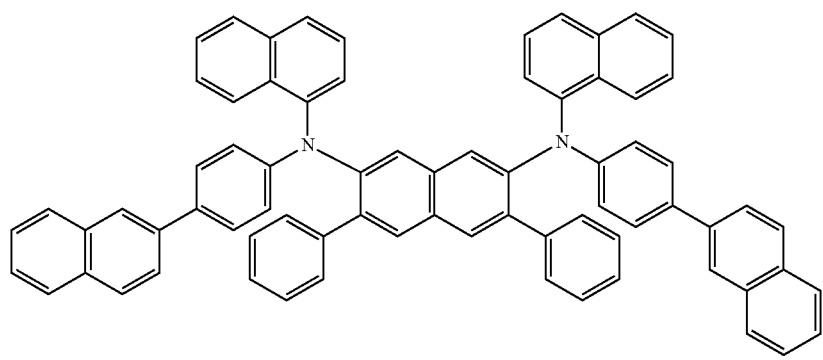
2-35
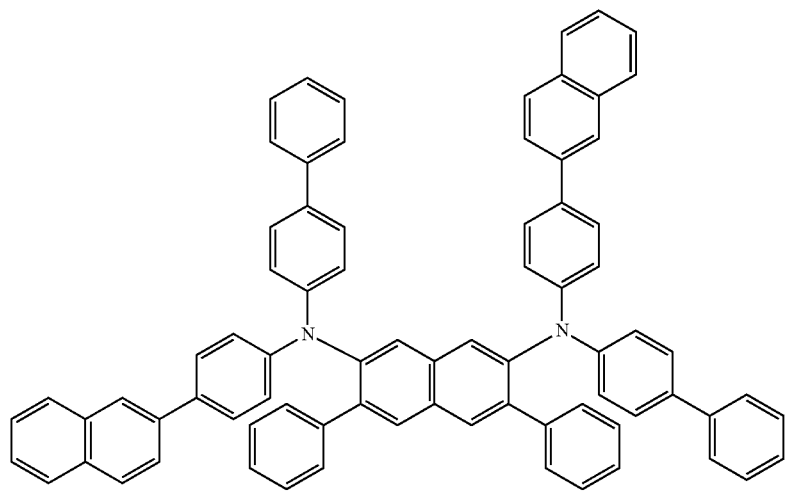

-continued
3-1
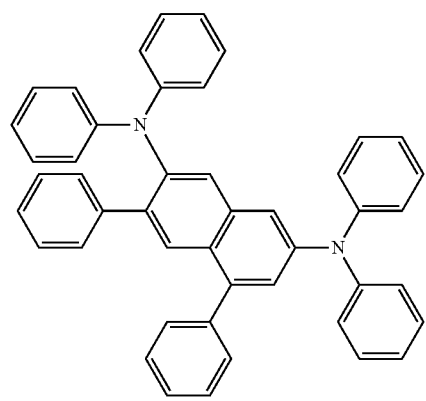
3-2
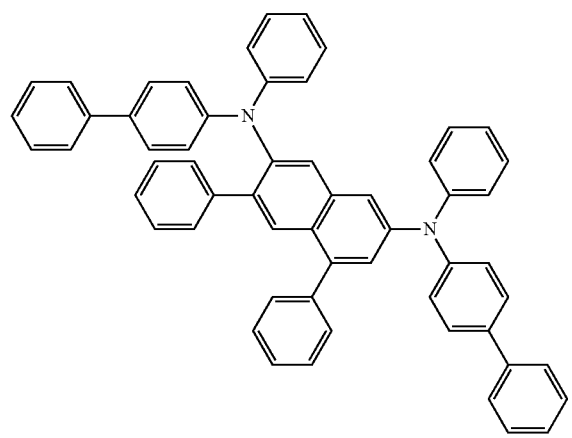
3-3
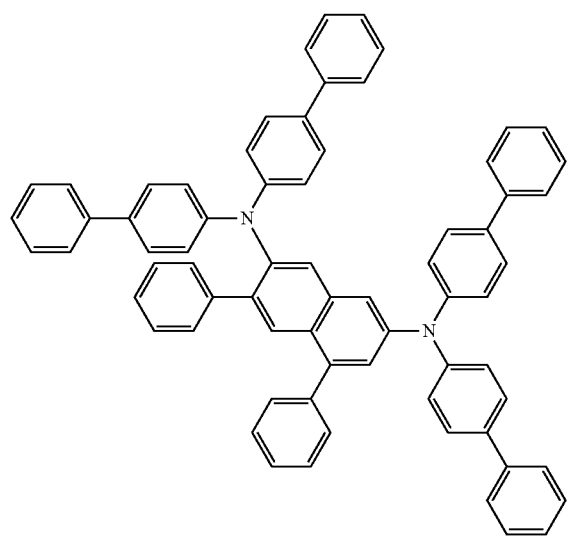
3-4
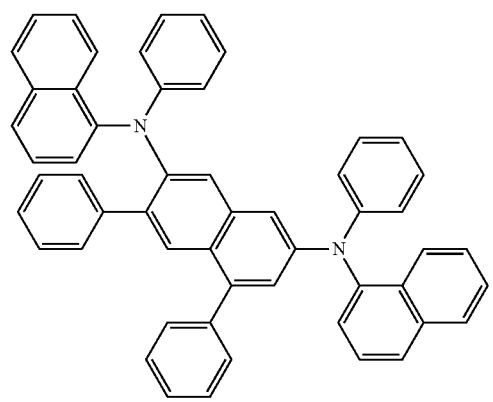
3-5
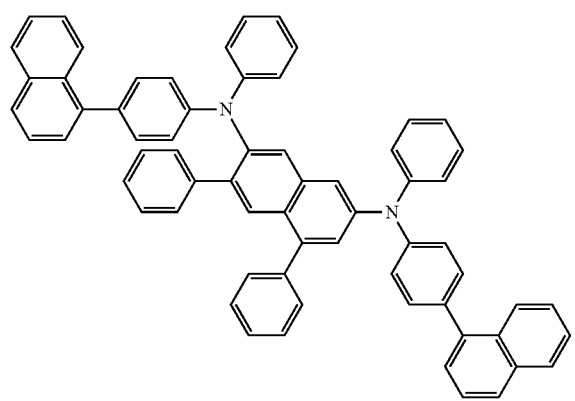
3-6
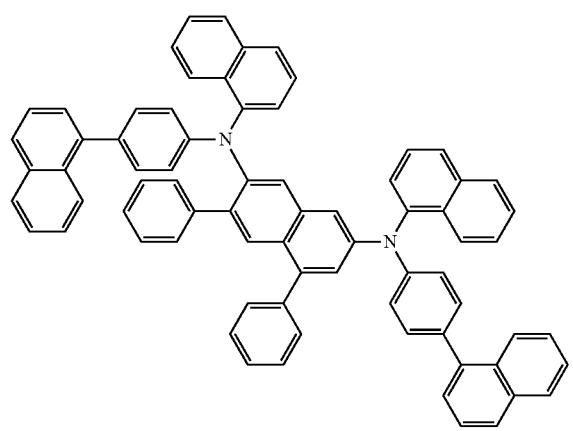

-continued
3-7
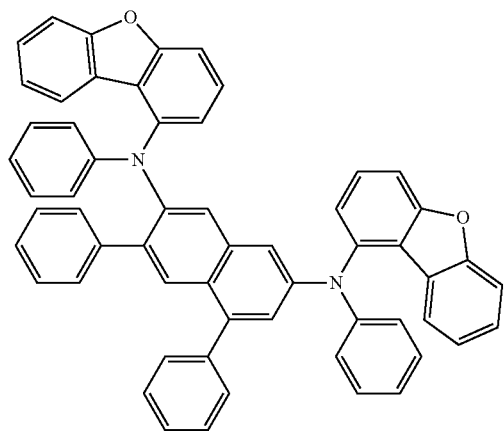
3-8
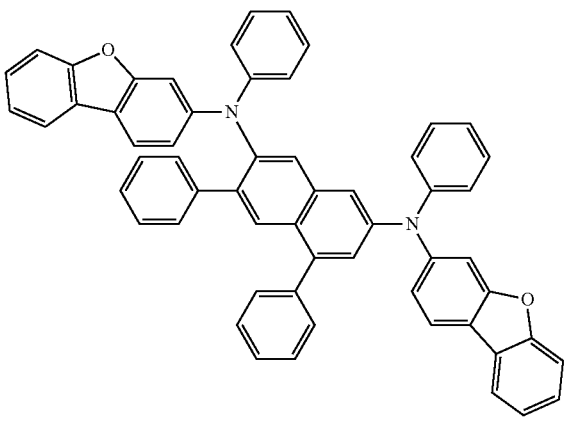
3-9
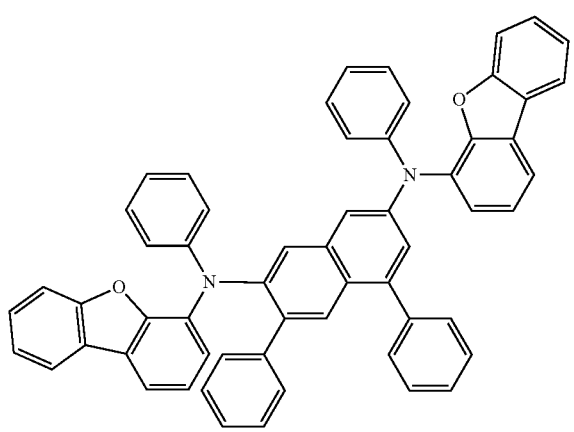
3-10
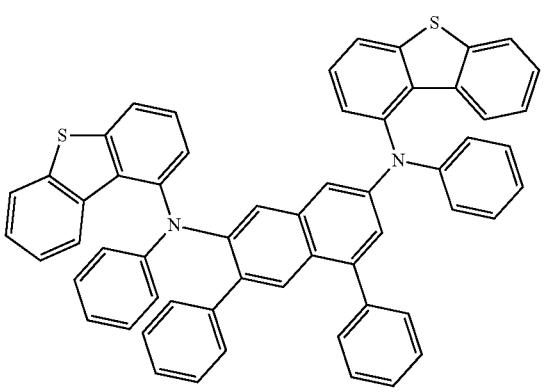
3-11
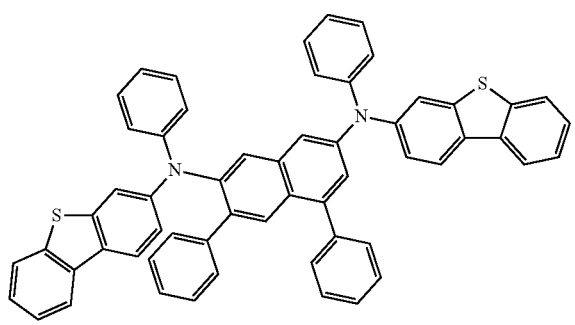
3-12
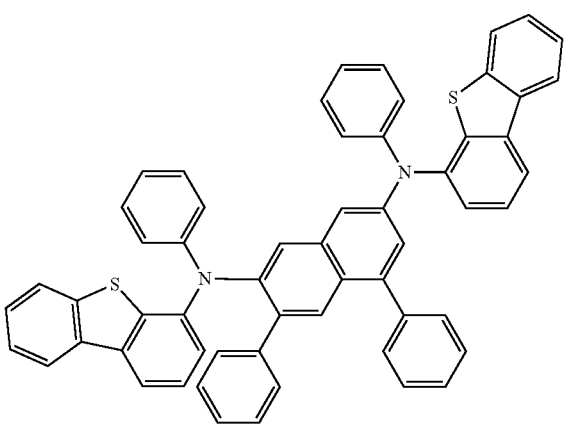

-continued
3-13
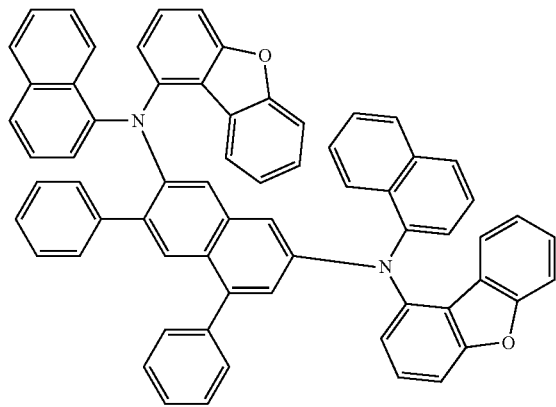
3-14
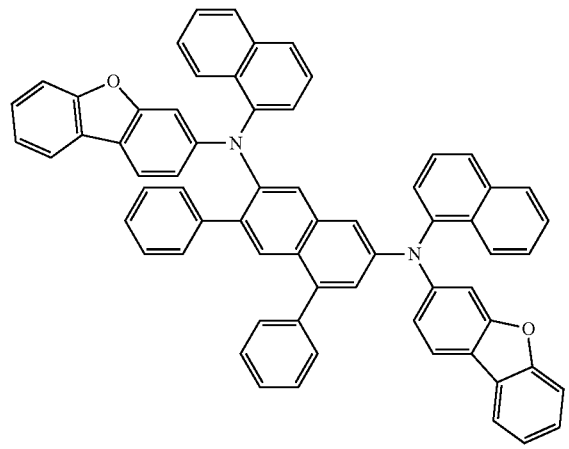
3-15
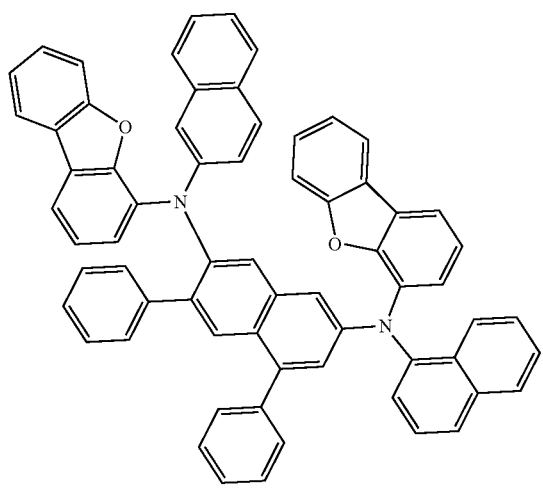
3-16
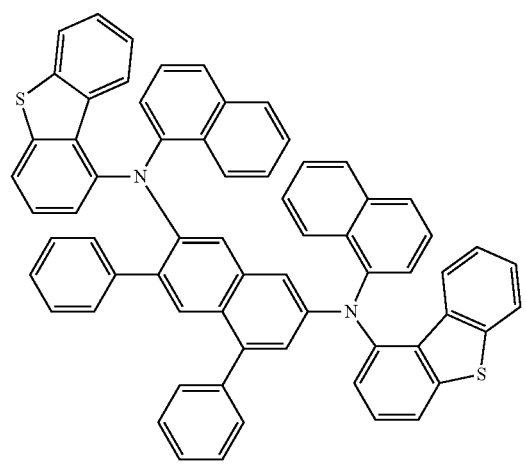
3-17
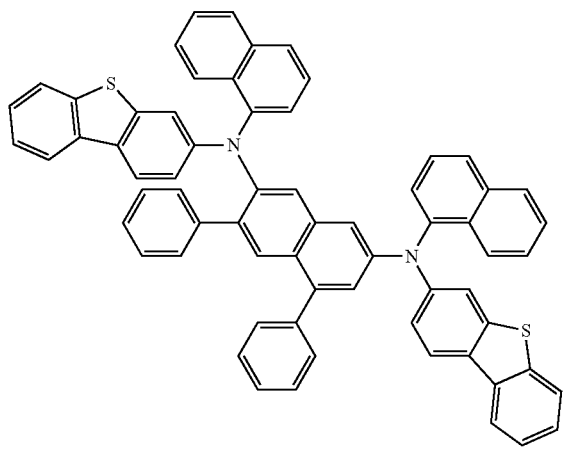
3-18
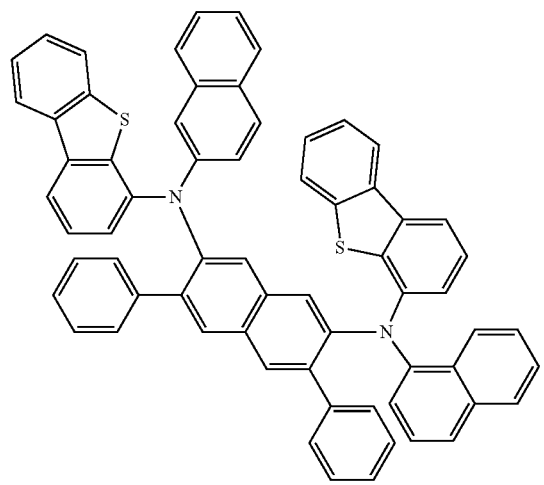

-continued
3-19
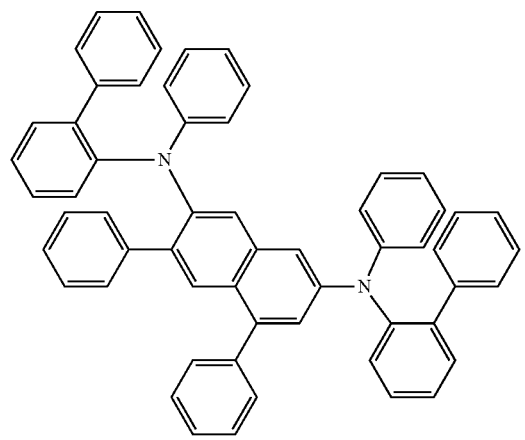
3-20
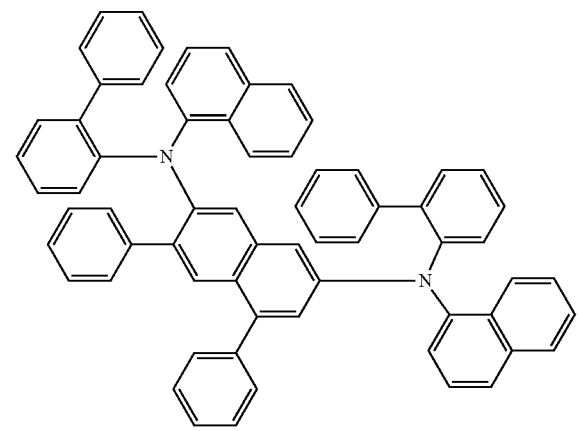
3-21
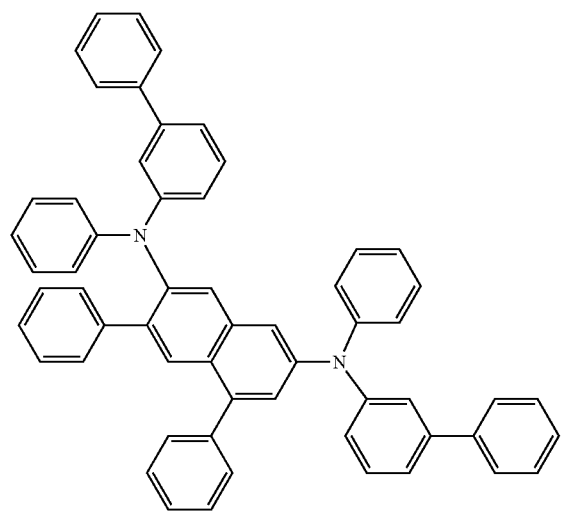
3-22
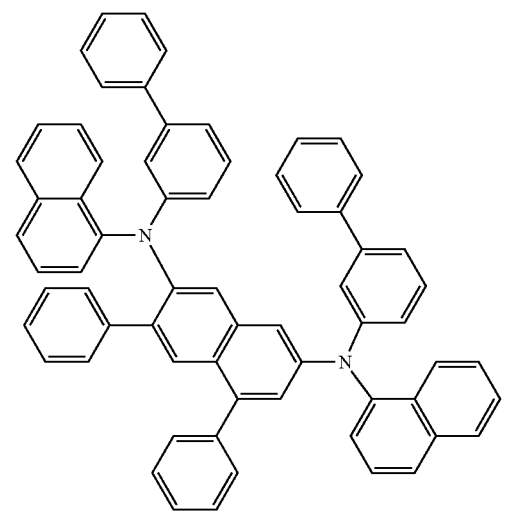
3-23
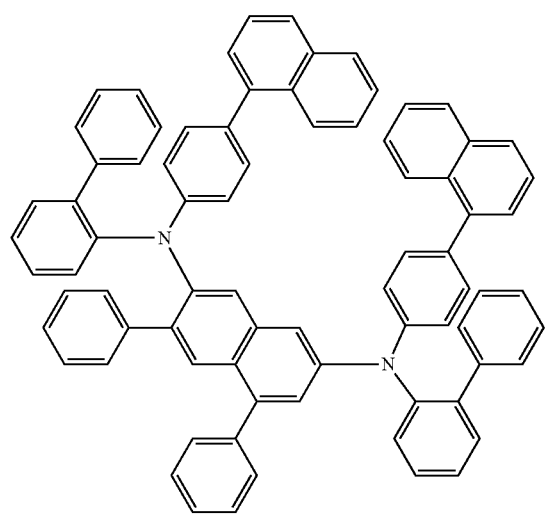
3-24
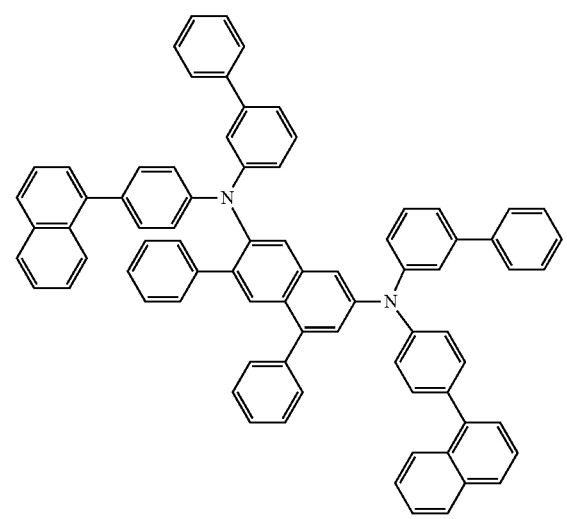

3-25
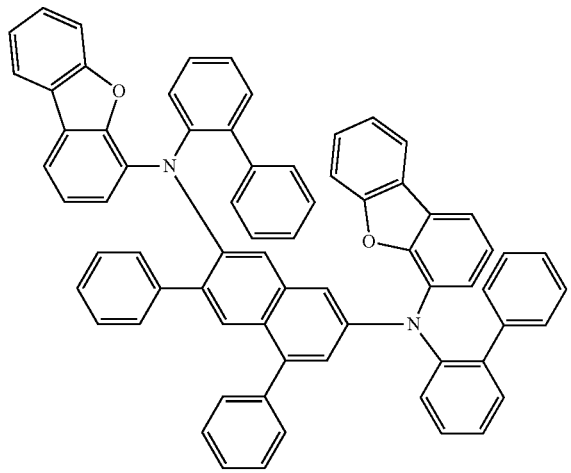
3-26
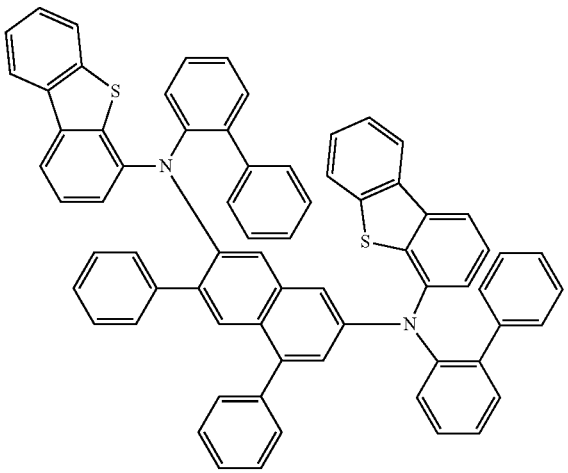
3-27
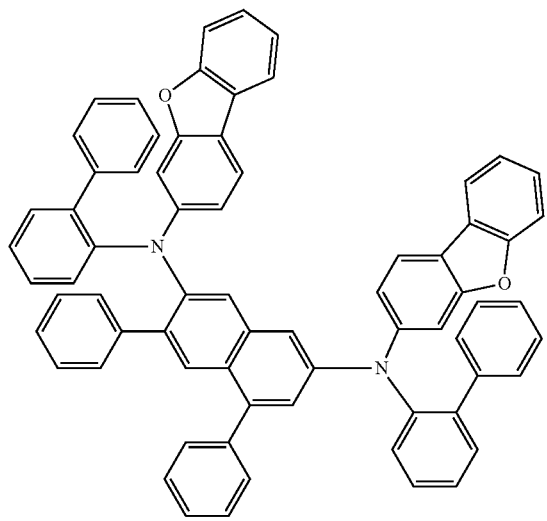
3-28
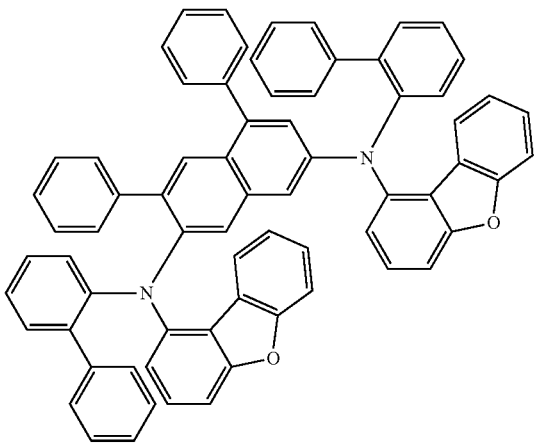
3-29
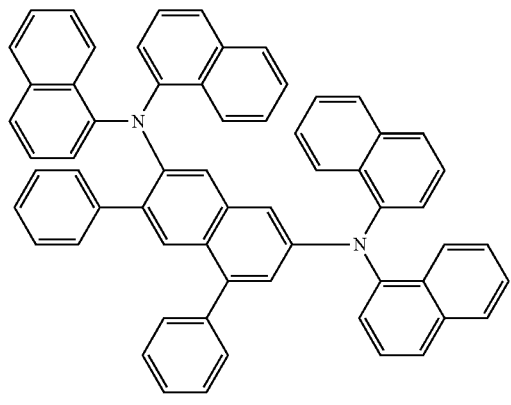
3-30
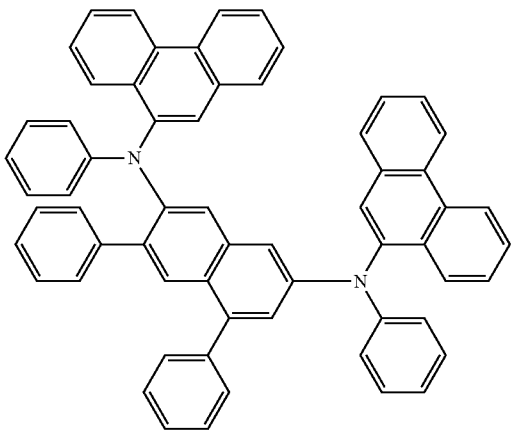

-continued
3-31
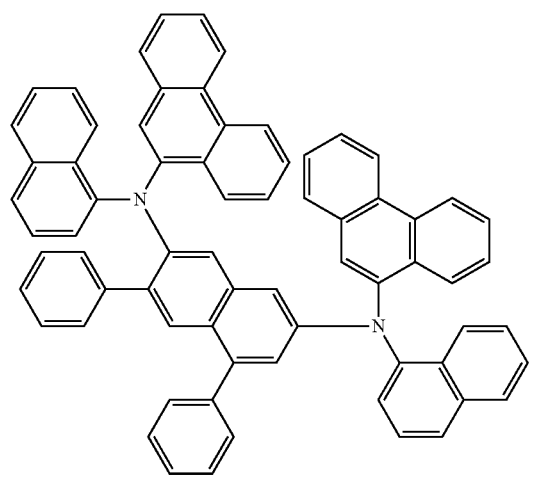
3-32
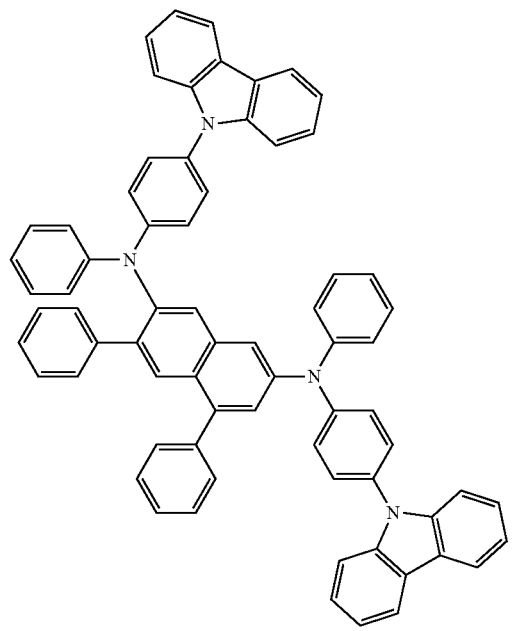
3-33
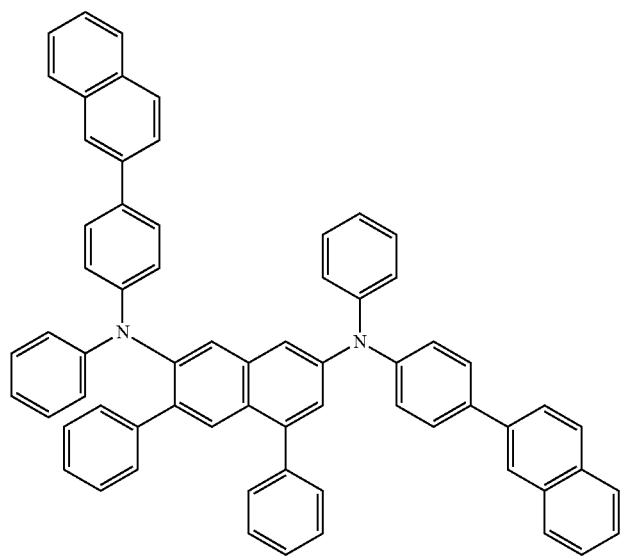
3-34
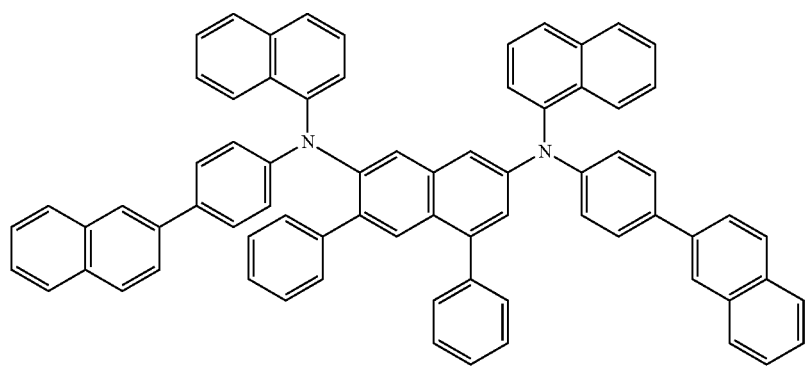

-continued
3-35
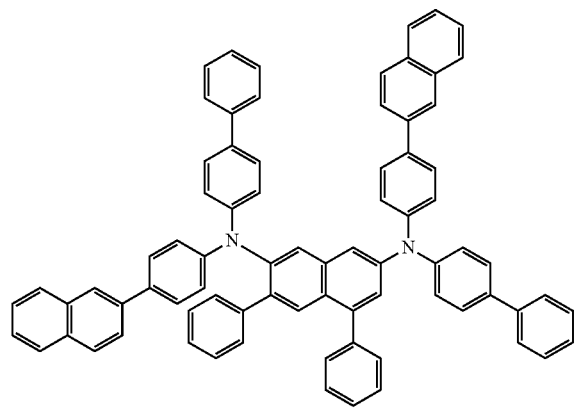
4-1
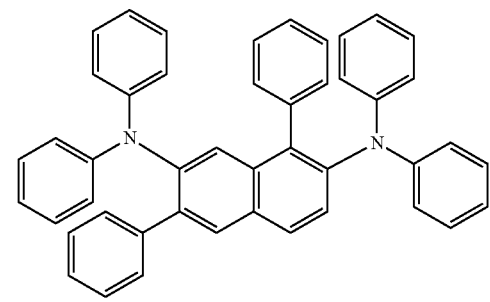
4-2
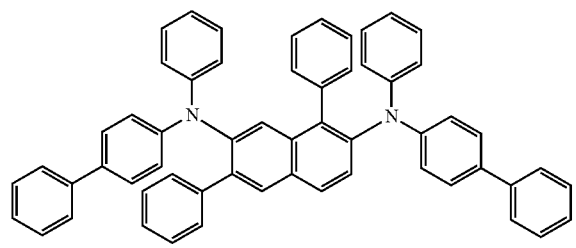
4-3
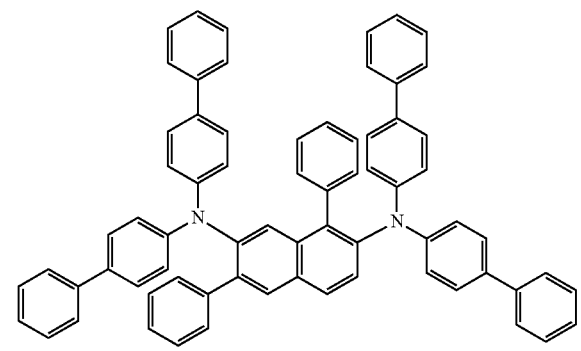
4-4
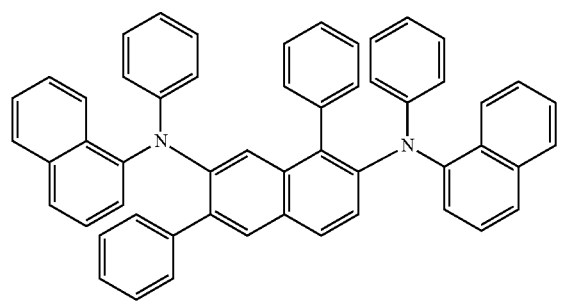
4-5
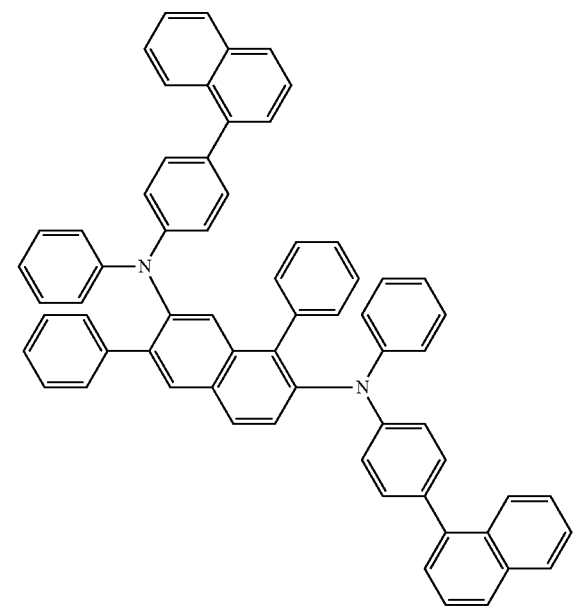

-continued
4-6
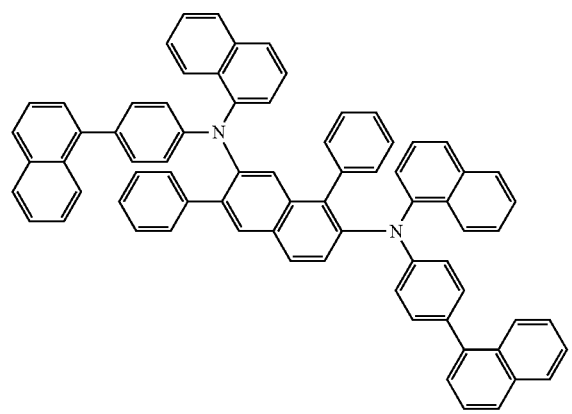
4-7
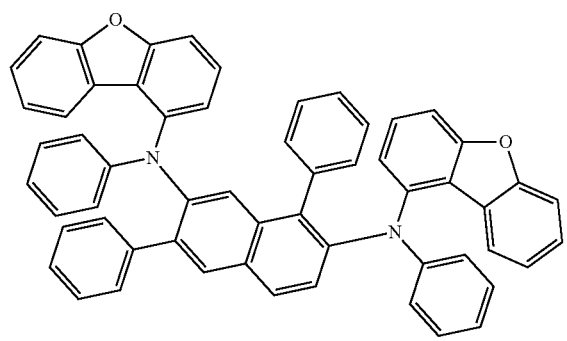
4-8
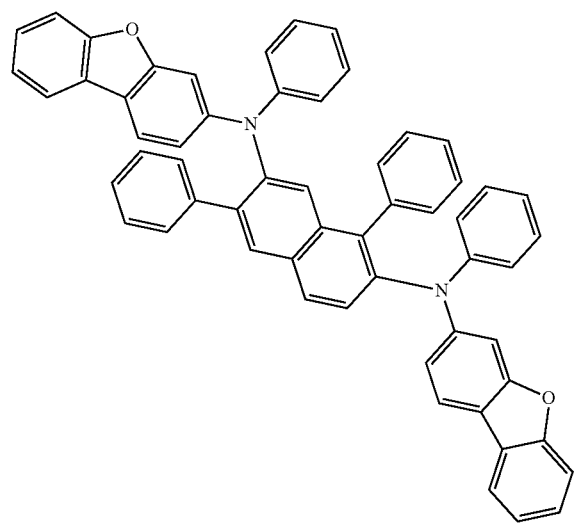
4-9
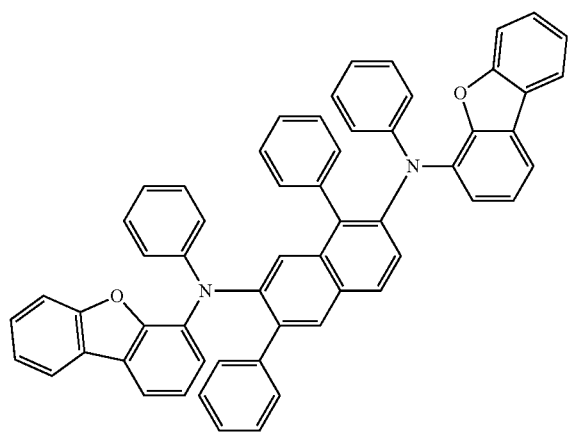
4-10
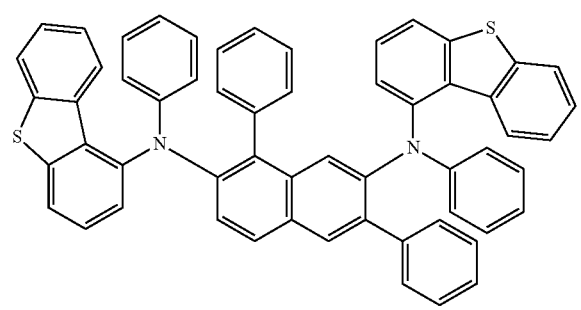
4-11
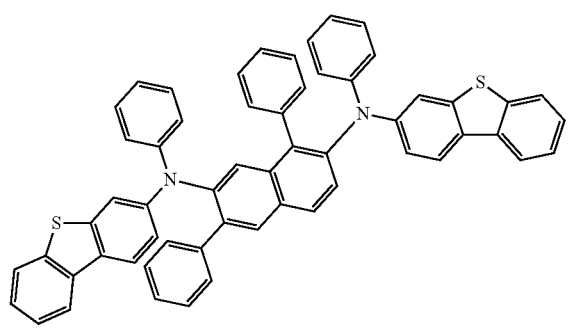

-continued
4-12
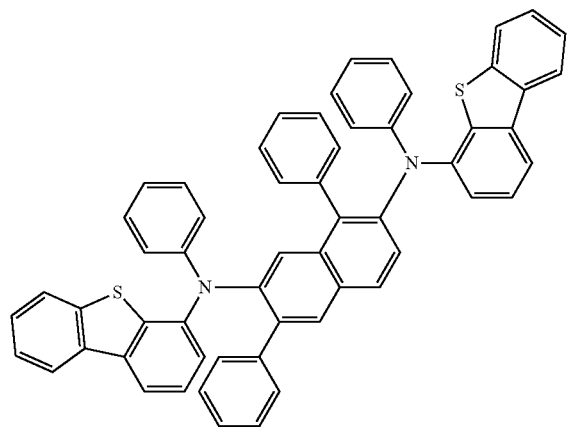
4-13
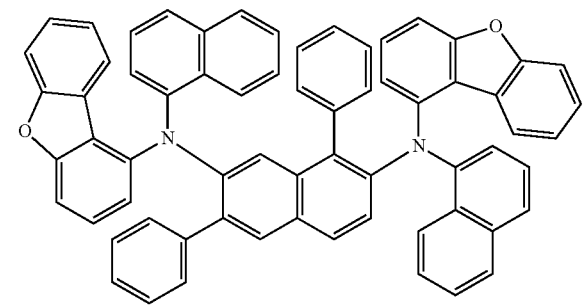
4-14
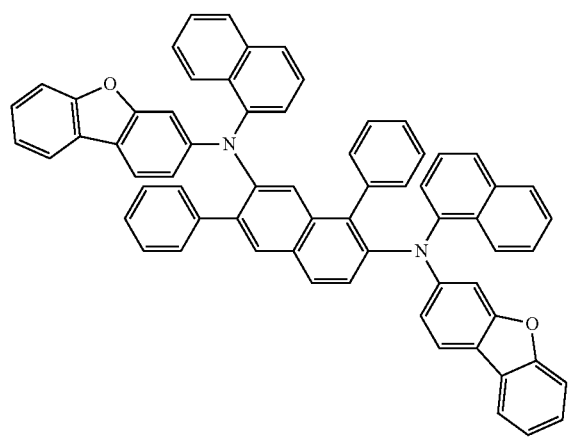
4-15
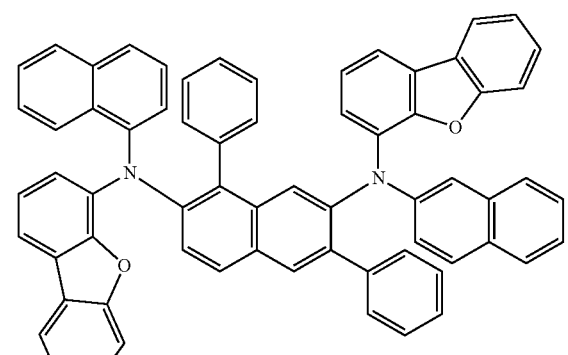
4-16
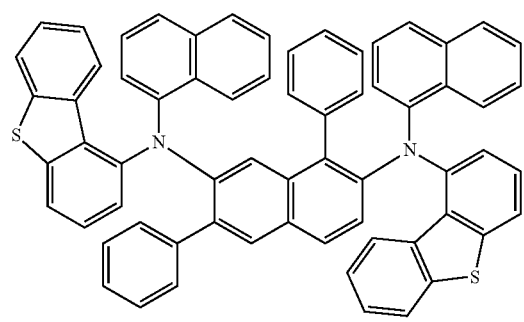
4-17
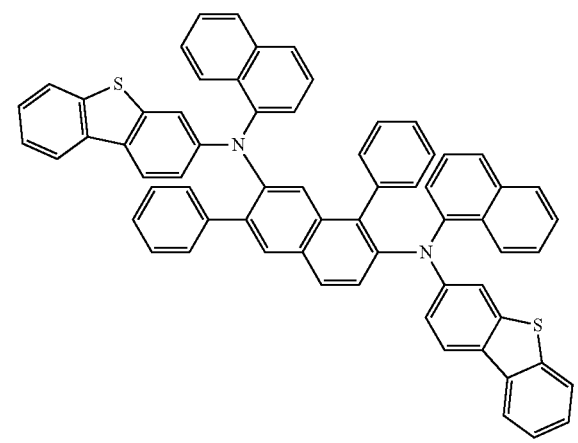

4-18
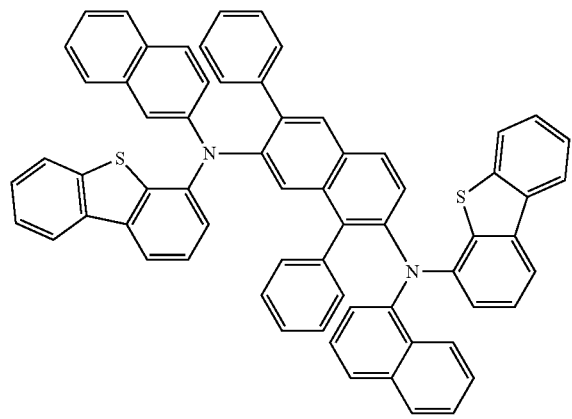
4-19
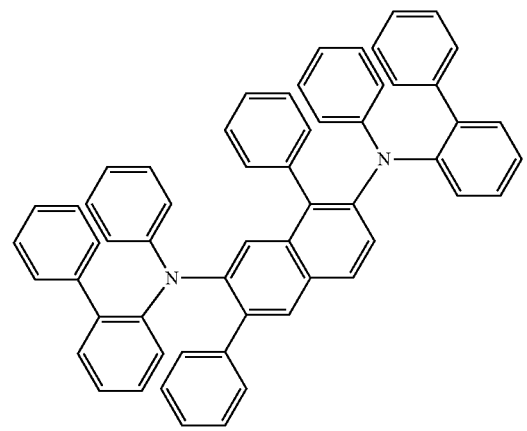
4-20
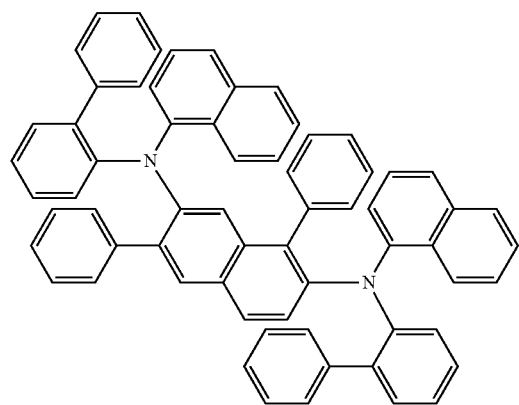
4-21
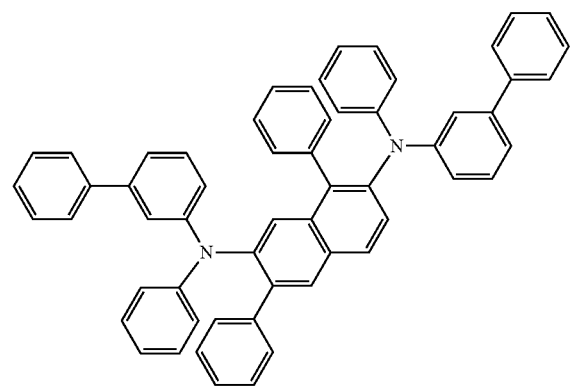
4-22
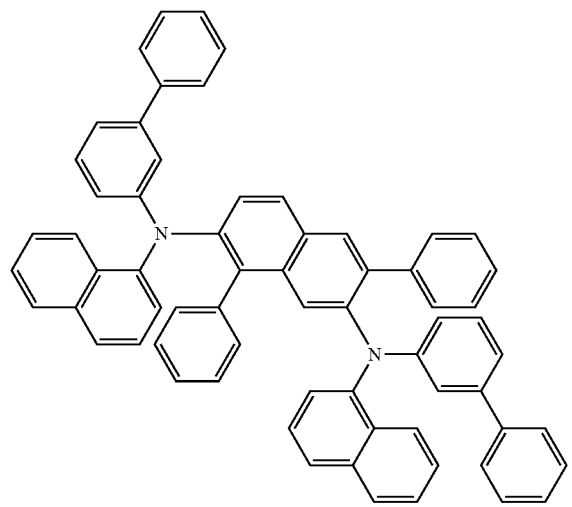
4-23
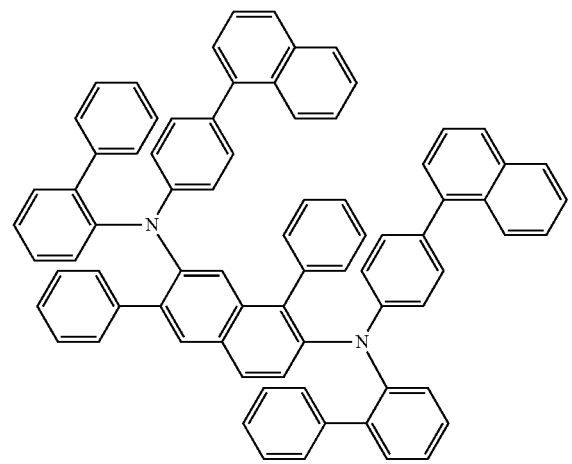

4-24
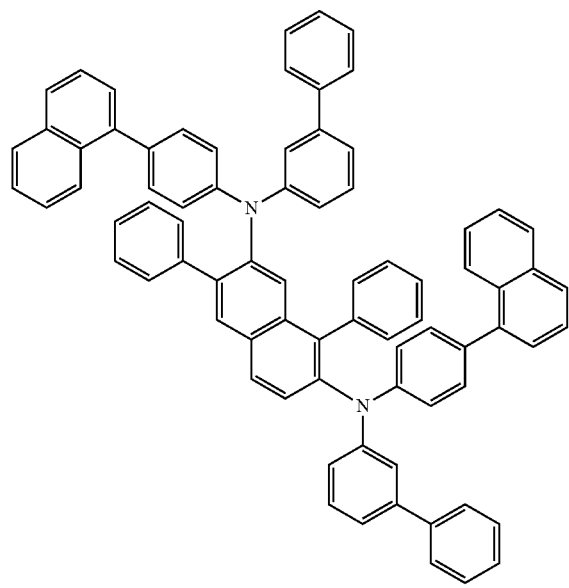
4-25
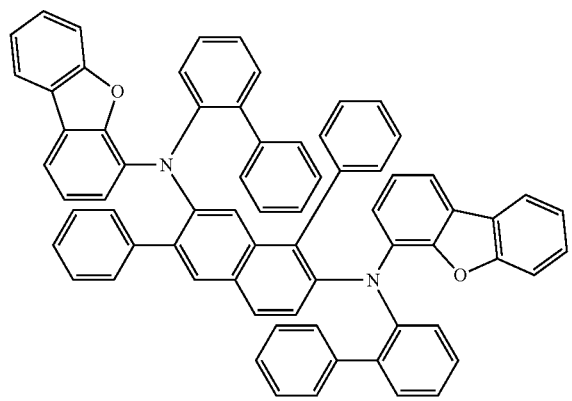
4-26
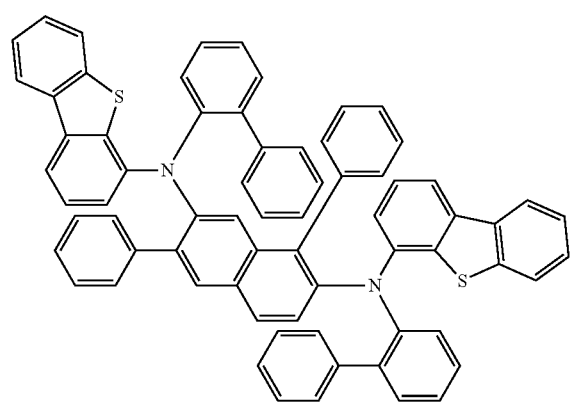
4-27
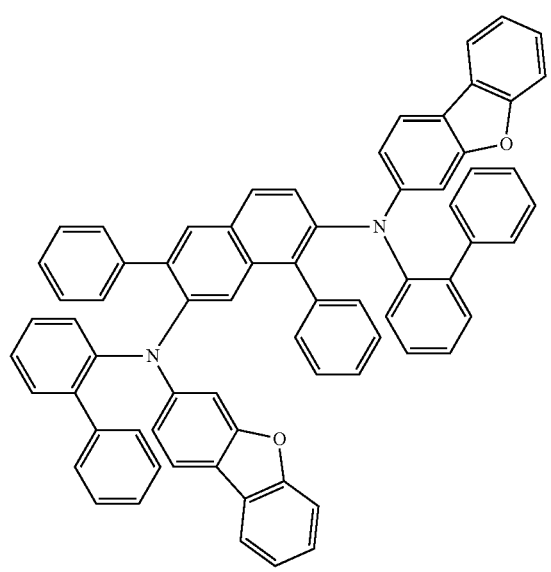

-continued
4-28
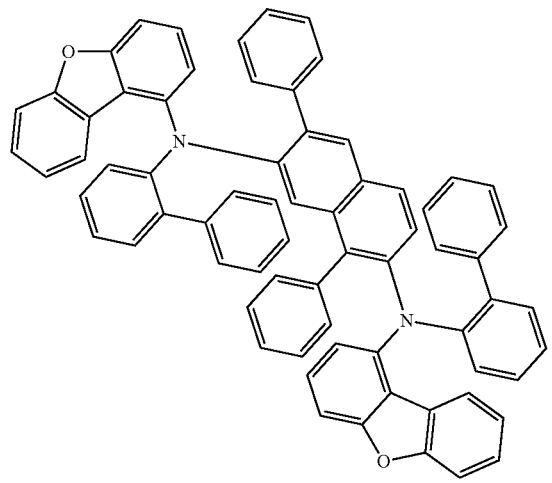
4-29
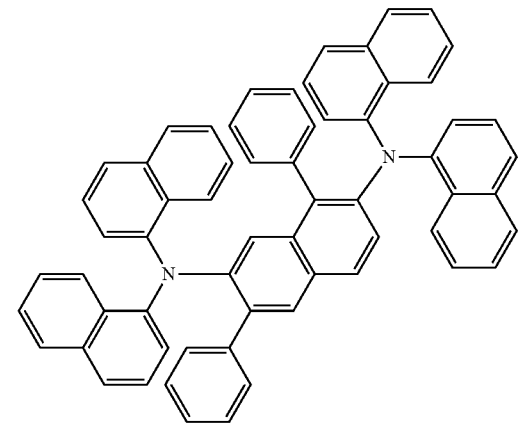
4-30
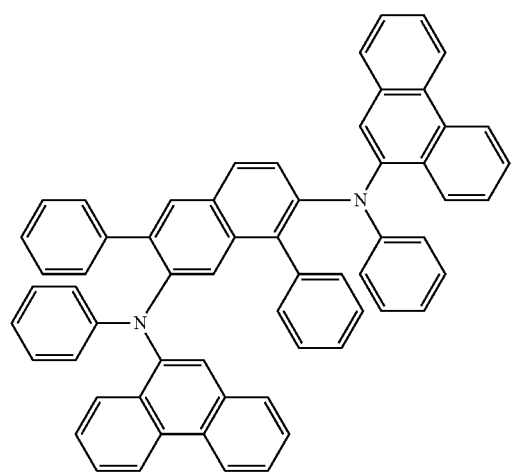
4-31
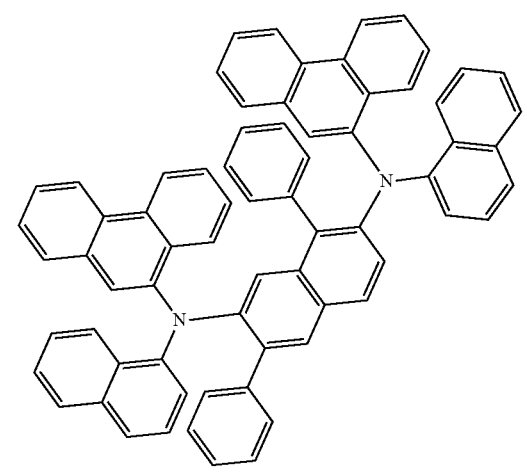
4-32
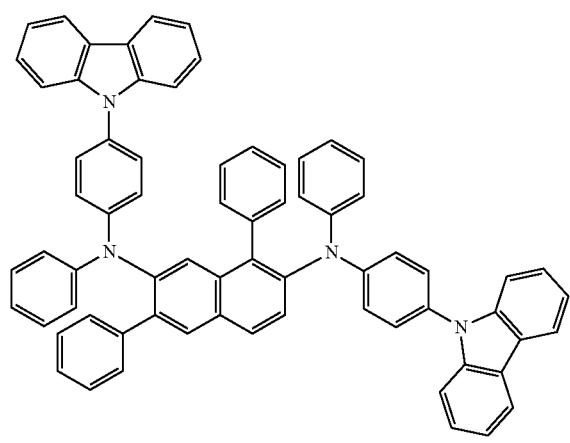
4-33
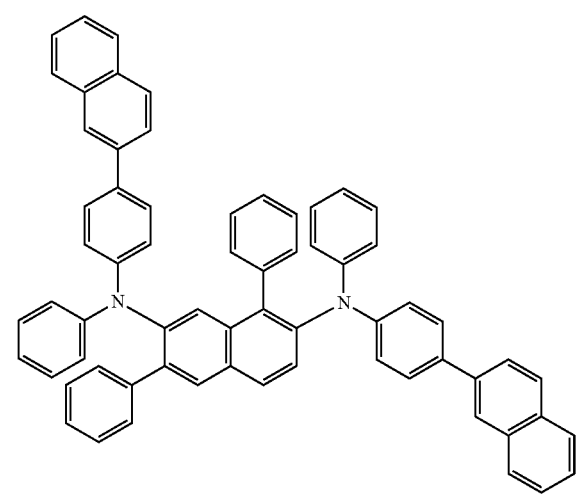

-continued
4-34
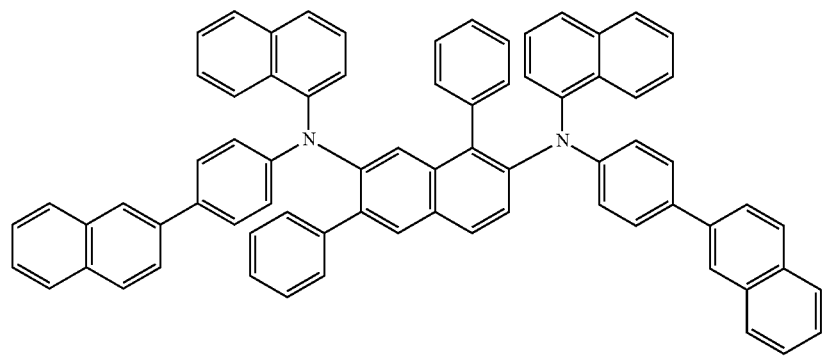
4-35
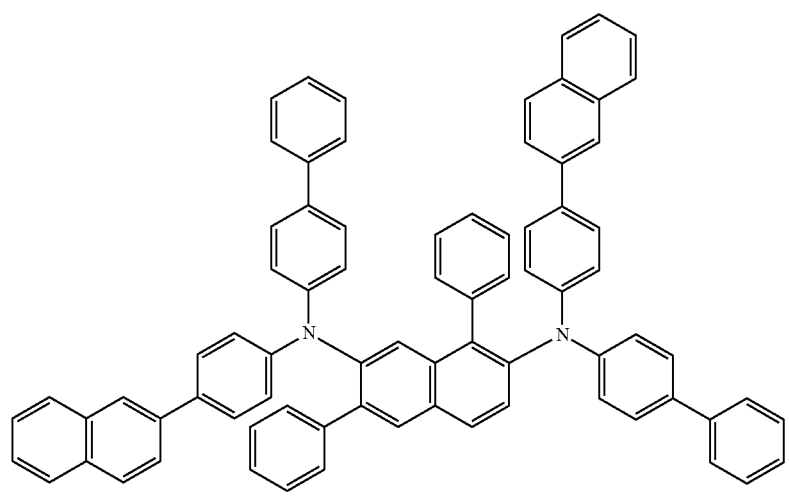
5-1
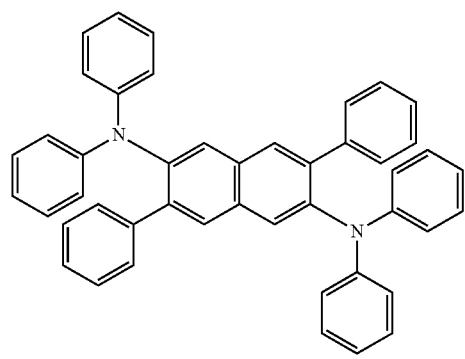
5-2
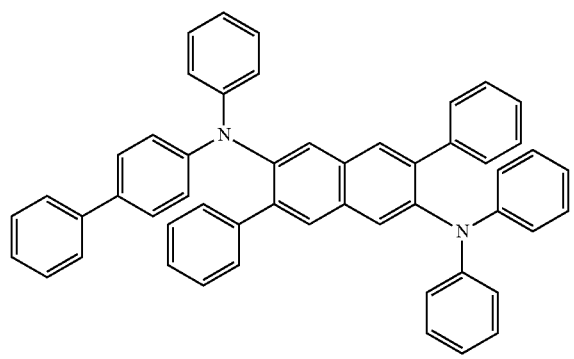

-continued
5-3
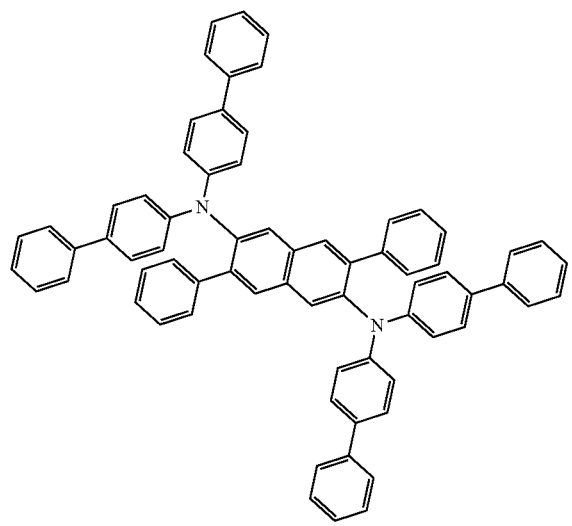
5-4
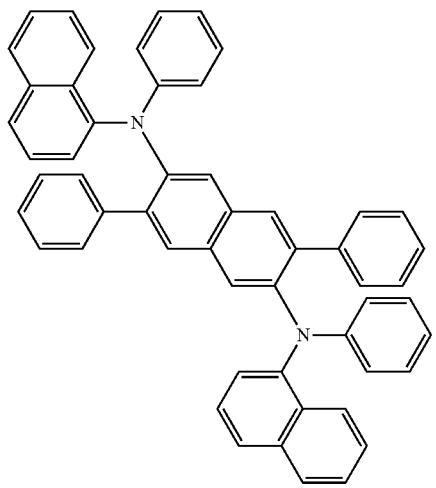
5-5
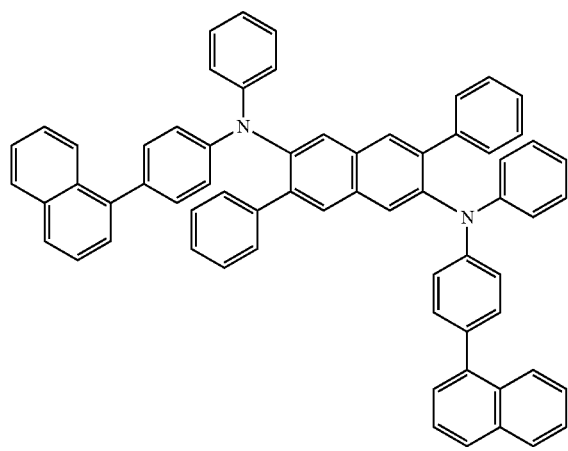
5-6
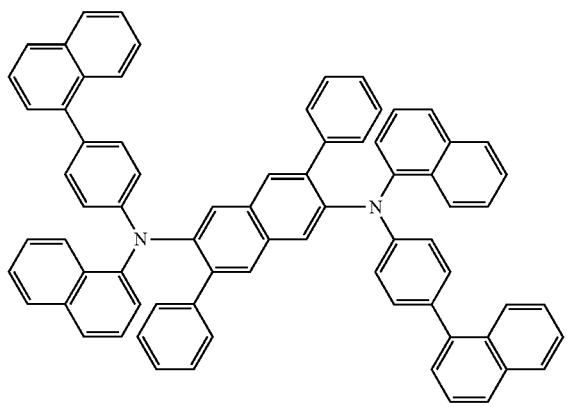
5-7
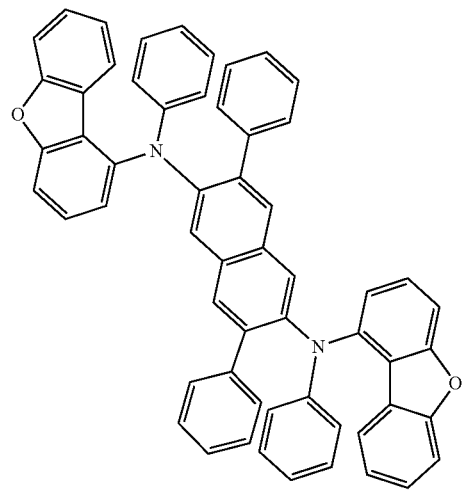
5-8
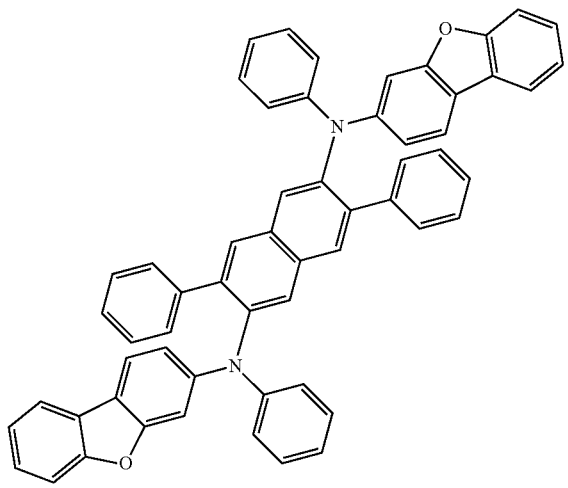

-continued
5-9
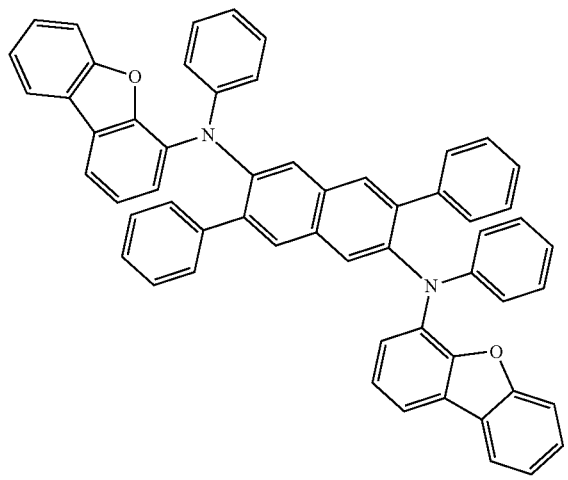
5-10
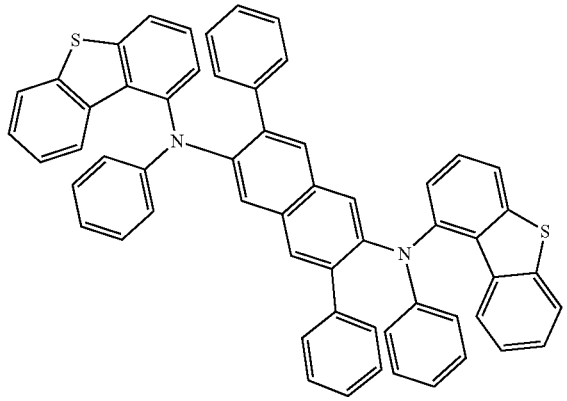
5-11
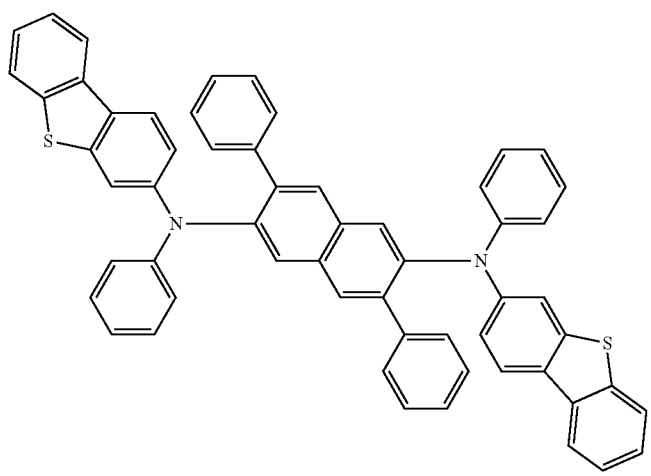
5-12
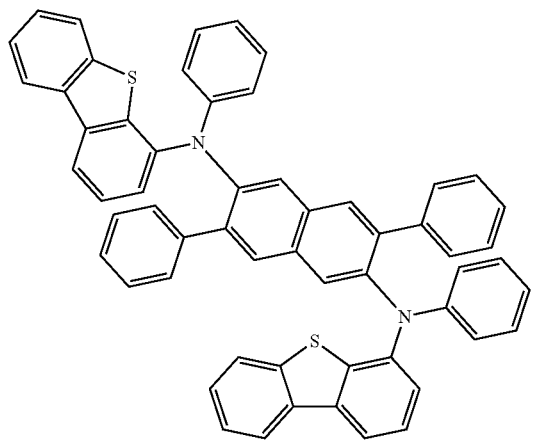
5-13
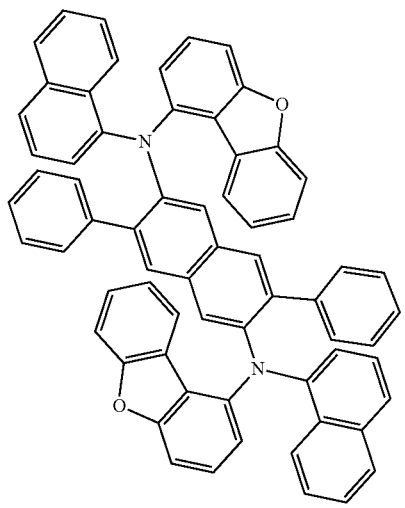

-continued
5-14
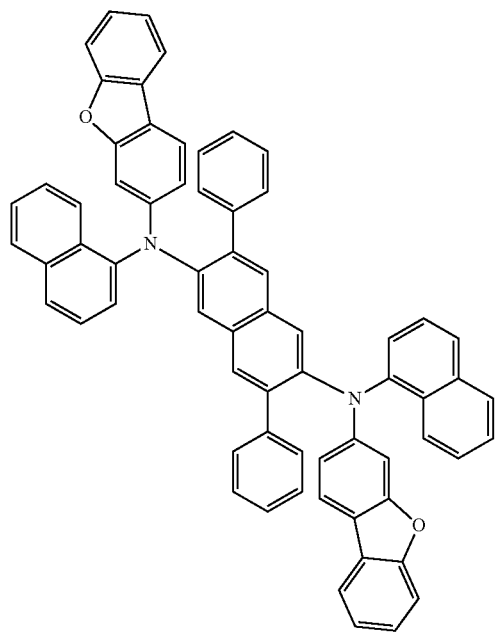
5-15
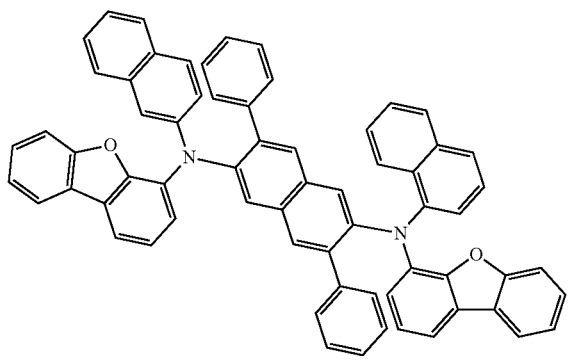
5-16
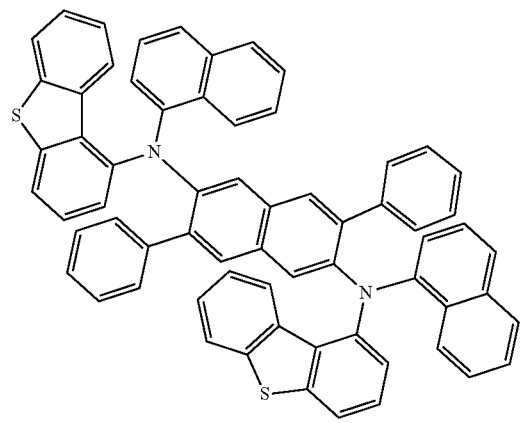
5-17
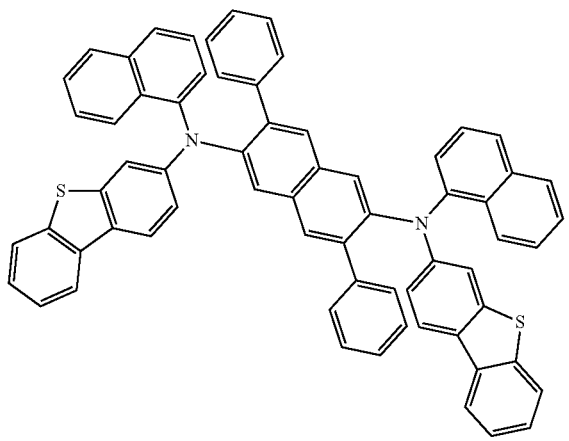
5-18
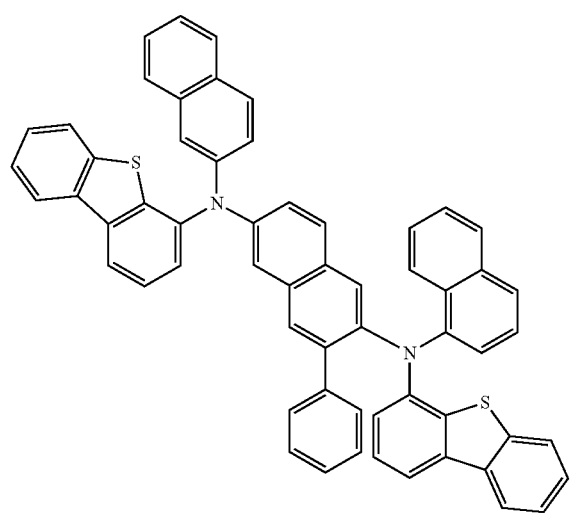
5-19
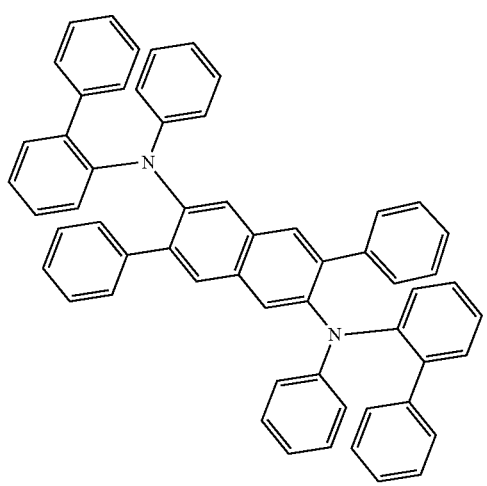

-continued
5-20
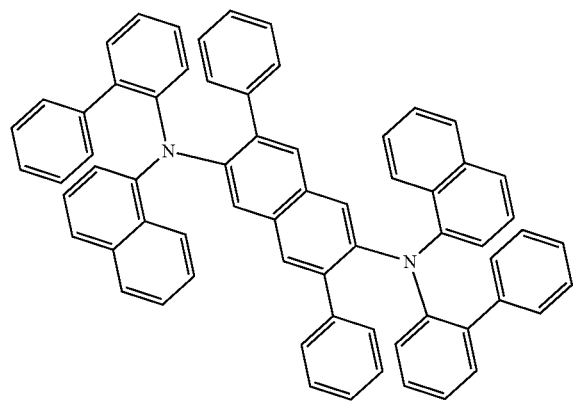
5-21
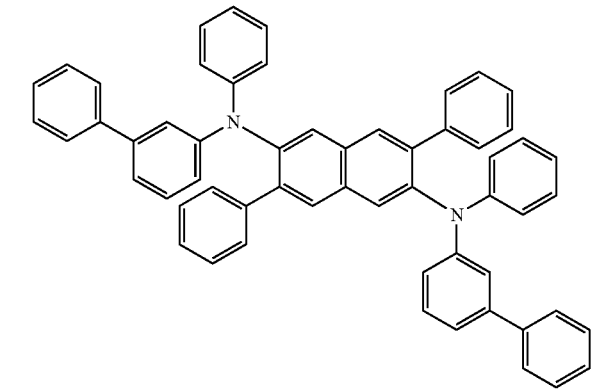
5-22
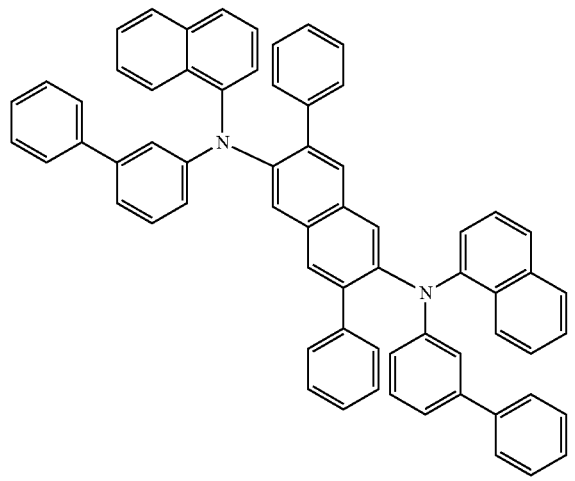
5-23
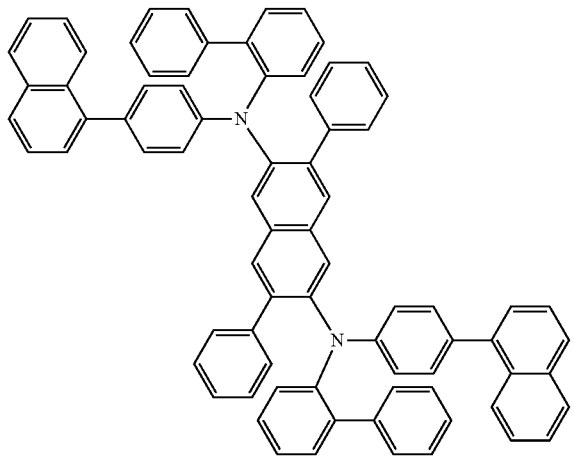
5-24
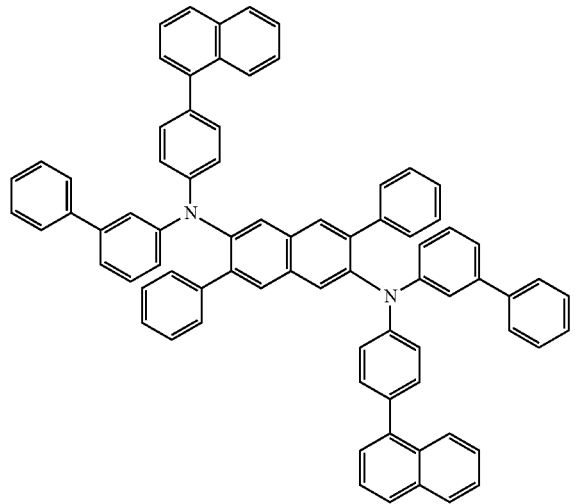
5-25
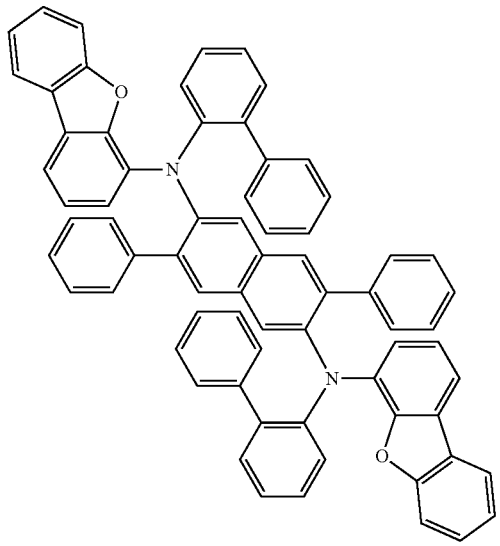

-continued
5-26
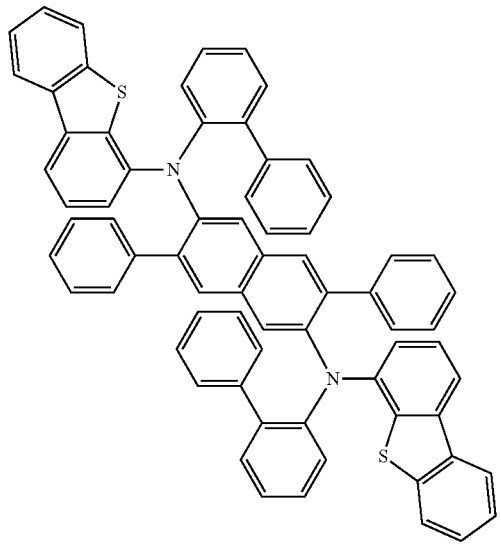
5-27
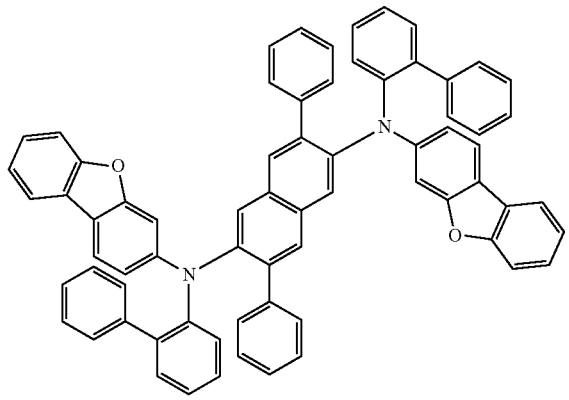
5-28
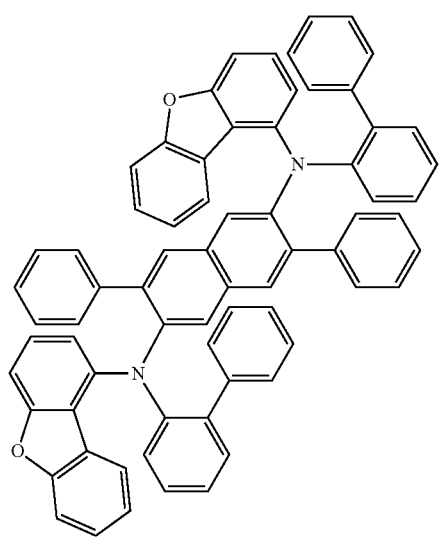
5-29
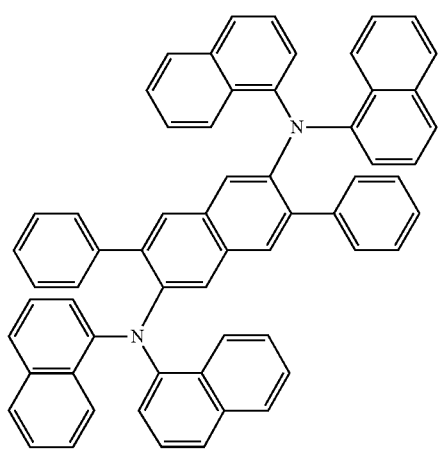
5-30
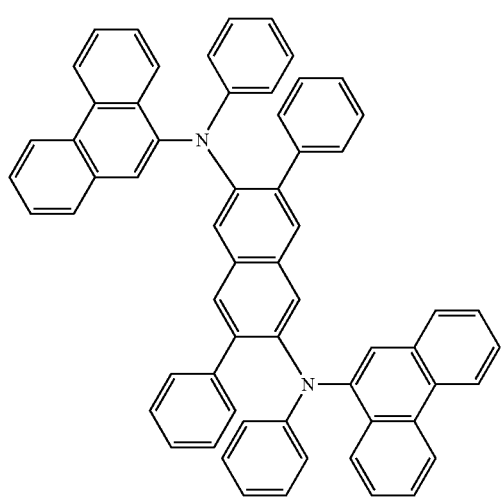
5-31
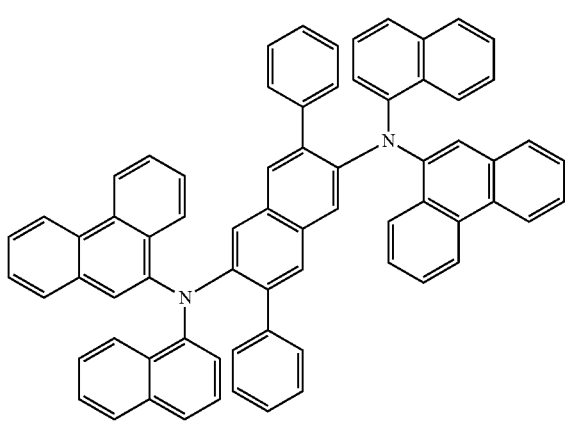

5-32
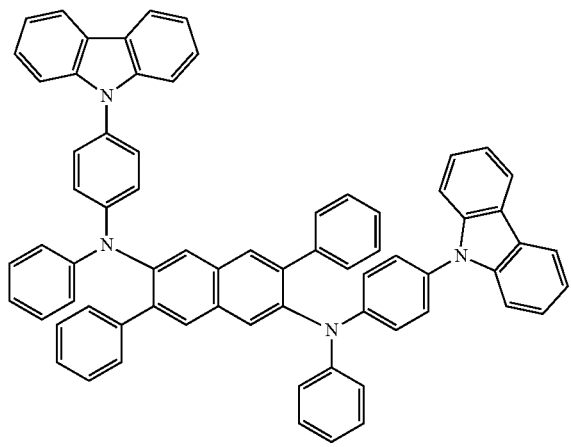
5-33
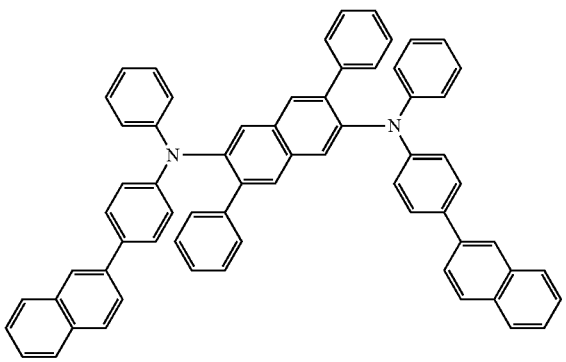
5-34
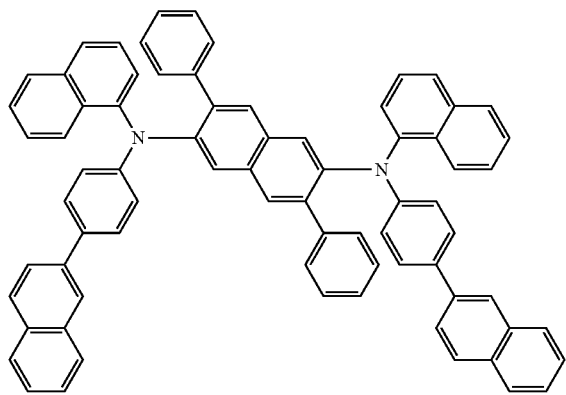
5-35
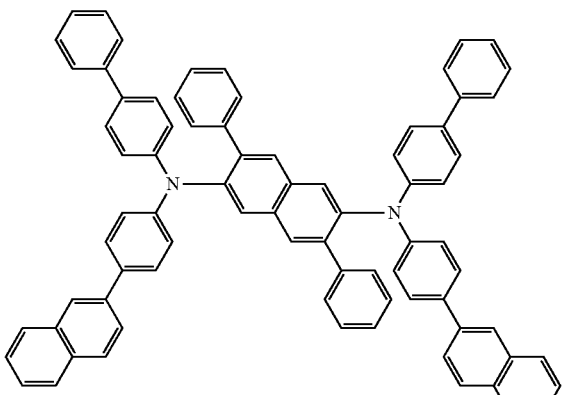
6-1
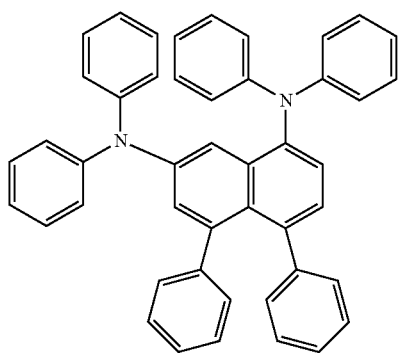
6-2
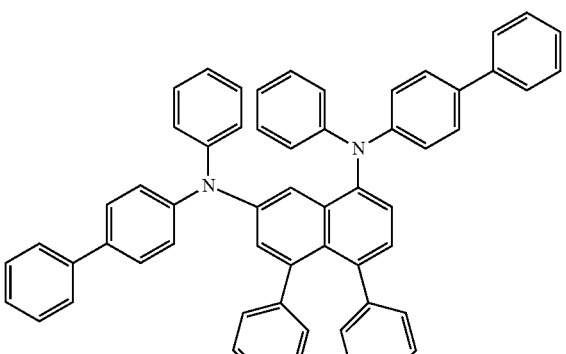

-continued
6-3
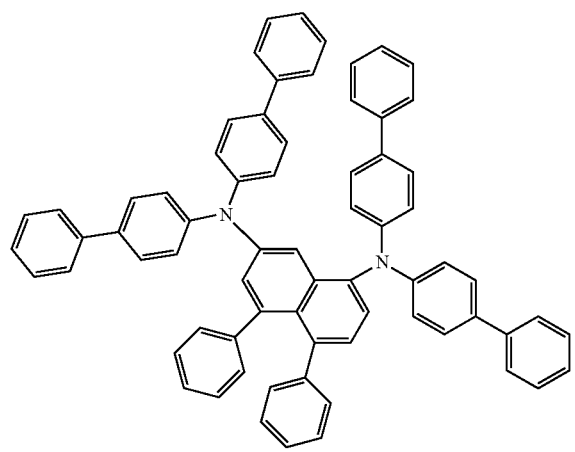
6-4
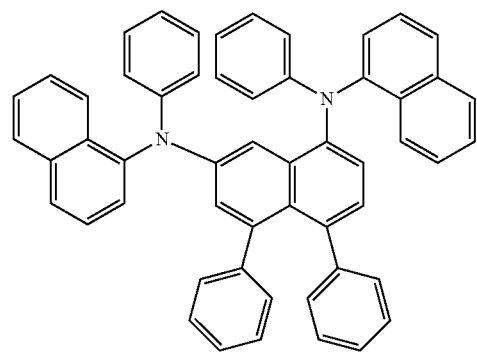
6-5
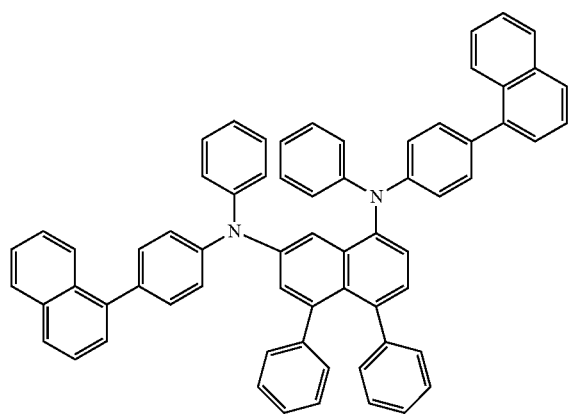
6-6
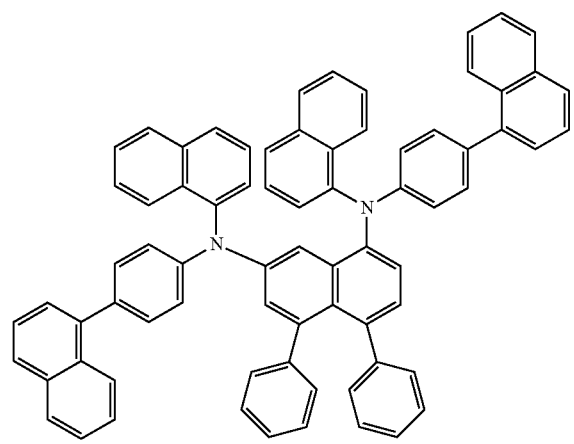
6-7
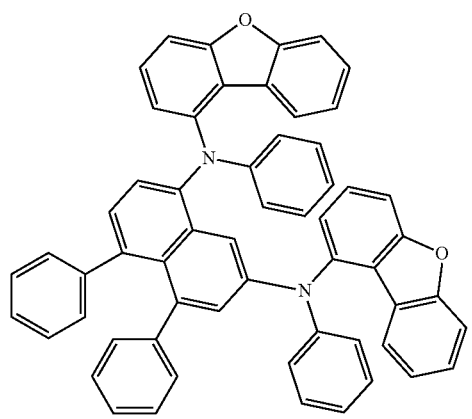
6-8
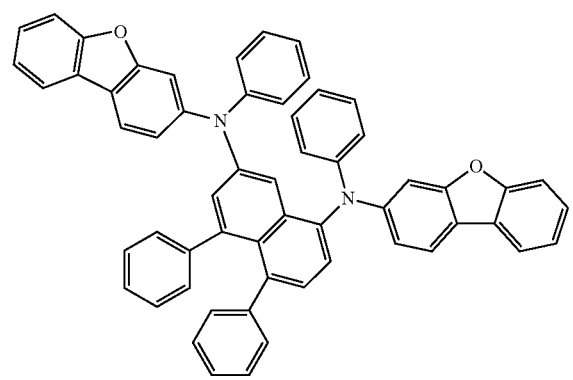

-continued
6-9
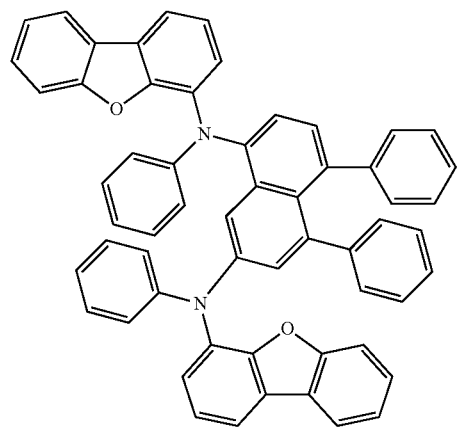
6-10
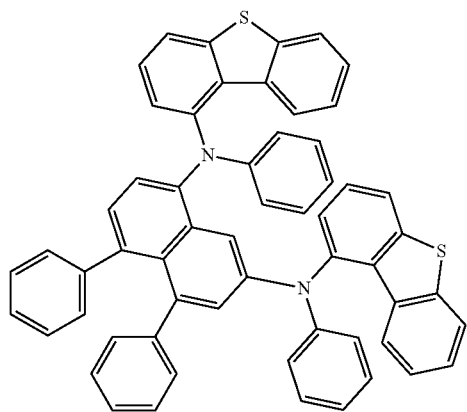
6-11
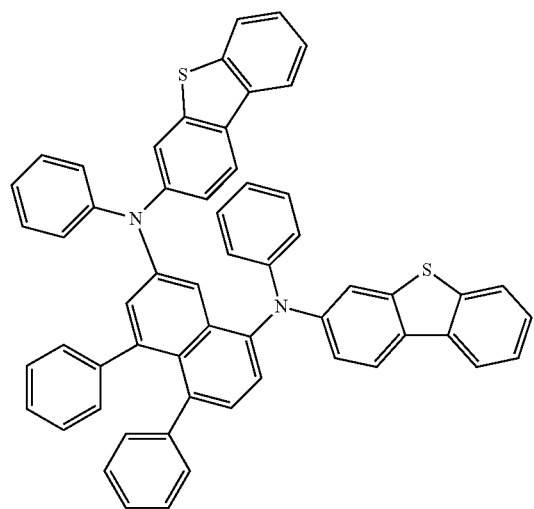
6-12
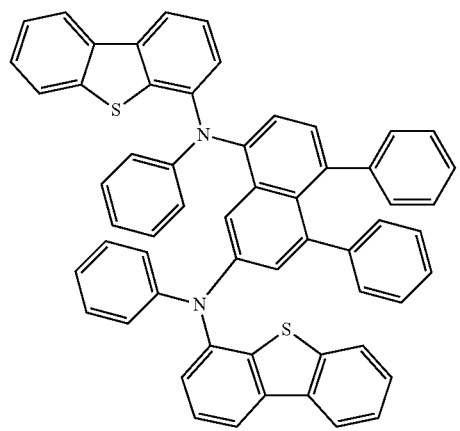
6-13
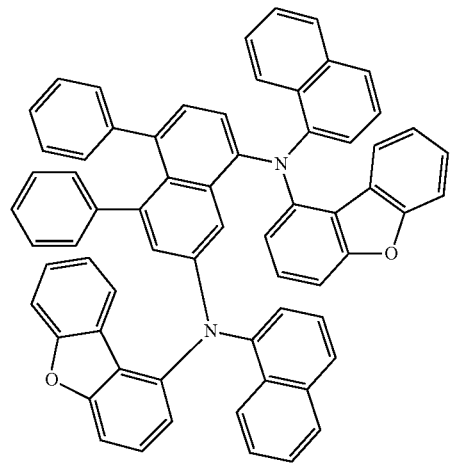
6-14
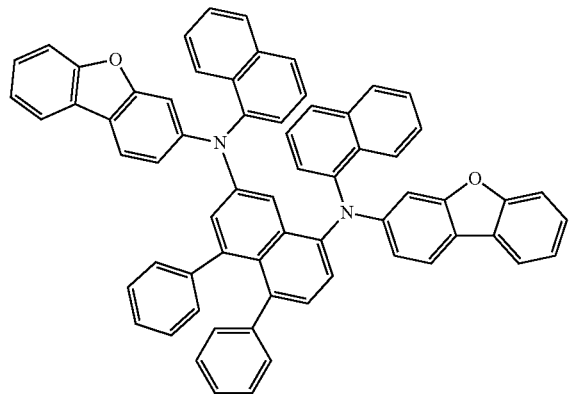

-continued
6-15
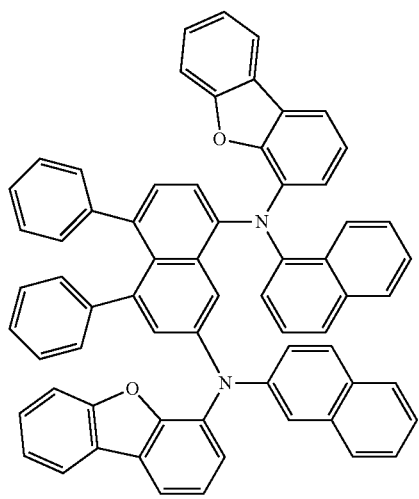
6-16
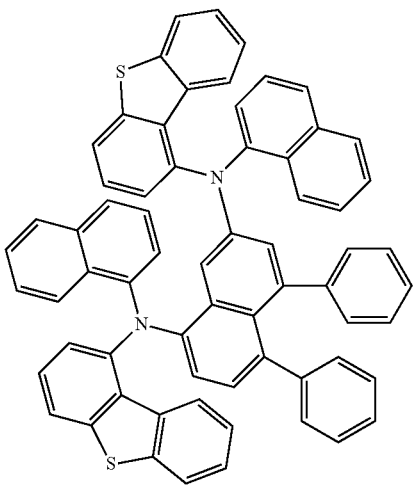
6-17
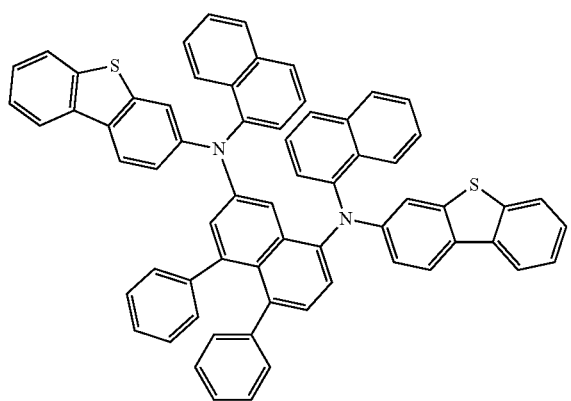
6-18
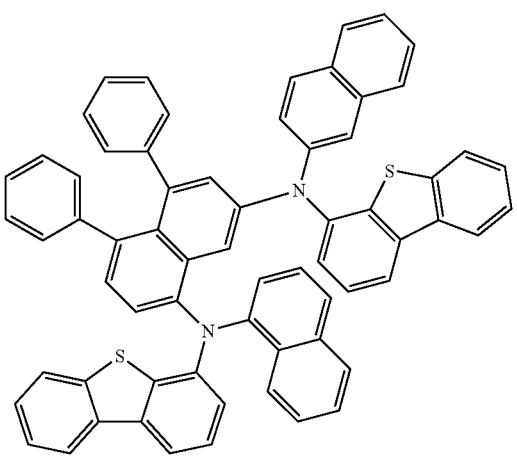
6-19
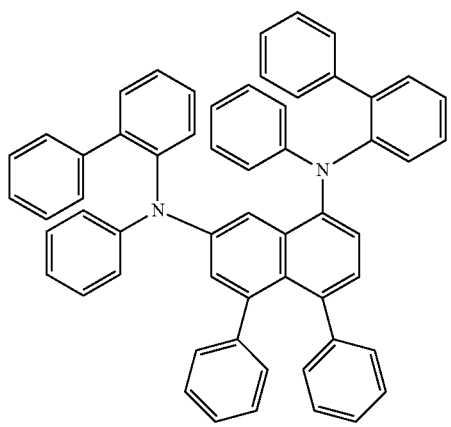
6-20
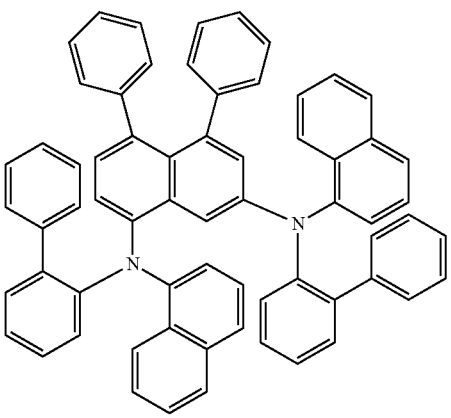

-continued
6-21
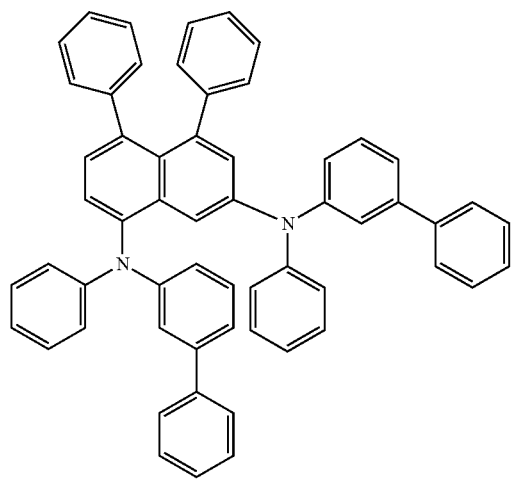
6-22
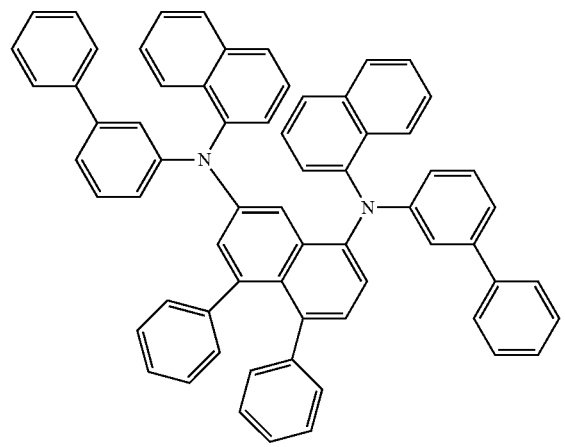
6-23
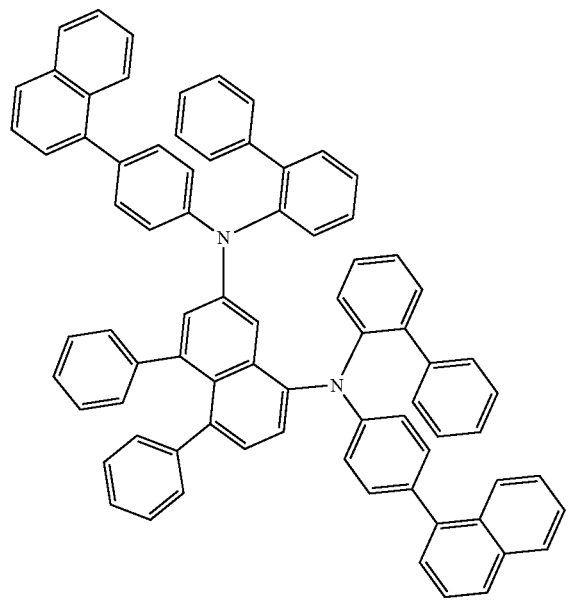
6-24
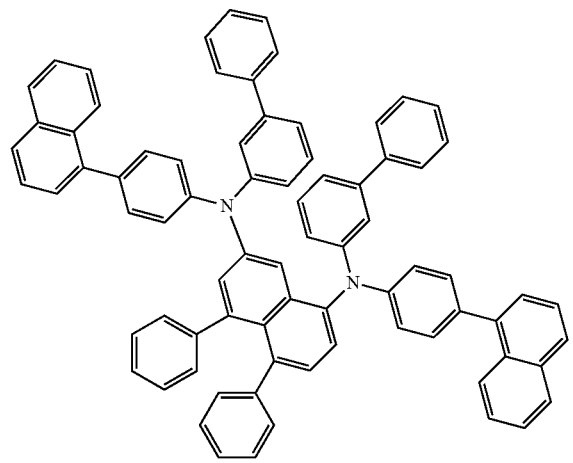
6-25
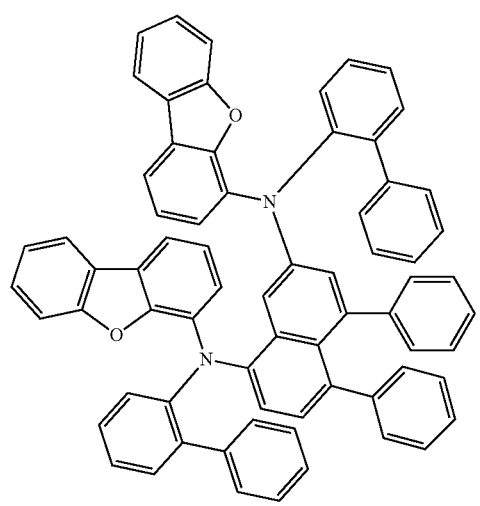
6-26
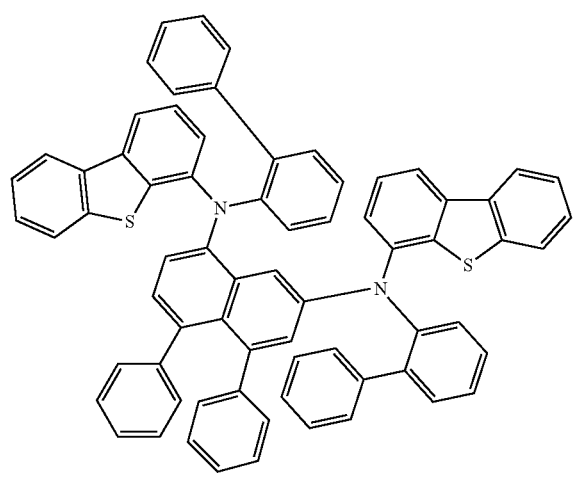

-continued
6-27
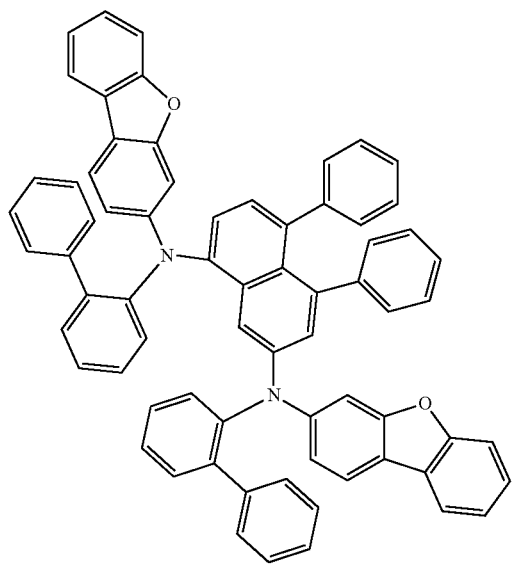
6-28
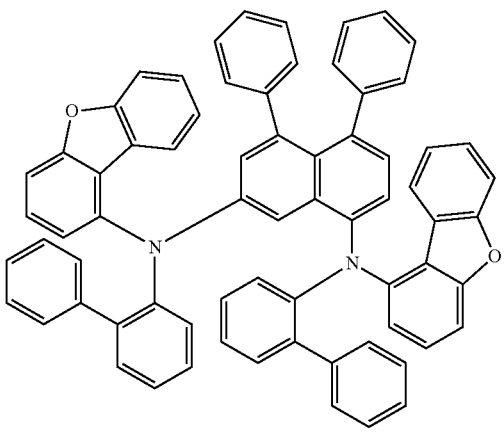
6-29
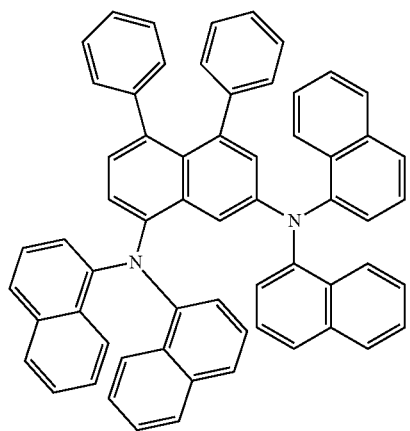
6-30
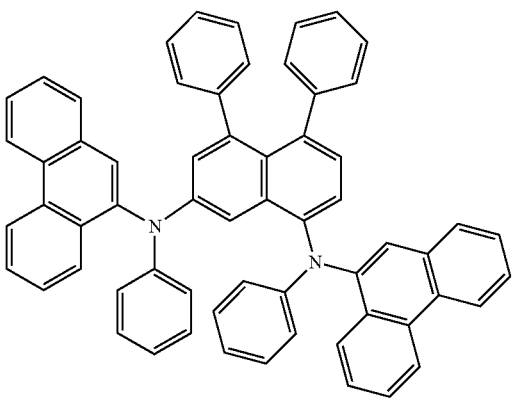
6-31
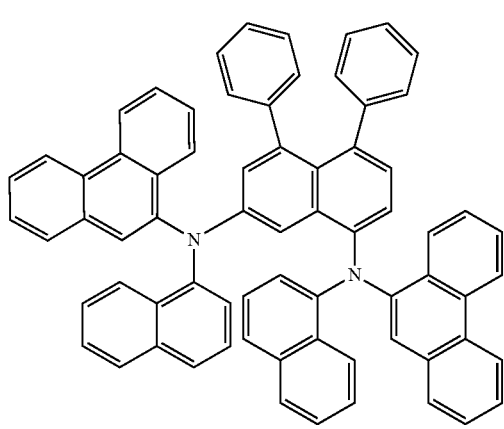
6-32
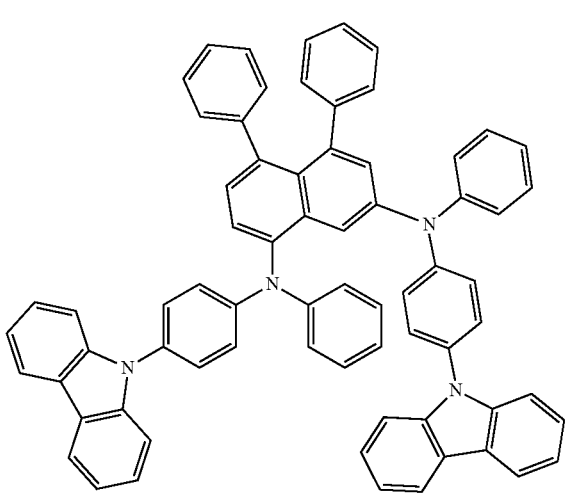

6-33
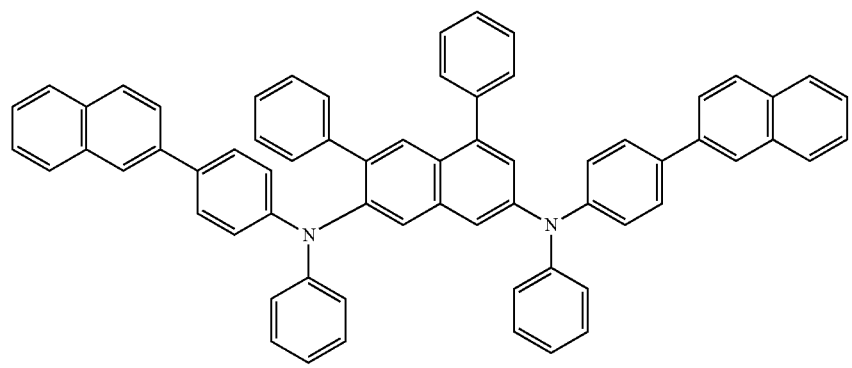
6-34
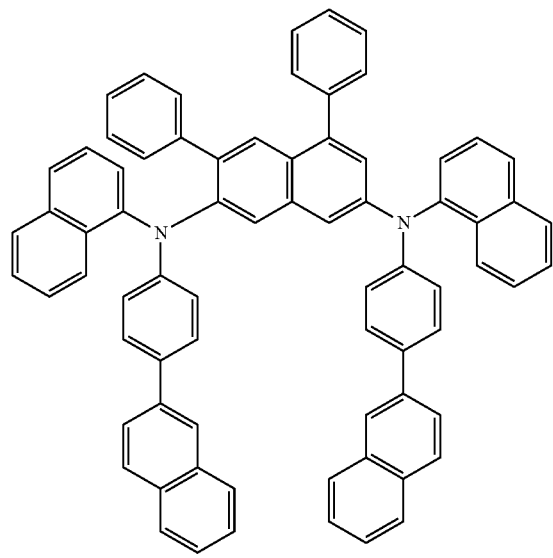
6-35
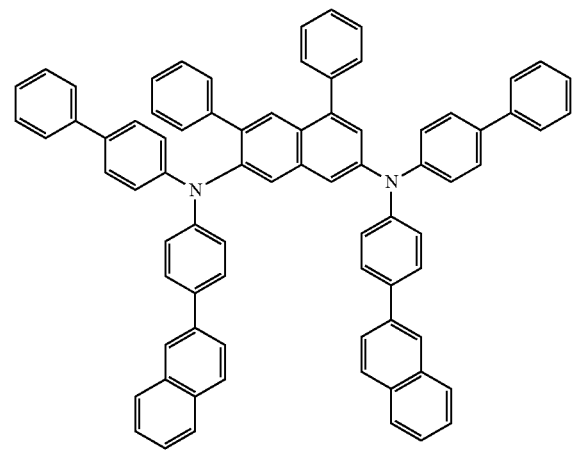
7-1
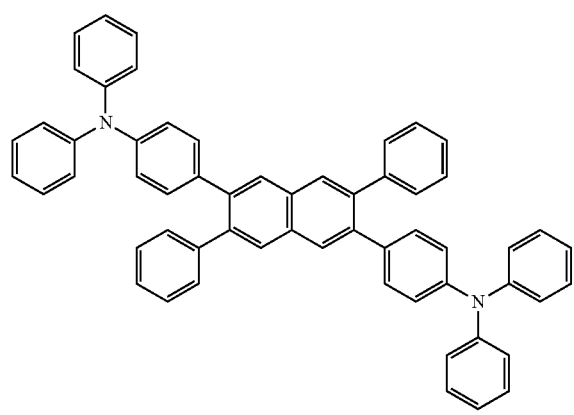
7-2
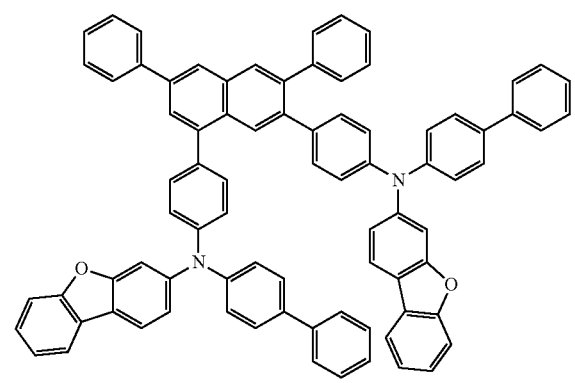

-continued
7-3
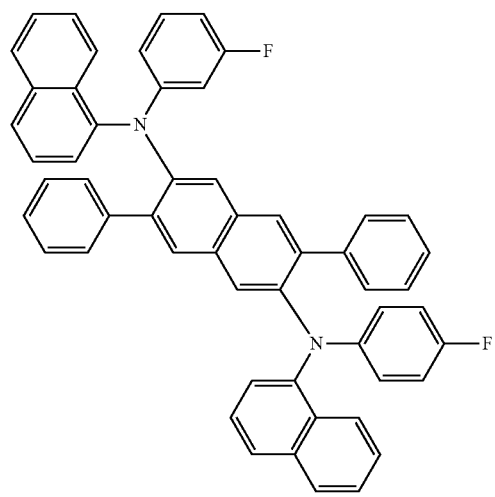
7-4
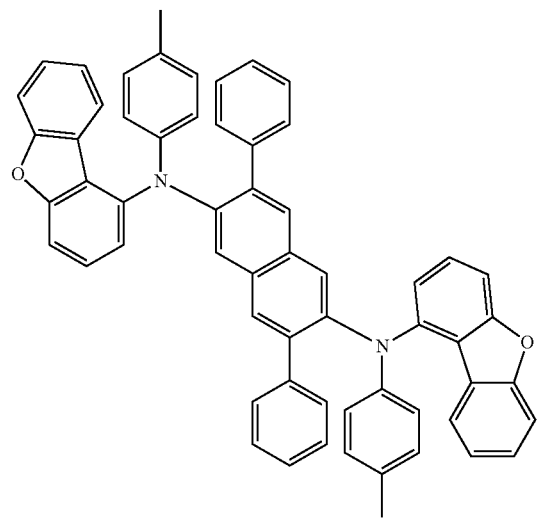
7-5
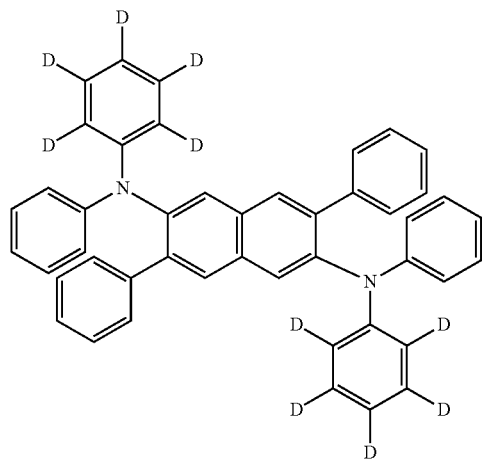
7-6
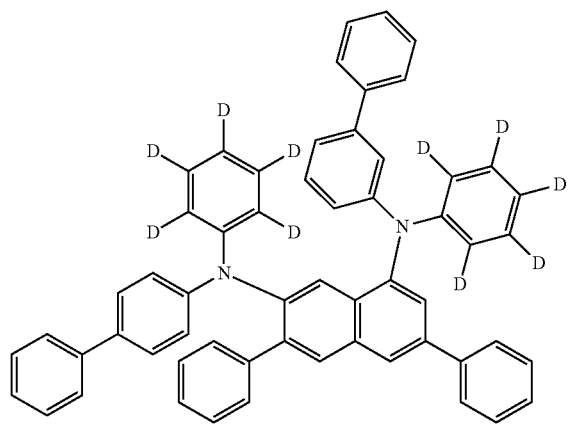
7-7
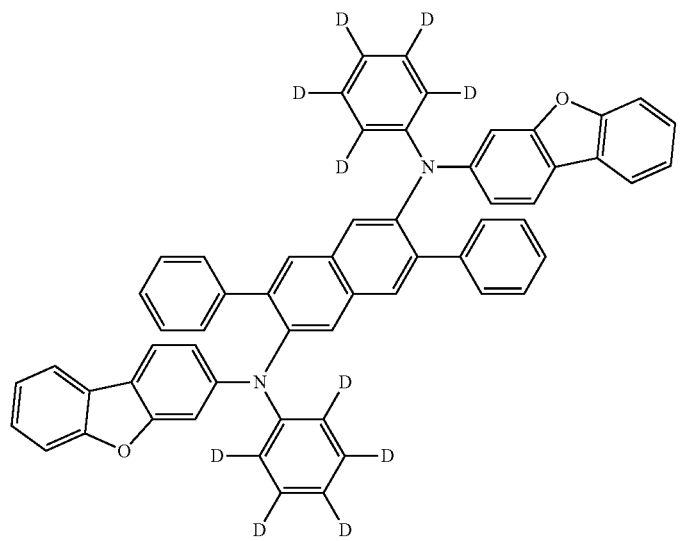

10. The diamine compound of claim 7, wherein Formula 6 is represented by Formula 6-1 or Formula 6-2:

[Formula 6-1]

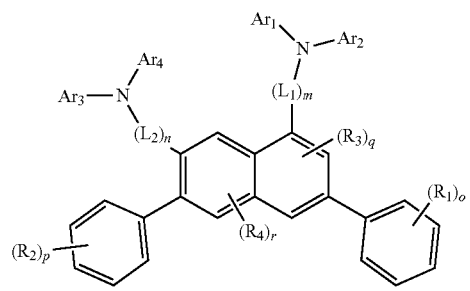

[Formula 6-2]

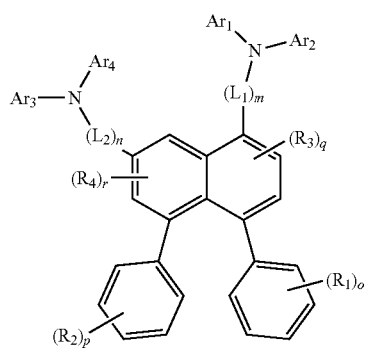

wherein in Formula 6-1 and Formula 6-2, $Ar_1$ to $Ar_4$, $L_1$, $L_2$, $R_1$ to $R_4$, and m to r are the same as defined in Formula 6.

11. The diamine compound of claim 7, wherein Formula 10 is represented by one of Formula 10-1 to Formula 10-3:

[Formula 10-1]

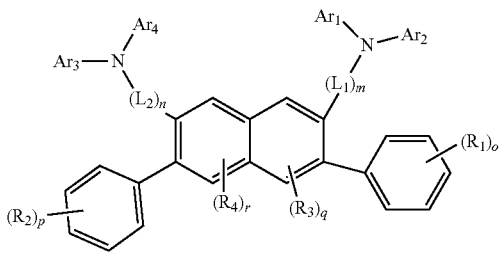

[Formula 10-2]

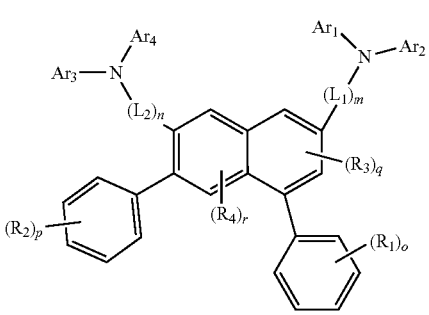

[Formula 10-3]

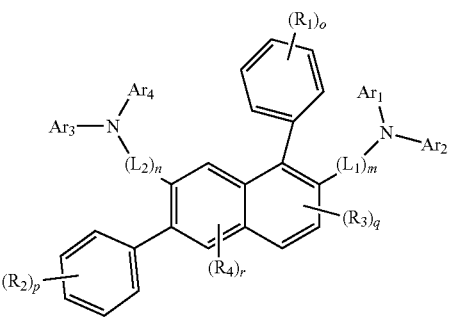

wherein in Formula 10-1 to Formula 10-3, $Ar_1$ to $Ar_4$, $L_1$, $L_2$, $R_1$ to $R_4$, and m to r are the same as defined in Formula 10.

* * * * *